(12) United States Patent
Georg et al.

(10) Patent No.: US 8,362,031 B2
(45) Date of Patent: Jan. 29, 2013

(54) LONIDAMINE ANALOGUES AND TREATMENT OF POLYCYSTIC KIDNEY DISEASE

(75) Inventors: Ingrid Gunda Georg, St. Paul, MN (US); Joseph S. Tash, Leawood, KS (US); Ramappa Chakrasali, St. Paul, MN (US); Sudhakar Rao Jakkaraj, Falcon Heights, MN (US); James P. Calvet, Lenexa, KS (US)

(73) Assignee: University of Kansas, Lawrence, KS (US)

(*) Notice: Subject to any disclaimer, the term of this patent is extended or adjusted under 35 U.S.C. 154(b) by 199 days.

(21) Appl. No.: 12/395,521

(22) Filed: Feb. 27, 2009

(65) Prior Publication Data

US 2009/0197911 A1 Aug. 6, 2009

Related U.S. Application Data

(63) Continuation-in-part of application No. 10/922,747, filed on Aug. 20, 2004, now Pat. No. 7,514,463.

(60) Provisional application No. 61/105,125, filed on Oct. 14, 2008.

(51) Int. Cl.
*A61K 31/4162* (2006.01)
*A61K 31/416* (2006.01)
*A61P 13/12* (2006.01)

(52) U.S. Cl. ........................ 514/303; 514/406
(58) Field of Classification Search .................. 514/303, 514/406
See application file for complete search history.

(56) References Cited

U.S. PATENT DOCUMENTS 4,609,659 A 9/1986 Hartman

FOREIGN PATENT DOCUMENTS

EP 0272824 6/1988

OTHER PUBLICATIONS

Gong et al., Journal of Membrane Biology, (2000), 178(3), p. 225-233 (Abstract from STN search report).*
Gong et al., Biology of Reproduction, (2000), 63(3), p. 833-838 (Abstract from STN search report).*
Okada et al. Human Reproduction, 14(1), (1999), p. 110-113.*
Ames, B. et al., "An improved bacterial test system for the detection and classification of mutagens and carcinogens," Proc. Natl. Acad. Sci. USA, 70, pp. 782-786, 1973.
Cancer, Principles and Practice of Oncology, Lippincott-Raven Ed., pp. 418-432, 1997.
Cancer, Principles and Practice of Oncology, Lippincott-Raven Ed., pp. 467-483, 1997.
Berge, S. M. et al., "Pharmaceutical Salts," J. Pharmaceutical Sciences, 66. pp. 1-19, 1977.
Bulinski, "Overexpression of MAP4 inhibits organelle motility and trafficking in vivo," Journal of Cell Science 110, pp. 3055-3064, 1997.
Davis et al., "Aromatic Biosynthesis, VII. Accumulation of Two Derivatives of Shikimic Acid by Bacterial Mutants," J. Bacteriol., 66(2), pp. 129-136, 1953.
Gilbert, R. I., The Analysis of Fluctuation Tests, Mutation Research, pp. 283-289, 1980.
Gonen, H., et al., "Protein synthesis elongation factor EF-1 alpha is essential for ubiquitin-dependent degradation of certain N alpha-acetylated proteins and may be substituted for by the bacterial elongation factor EF-Tu," Proc. Natl. Acad. Sci. U S A., 91(16), pp. 7648-7652, 1994.
Higuchi, T. & V. Stella, "Prodrugs as Novel delivery Systems," vol. 14, ACS Symposium Series; American Chemical Society: Washington, DC, 1975.
George, Journal of Chemical Society Perkin Trans 1: Organic and Bio-organic Chemistry, 9, pp. 2409-2415, 1990.
Komin, A. P. et al., "The Chemistry of 1, 2, 5-Thiadiazoles vs. Synthesis of 3,4-Diamino 1, 2, 5-thiadiazole [1,2,5] thiadiazolo and [3,4-b] pyrazides," J. Het. Chem., vol. 13, pp. 13-22, 1976.
Laemmli, "Cleavage of Structural Proteins During the Assembly of the Head of Bacteriophage T4," Nature, vol. 228, pp. 680-685, 1970.
Magenheimer, BS et al., "Early Embryonic Renal Tubules of Wild-Type and Polycystic Kidney Disease Kidneys Respond to cAMP Stimulation with Cystic Fibrosis Transmembrane Conductance Regulator/Na+,K+,2CI- Co-Transporter-Dependent Cystic Dilation," J. Am. Soc. Nephrol. 17, pp. 3424-3437, 2006.
McCann, J. et al. "Detection of carcinogens as mutagens in the *Salmonella*/microsome test: Assay of 300 chemicals," Proc. Nat. Acad. Sci. USA, vol. 72, No. 12, pp. 5135-5139, 1975.
Muhlradt, "Epothilone B Stabilizes Microtubuli of Macrophages Like Taxol without Showing Taxol-like Endotoxin Activity," Cancer Research 57, pp. 3344-3346, 1997.
Nicolaou, "Synthesis of Epothilones A and B in Solid and Solution Phase," Letters to Nature, Nature, vol. 387, pp. 268-272,1997.
Osdene, T.S., et al., "2,4,7-Triamino-6-ortho-substituted Arylpteridiiies—A New Series of Potent Antimalarial Agents," J. Med. Chem., 10(3), pp. 431-434, 1967.
Panda, D. et al., "Differential Effects of Vinblastine on Polymerization and Dynamics at Opposite Microtubule Ends," The Journal of Biological Chemistry, vol. 271, No. 47, Issue of Nov. 22, pp. 29807-29812, 1996.
Panda, D. et al., "Stabilization of microtubule dynamics by estramustine by binding to a novel site in tubulin: A possible mechanistic basis for its antitumor action," Proc. Natl. Acad. Sci. USA, vol. 94, pp. 10560-10564, 1997.
Reich, M.F. et al, "Pyrido[3,4-e]-1,2,4-triazines and Related Heterocycles as Potential Antifungal Agents," J. Med. Chem.,32, pp. 2474-2485, 1989.

(Continued)

*Primary Examiner* — Yong Chu
(74) *Attorney, Agent, or Firm* — Workman Nydegger

(57) ABSTRACT

Lonidamine derivatives can be useful in methods of treating, inhibiting, and/or preventing polycystic kidney disease (PKD). Accordingly, lonidamine derivatives can be administered in a therapeutically effective amount for inhibiting, and/or preventing polycystic kidney disease (PKD) in the subject. This can include administering a therapeutically effective amount of the lonidamine derivatives for inhibiting CFTR and/or Hsp90 or biological pathway thereof. Also, the method can include administering the lonidamine derivatives in a therapeutically effective amount for inhibiting ErbB2, Src, Raf-1, B-Raf, MEK, Cdk4, NKCC1, or combinations thereof. For example, the therapeutically effective amount of the lonidamine derivatives can be configured so as to provide a concentration in or adjacent to a kidney cell of about 0.25 uM or more or less.

12 Claims, 45 Drawing Sheets

OTHER PUBLICATIONS

Roche, E.B., "Bioreversable Carriers in Drug Design," American Pharmaceutical Association and Pergamon Press, 1987.

Service, R.F., "Chemical Synthesis: Tumor-Killer Made; How Does It Work?" Science, Dec. 20, 1996: vol. 274. No. 5295, pp. 2009.

Shevchenko, A. et al., "Mass Spectrometric Sequencing of Proteins from Silver-Stained Polyacrylamide Gels," Anal. Chem., 68, pp. 850-858, 1996.

Tash, J.S., "Gamendazole, an Orally Active Indazole Carboxylic Acid Male Contraceptive Agent, Targets HSP90AB1 (HSP90BETA) and EEF1A1 (eEF1A), and Stimulates IIIa Transcription in Rat Sertoli Cells," Biology of Reproduction, 78, pp. 13139-1152, 2008.

Trecourt, "Improved Synthesis of 2,3-Disubstituted Pyridines by Metallation of 2-Chloropyridine: a Convenient Route to Fused Polyheterocycles," J. Chem. Soc. Perkin Trans. 1, pp. 2409-2415,1990.

Vasquez, "Nanomolar Concentrations of Nocodazole Alter Microtubule Dynamic Instability In Vivo and In Vitro," Molecular Biology of the Cell, vol. 8, pp. 973-985, 1997.

Whitsett, J.M., Effect of transitional photoperiods on testicular development and puberty in male deer mice (*Peromyscus maniculatus*), J. Reprod. Fert., 72, pp. 277-286, 1984.

Yue, L. et al., "Genetic Analysis of Viable Hsp90 Alleles Reveals a Critical Role in *Drosophila Spermatogenesis*," Genetics, 151, pp. 1065-1079, 1999.

Mortelmans, K. et al., "The Ames *Salmonella*/Microsome Mutagenicity Assay," Mutat Res. 455, pp. 29-60, 2000.

* cited by examiner

LONIDAMINE ANALOGUES AND TREATMENT OF POLYCYSTIC KIDNEY DISEASE

CROSS-REFERENCE TO RELATED APPLICATIONS

The present invention claims is a continuation-in-part of U.S. patent application Ser. No. 10/922,747, filed Aug. 20, 2004 and claims benefit U.S. Provisional Application Ser. No. 61/105,125, filed Oct. 14, 2008, which applications are incorporated herein by specific reference in their entirety.

STATEMENT REGARDING FEDERALLY SPONSORED RESEARCH OR DEVELOPMENT

This invention was made with government support under NO1-HD-1-3313 and P50 DK05301 awarded by the National Institutes of Health. The government has certain rights in the invention.

FIELD OF THE INVENTION

The present invention relates to novel analogues of lonidamine, such as gamendazole and H2-gamendazole, and others. In particular, some of the novel analogues of lonidamine, such as gamendazole and H2-gamendazole, are useful in treating polycystic kidney disease.

BACKGROUND OF THE INVENTION

A number of renal cystic diseases (RCD), including Von Hippel-Lindau (VHL), tuberous sclerosis (TSC), polycystic kidney disease (PKD), and acquired cystic disease (AcCD) are characterized by epithelial neoplastic growth, cyst formation and enlargement, and progression to adenoma and various malignancies, including oncocytoma, clear cell carcinoma, and papillary renal cell carcinoma. While the degree varies to which these disorders progress to metastasis, they all have in common 1) cyst formation, 2) neoplastic growth, and 3) tumor formation. VHL, TSC, and PKD are inherited diseases caused by mutation of tumor-suppressor genes (VHL, TSC1, TSC2) or tumor suppressor-like genes (PKD1, PKD2, PKHD1). All have extrarenal pathology as well. Acquired cystic disease is environmental, caused principally by kidney dialysis.

Polycystic kidney disease (PKD or PCKD, also known as polycystic kidney syndrome) is a cystic genetic disorder of the kidneys and other organs. It occurs in humans and other animals. PKD is characterized by the presence of multiple cysts (hence, "polycystic") in both kidneys. The disease can also damage the liver, pancreas, and rarely, the heart and brain vasculature. The two major forms of polycystic kidney disease are distinguished by their patterns of inheritance.

Autosomal dominant polycystic kidney disease (ADPKD) is generally a late-onset disorder characterized by progressive cyst development and bilaterally enlarged kidneys with multiple cysts. Kidney manifestations in this disorder include renal function abnormalities, hypertension, renal pain, and renal insufficiency. ADPKD is a very common inherited disease, affecting one in 500-1,000 individuals. Two genes give rise to ADPKD in humans—mutations in PKD1 cause ~85% of ADPKD cases and mutations in PKD2 cause ~15% of ADPKD cases. In mice, homozygous Pkd1 and Pkd2 null mutations have late-embryo lethal phenotypes and cystic kidneys. The protein products of PKD1 and PKD2 are polycystin-1 (PC1) and polycystin-2 (PC2). A less-common autosomal recessive polycystic kidney disease (ARPKD) is caused by mutations in the PKHD1 (polycystic kidney and hepatic disease-1) gene.

Approximately 50% of patients with ADPKD have end-stage renal disease (ESRD) by the age of 60. ADPKD is a systemic disease with cysts in other organs such as the liver (which may lead to cirrhosis), seminal vesicles, pancreas, and arachnoid mater and non-cystic abnormalities such as intracranial aneurysms and dolichoectasias, dilation of the aortic root and dissection of the thoracic aorta, mitral valve prolapse, and abdominal wall hernias. Initial simian and human symptoms are hypertension, fatigue, and mild to severe back or flank pain and urinary tract infections. The disease often leads to chronic renal failure and may result in total loss of kidney function, known as end stage renal disease (ESRD), which requires some form of renal replacement therapy (e.g. dialysis or transplantation).

Autosomal recessive polycystic kidney disease (ARPKD) is much rarer than ADPKD and is often fatal in utero or during the first month of life. The signs and symptoms of the condition are usually apparent at birth or in early infancy.

There is no cure for PKD. The option of a transplant generally only arises after the patient reaches ESRD. Therefore, it would be advantageous to find a therapy to treat, inhibit, and/or prevent PKD of either type.

BRIEF SUMMARY OF THE INVENTION

The present invention is directed to novel compounds which are useful in methods of treating, inhibiting, and/or preventing polycystic kidney disease (PKD). Accordingly, the compounds can be administered in a therapeutically effective amount for inhibiting, and/or preventing polycystic kidney disease (PKD) in the subject. This can include administering a therapeutically effective amount of the compound for inhibiting CFTR and/or Hsp90 or biological pathways thereof. Also, the method can include administering the compound in a therapeutically effective amount for inhibiting ErbB2, Src, Raf-1, B-Raf, MEK, Cdk4, NKCC1, or combinations thereof. For example, the therapeutically effective amount of the compound can be configured so as to provide a concentration in or adjacent to a kidney cell of at least about 0.25 uM.

BRIEF DESCRIPTION OF THE DRAWINGS

FIG. 10B is a graph for an MTT assay that shows gamendazole significantly inhibited serum, cAMP, and EGF-induced proliferation of PKD (e.g., ADPKD) cells in a dose-dependent manner (5 uM-100 uM GMZ for 72 h).

DETAILED DESCRIPTION OF PREFERRED EMBODIMENT

Figure 1A:
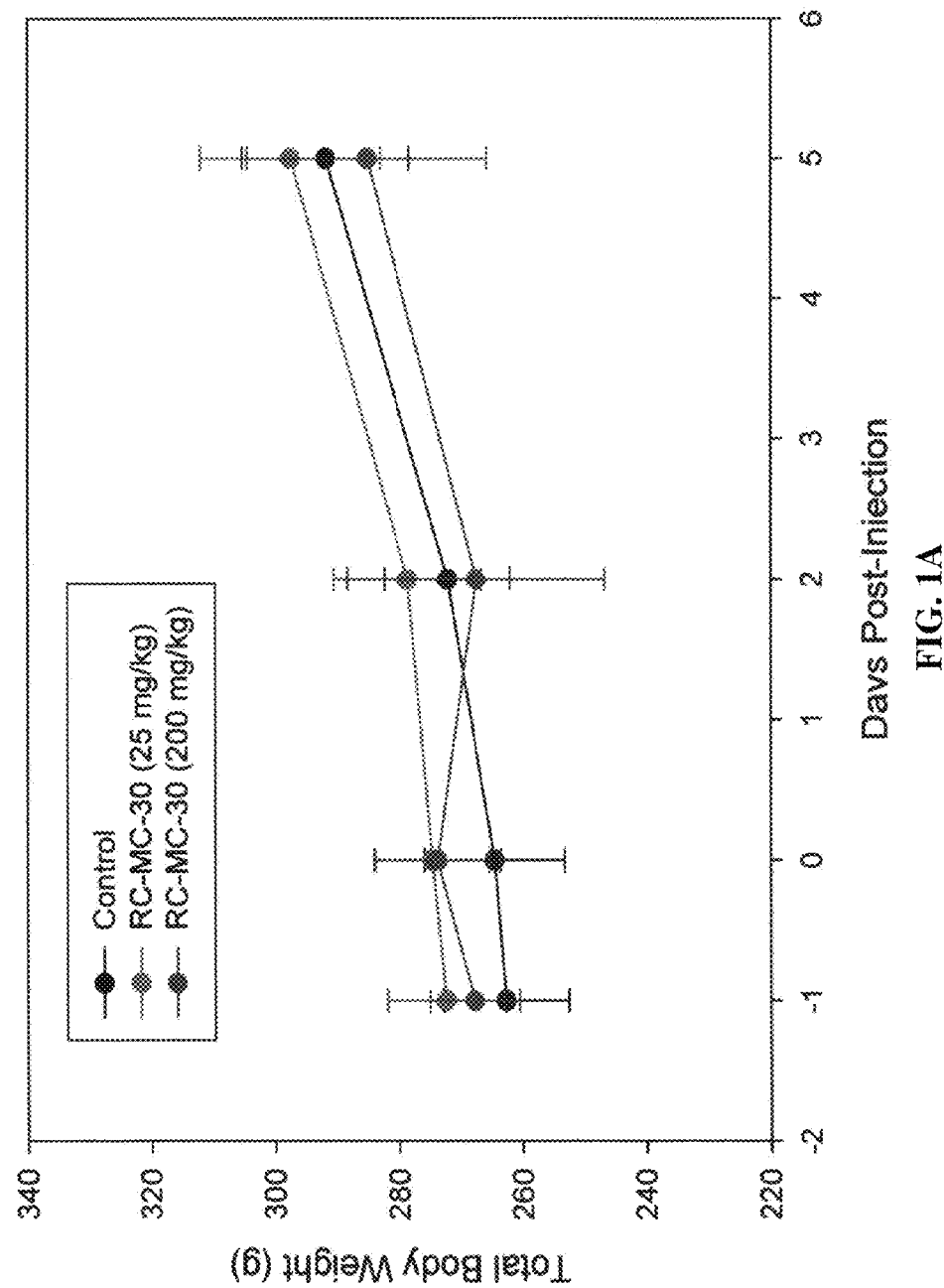
FIG. 1A illustrates the change in total body weight of animals receiving 25 mg/kg and 200 mg/kg of RC-MC-30 compared with the control.
Figure 1B:
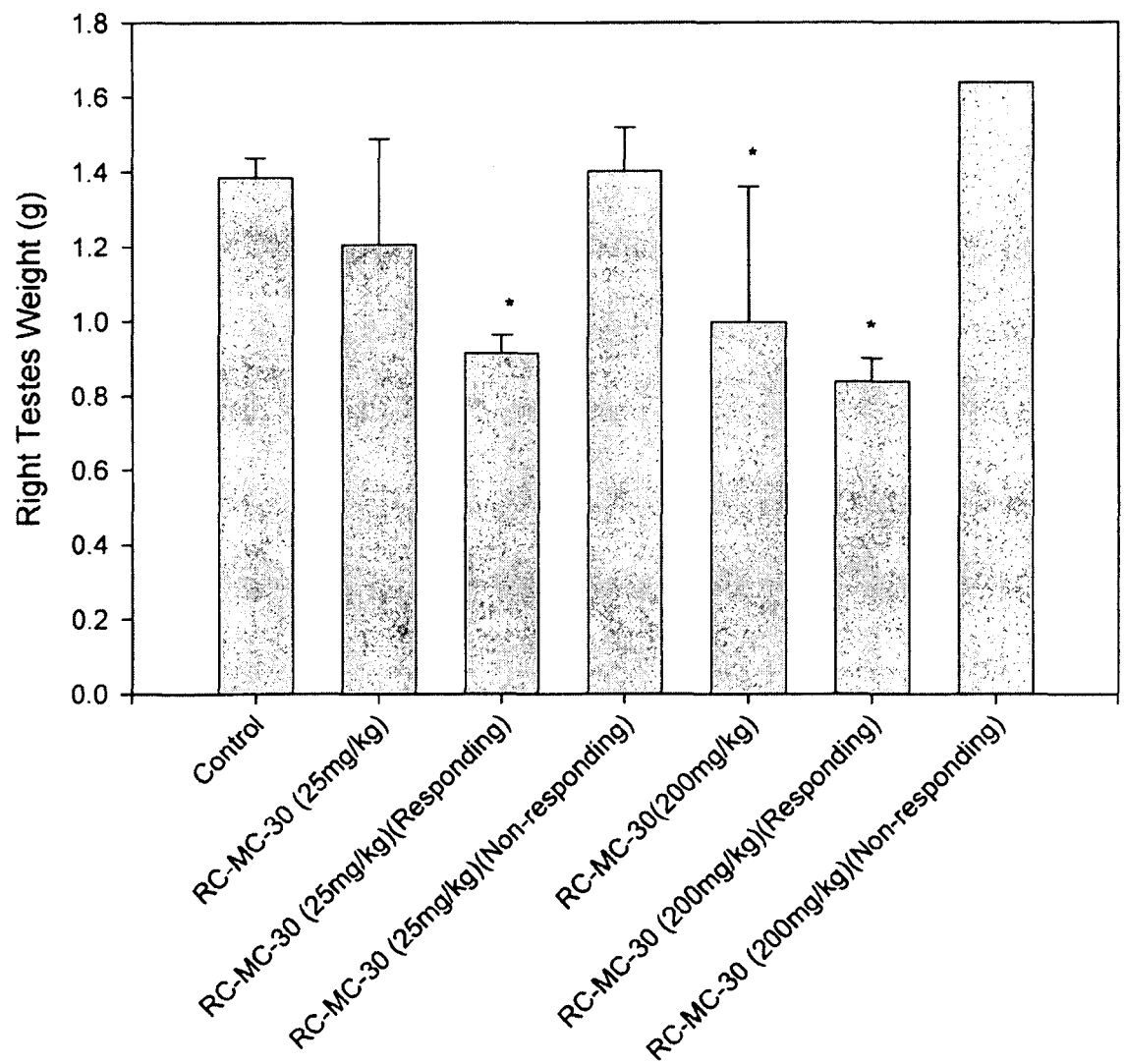
FIG. 1B illustrates the right testes weight of animals receiving 25 mg/kg and animals receiving 200 mg/kg of RC-MC-30 compared with the control.
Figure 1C:
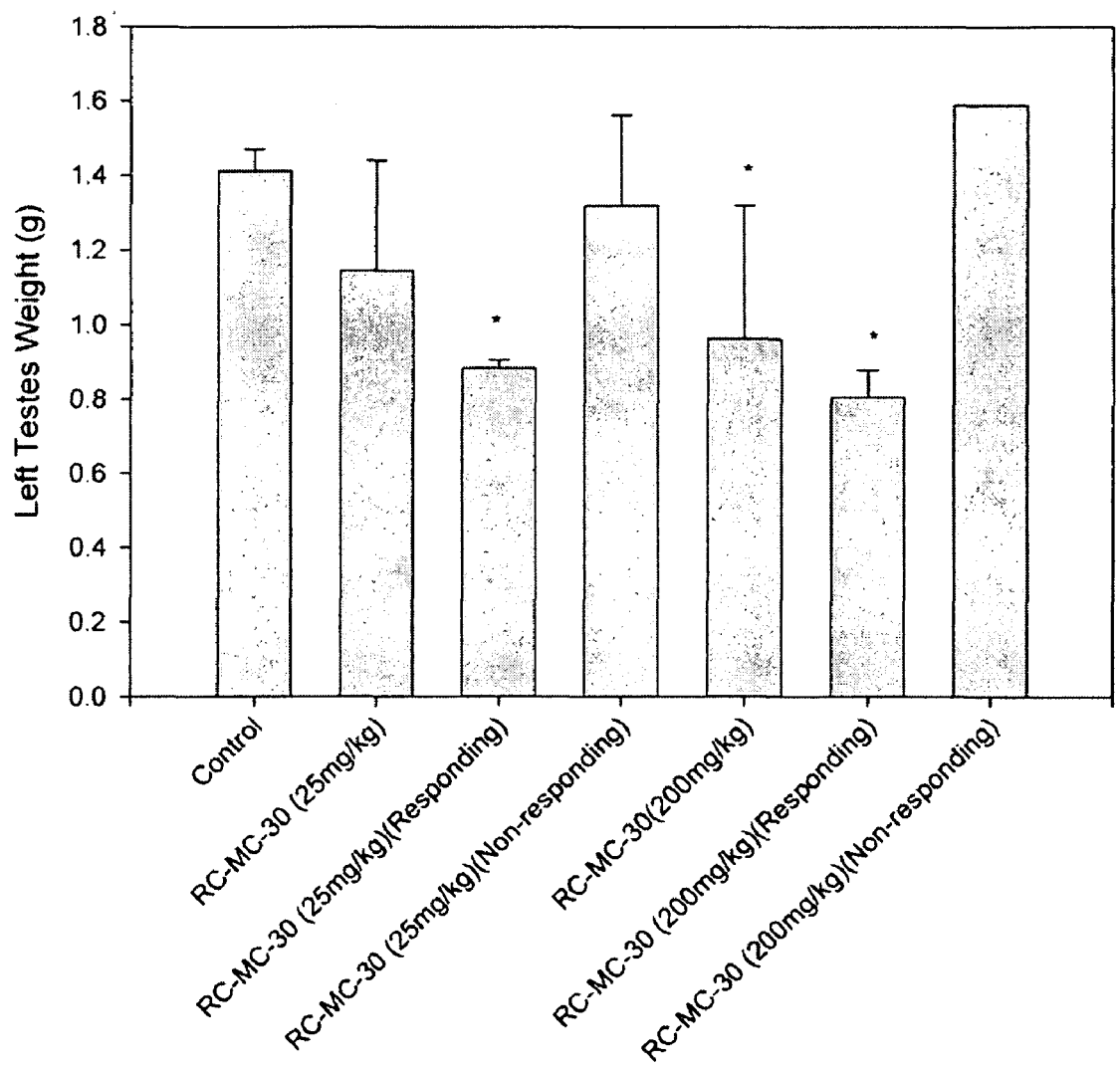
FIG. 1C illustrates the left testes weight of animals receiving 25 mg/kg and animals receiving 200 mg/kg of RC-MC-30 compared with the control.
Figure 1D:
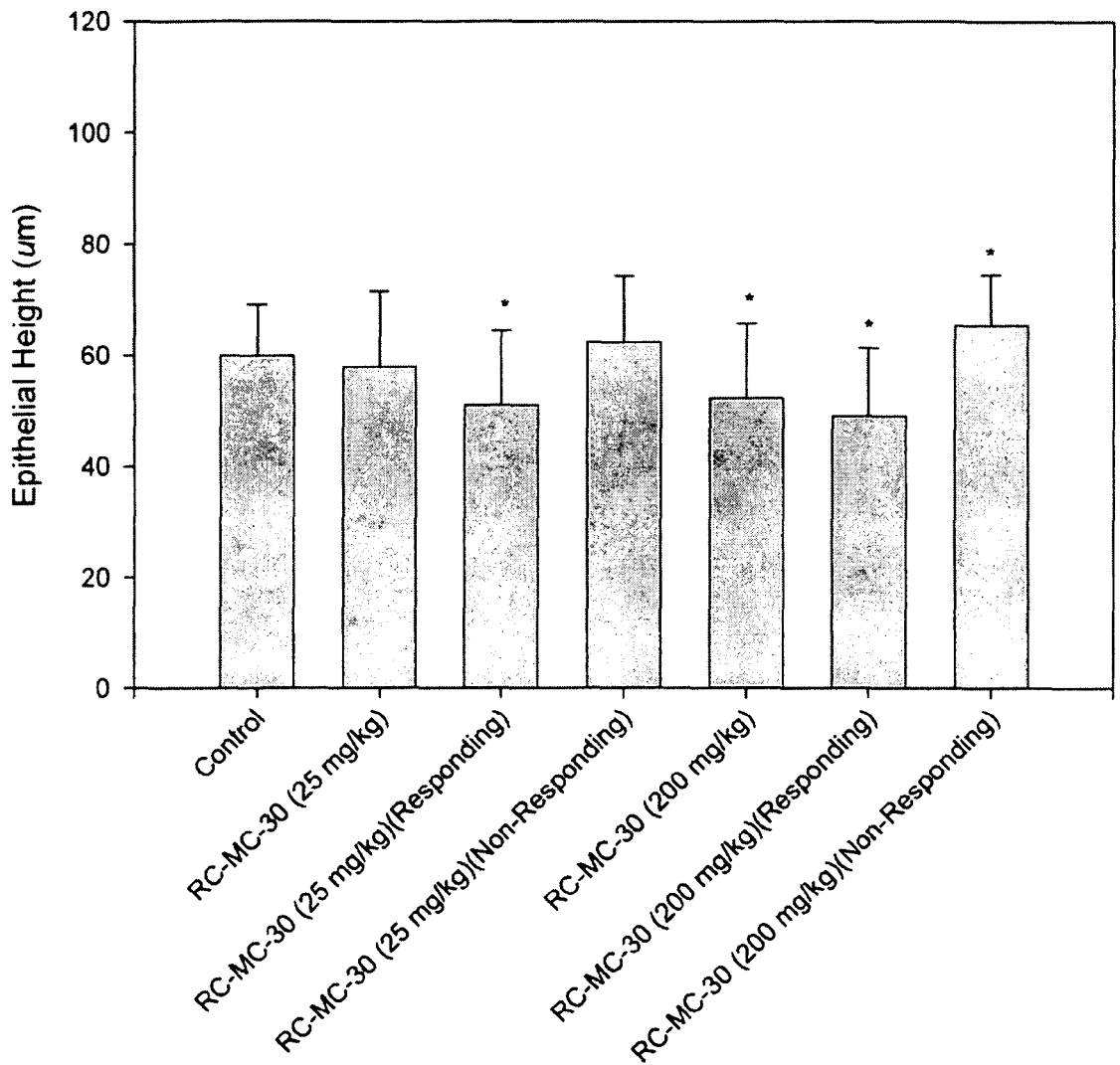
FIG. 1D illustrates the epithelial height of the seminiferous tubule epithelium of animals receiving 25 mg/kg and animals receiving 200 mg/kg of RC-MC-30 compared with the control.
Figure 1E:
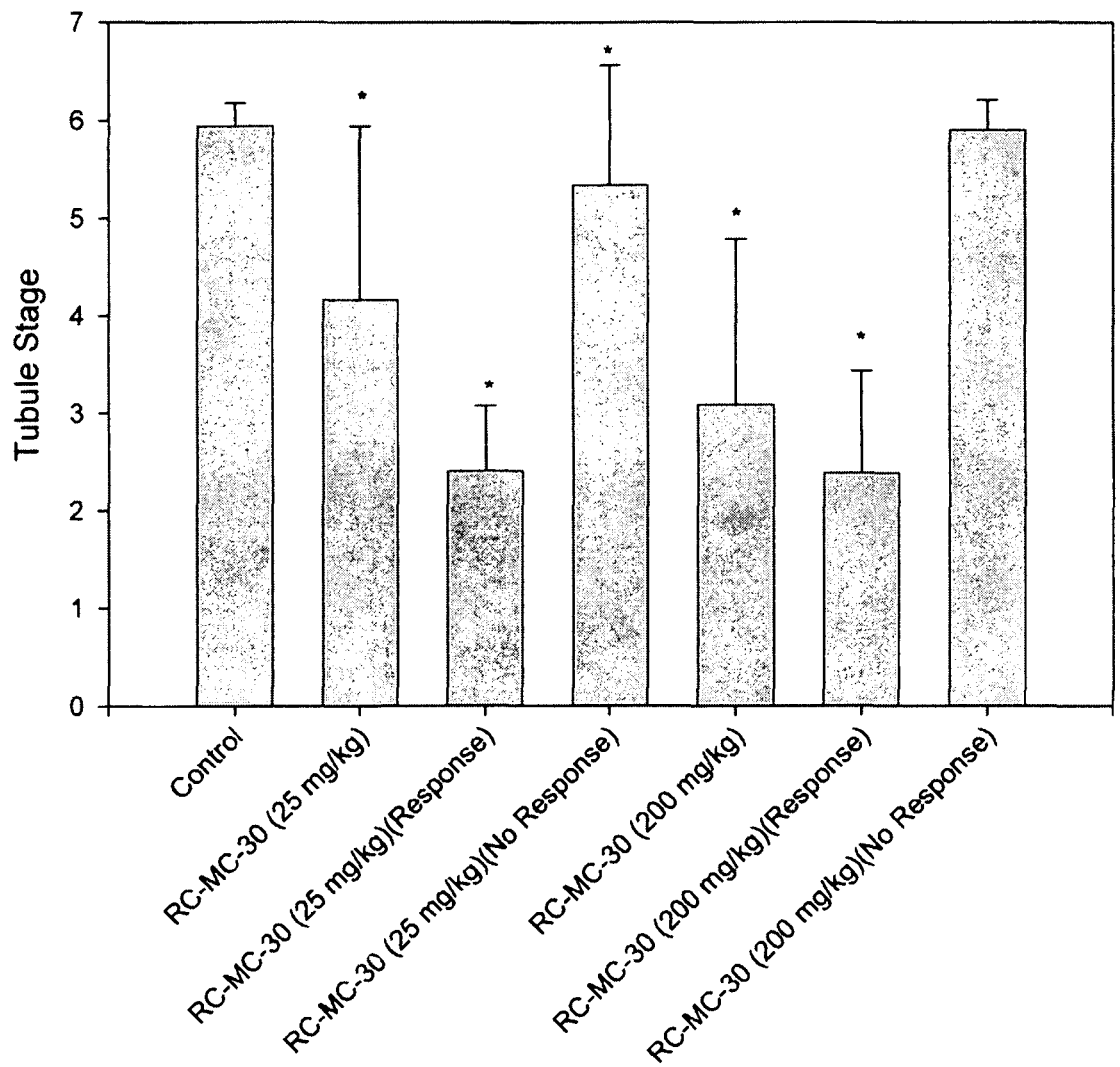
FIG. 1E illustrates seminiferous tubule staging of animals receiving 25 mg/kg and animals receiving 200 mg/kg of RC-MC-30 compared with the control.
Figure 2A:
FIG. 2A is a histologic photograph of the testes of a rat receiving 25 mg/kg of RC-MC-30.
Figure 2B:
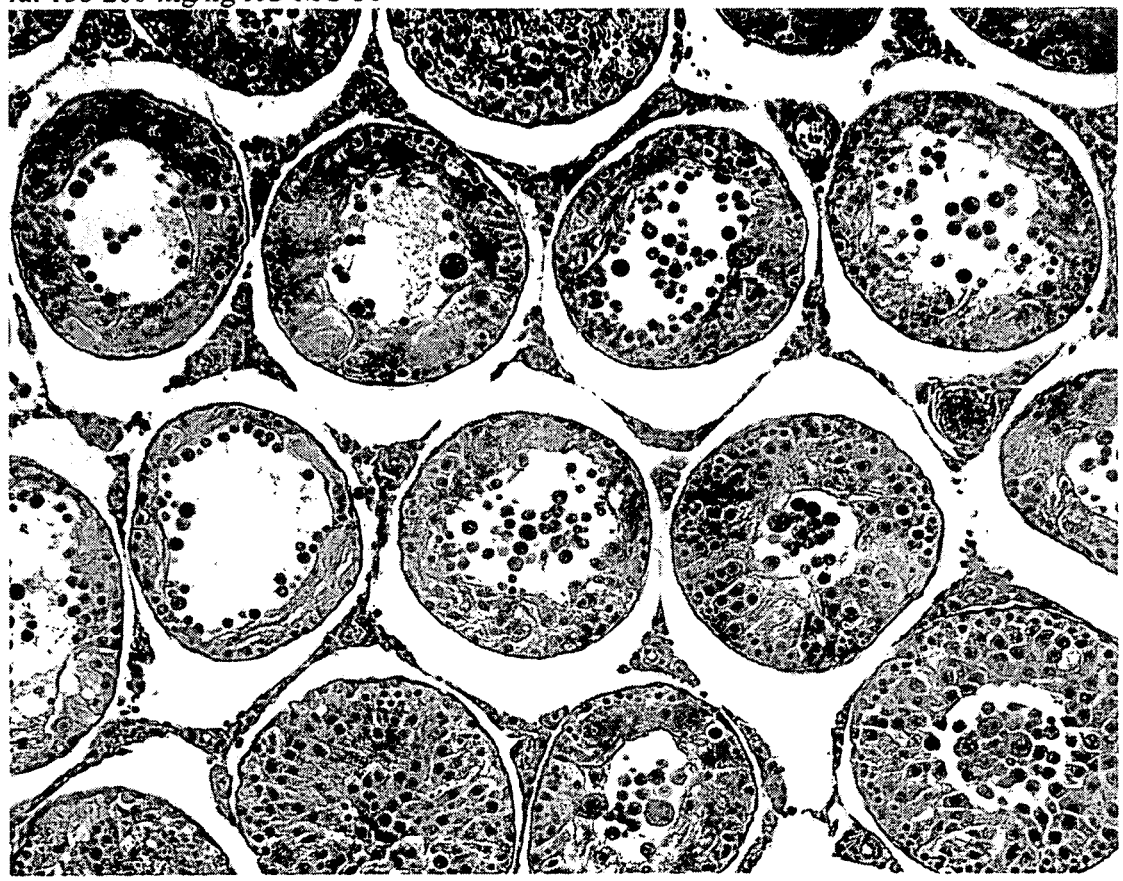
FIG. 2B is a histologic photograph of the testes of a rat receiving 200 mg/kg of RC-MC-30.
Figure 3A:
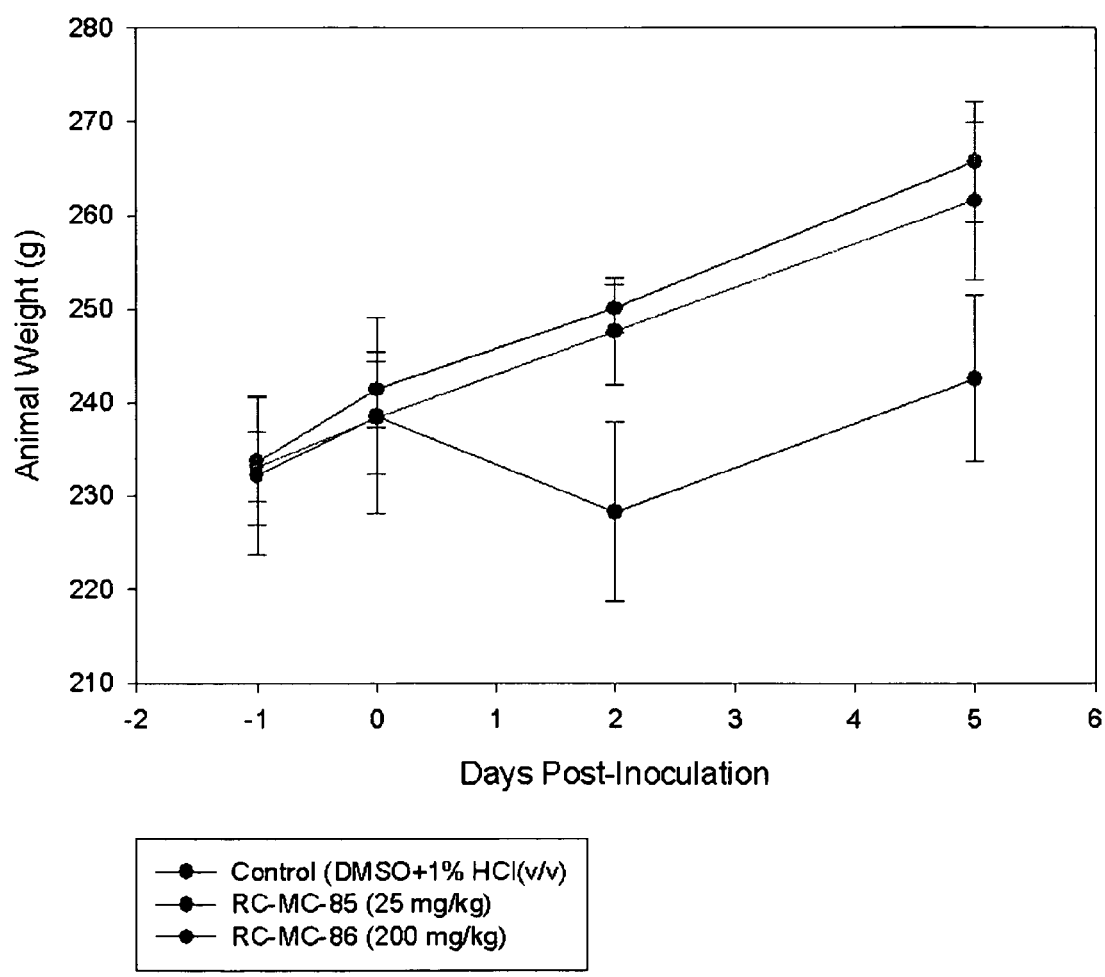
FIG. 3A illustrates the change in total body weight of animals receiving 25 mg/kg and 200 mg/kg of RC-MC-86 compared with the control.
Figure 3B:
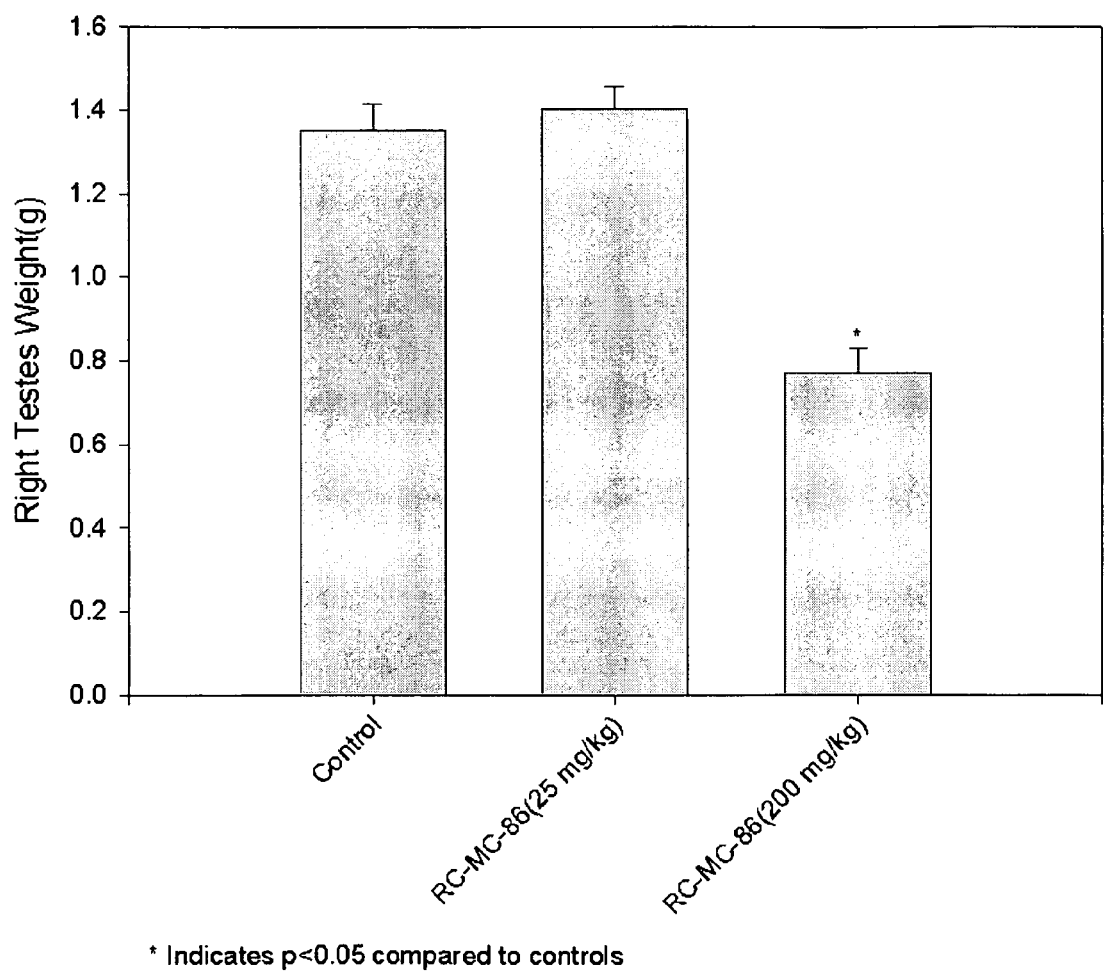
FIG. 3B illustrates the right testes weight of animals receiving 25 mg/kg and animals receiving 200 mg/kg of RC-MC-86 compared with the control.
Figure 3C:
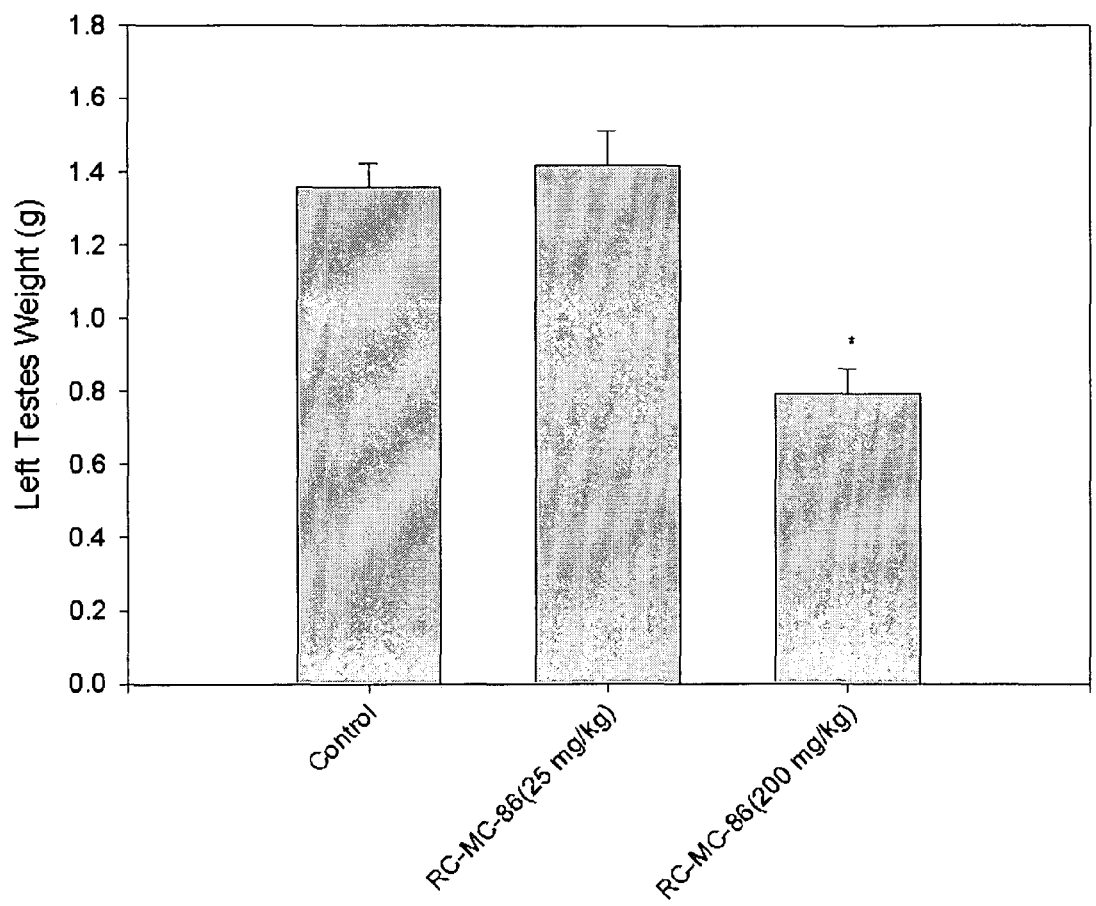
FIG. 3C illustrates the left testes weight of animals receiving 25 mg/kg and animals receiving 200 mg/kg of RC-MC-86 compared with the control.
Figure 3D:
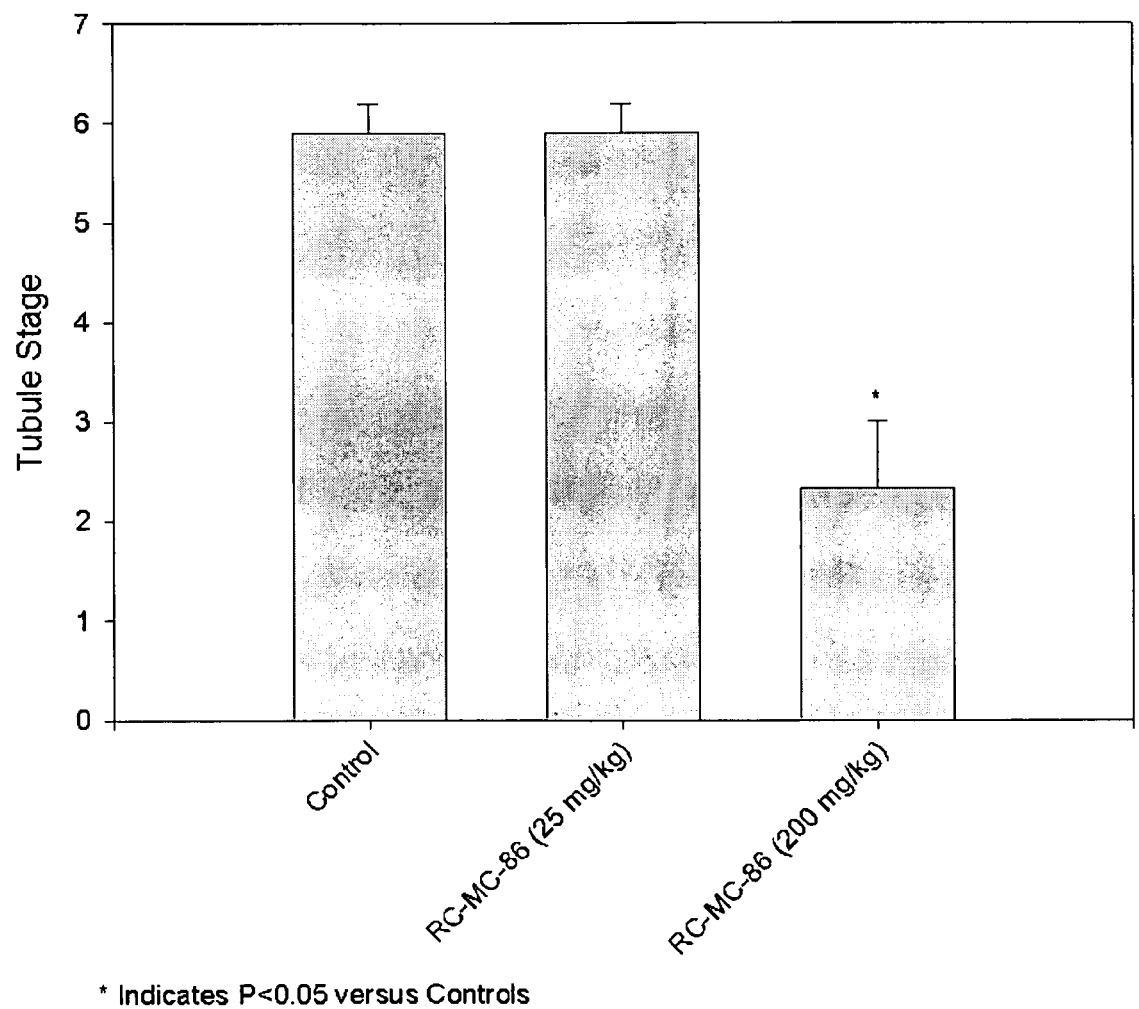
FIG. 3D illustrates the epithelial height of the seminiferous tubule epithelium of animals receiving 25 mg/kg and animals receiving 200 mg/kg of RC-MC-86 compared with the control.
Figure 3E:
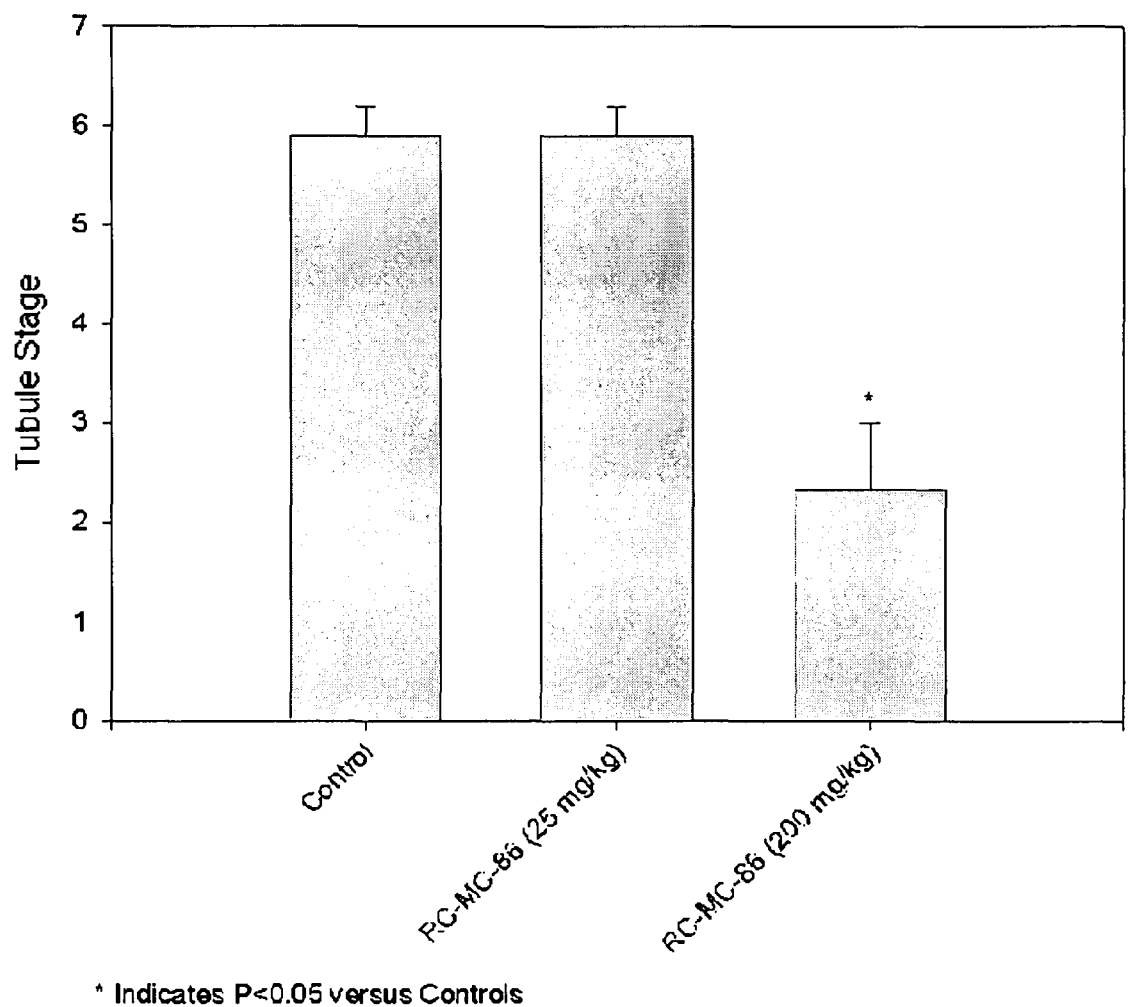
FIG. 3E illustrates seminiferous tubule staging of animals receiving 25 mg/kg and animals receiving 200 mg/kg of RC-MC-86 compared with the control.
Figure 4A:
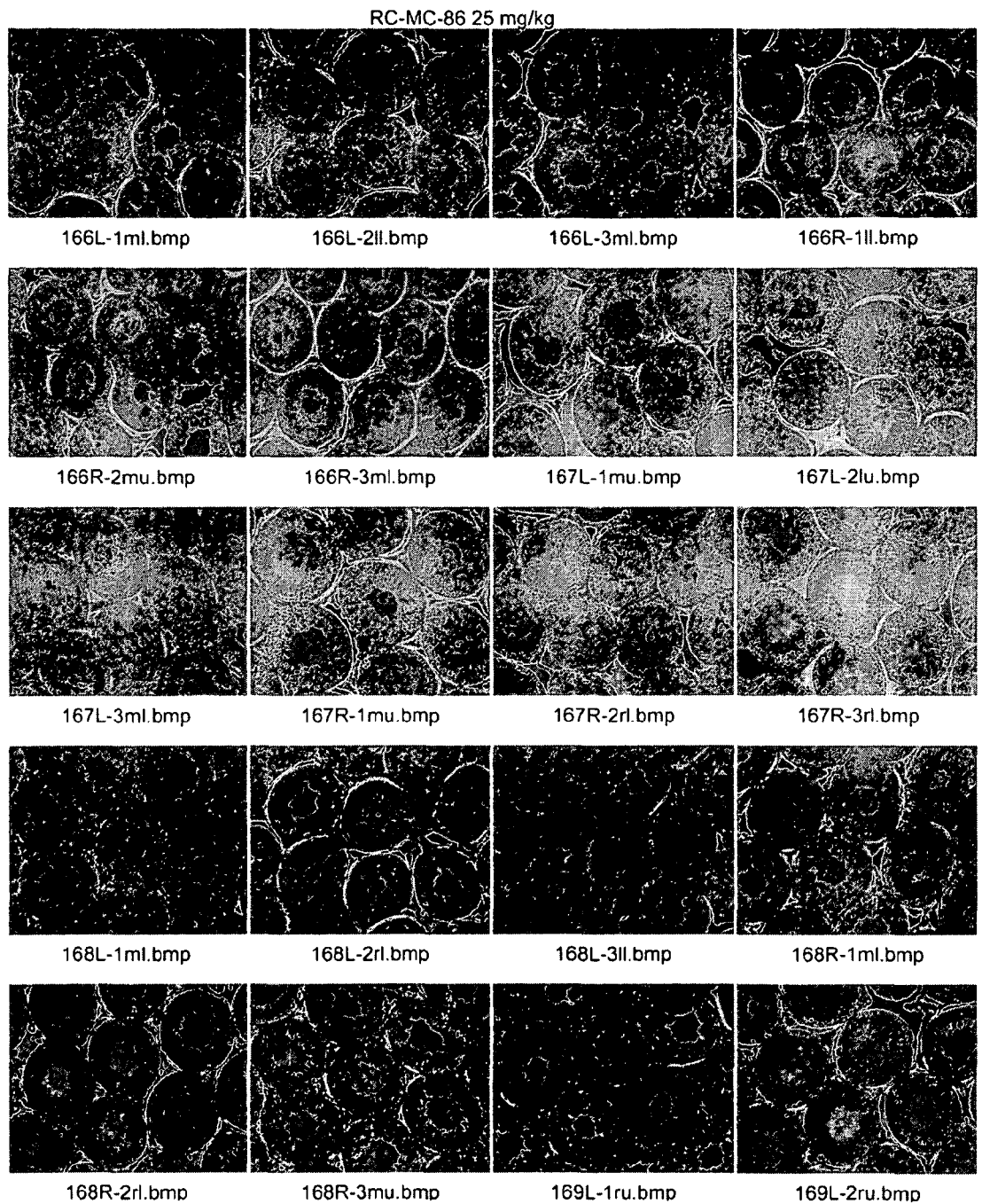
FIG. 4A is a histologic photograph of the testes of a rat receiving 25 mg/kg of RC-MC-86.
Figure 4B:
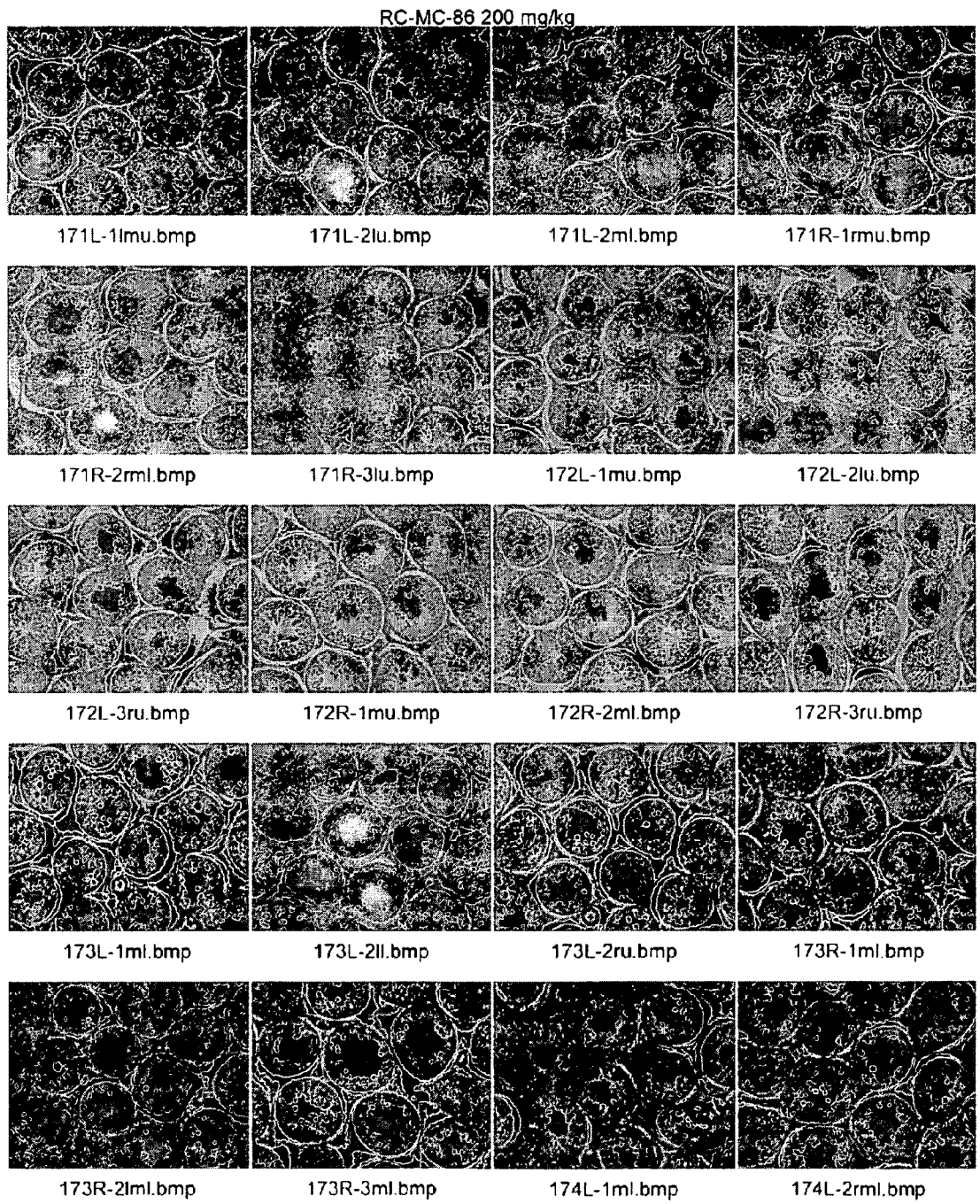
FIG. 4B is a histologic photograph of the testes of a rat receiving 200 mg/kg of RC-MC-86.
Figure 5A:
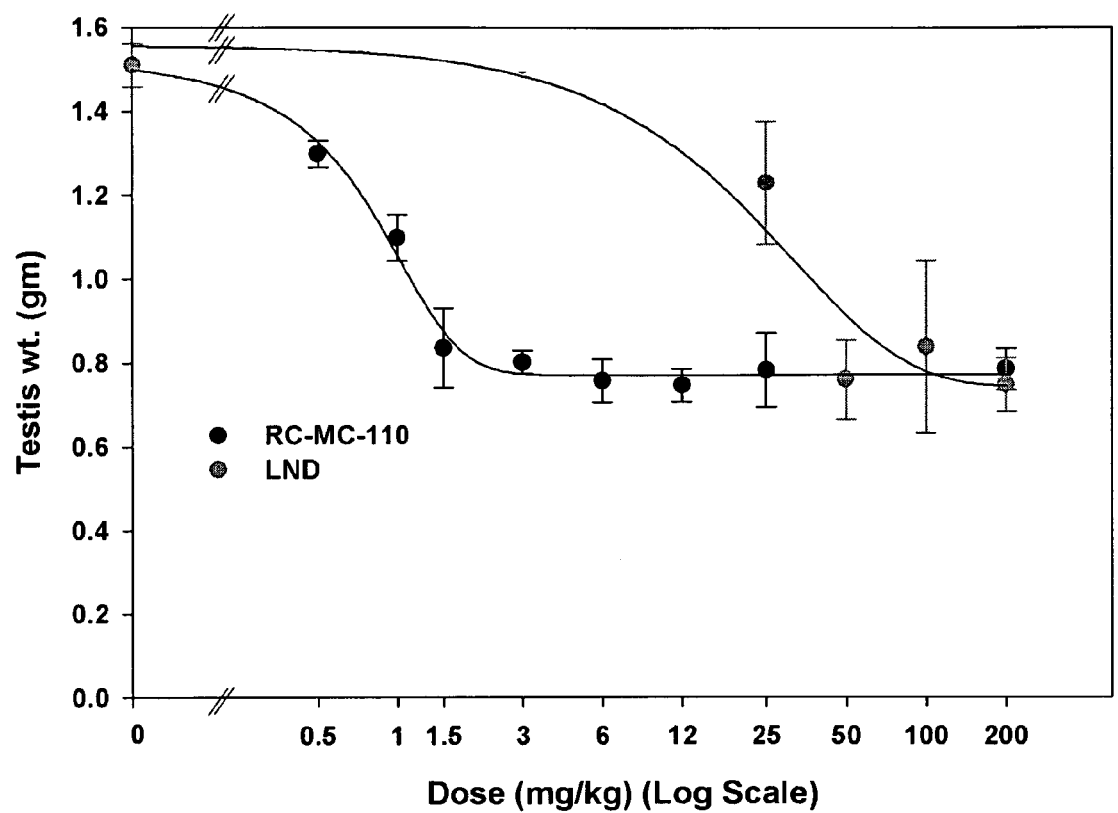
FIG. 5A illustrates the dose-dependent effects of lonidamine compared to RC-MC-110 on testes weight.
Figure 5B:
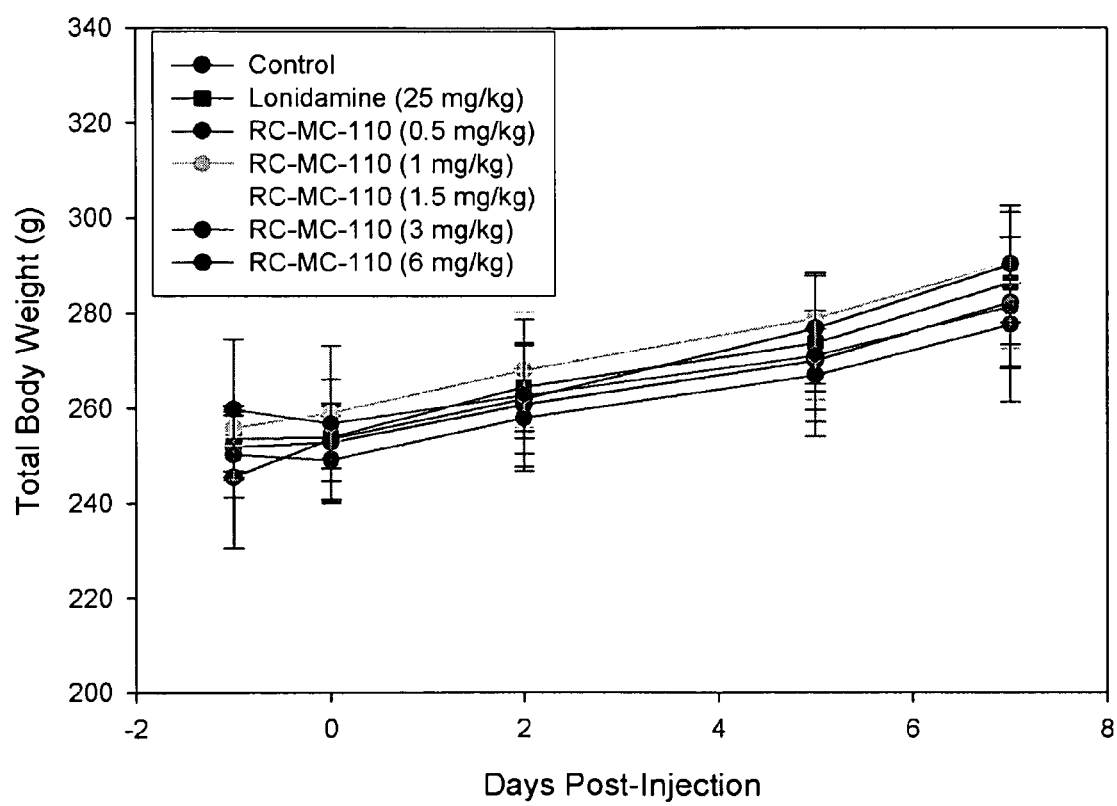
FIG. 5B illustrates the total body weight of animals receiving 6.0, 3.0, 1.5, 1, and 0.5 mg/kg of RC-MC-110 and animals compared to 25 mg/kg lonidamine and a control.
Figure 5C:
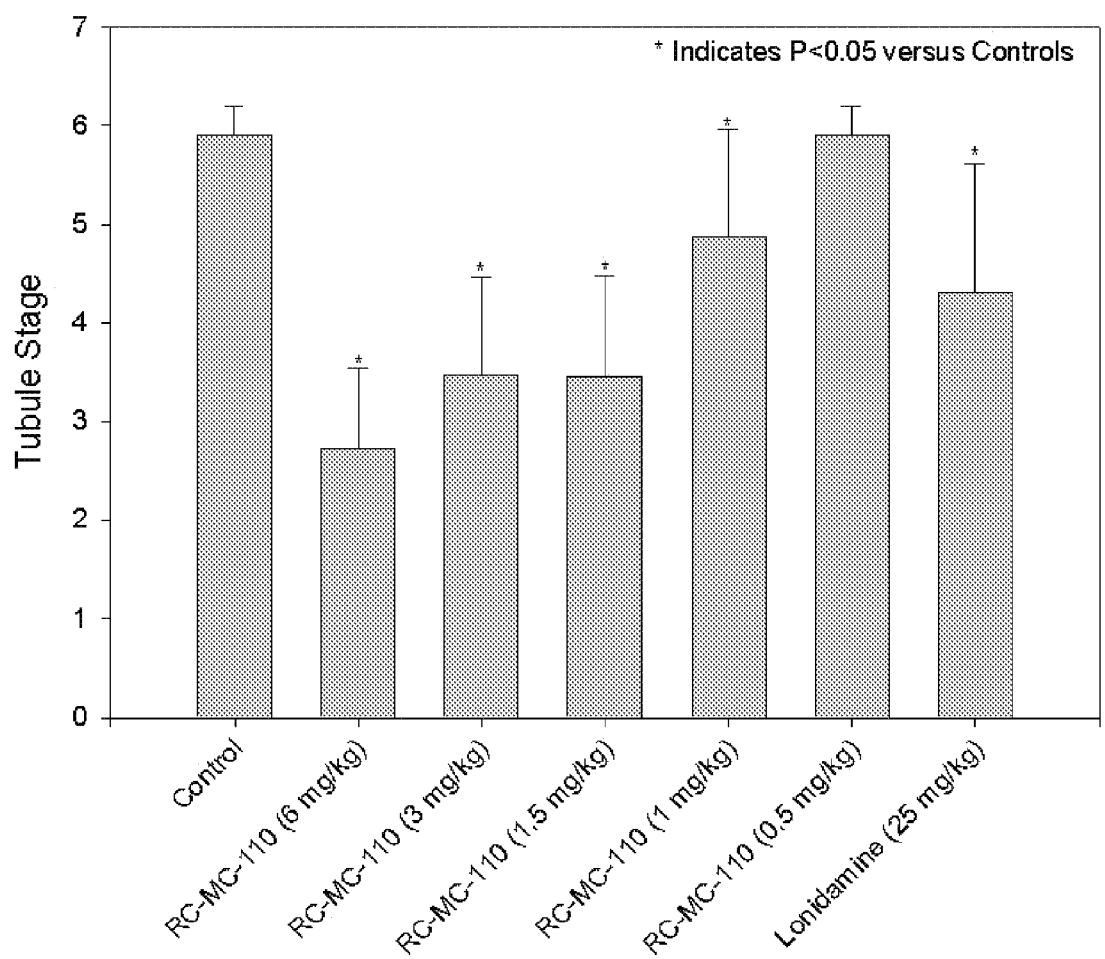
FIG. 5C illustrates tubule staging of animals receiving 6.0, 3.0, 1.5, 1, and 0.5 mg/kg of RC-MC-110 and animals compared to 25 mg/kg lonidamine and a control.
Figure 5D:
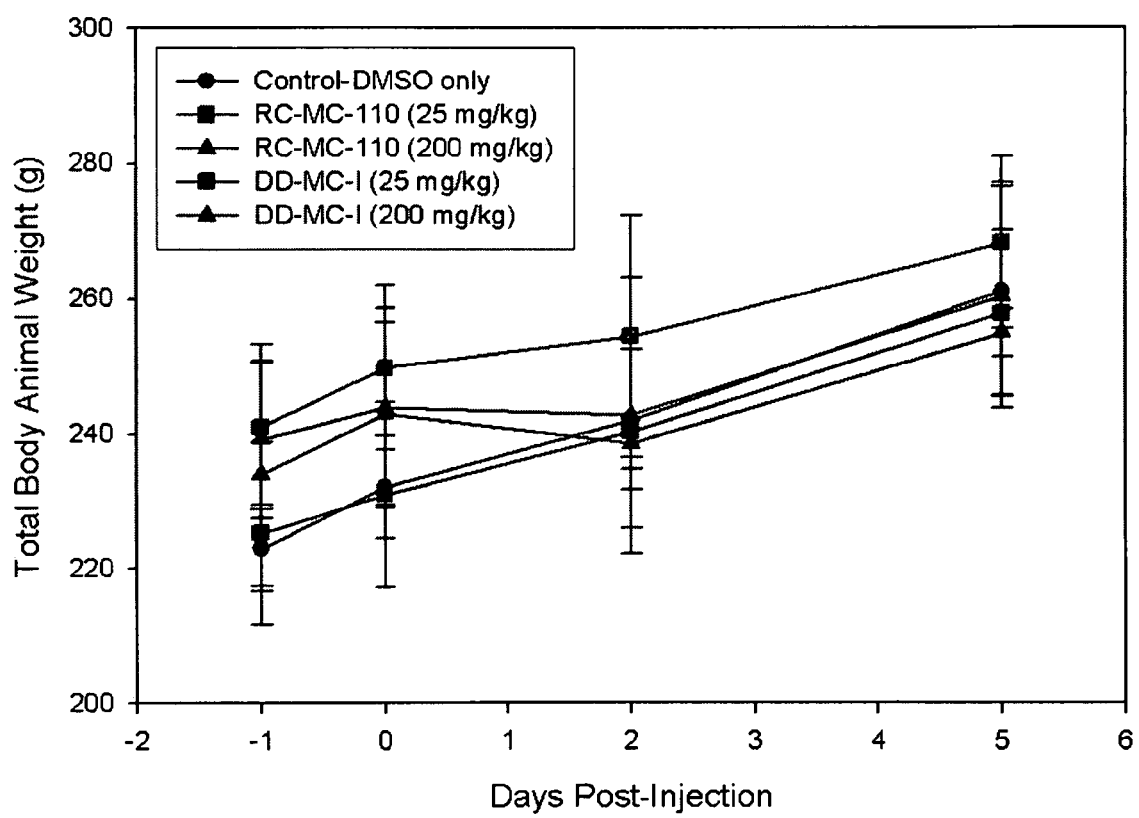
FIG. 5D illustrates the total body weight of animals receiving 25 mg/kg and 200 mg/kg of RC-MC-110 and DD-MC-I.
Figure 5E:
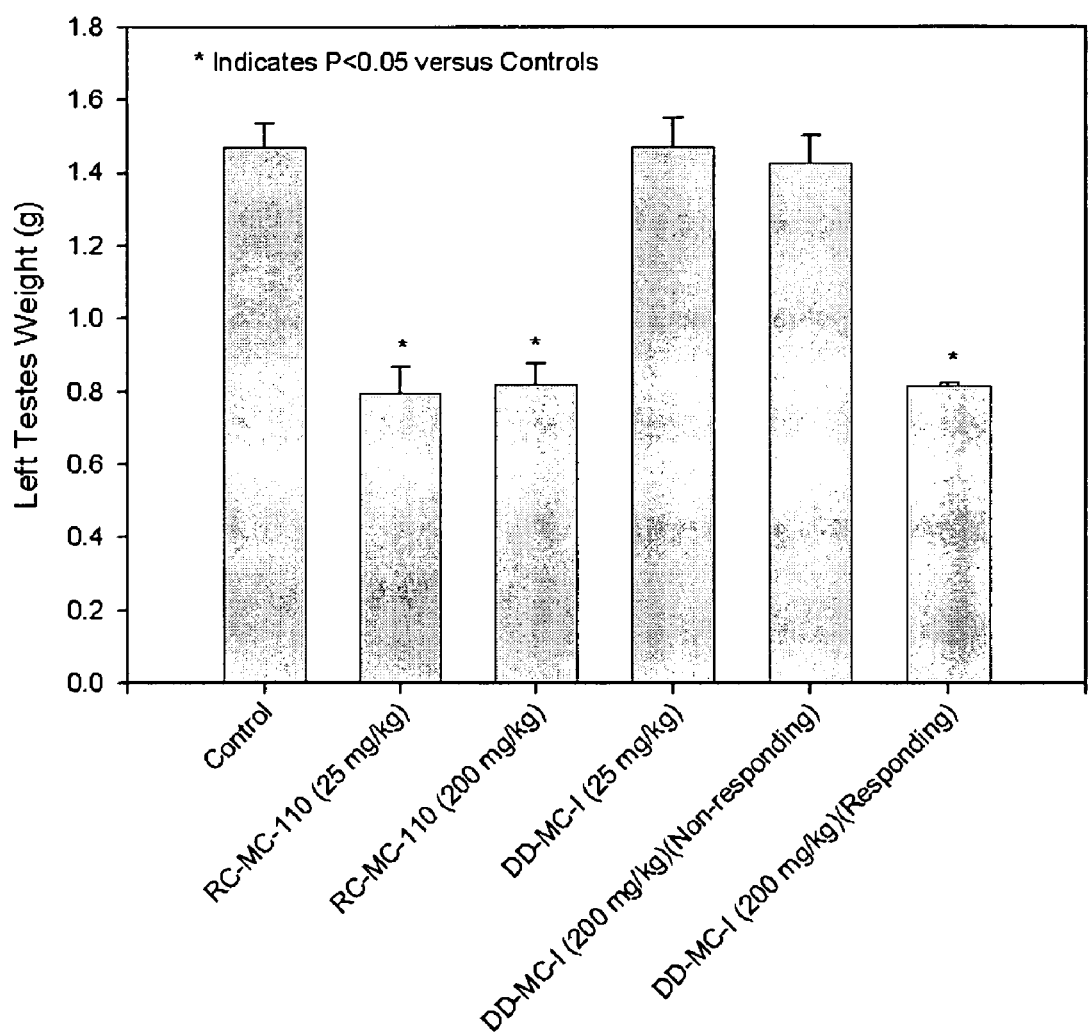
FIG. 5E illustrates the left testes weight of animals receiving 25 mg/kg and 200 mg/kg of RC-MC-110 compared to that of comparative compound, DD-MC-I (1-(2,4-dichlorobenzyl)-6-chloro-1H-indazole-3-carboxylic acid).
Figure 6A:
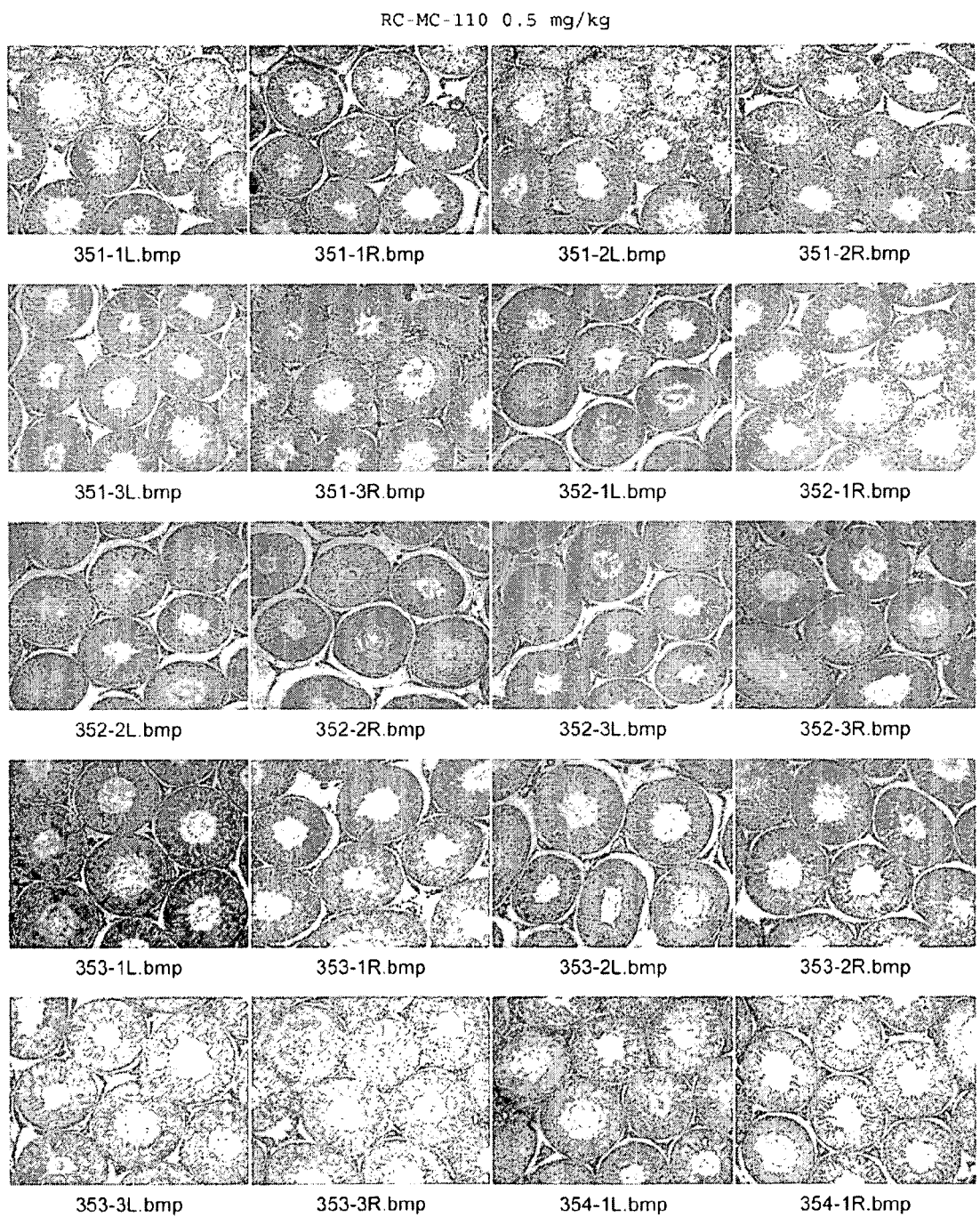
FIG. 6A is a histologic photograph of the testes of a rat receiving 0.5 mg/kg of RC-MC-110.
Figure 6B:
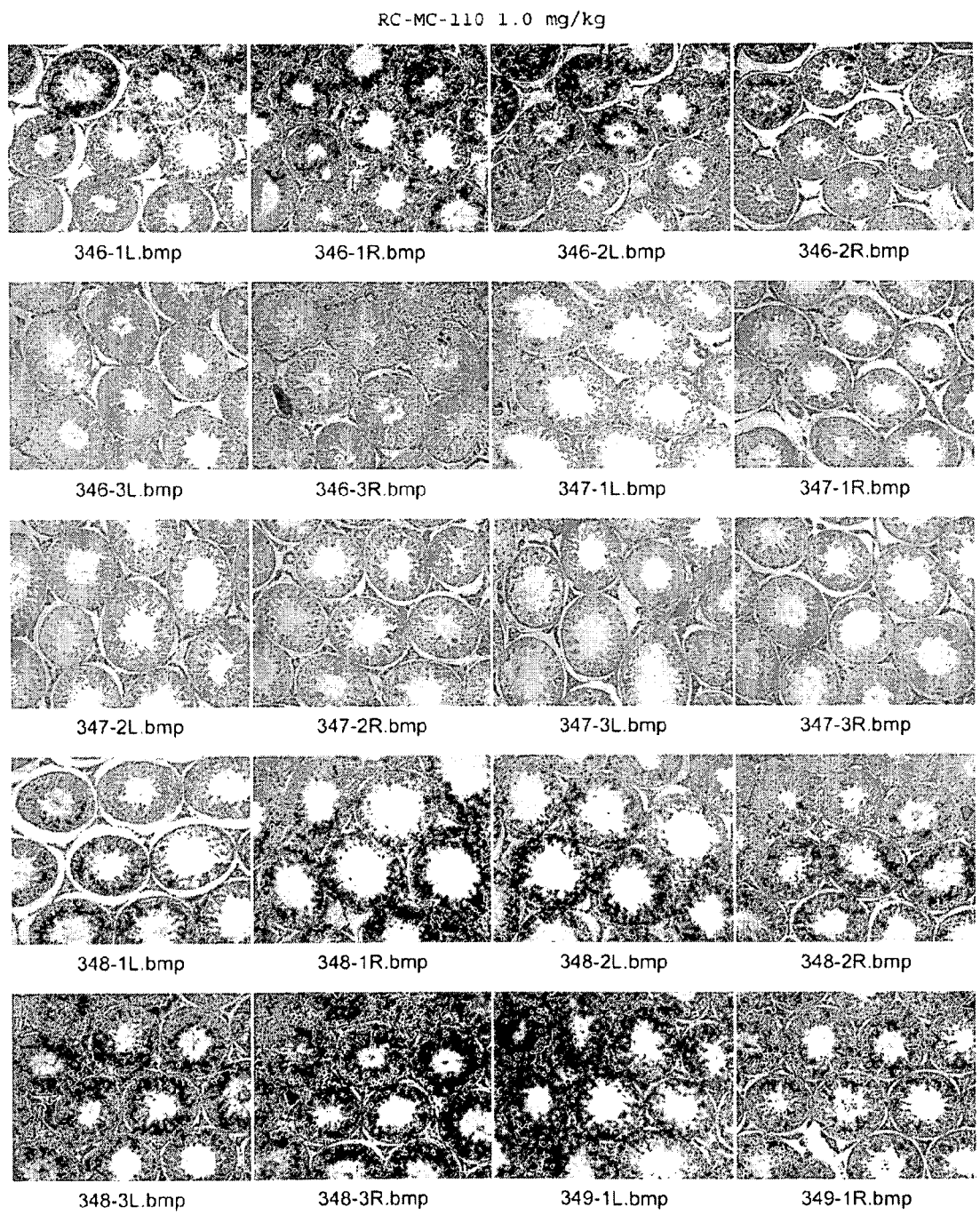
FIG. 6B is a histologic photograph of the testes of a rat receiving 1.0 mg/kg of RC-MC-110.
Figure 6C:
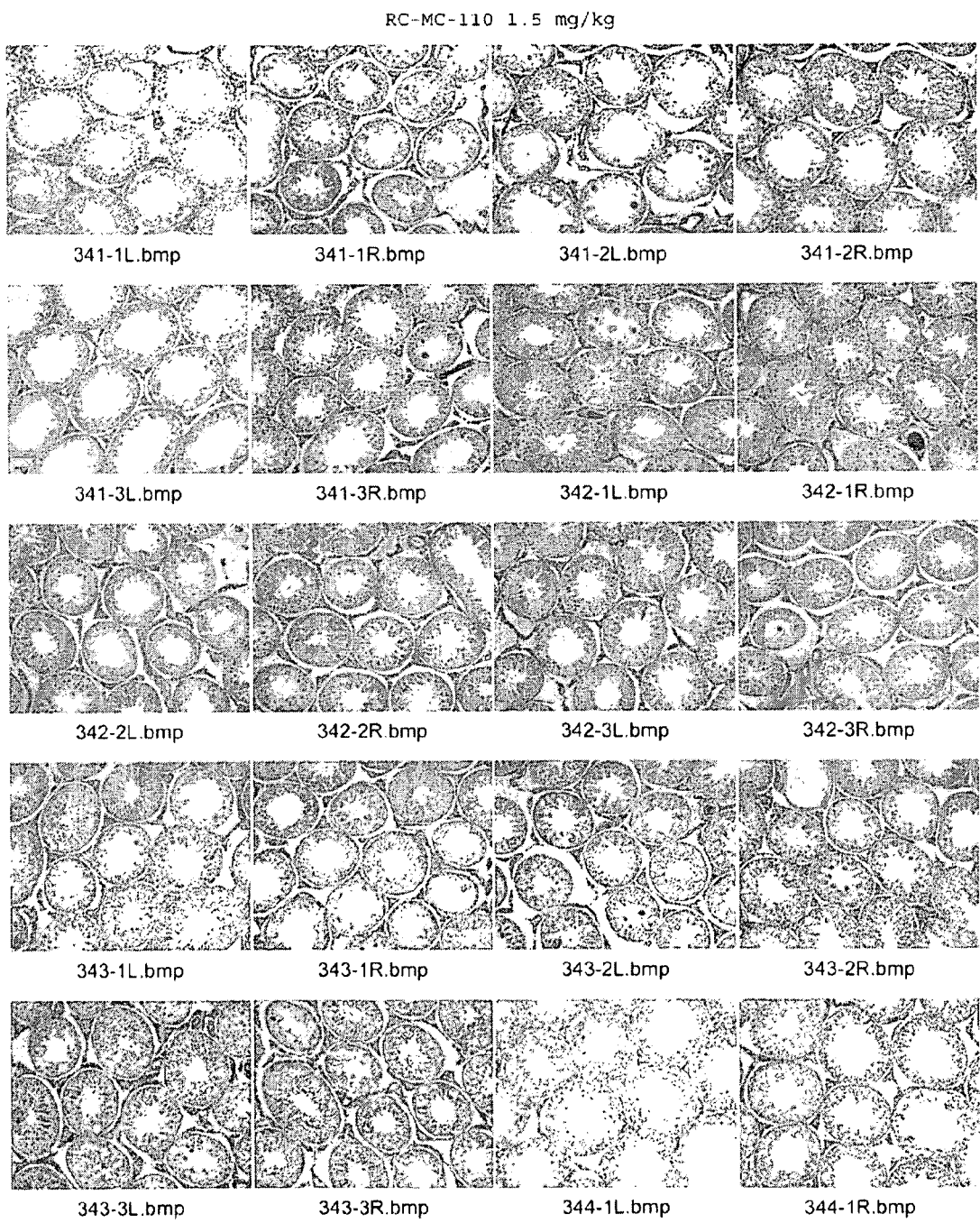
FIG. 6C is a histologic photograph of the testes of a rat receiving 1.5 mg/kg of RC-MC-110.
Figure 6D:
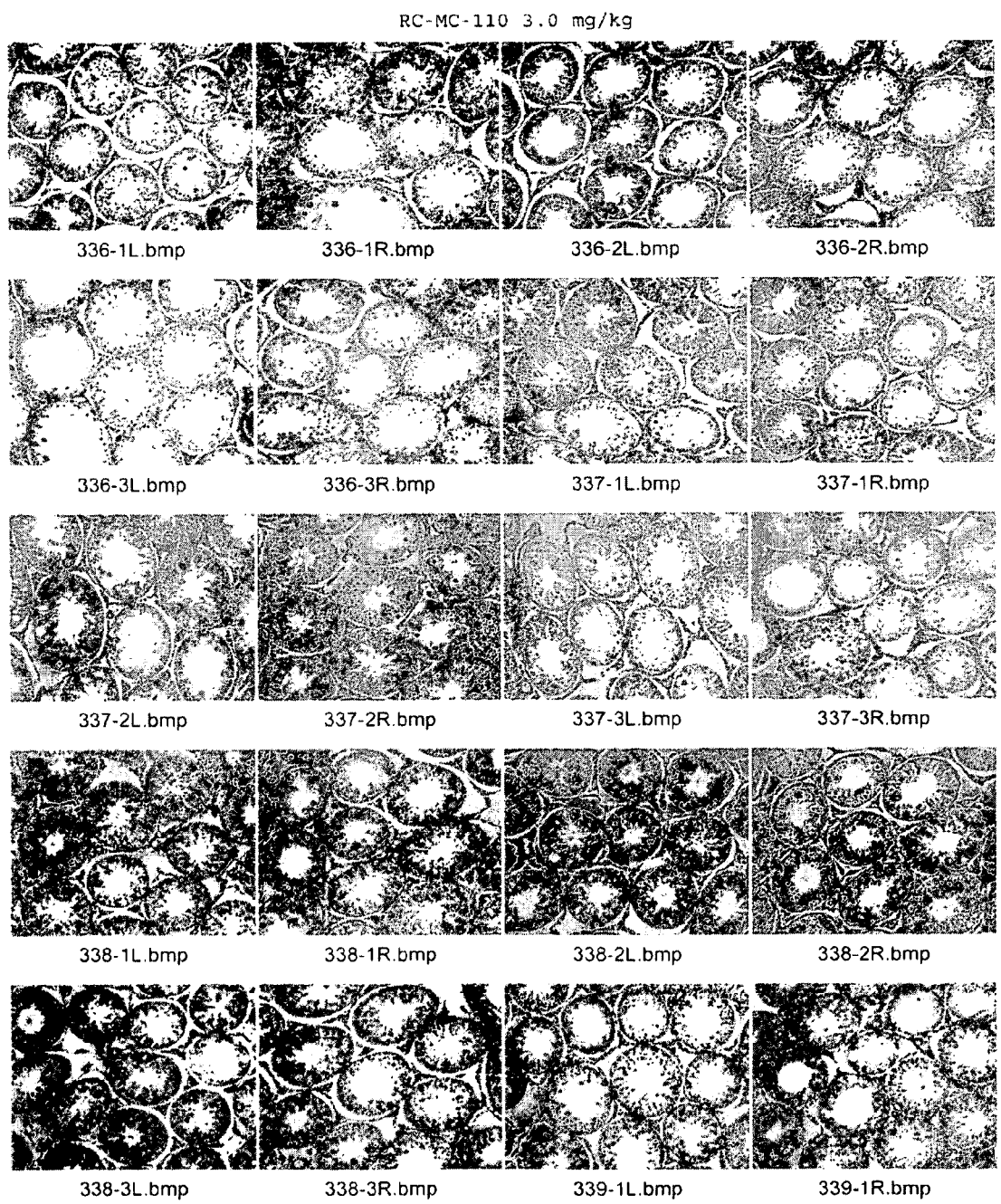
FIG. 6D is a histologic photograph of the testes of a rat receiving 3.0 mg/kg of RC-MC-110.
Figure 6E:
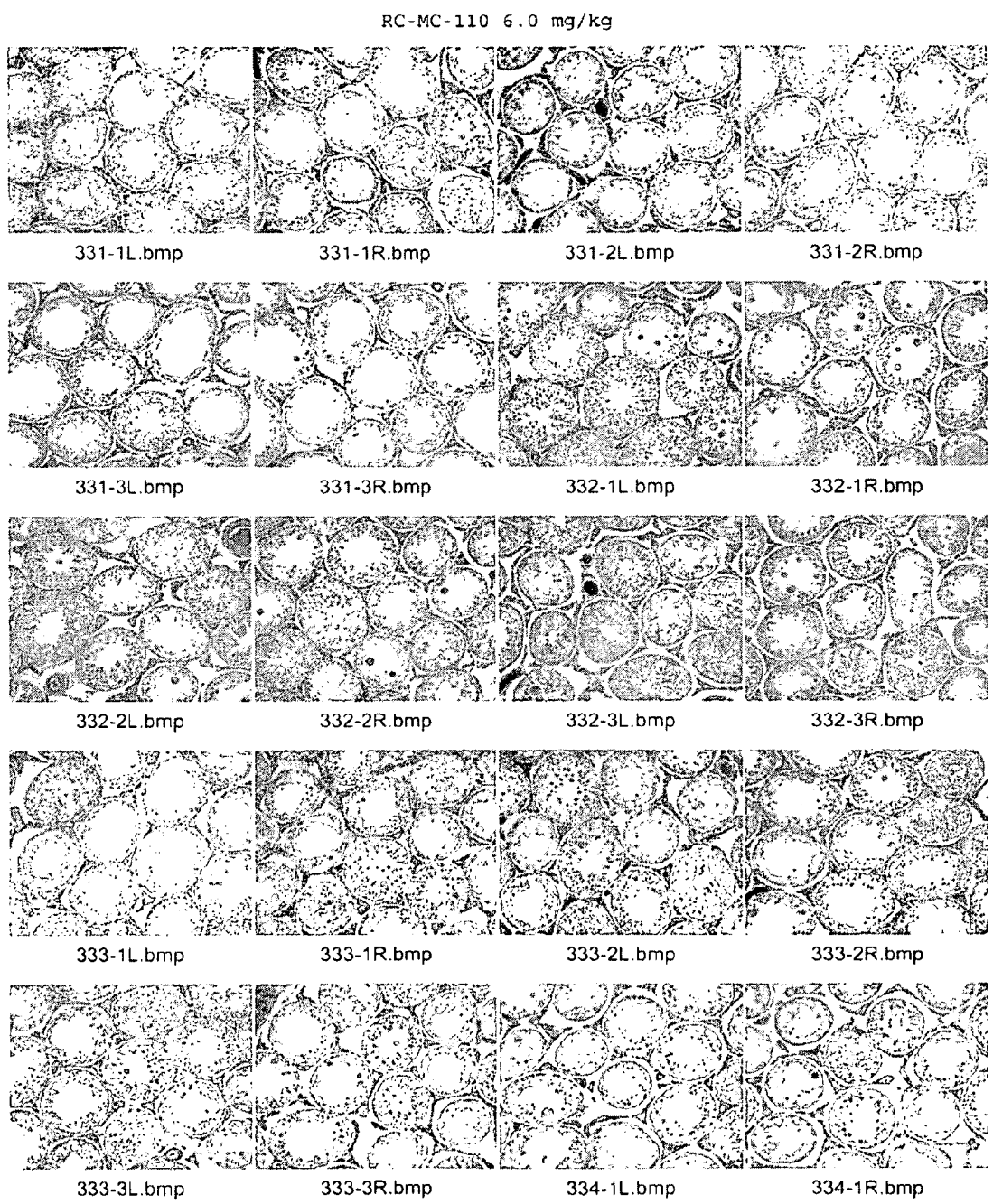
FIG. 6E is a histologic photograph of the testes of a rat receiving 6.0 mg/kg of RC-MC-110.
Figure 6F:
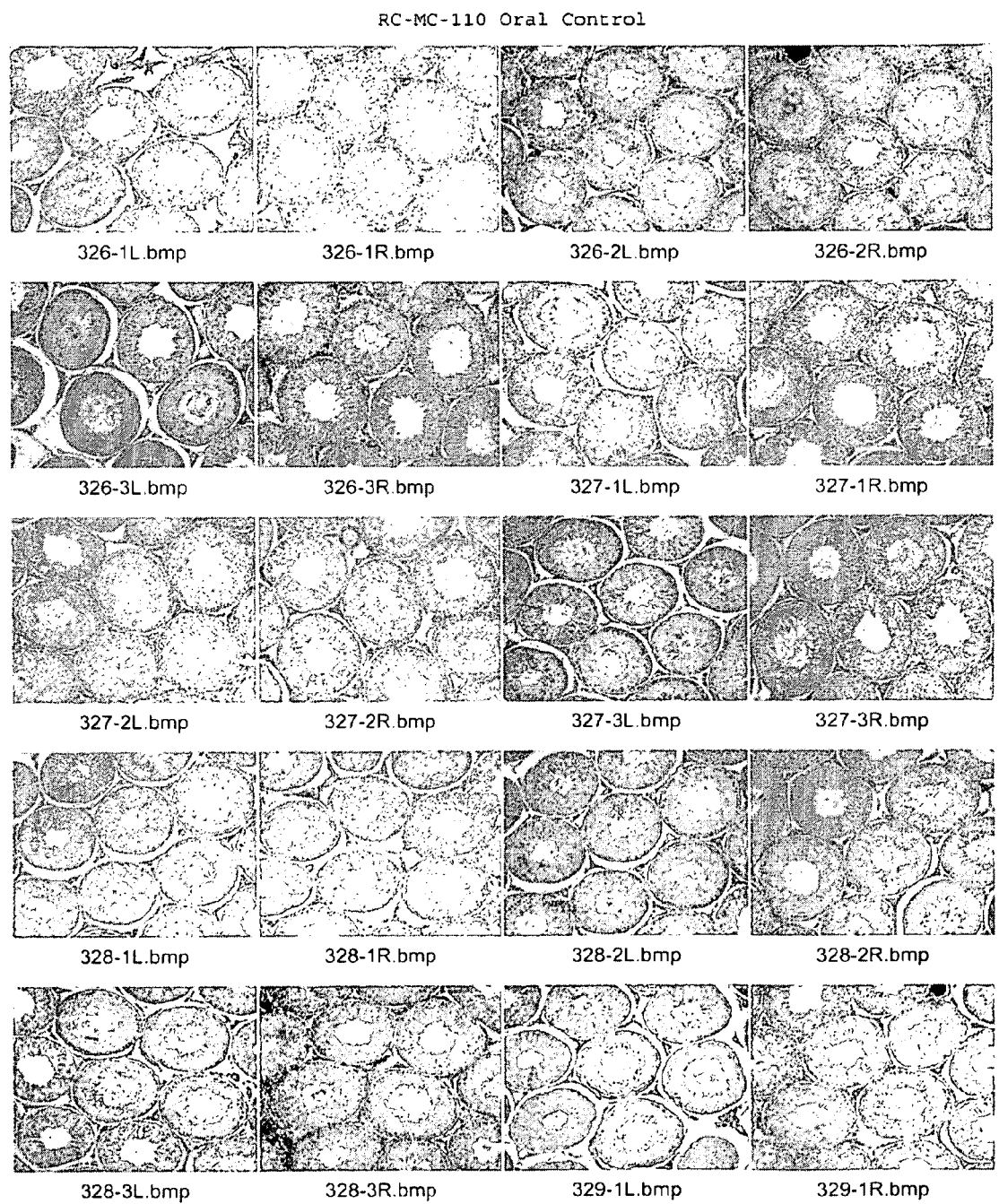
FIG. 6F is a histologic photograph of the testes of a rat receiving corn oil as a control for the RC-MC-110 studies.

It is contemplated that some of the compounds of the present invention exert their anti-cancer effects by binding either directly or indirectly to heat shock proteins. In recent years, heat shock 90 proteins ("Hsp90"), the molecular chaperones responsible for protein folding and maturation in vivo have been found at higher levels in cancerous cells than in normal cells. It is thought that Hsp90 is involved in the development of polycystic kidney disease (PKD) in a manner similar to its involvement in cancer cell proliferation: it helps cells divide and proliferate. Therefore, inhibitors of Hsp90 and/or related proteins in the biological pathways of cell division and propagation may also be useful for treating, inhibiting, and/or preventing PKD, such as ADPKD and ARPKD.

The 90 kDa heat shock proteins belong to a family of chaperones that regulate intracellular functions and are required for the refolding of denatured proteins following heat shock, as well as the conformational maturation of a large number of key proteins involved in cellular processes. In yeast, a homologue of Hsp90 with a slightly lower molecular weight at 83 kDa (Hsp83) serves an identical function. The Hsp90 family of chaperones is comprised of four different isoforms. Hsp90 α and Hsp90 β are found predominately in the cytosol, the 94 kDa glucose-regulated protein ("GRP94") is localized to the endoplasmic reticulum, and Hsp75/tumour necrosis factor receptor associated protein 1 ("TRAP-1") resides mainly in the mitochondrial matrix. These Hsp90s bind to client proteins in the presence of cochaperones, immunophilins, and partner proteins to make the multiprotein complex responsible for conformational maturation of newly formed nascent peptides into biologically active three-dimensional structures.

As discussed more fully below, Hsp90 is an ATP-dependent protein with an ATP binding site in the N-terminal region of the active homodimer. Disruption of the ATPase activity of Hsp90 results in the stabilization of multiprotein complexes and subsequent ubiquitination of the client protein, which undergoes proteasome-mediated hydrolysis.

More specifically, in an ATP-dependent fashion, Hsp70 binds to newly synthesized proteins cotranslationally and/or posttranslationally to stabilize the nascent peptide by preventing aggregation. Stabilization of the Hsp70/polypeptide binary complex is dependent upon the binding of Hsp70 interacting protein ("HIP"), which occurs after Hsp70 binds to the newly formed peptide. Hsp70-Hsp90 organizing protein ("HOP") contains highly conserved TPRs (tetratricopeptide repeats) that are recognized by both Hsp70 and Hsp90, promoting the union of Hsp70/HIP and Hsp90, which results in a heteroprotein complex. In the case of telomerase and steroid hormone receptors, the client protein is transferred from the Hsp70 system to the Hsp90 homodimer with concomitant release of Hsp70, HIP, and HOP. Upon binding of ATP and an immunophilin with cis/trans prolyl-isomerase activity (FKBP51, FKBP-52, or CyP A), the ensemble folds the client protein into its three-dimensional structure. In a subsequent event, p23 binds Hsp90 near the N-terminal region promoting the hydrolysis of ATP and release of the folded protein Hsp90 partner proteins, and ADP.

Examples of proteins dependent upon Hsp90 for conformational maturation include: oncogenic Src kinase, Raf, p185, mutant p53 (not normal p53), telomerase, steroid hormone receptors, polo-like kinase ("PLK"), protein kinase B ("AKT"), death domain kinase ("RIP"), MET kinase, focal adhesion kinase ("FAK"), aryl hydrocarbon receptor, RNA-dependent protein kinase ("PKR"), nitric oxide synthase ("NOS"), centrosomal proteins, and others. In addition, other proteins, such as cyclin dependent kinase 4 ("CDK4"), cyclin dependent kinase 6 ("CDK6"), and human epidermal growth factor receptor 2 ("Her-2") are thought to be client proteins of Hsp90. Of these Hsp90 client proteins, Raf, PLK, RIP, AKT, FAK, telomerase, and MET kinase are directly associated with the six hallmarks of cancer and possibly other uncontrolled cell proliferation states, such as PKD: (1) self-sufficiency in growth signals; (2) sensitivity to antigrowth signals; (3) evasion of apoptosis; (4) unlimited replication potential; (5) sustained angiogenesis; and (6) tissue invasion/metastasis. Consequently, Hsp90 inhibition is a target for the development of therapeutics that inhibit uncontrolled or abnormal cell proliferation because multiple signaling pathways can be simultaneously inhibited by disruption of the Hsp90 protein folding machinery.

Known inhibitors of Hsp90 include the anti-tumor antibiotics geldanamycin ("GDA"), radicicol ("RDC"), herbimycin A ("HB"), a 17-allylamino derivative of GDA ("17-AAG"), and the synthetic ATP analog called PU3. These molecules exert their activity by binding to the N-terminal ATP binding pocket and inhibit the ATPase activity of Hsp90. Novobiocin (a DNA gyrase ATP binding site inhibitor) has been found to selectively bind to the C-terminal domain of Hsp90. In all cases, these complex structures, however, are very difficult to isolate and/or synthesize. As such, there remains a need to develop other Hsp90 inhibitors useful as anti-cancer agents. Most preferably, these new Hsp90 inhibitors have decreased toxicity, increased solubility, and/or increased selectivity for Hsp90. These Hsp90 inhibitors may operate by binding to the N-terminal region, the C-terminal region, or another region of the homodimer that causes a conformational change. Now, it has been found that lonidamine analogs, such as those described herein, can be used as Hsp90 inhibitors, and thereby, can be used to treat, inhibit, and/or prevent PKD.

Accordingly, the present invention is directed to novel compounds (e.g., lonidamine analogs) which are based on the lonidamine structure. Lonidamine (1-(2,4,-dichlorobenzyl)-1H-indazole-3-carboxylic acid) belongs to a group of indazole-carboxylic acid compounds. Some examples of lonidamine analogs that can be used in therapies for PKD are described as follows.

In one aspect of the present invention, compounds according to the Formula I are provided:

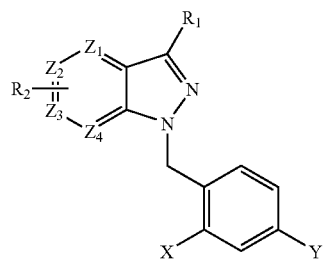

Formula I wherein $R_1$ is carboxyl, acryl, or carboxylic acid hydrazide;

wherein $R_2$ is hydrogen, halogen, alcohol, alkyl, alkoxy, aralkyl, cycloalkyl, haloalkyl, haloalkoxy, amino, or carboxyl;

wherein X and Y are the same or different from each other and are halogen or lower alkyl;

wherein $Z_1$, $Z_2$, $Z_3$, and $Z_4$ are independently nitrogen or carbon, and pharmaceutically salts and esters thereof.

When $R_2$ is anything other than hydrogen, $R_1$ can be —COOCH$_3$, —COOCH$_2$CH$_3$, —CH=CHCOOH, —CH=CHCOOCH$_3$, —CONHNH$_2$, —CONHNHCH$_3$, or —CONHN(CH$_3$)$_2$. When $R_2$ is hydrogen, then either: at least one of $Z_1$, $Z_2$, $Z_3$, and $Z_4$ is nitrogen and the remainder are independently carbon or nitrogen; or $R_1$ is not —COOH, —CONHNH$_2$, —CONHN(CH$_3$)$_2$, —CH=CHCOOH. Also, $R_1$ can be carboxylic acid or carboxylic acid ester selected from the group consisting of propionic acid, 2-methyl propionic acid, oxirane-carboxylic acid, cyclopropane carboxylic acid, propionic acid methyl ester, 2-methyl propionic acid methyl ester, oxirane-carboxylic acid methyl ester, cyclopropane carboxylic acid methyl ester In one aspect of the present invention, a compound comprising 1-(2,4-dichlorobenzyl)indazole-3-carboxylic acid methyl ester (also referred herein as RC-MC-30) is provided.

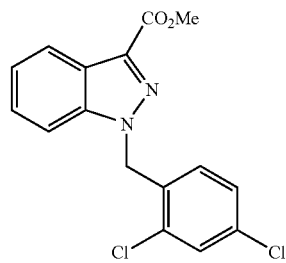 [SMILES: COC(=O)c1nn(Cc2ccc(Cl)cc2Cl)c2ccccc12]

In another aspect of the present invention, a compound comprising 1-[(2,4-dichlorobenzyl)-1H-indazole]-3-carboxylic acid ethyl ester (RC-MC-156) is provided.

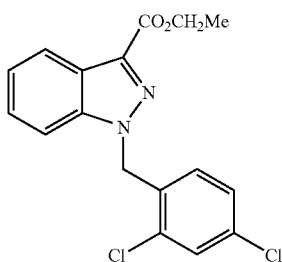

Still in another aspect of the present invention, a compound comprising 1-[(2,4-dichlorobenzyl)-1H-indazole]-3-carboxylic acid propyl ester (RC-MC-158) is provided.

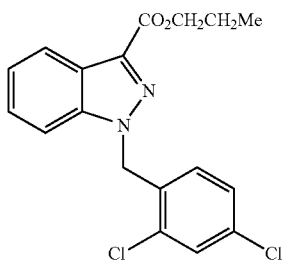

Still in another aspect of the present invention, a compound comprising 1-(2,4-dichlorobenzyl)-1H-indazole-3-carboxylic acid N-methyl hydrazide (RC-MC-120) is provided.

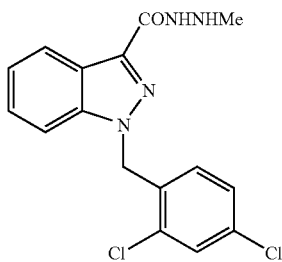

In another aspect of the present invention, a compound comprising 6-chloro-1-(2,4-dichlorobenzyl)-1H-indazole-3-carboxylic acid (DD-MC-I) is provided.

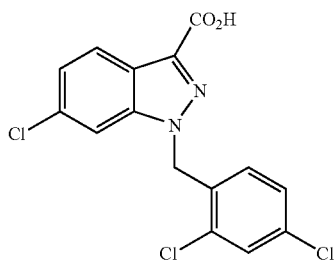 [SMILES: O=C(O)c1nn(Cc2ccc(Cl)cc2Cl)c2cc(Cl)ccc12]

In yet another aspect, the present invention includes a compound comprising 1-(2,4-difluorobenzyl)-6-chloro-1H-indazole-3-carboxylic acid (JSW-1-284).

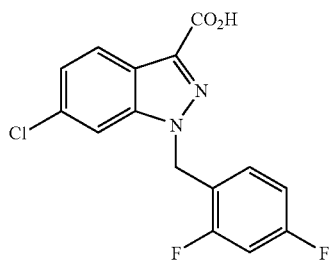 [SMILES: O=C(O)c1nn(Cc2ccc(F)cc2F)c2cc(Cl)ccc12]

Still in another aspect of the present invention, a compound comprising 1-(2-chloro-4-fluorobenzyl)-6-chloro-1H-indazole-3-carboxylic acid (JWS-2-20) is provided.

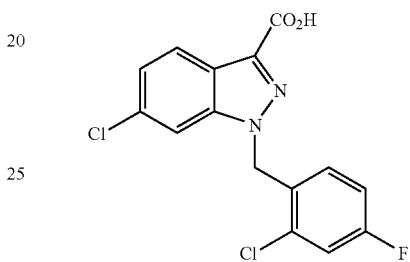

Still in another aspect of the present invention, a compound comprising 1-(2,4-difluorobenzyl)-6-chloro-1H-indazole-3-carboxylic acid methyl ester (JWS-1-280) is provided.

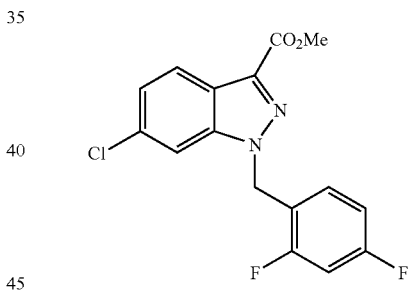

Yet, still in another aspect of the present invention, a compound comprising 1-(2-chloro-4-fluorobenzyl)-6-chloro-1H-indazole-3-carboxylic acid methyl ester (JWS-2-18) is provided.

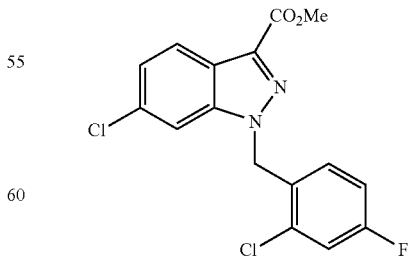

Still in another aspect of the present invention, a compound comprising 3-[1-(2,4-dichlorobenzyl)-6-chloro-1H-indazol-3-yl]-acrylic acid (JWS-1-190) is provided.

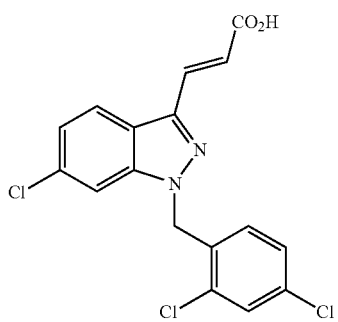 [SMILES: O=C(O)/C=C/c1nn(Cc2ccc(Cl)cc2Cl)c2cc(Cl)ccc12]

Still in another aspect of the present invention, a compound comprising 3-[1-(2,4-dichlorobenzyl)-6-chloro-1H-indazol-3-yl]-propionic acid is provided.

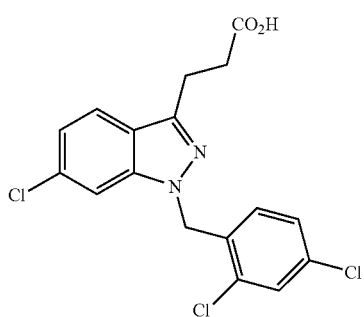 [SMILES: O=C(O)CCc1nn(Cc2ccc(Cl)cc2Cl)c2cc(Cl)ccc12]

Still in another aspect of the present invention, a compound comprising 3-[1-(2,4-difluorobenzyl)-6-chloro-1H-indazol-3-yl]-acrylic acid (JWS-1-298) is provided.

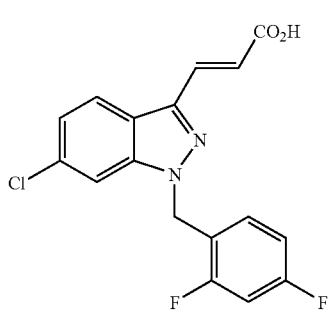 [SMILES: O=C(O)/C=C/c1nn(Cc2ccc(F)cc2F)c2cc(Cl)ccc12]

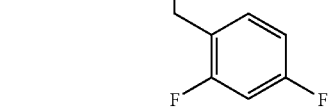

Still in another aspect of the present invention, a compound comprising 3-[1-(2-chloro, 4-fluorobenzyl)-6-chloro-1H-indazol-3-yl]-acrylic acid (JWS-2-36) is provided.

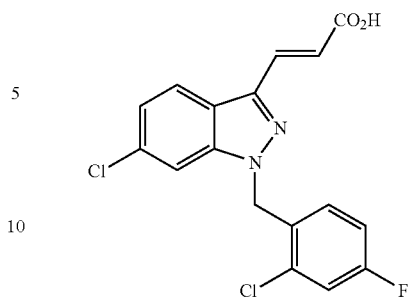

In yet another aspect of the present invention, a compound comprising 6-chloro-1-(2,4-dichlorobenzyl)-1H-indazole-3-carboxylic acid hydrazide (DD-MC-II) is provided.

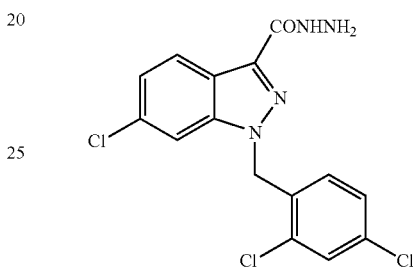

Still in another aspect of the present invention, a compound comprising 1-(2,4-difluorobenzyl)-6-chloro-1H-indazole-3-carboxylic acid hydrazide (JWS-1-282) is provided.

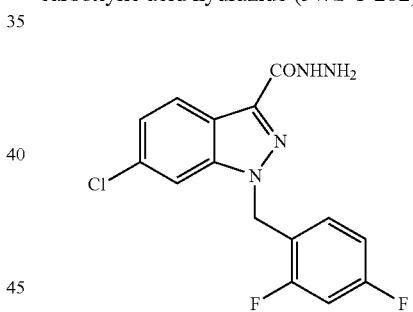

Still in another aspect of the present invention, a compound comprising 1-(2-chloro, 4-fluorobenzyl)-6-chloro-1H-indazole-3-carboxylic acid hydrazide (JWS-2-22) is provided.

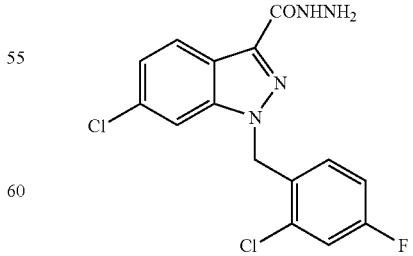

Still in another aspect of the present invention, a compound comprising 1-(2,4-dichlorobenzyl)-6-fluoro-1H-indazole-3-carboxylic acid (JWS-1-162) is provided.

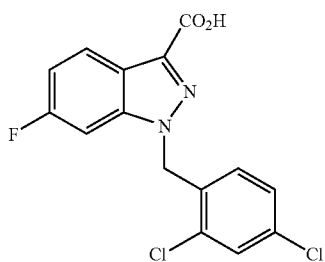 [SMILES: O=C(O)c1nn(Cc2ccc(Cl)cc2Cl)c2cc(F)ccc12]

Still in another aspect of the present invention, a compound comprising 1-(2,4-dichlorobenzyl)-6-fluoro-1H-indazole-3-carboxylic acid methyl ester (JWS-1-158) is provided.

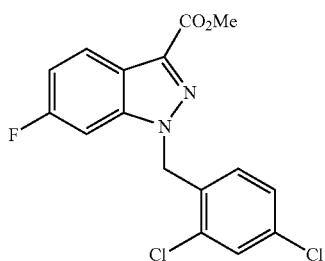 [SMILES: COC(=O)c1nn(Cc2ccc(Cl)cc2Cl)c2cc(F)ccc12]

In still another aspect of the present invention, a compound comprising 3-[1-(2,4-dichlorobenzyl)-6-fluoro-1H-indazol-3-yl]-acrylic acid (JWS-1-170) is provided.

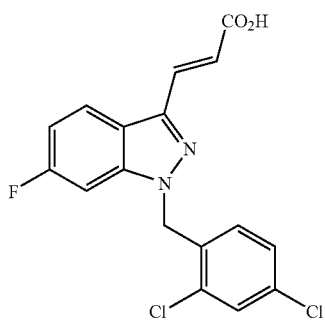 [SMILES: O=C(O)/C=C/c1nn(Cc2ccc(Cl)cc2Cl)c2cc(F)ccc12]

It is still another aspect of the present invention to provide a compound comprising 1-(2,4-dichlorobenzyl)-6-fluoro-1H-indazole-3-carboxylic acid hydrazide (JWS-1-160).

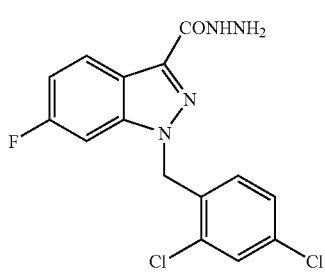

Still in another aspect of the present invention, a compound comprising 1-(2,4-dichlorobenzyl)-6-trifluoromethyl-1H-indazole-3-carboxylic acid (RC-MC-100) is provided.

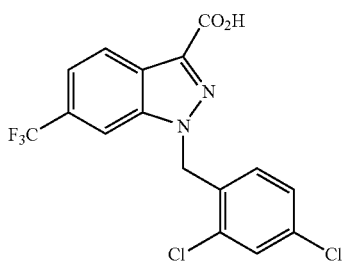 [SMILES: O=C(O)c1nn(Cc2ccc(Cl)cc2Cl)c2cc(C(F)(F)F)ccc12]

In a further aspect of the present invention, a compound comprising 1-(2,4-difluorobenzyl)-6-trifluoromethyl-1H-indazole-3-carboxylic acid (JWS-1-276) is provided.

Further, in another aspect of the present invention, a compound comprising 1-(2-chloro-4-fluorobenzyl)-6-trifluoromethyl-1H-indazole-3-carboxylic acid (JWS-2-14) is provided.

In another aspect of the present invention, a compound comprising 1-(2,4-difluorobenzyl)-6-trifluoromethyl-1H-indazole-3-carboxylic acid methyl ester (JWS-1-270) is provided.

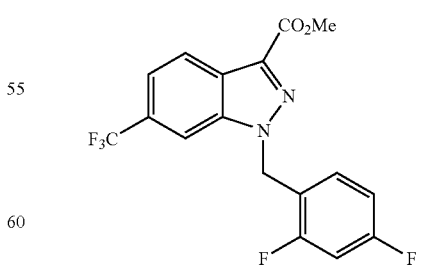

Still in another aspect of the present invention, a compound comprising 1-(2-fluoro-4-chlorobenzyl)-6-trifluoromethyl-1H-indazole-3-carboxylic acid methyl ester (JWS-2-12) is provided.

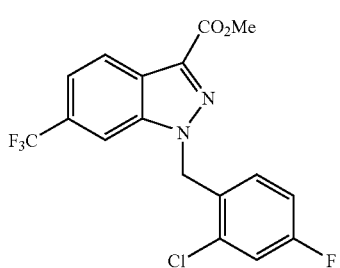 [SMILES: O=C(O)c1nn(Cc2ccc(F)cc2Cl)c2cc(C(F)(F)F)ccc12]

Still in another aspect of the present invention, a compound comprising trans 3-[1-(2,4-dichlorobenzyl)-6-trifluoromethyl-1H-indazol-3-yl]-acrylic acid (RC-MC-110) is provided.

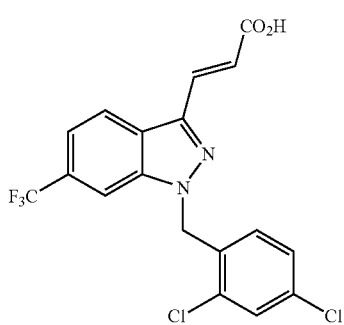 [SMILES: O=C(O)/C=C/c1nn(Cc2ccc(Cl)cc2Cl)c2cc(C(F)(F)F)ccc12]

In still a further aspect of the present invention, a compound comprising cis 3-[1-(2,4-dichlorobenzyl)-6-trifluoromethyl-1H-indazol-3-yl]-acrylic acid (cis RC-MC-110) is provided

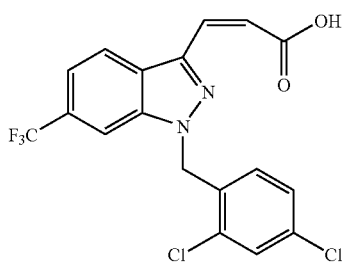 [SMILES: O=C(O)/C=C\c1nn(Cc2ccc(Cl)cc2Cl)c2cc(C(F)(F)F)ccc12]

Still in another aspect of the present invention, a compound comprising 3-[1-(2,4-difluorobenzyl)-6-trifluoromethyl-1H-indazol-3-yl]-acrylic acid (JWS-1-294) is provided.

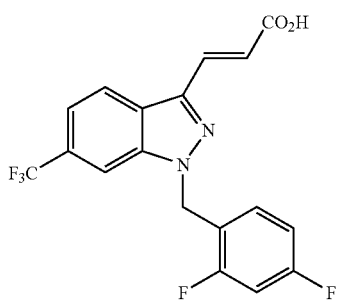 [SMILES: O=C(O)/C=C/c1nn(Cc2ccc(F)cc2F)c2cc(C(F)(F)F)ccc12]

Still in another aspect of the present invention, a compound comprising 3-[1-(2-chloro, 4-fluorobenzyl)-6-trifluoromethyl-1H-indazol-3-yl]-acrylic acid (JWS-2-40) is provided.

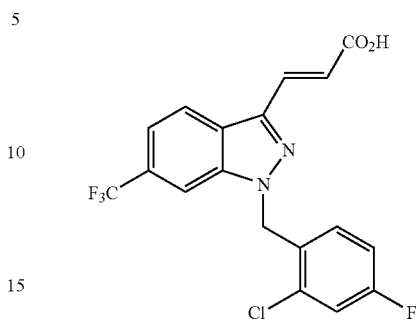

In still a further aspect of the present invention, a compound comprising 3-[1-(2,4-dichlorobenzyl)-6-trifluoromethyl-1H-indazol-3-yl]-2-methyl-acrylic acid (RC-MC-217) is provided.

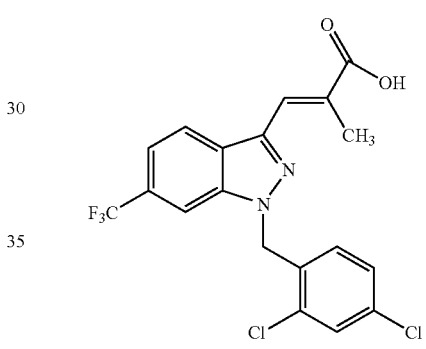

In a further aspect of the present invention, a compound comprising trans 3-[1-(2,4-dichlorobenzyl)-6-trifluoromethyl-1H-indazol-3-yl]-acrylic acid methyl ester (trans RC-MC-200) is provided.

In still a further aspect of the present invention, a compound comprising cis 3-[1-(2,4-dichlorobenzyl)-6-trifluoromethyl-1H-indazol-3-yl]-acrylic acid methyl ester (cis RC-MC-200) is provided.

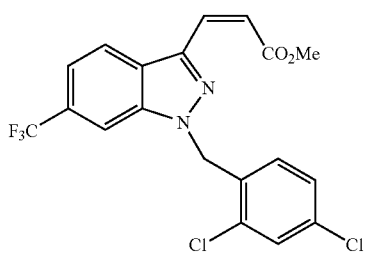 [SMILES: COC(=O)/C=C\c1nn(Cc2ccc(Cl)cc2Cl)c2cc(C(F)(F)F)ccc12]

Still in another aspect of the present invention, a compound comprising 1-(2,4-dichlorobenzyl)-6-trifluoromethyl-1H-indazole-3-carboxylic acid hydrazide (RC-MC-101) is provided.

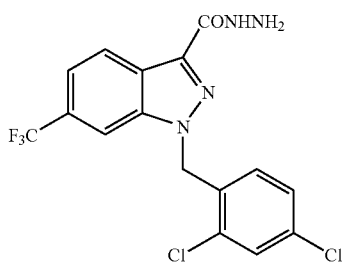

Still in another aspect of the present invention, a compound comprising 1-(2,4-difluorobenzyl)-6-trifluoromethyl-1H-indazole-3-carboxylic acid hydrazide (JWS-1-274) is provided.

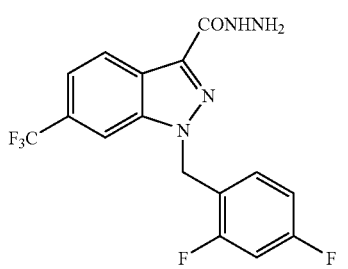

Still in another aspect of the present invention, a compound comprising 1-(2-chloro-4-fluorobenzyl)-6-trifluoromethyl-1H-indazole-3-carboxylic acid hydrazide (JWS-2-16) is provided.

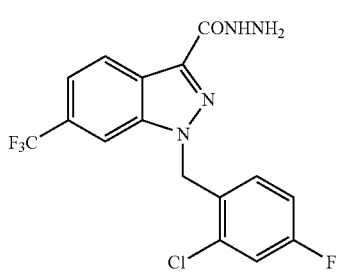

In still a further aspect of the present invention, a compound comprising 3-[1-(2,4-dichlorobenzyl)-6-trifluoromethyl-1H-indazol-3-yl]-propionic acid (JWS-2-72; H2-gamendazole) is provided. Also, gamendazole can be used as described herein.

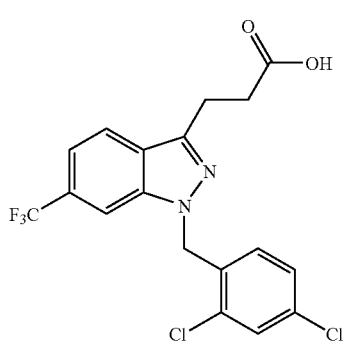 [SMILES: CCOC(=O)CCc1nn(Cc2ccc(Cl)cc2Cl)c2cc(C(F)(F)F)ccc12]

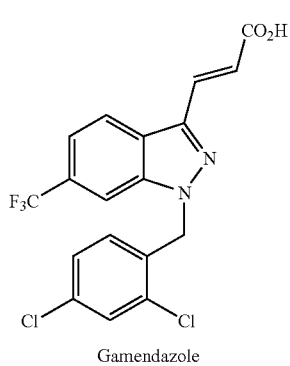

Gamendazole

In still a further aspect of the present invention, a compound comprising 3-[1-(2,4-dichlorobenzyl)-6-trifluoromethyl-1H-indazol-3-yl]-2-methylpropionic acid is provided (RC-MC-294).

In still a further aspect of the present invention, a compound comprising 3-[1-(2,4-dichlorobenzyl)-6-trifluoromethyl-1H-indazol-3-yl]-propionic acid ethyl ester (JWS-2-70) is provided.

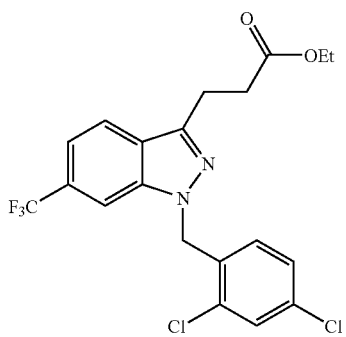

In still a further aspect of the present invention, a compound comprising 1-(4-chloro-2-methyl-benzyl)-6-trifluoromethyl-1H-indazole-3-carboxylic acid (JWS-2-212) is provided.

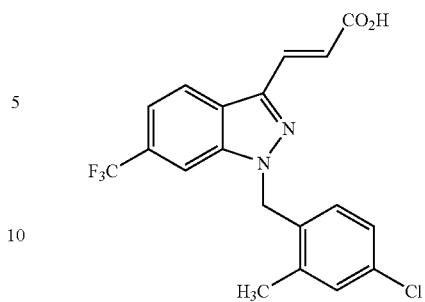

In still a further aspect of the present invention, compounds comprising cis- and trans-3-[1-(2,4-dichlorobenzyl)-6-trifluoromethyl-1H-indazol-3-yl]-oxirane-2-carboxylic acid (RC-MC-228) are provided.

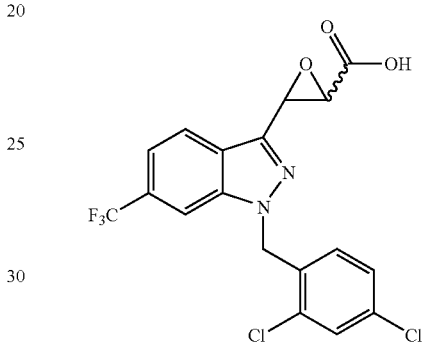

In still a further aspect of the present invention, compounds comprising cis- and trans-2-[1-(2,4-dichloro-benzyl)-6-trifluoromethyl-1H-indazol-3-yl]-cyclopropanecarboxylic acid (JWS-3-6) are provided.

In still a further aspect of the present invention, a compound comprising 1-(4-chloro-2-methyl-benzyl)-6-trifluoromethyl-1H-indazole-3-carboxylic acid methyl ester (JWS-2-210) is provided.

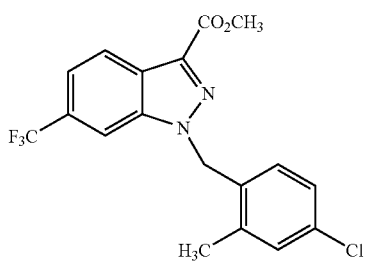 [SMILES: COC(=O)c1nn(Cc2ccc(Cl)cc2C)c2cc(C(F)(F)F)ccc12]

In still a further aspect of the present invention, a compound comprising 3-[1-(4-chloro-2-methyl-benzyl)-6-trifluoromethyl-1H-indazol-3-yl]-acrylic acid (JWS-2-224) is provided.

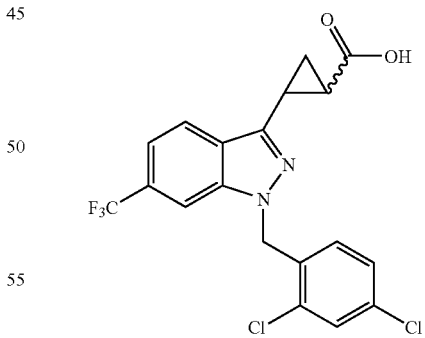

In still a further aspect of the present invention, a compound comprising 3-[1-(2,4-dichlorobenzyl)-6-trifluoromethyl-1H-indazol-3-yl]-prop-2-en-1-ol (RC-MC-223) is provided.

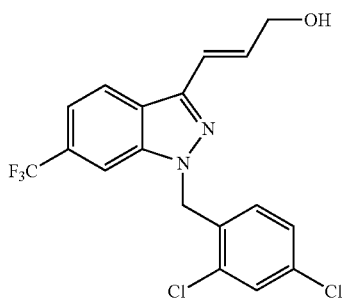 [SMILES: OC/C=C/c1nn(Cc2ccc(Cl)cc2Cl)c2cc(C(F)(F)F)ccc12]

In still a further aspect of the present invention, a compound comprising trans-3-[1-(2,4-dichlorobenzyl)-6-trifluoromethyl-1H-indazol-3-yl]-acrylonitrile is provided (RC-MC-222 Trans).

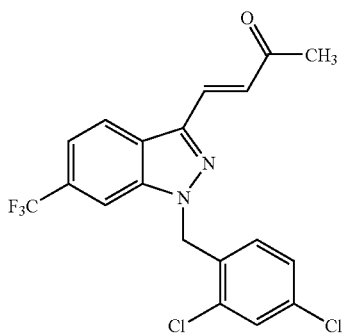

In still a further aspect of the present invention, a compound comprising 1-(2,4-dichloro-benzyl)-3-[2-(1H-tetrazol-5-yl)-vinyl]-6-trifluoromethyl-1H-indazole (RC-MC-225) is provided.

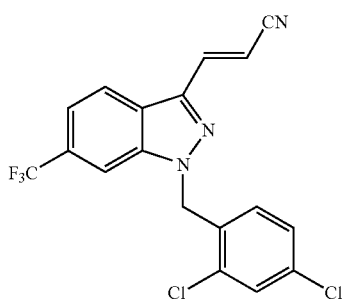 [SMILES: N#C/C=C/c1nn(Cc2ccc(Cl)cc2Cl)c2cc(C(F)(F)F)ccc12]

In still a further aspect of the present invention, a compound comprising cis-3-[1-(2,4-dichlorobenzyl)-6-trifluoromethyl-1H-indazol-3-yl]-acrylonitrile is provided (RC-MC-222 cis).

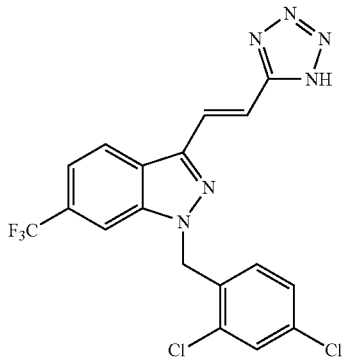

In a further aspect of the present invention, a compound comprising 3-[1-(2,4-dichlorobenzyl)-6-trifluoromethyl-1H-indazol-3-yl]-acrylic acid hydrazide (RC-MC-205) is provided.

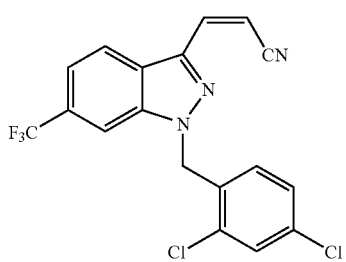 [SMILES: N#C/C=C\c1nn(Cc2ccc(Cl)cc2Cl)c2cc(C(F)(F)F)ccc12]

In still a further aspect of the present invention, a compound comprising 4-[1-(2,4-dichloro-benzyl)-6-trifluoromethyl-1H-indazol-3-yl]-but-3-en-2-one (RC-MC-216) is provided.

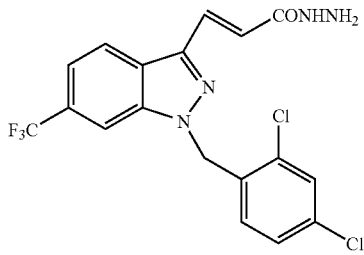

Further, in another aspect of the present invention, a compound comprising 1-(2,4-dichlorobenzyl)-6-difluoromethyl-1H-indazole-3-carboxylic acid (RC-MC-288) is provided.

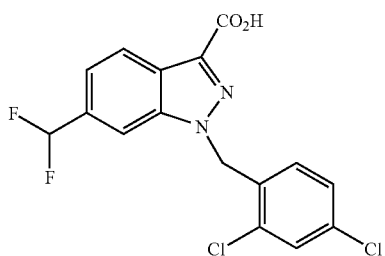 [SMILES: O=C(O)c1nn(Cc2ccc(Cl)cc2Cl)c2cc(C(F)F)ccc12]

Further, in another aspect of the present invention, a compound comprising 1-(2,4-dichlorobenzyl)-6-difluoromethyl-1-indazole-3-carboxylic acid methyl ester (RC-MC-287) is provided.

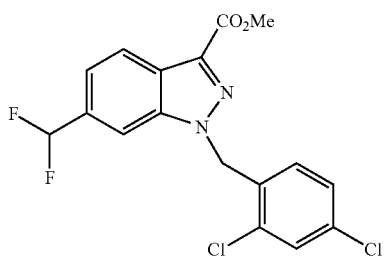

Still in another aspect of the present invention, a compound comprising 3-[1-(2,4-dichlorobenzyl)-6-difluoromethyl-1H-indazol-3-yl]-acrylic acid (RC-MC-292) is provided.

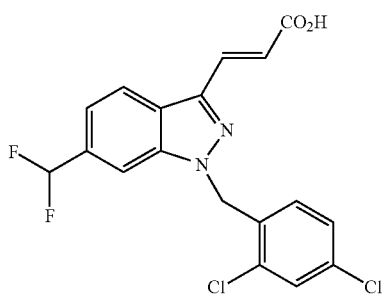 [SMILES: O=C(O)/C=C/c1nn(Cc2ccc(Cl)cc2Cl)c2cc(C(F)F)ccc12]

In a further aspect of the present invention, a compound comprising 3-[1-(2,4-dichlorobenzyl)-6-difluoromethyl-1H-indazol-3-yl]-acrylic acid methyl ester (RC-MC-291) is provided.

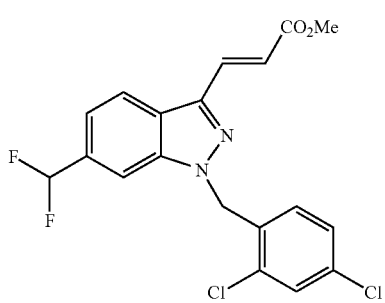

Further, in another aspect of the present invention, a compound comprising 1-(2,4-dichlorobenzyl)-6-fluoromethyl-1H-indazole-3-carboxylic acid (RC-MC-263) is provided.

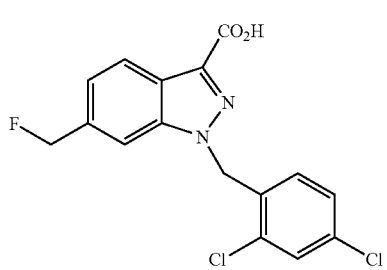 [SMILES: O=C(O)c1nn(Cc2ccc(Cl)cc2Cl)c2cc(CF)ccc12]

In still another aspect of the present invention, a compound comprising 1-(2,4-dichlorobenzyl)-6-fluoromethyl-1H-indazole-3-carboxylic acid methyl ester (RC-MC-262) is provided.

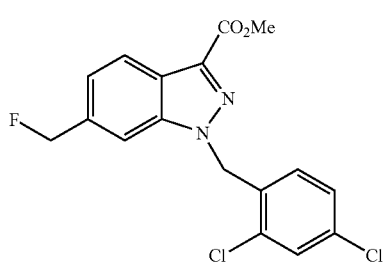 [SMILES: COC(=O)c1nn(Cc2ccc(Cl)cc2Cl)c2cc(CF)ccc12]

Still in another aspect of the present invention, a compound comprising 3-[1-(2,4-dichlorobenzyl)-6-fluoromethyl-1H-indazol-3-yl]-acrylic acid (RC-MC-265) is provided.

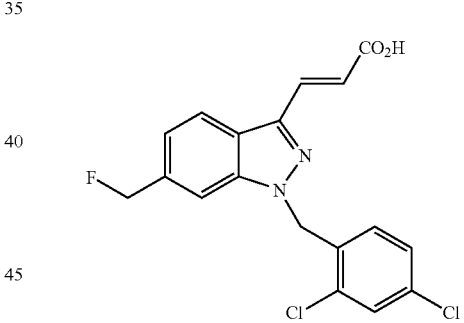

In a further aspect of the present invention, a compound comprising 3-[1-(2,4-dichlorobenzyl)-6-fluoromethyl-1H-indazol-3-yl]-acrylic acid methyl ester (RC-MC-264) is provided.

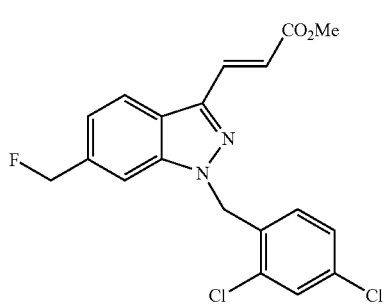 [SMILES: COC(=O)/C=C/c1nn(Cc2ccc(Cl)cc2Cl)c2cc(CF)ccc12]

In still a further aspect of the present invention, a compound comprising 1-(2,4-dichlorobenzyl)-6-trifluoromethoxy-1H-indazole-3-carboxylic acid (JWS-2-102) is provided.

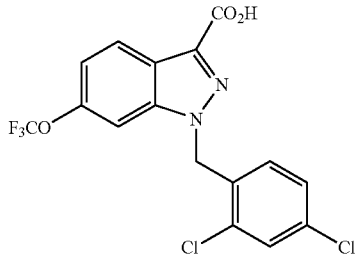 [SMILES: O=C(O)c1nn(Cc2ccc(Cl)cc2Cl)c2cc(OC(F)(F)F)ccc12]

In still a further aspect of the present invention, a compound comprising 1-(2,4-dichlorobenzyl)-6-trifluoromethoxy-1H-indazole-3-carboxylic acid methyl ester (JWS-2-100) is provided.

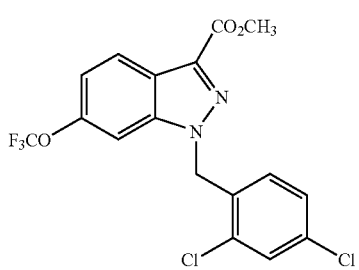 [SMILES: COC(=O)c1nn(Cc2ccc(Cl)cc2Cl)c2cc(OC(F)(F)F)ccc12]

In still a further aspect of the present invention, a compound comprising 3-[1-(2,4-dichlorobenzyl)-6-trifluoromethoxy-1H-indazol-3-yl]acrylic acid (JWS-2-112) is provided.

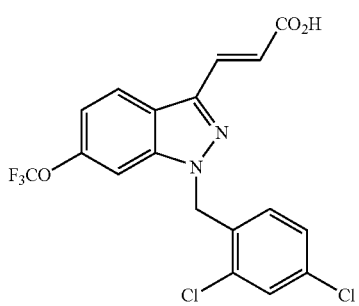 [SMILES: O=C(O)/C=C/c1nn(Cc2ccc(Cl)cc2Cl)c2cc(OC(F)(F)F)ccc12]

In still a further aspect of the present invention, a compound comprising 3-[1-(2,4-dichlorobenzyl)-6-trifluoromethoxy-1H-indazol-3-yl]acrylic acid methyl ester (JWS-2-110) is provided.

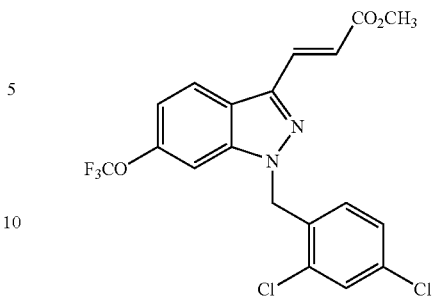

In still a further aspect of the present invention, a compound comprising 1-(2,4-dichlorobenzyl)-6-trifluoromethoxy-1H-indazole-3-carboxylic acid hydrazide (JWS-2-104) is provided.

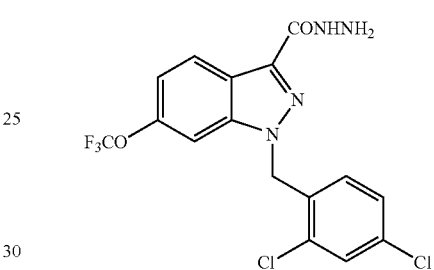

In still a further aspect of the present invention, a compound comprising 1-(4-chloro-2-methyl-benzyl)-6-trifluoromethoxy-1H-indazole-3-carboxylic acid (JWS-2-216) is provided.

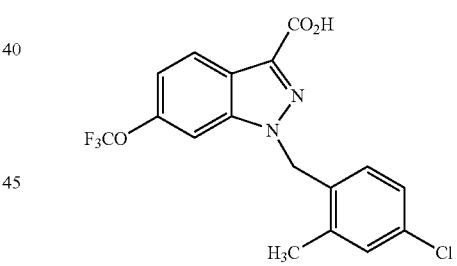

In still a further aspect of the present invention, a compound comprising 1-(4-chloro-2-methyl-benzyl)-6-trifluoromethoxy-1H-indazole-3-carboxylic acid methyl ester (JWS-2-214) is provided.

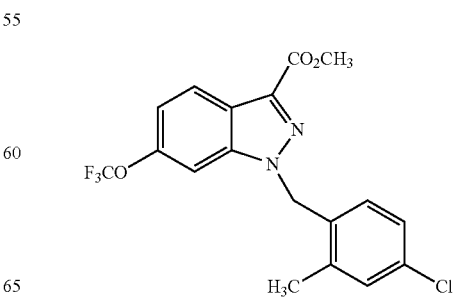

In still a further aspect of the present invention, a compound comprising 3-[1-(4-chloro-2-methyl-benzyl)-6-trifluoromethoxy-1H-indazol-3-yl]-acrylic acid (JWS-2-232) is provided.

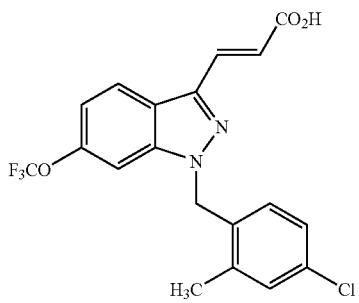 [SMILES: Cc1cc(Cl)ccc1Cn1nc(/C=C/C(=O)O)c2ccc(OC(F)(F)F)cc21]

Still in another aspect of the present invention, a compound comprising 1-(2,4-dichlorobenzyl)-6-methyl-1H-indazole-3-carboxylic acid (TH-2-178) is provided.

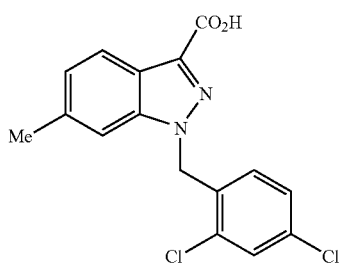 [SMILES: Cc1ccc2c(C(=O)O)nn(Cc3ccc(Cl)cc3Cl)c2c1]

In a further aspect of the present invention, a compound comprising 3-[1-(2,4-dichlorobenzyl)-6-methyl-1H-indazol-3-yl]acrylic acid (TH-2-192) is provided.

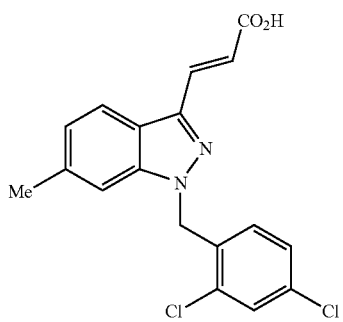 [SMILES: Cc1ccc2c(/C=C/C(=O)O)nn(Cc3ccc(Cl)cc3Cl)c2c1]

Still in another aspect of the present invention, a compound comprising 1-(2,4-dichlorobenzyl)-6-methyl-1H-indazole-3-carboxylic acid hydrazide (TH-2-179) is provided.

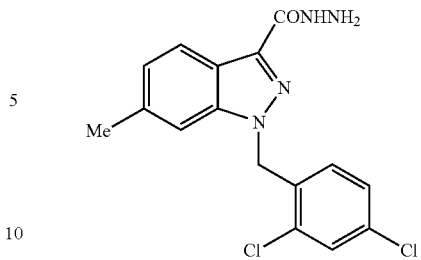

In still a further aspect of the present invention, a compound comprising 1-(2,4-dichlorobenzyl)-6-methoxy-1H-indazole-3-carboxylic acid (JWS-2-122) is provided.

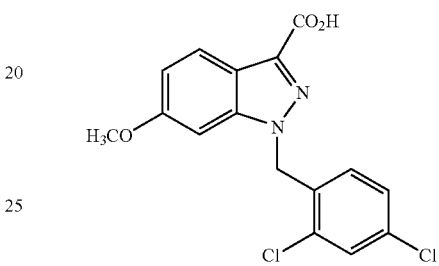

In still a further aspect of the present invention, a compound comprising 1-(2,4-dichlorobenzyl)-6-methoxy-1H-indazole-3-carboxylic acid methyl ester (JWS-2-120) is provided.

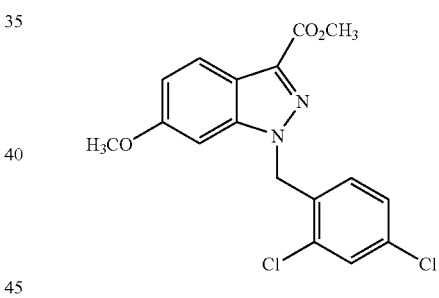

In still a further aspect of the present invention, a compound comprising 3-[1-(2,4-dichlorobenzyl)-6-methoxy-1H-indazol-3-yl]acrylic acid (JWS-2-132) is provided.

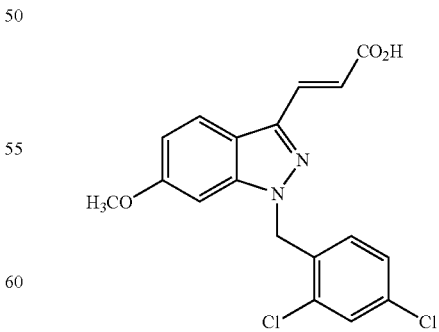

In still a further aspect of the present invention, a compound comprising 1-(2,4-dichlorobenzyl)-6-methoxy-1H-indazole-3-carboxylic acid hydrazide (JWS-2-124) is provided.

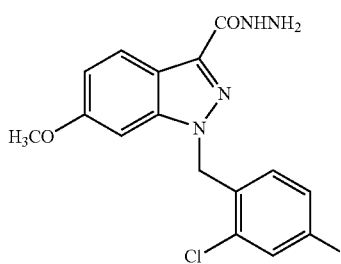

Yet, in another aspect of the present invention, a compound comprising 1-(2,4-dichlorobenzyl)-6-hydroxymethyl-1H-indazole-3-carboxylic acid (RC-MC-260) is provided.

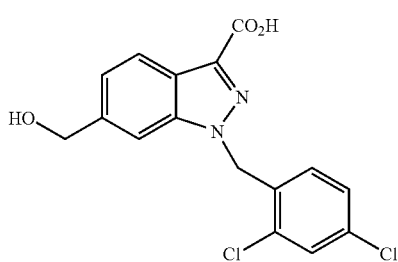 [SMILES: O=C(O)c1nn(Cc2ccc(Cl)cc2Cl)c2cc(CO)ccc12]

Yet, in another aspect of the present invention, a compound comprising 1-(2,4-dichlorobenzyl)-6-hydroxymethyl-1H-indazole-3-carboxylic acid methyl ester (RC-MC-251) is provided.

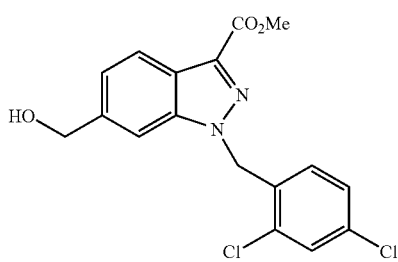 [SMILES: COC(=O)c1nn(Cc2ccc(Cl)cc2Cl)c2cc(CO)ccc12]

Still in another aspect of the present invention, a compound comprising 3-[1-(2,4-dichlorobenzyl)-6-hydroxymethyl-1H-indazol-3-yl]-acrylic acid (RC-MC-261) is provided.

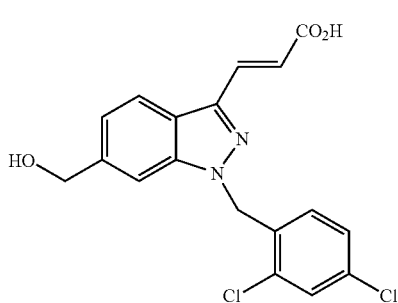 [SMILES: O=C(O)/C=C/c1nn(Cc2ccc(Cl)cc2Cl)c2cc(CO)ccc12]

In still a further aspect of the present invention, a compound comprising 3-[1-(2,4-dichlorobenzyl)-6-hydroxymethyl-1H-indazol-3-yl]acrylic acid methyl ester (RC-MC-257) is provided.

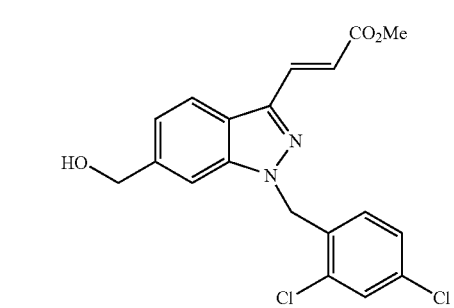 [SMILES: COC(=O)/C=C/c1nn(Cc2ccc(Cl)cc2Cl)c2cc(CO)ccc12]

Yet, in another aspect of the present invention, a compound comprising 1-(2,4-dichloro-benzyl)-1H-indazole-3,6-dicarboxylic acid (RC-MC-247) is provided.

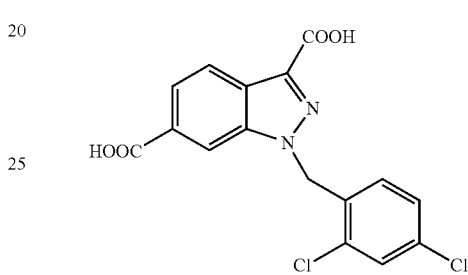

Yet, in another aspect of the present invention, a compound comprising 1-(2,4-dichloro-benzyl)-1H-indazole-3,6-dicarboxylic acid-3-methyl ester (RC-MC-252) is provided.

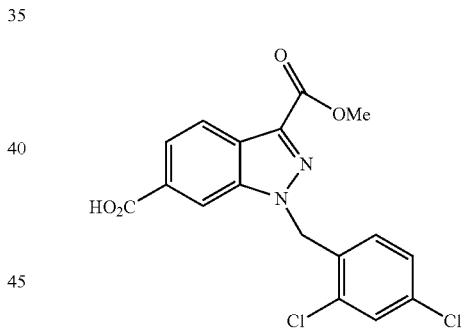

In still a further aspect of the present invention, a compound comprising 3-(2-carboxy-vinyl)-1-(2,4-dichloro-benzyl)-1H-indazole-6-carboxylic acid (RC-MC-259) is provided

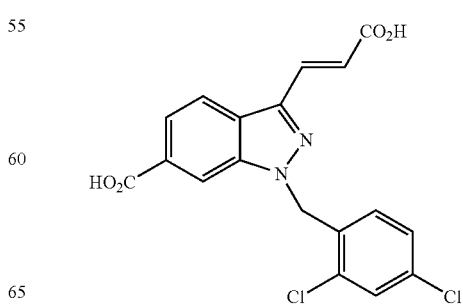

In still a further aspect of the present invention, a compound comprising 1-(2,4-dichloro-benzyl)-3-(2-methoxy-carbonyl-vinyl)-1H-indazole-6-carboxylic acid (RC-MC-258) is provided.

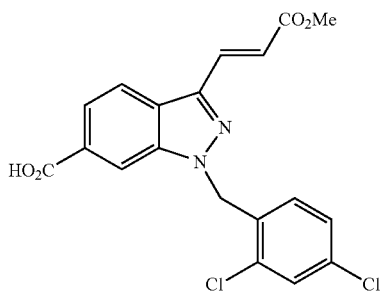 [SMILES: COC(=O)/C=C/c1nn(Cc2ccc(Cl)cc2Cl)c2cc(C(=O)O)ccc12]

Still in another aspect of the present invention, a compound comprising 1-(2,4-dichlorobenzyl)-5-trifluoromethyl-1H-indazole-3-carboxylic acid (JWS-1-260) is provided.

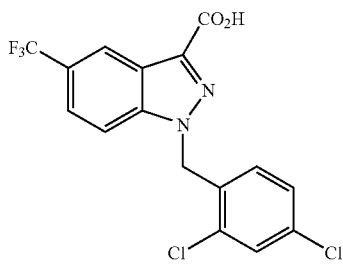 [SMILES: O=C(O)c1nn(Cc2ccc(Cl)cc2Cl)c2ccc(C(F)(F)F)cc12]

Still in another aspect of the present invention, a compound comprising 1-(2,4-difluorobenzyl)-5-trifluoromethyl-1H-indazole-3-carboxylic acid (JWS-2-1) is provided.

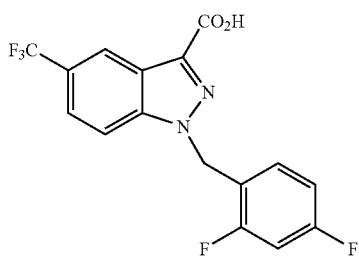 [SMILES: O=C(O)c1nn(Cc2ccc(F)cc2F)c2ccc(C(F)(F)F)cc12]

Yet, in another aspect of the present invention, a compound comprising 1-(2,4-dichlorobenzyl)-5-trifluoromethyl-1H-indazole-3-carboxylic acid methyl ester (JWS-1-254) is provided.

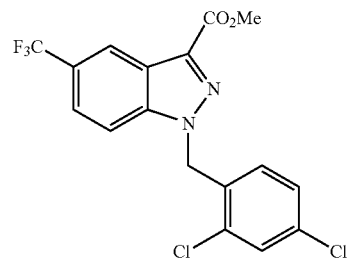 [SMILES: COC(=O)c1nn(Cc2ccc(Cl)cc2Cl)c2ccc(C(F)(F)F)cc12]

Still in another aspect of the present invention, a compound comprising 1-(2,4-difluorobenzyl)-5-trifluoromethyl-1H-indazole-3-carboxylic acid methyl ester (JWS-1-300) is provided.

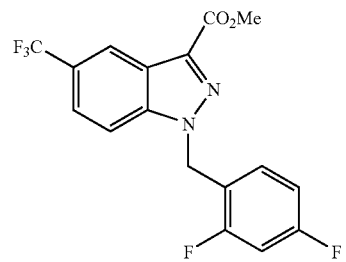 [SMILES: COC(=O)c1nn(Cc2ccc(F)cc2F)c2ccc(C(F)(F)F)cc12]

In yet another aspect of the present invention, a compound comprising 3-[1-(2,4-dichlorobenzyl)-5-trifluoromethyl-1H-indazol-3-yl]-acrylic acid (JWS-1-268) is provided.

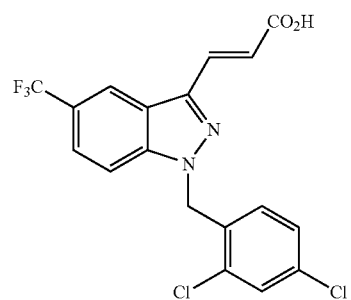 [SMILES: O=C(O)/C=C/c1nn(Cc2ccc(Cl)cc2Cl)c2ccc(C(F)(F)F)cc12]

Still in another aspect of the present invention, a compound comprising 3-[1-(2,4-difluorobenzyl)-5-trifluoromethyl-1H-indazol-3-yl]-acrylic acid (JWS-2-10) is provided.

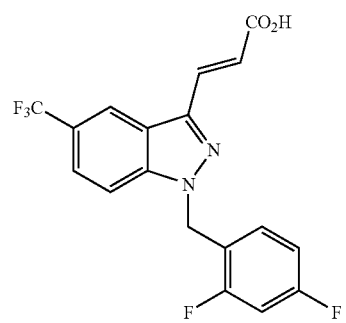 [SMILES: O=C(O)/C=C/c1nn(Cc2ccc(F)cc2F)c2ccc(C(F)(F)F)cc12]

Further, in another aspect of the present invention, a compound comprising 1-(2,4-dichlorobenzyl)-5-trifluoromethyl-1H-indazole-3-carboxylic acid hydrazide (JWS-1-258) is provided.

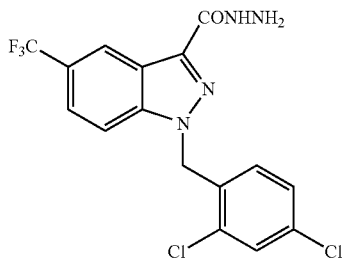

Still in another aspect of the present invention, a compound comprising 1-(2,4-difluorobenzyl)-5-trifluoromethyl-1H-indazole-3-carboxylic acid hydrazide (JWS-1-302) is provided.

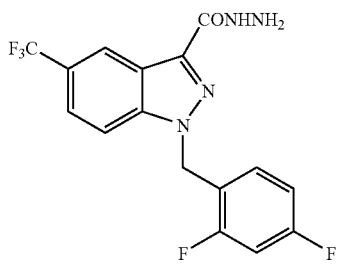

In still a further aspect of the present invention, a compound comprising 1-(2,4-dichloro-benzyl)-6-dimethylamino-1H-indazole-3-carboxylic acid (JWS-2-270) is provided.

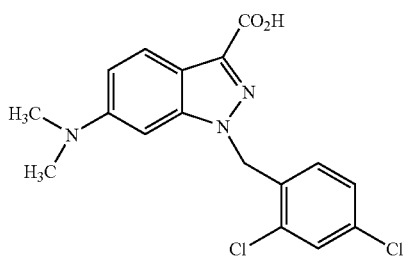 [SMILES: CN(C)c1ccc2c(C(=O)O)nn(Cc3ccc(Cl)cc3Cl)c2c1]

In still a further aspect of the present invention, a compound comprising 1-(2,4-dichloro-benzyl)-6-dimethylamino-1H-indazole-3-carboxylic acid methyl ester (JWS-2-268) is provided.

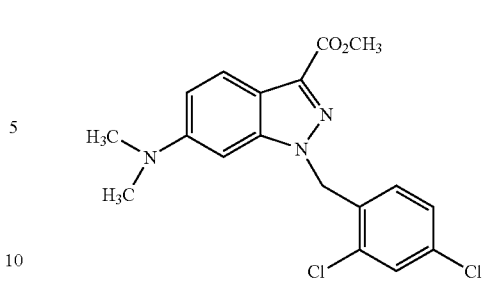

In still a further aspect of the present invention, a compound comprising 3-[1-(2,4-dichlorobenzyl)-6-dimethylamino-1H-indazol-3-yl]-acrylic acid (JWS-2-278) is provided.

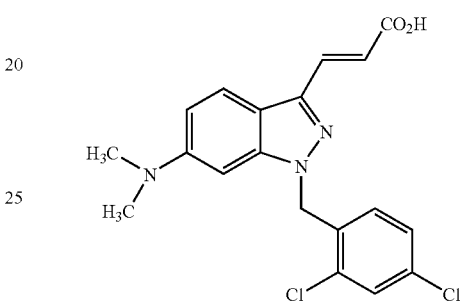

In still a further aspect of the present invention, a compound comprising 1-(2,4-dichlorobenzyl)-4-methyl-1H-indazole-3-carboxylic acid (JWS-2-94) is provided.

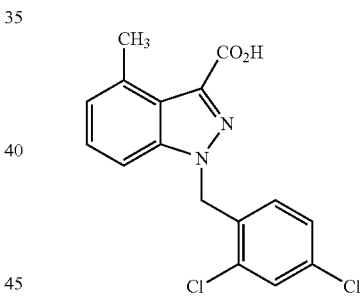

In still a further aspect of the present invention, a compound comprising 1-(2,4-dichlorobenzyl)-4-methyl-1H-indazole-3-carboxylic acid methyl ester (JWS-2-92) is provided.

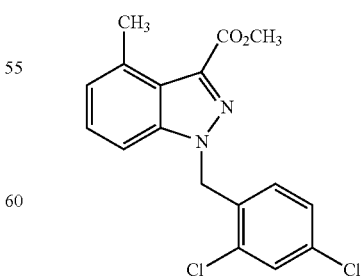

In still another aspect, compounds according to Formula II(A), are provided, where the substituents are the same as described in connection to Formula I:

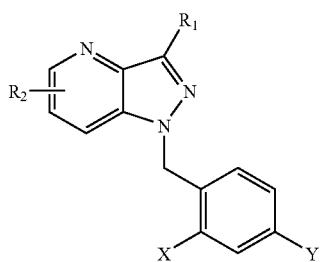

Examples of Formula II(A) derivatives include: 1-(2,4-difluorobenzyl)-1H-pyrazolo[4,3-b]pyridine-3-carboxylic acid; 1-(2-chloro-4-fluorobenzyl)-1H-pyrazolo[4,3-b]pyridine-3-carboxylic acid; 1-(2-fluoro-4-chlorobenzyl)-1H-pyrazolo[4,3-b]pyridine-3-carboxylic acid; 1-(2,4-difluorobenzyl)-1H-pyrazolo[4,3-b]pyridine]-3-carboxylic acid methyl ester; 1-(2-chloro-4-fluorobenzyl)-1H-pyrazolo[4,3-b]pyridine]-3-carboxylic acid methyl ester; 1-(2-fluoro-4-chlorobenzyl)-1H-pyrazolo[4,3-b]pyridine]-3-carboxylic acid methyl ester; 3-[1-(2,4-difluorobenzyl)-1H-pyrazolo[4,3-b]pyridin-3-yl]acrylic acid; 3-[1-(2-chloro-4-fluorobenzyl)-1H-pyrazolo[4,3-b]pyridin-3-yl]acrylic acid; 3-[1-(2-fluoro-4-chlorobenzyl)-1H-pyrazolo[4,3-b]pyridin-3-yl] acrylic acid; 1-(2,4-difluorobenzyl)-1H-pyrazolo[4,3-b]pyridine-3-carboxylic acid hydrazide; 1-(2-chloro-4-fluorobenzyl)-1H-pyrazolo[4,3-b]pyridine-3-carboxylic acid hydrazide; and 1-(2-fluoro-4-chlorobenzyl)-1H-pyrazolo[4,3-b]pyridine-3-carboxylic acid hydrazide. Additional examples are provided herein.

In still another aspect of the present invention, a compound comprising 1-(2,4-dichlorobenzyl)-1H-pyrazolo[4,3-b]pyridine-3-carboxylic acid (JWS-1-114) is provided.

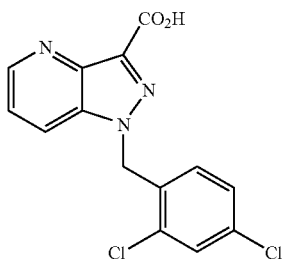 [SMILES: O=C(O)c1nn(Cc2ccc(Cl)cc2Cl)c2cccnc12]

In another aspect of the present invention, a compound comprising 1-(2,4-dichlorobenzyl)-1H-pyrazolo[4,3-b]pyridine]-3-carboxylic acid methyl ester (JWS-1-110) is provided.

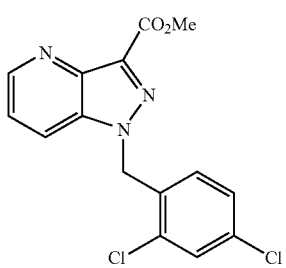 [SMILES: COC(=O)c1nn(Cc2ccc(Cl)cc2Cl)c2cccnc12]

In still a further aspect of the present invention, a compound comprising 3-[1-(2,4-dichlorobenzyl)-1H-pyrazolo[4,3-b]pyridin-3-yl]acrylic acid (JWS-2-176) is provided.

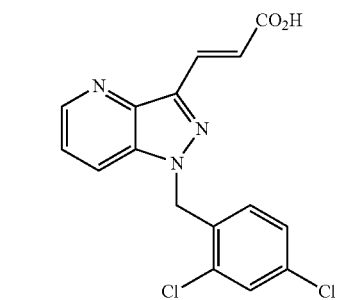 [SMILES: O=C(O)/C=C/c1nn(Cc2ccc(Cl)cc2Cl)c2cccnc12]

In still another aspect of the present invention, a compound comprising 1-(2,4-dichlorobenzyl)-1H-pyrazolo[4,3-b]pyridine-3-carboxylic acid hydrazide (JWS-1-112) is provided.

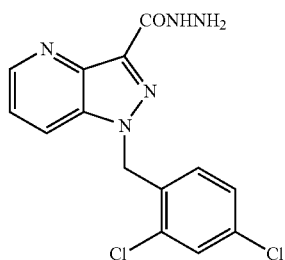

Further, the present invention includes a compound comprising 1-(2,4-dichlorobenzyl)-6-trifluoromethyl-1H-pyrazolo[4,3-b]pyridine-3-carboxylic acid (JWS-1-230).

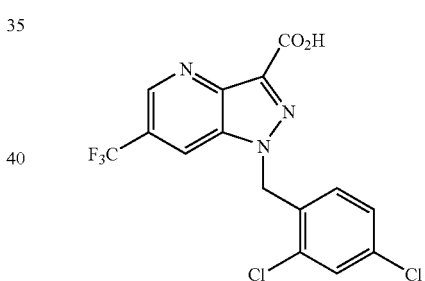

In another aspect of the present invention, a compound comprising 1-(2,4-dichlorobenzyl)-6-trifluoromethyl-1H-pyrazolo[4,3-b]pyridine-3-carboxylic acid methyl ester (JWS-1-228) is provided.

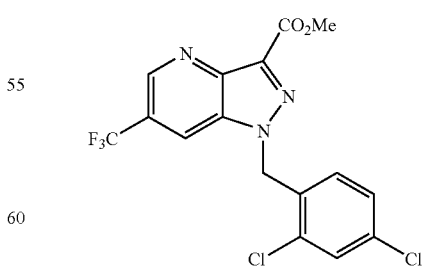

Further, the present invention includes a compound comprising 1-(2,4-dichlorobenzyl)-6-trifluoromethyl-1H-pyrazolo[4,3-b]pyridine-3-carboxylic acid hydrazide (JWS-1-232).

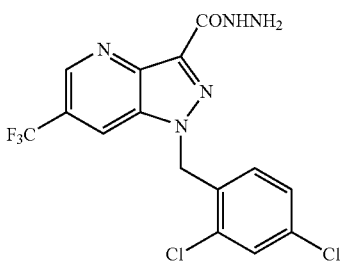

Further, the present invention includes a compound comprising 1-(2,4-dichlorobenzyl)-5-methoxy-1H-pyrazolo[4,3-b]pyridine-3-carboxylic acid (JWS-1-144).

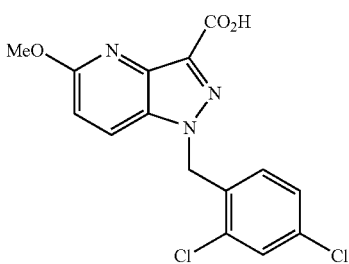 [SMILES: COc1ccc2c(n1)c(C(=O)O)nn2Cc1ccc(Cl)cc1Cl]

In another aspect of the present invention, a compound comprising 1-(2,4-dichlorobenzyl)-5-methoxy-1H-pyrazolo[4,3-b]pyridine-3-carboxylic acid methyl ester (JWS-1-142) is provided.

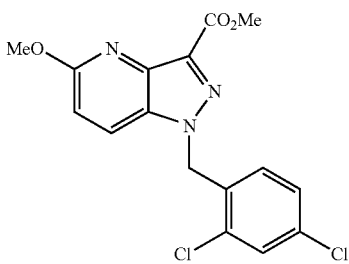 [SMILES: COC(=O)c1nn(Cc2ccc(Cl)cc2Cl)c2ccc(OC)nc12]

Further, the present invention includes a compound comprising 1-(2,4-dichlorobenzyl)-5-methoxy-1H-pyrazolo[4,3-b]pyridine-3-carboxylic acid hydrazide (JWS-1-146) is provided.

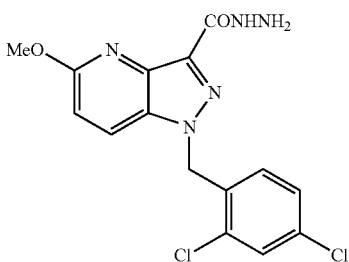

In yet another aspect, compounds according Formula II(B) are provided:

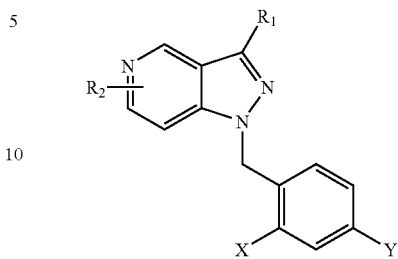

In still another aspect, the compounds according to Formula II(C) are provided, where the substituents are the same as described in connection to Formula I:

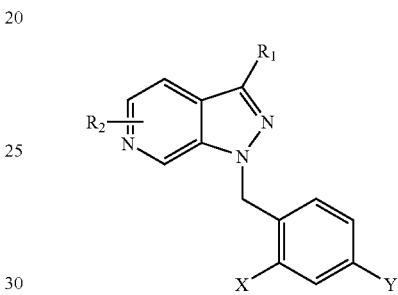

Examples of Formula II(C) derivatives include: 3-[1-(2,4-dichlorobenzyl)-1H-pyrazolo[3,4-c]pyridin-3-yl]acrylic acid; 1-(2,4-dichlorobenzyl)-1H-pyrazolo[3,4-c]pyridine-3-carboxylic acid hydrazide; 1-(2,4-dichlorobenzyl)-6-trifluoromethyl-1H-pyrazolo[3,4-c]pyridine-3-carboxylic acid; 1-(2,4-difluorobenzyl)-6-trifluoromethyl-1H-pyrazolo[3,4-c]pyridine-3-carboxylic acid; 1-(2,4-dichlorobenzyl)-6-trifluoromethyl-1H-pyrazolo[3,4-c]pyridine-3-carboxylic acid methyl ester; 1-(2,4-difluorobenzyl)-6-trifluoromethyl-1H-pyrazolo[3,4-c]pyridine-3-carboxylic acid methyl ester; 3-[1-(2,4-dichlorobenzyl)-6-trifluoromethyl-1H-pyrazolo[3,4-c]pyridin-3-yl]acrylic acid; 3-[1-(2,4-difluorobenzyl)-6-trifluoromethyl-1H-pyrazolo[3,4-c]pyridin-3-yl]acrylic acid; 1-(2,4-dichlorobenzyl)-6-trifluoromethyl-1H-pyrazolo[3,4-c]pyridine-3-carboxylic acid hydrazide; and 1-(2,4-difluorobenzyl)-6-trifluoromethyl-1H-pyrazolo[3,4-c]pyridine-3-carboxylic acid hydrazide. Additional examples are provided herein.

In still another aspect of the present invention, a compound comprising 1-(2,4-dichlorobenzyl)-1H-pyrazolo[3,4-c]pyridine-3-carboxylic acid (JWS-1-132) is provided.

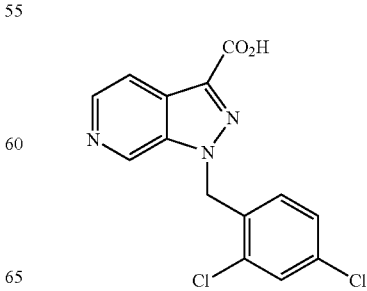

In another aspect of the present invention, a compound comprising 1-(2,4-dichlorobenzyl)-1H-pyrazolo[3,4-c]pyridine-3-carboxylic acid methyl ester (JWS-1-130) is provided.

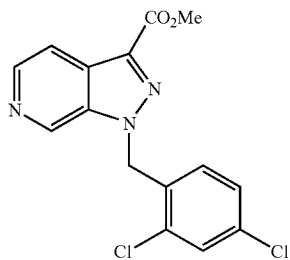 [SMILES: COC(=O)c1nn(Cc2ccc(Cl)cc2Cl)c2cnccc12]

In still another aspect, the compounds according to Formula II(D) are provided, where the substituents are the same as described in connection to Formula I:

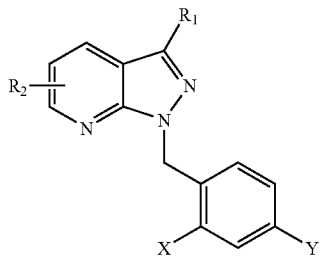

Examples of Formula II(D) derivatives include: 1-(2,4-dichlorobenzyl)-1H-pyrazolo[3,4-b]pyridine-3-carboxylic acid methyl ester; 1-(2,4-dichlorobenzyl)-6-trifluoromethyl-1H-pyrazolo[3,4-b]pyridine-3-carboxylic acid; 1-(2,4-dichlorobenzyl)-6-trifluoromethyl-1H-pyrazolo[3,4-b]pyridine-3-carboxylic acid methyl ester; 3-[1-(2,4-dichlorobenzyl)-6-trifluoromethyl-1H-pyrazolo[3,4-b]pyridine-3-yl]-acrylic acid; and 1-(2,4-dichlorobenzyl)-6-trifluoromethyl-1H-pyrazolo[3,4-b]pyridine-3-carboxylic acid hydrazide.

In still a further aspect of the present invention, a compound comprising 1-(2,4-dichlorobenzyl)-1H-pyrazolo[3,4-b]pyridine-3-carboxylic acid (RC-MC-86) is provided.

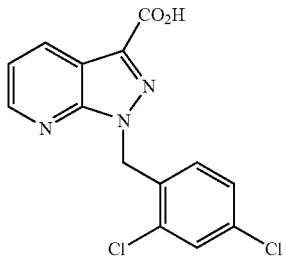 [SMILES: O=C(O)c1nn(Cc2ccc(Cl)cc2Cl)c2ncccc12]

In yet another aspect of the present invention, a compound comprising 3-[1-(2,4-dichlorobenzyl)-1H-pyrazolo[3,4-b]pyridine-3-yl]-acrylic acid (RC-MC-65) is provided.

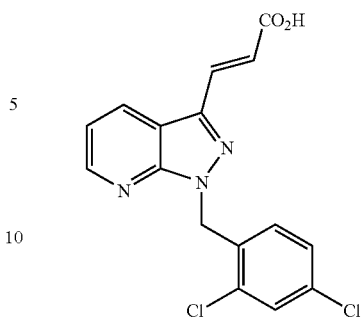

In yet another aspect of the present invention, a compound comprising 1-(2,4-dichlorobenzyl)-1H-pyrazolo[3,4-b]pyridine-3-carboxylic acid hydrazide (RC-MC-60) is provided.

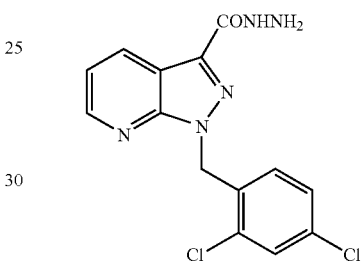

In still another aspect, the compounds encompassed by the Formula II(F) are provided, where the substituents are the same as described in connection to Formula I:

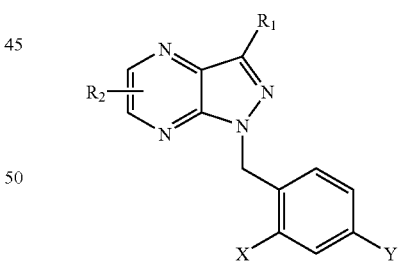

Examples of Formula II(F) derivatives include: 1-(2,4-dichlorobenzyl)-1H-pyrazolo[3,4-b]pyrazine-3-carboxylic acid hydrazide; 1-(2,4-dichlorobenzyl)-6-trifluoromethyl-1H-pyrazolo[3,4-b]pyrazin-3-carboxylic acid; 1-(2,4-dichlorobenzyl)-6-trifluoromethyl-1H-pyrazolo[3,4-b]pyrazin-3-carboxylic acid methyl ester; 3-[1-(2,4-dichlorobenzyl)-6-trifluoromethyl-1H-pyrazolo[3,4-b]pyrazin-3-yl]-acrylic acid; and 1-(2,4-dichlorobenzyl)-6-trifluoromethyl-1H-pyrazolo[3,4-b]pyrazin-3-carboxylic acid hydrazide.

In still a further aspect of the present invention, a compound comprising 1-(2,4-dichloro-benzyl)-1H-pyrazolo[3,4-b]pyrazine-3-carboxylic acid (JWS-2-298) is provided.

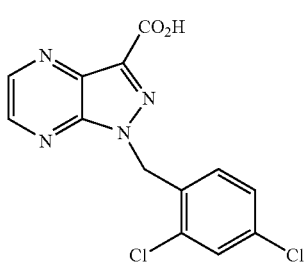 [SMILES: O=C(O)c1nn(Cc2ccc(Cl)cc2Cl)c2nccnc12]

In still a further aspect of the present invention, a compound comprising 1-(2,4-dichloro-benzyl)-1H-pyrazolo[3,4-b]pyrazine-3-carboxylic acid methyl ester (JWS-2-296) is provided.

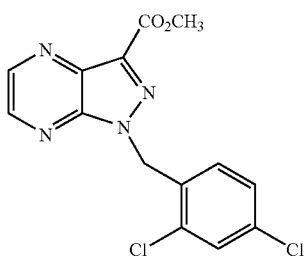 [SMILES: COC(=O)c1nn(Cc2ccc(Cl)cc2Cl)c2nccnc12]

In still a further aspect of the present invention, a compound comprising 3-[1-(2,4-dichlorobenzyl)-1H-pyrazolo[3,4-b]pyrazin-3-yl]-acrylic acid (JWS-3-1) is provided.

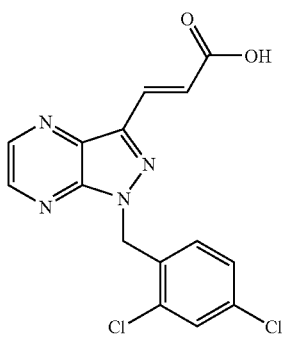 [SMILES: O=C(O)/C=C/c1nn(Cc2ccc(Cl)cc2Cl)c2nccnc12]

In yet another aspect, the compounds according encompassed by the Formula II(E) are provided, where the substituents are the same as described in connection to Formula I:

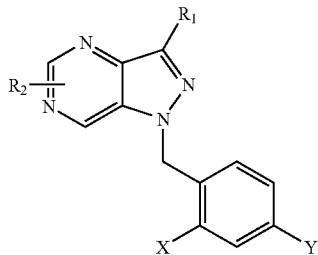

Examples of Formula II(E) derivatives include: 1-(2,4-dichlorobenzyl)-1H-pyrazolo[4,3-d]pyrimidine-3-carboxylic acid hydrazide; 1-(2,4-dichlorobenzyl)-6-trifluoromethyl-1H-pyrazolo[4,3-d]pyrimidine-3-carboxylic acid; 1-(2,4-dichlorobenzyl)-6-trifluoromethyl-1H-pyrazolo[4,3-d]pyrimidine-3-carboxylic acid methyl ester; 3-[1-(2,4-dichlorobenzyl)-6-trifluoromethyl-1H-pyrazolo[4,3-d]pyrimidin-3-yl]-acrylic acid; and 1-(2,4-dichlorobenzyl)-6-trifluoromethyl-1H-pyrazolo[4,3-d]pyrimidin-3-carboxylic acid hydrazide.

In still a further aspect of the present invention, a compound comprising 1-(2,4-dichloro-benzyl)-1H-pyrazolo[4,3-d]pyrimidine-3-carboxylic acid (JWS-2-256) is provided.

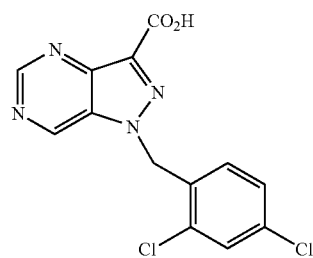 [SMILES: O=C(O)c1nn(Cc2ccc(Cl)cc2Cl)c2cncnc12]

In still a further aspect of the present invention, a compound comprising [1-(2,4-dichloro-benzyl)-1H-pyrazolo[4,3-d]pyrimidine-3-carboxylic acid methyl ester (JWS-2-246) is provided.

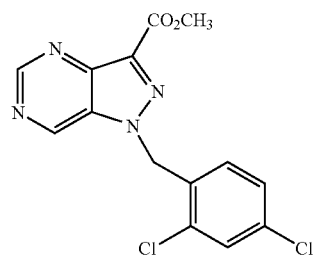 [SMILES: COC(=O)c1nn(Cc2ccc(Cl)cc2Cl)c2cncnc12]

In still a further aspect of the present invention, a compound comprising 3-[1-(2,4-dichloro-benzyl)-1H-pyrazolo[4,3-d]pyrimidin-3-yl]-acrylic acid (JWS-2-254) is provided.

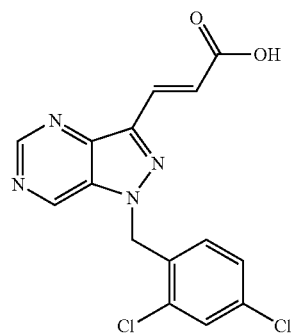 [SMILES: O=C(O)/C=C/c1nn(Cc2ccc(Cl)cc2Cl)c2cncnc12]

The present invention is further described by the following description, which should not be construed as a limitation on the invention.

In addition to the foregoing, the derivatives in accordance with Formula I can include $R_2$ at the 6-position being halogen, alkoxy, or carboxylic acid such as: 1-(2,4-dichlorobenzyl)-6-chloro-1H-indazole-3-carboxylic acid methyl ester; 1-(2-fluoro-4-chlorobenzyl)-6-chloro-1H-indazole-3-carboxylic acid methyl ester; 3-[1-(2-fluoro-4-chlorobenzyl)-6-chloro-1H-indazol-3-yl]-acrylic acid; 3-[1-(2,4-dichlorobenzyl)-6-chloro-1H-indazol-3-yl]-acrylic acid methyl ester; 3-[1-(2,4-difluorobenzyl)-6-chloro-1H-indazol-3-yl]-acrylic acid methyl ester; 3-[1-(2-chloro-4-fluorobenzyl)-6-chloro-1H-indazol-3-yl]-acrylic acid methyl ester; 3-[1-(2-fluoro-4-chlorobenzyl)-6-chloro-1H-indazol-3-yl]-acrylic acid; 1-(2-fluoro-4-chlorobenzyl)-6-chloro-1H-indazole-3-carboxylic acid hydrazide; 1-(2,4-dichlorobenzyl)-5-chloro-1H-indazole-3-carboxylic acid methyl ester; 1-(2,4-difluorobenzyl)-5-chloro-1H-indazole-3-carboxylic acid methyl ester; 1-(2-chloro-4-fluorobenzyl)-5-chloro-1H-indazole-3-carboxylic acid methyl ester; 1-(2-fluoro-4-chlorobenzyl)-5-chloro-1H-indazole-3-carboxylic acid methyl ester; 3-[1-(2,4-dichlorobenzyl)-5-chloro-1H-indazol-3-yl]-acrylic acid; 3-[1-(2,4-difluorobenzyl)-5-chloro-1H-indazol-3-yl]-acrylic acid; 3-[1-(2-chloro-4-fluorobenzyl)-5-chloro-1H-indazol-3-yl]-acrylic acid; 3-[1-(2-fluoro-4-chlorobenzyl)-5-chloro-1H-indazol-3-yl]-acrylic acid; 3-[1-(2,4-dichlorobenzyl)-5-chloro-1H-indazol-3-yl]-acrylic acid methyl ester; 3-[1-(2,4-difluorobenzyl)-5-chloro-1H-indazol-3-yl]-acrylic acid methyl ester; 3-[1-(2-chloro-4-fluorobenzyl)-5-chloro-1H-indazol-3-yl]-acrylic acid methyl ester; 3-[1-(2-fluoro-4-chlorobenzyl)-5-chloro-1H-indazol-3-yl]-acrylic acid; 5-chloro-1-(2,4-dichlorobenzyl)-1H-indazole-3-carboxylic acid hydrazide; 1-(2,4-difluorobenzyl)-5-chloro-1H-indazole-3-carboxylic acid hydrazide; 1-(2-chloro-4-fluorobenzyl)-5-chloro-1H-indazole-3-carboxylic acid hydrazide; 1-(2-fluoro-4-chlorobenzyl)-5-chloro-1H-indazole-3-carboxylic acid hydrazide; 1-(2,4-difluorobenzyl)-6-fluoro-1H-indazole-3-carboxylic acid methyl ester; 1-(2-chloro-4-fluorobenzyl)-6-fluoro-1H-indazole-3-carboxylic acid methyl ester; 1-(2-fluoro-4-chlorobenzyl)-6-fluoro-1H-indazole-3-carboxylic acid methyl ester; 3-[1-(2,4-difluorobenzyl)-6-fluoro-1H-indazol-3-yl]-acrylic acid; 3-[1-(2-chloro-4-fluorobenzyl)-6-fluoro-1H-indazol-3-yl]-acrylic acid; 3-[1-(2-fluoro-4-chlorobenzyl)-6-fluoro-1H-indazol-3-yl]-acrylic acid; 1-(2,4-difluorobenzyl)-6-fluoro-1H-indazole-3-carboxylic acid hydrazide; 1-(2-chloro-4-fluorobenzyl)-6-fluoro-1H-indazole-3-carboxylic acid hydrazide; 1-(2-fluoro-4-chlorobenzyl)-6-fluoro-1H-indazole-3-carboxylic acid hydrazide; 1-(2,4-difluorobenzyl)-6-methoxy-1H-indazole-3-carboxylic acid methyl ester; 1-(2-chloro-4-fluorobenzyl)-6-methoxy-1H-indazole-3-carboxylic acid methyl ester; 1-(2-fluoro-4-chlorobenzyl)-6-methoxy-1H-indazole-3-carboxylic acid methyl ester; 3-[1-(2,4-difluorobenzyl)-6-methoxy-1H-indazol-3-yl]-acrylic acid; 3-[1-(2-chloro-4-fluorobenzyl)-6-methoxy-1H-indazol-3-yl]-acrylic acid; 3-[1-(2-fluoro-4-chlorobenzyl)-6-methoxy-1H-indazol-3-yl]-acrylic acid; 1-(2,4-difluorobenzyl)-6-methoxy-1H-indazole-3-carboxylic acid hydrazide; 1-(2-chloro-4-fluorobenzyl)-6-methoxy-1H-indazole-3-carboxylic acid hydrazide; 1-(2-fluoro-4-chlorobenzyl)-6-methoxy-1H-indazole-3-carboxylic acid hydrazide; 1-(2,4-difluoro-benzyl)-1H-indazole-3,6-dicarboxylic acid-3-methyl ester; 1-(2-chloro-4-fluoro-benzyl)-1H-indazole-3,6-dicarboxylic acid-3-methyl ester; 1-(2-fluoro-4-chloro-benzyl)-1H-indazole-3,6-dicarboxylic acid-3-methyl ester; 3-(2-carboxy-vinyl)-1-(2,4-difluoro-benzyl)-1H-indazole-6-carboxylic acid; 3-(2-carboxy-vinyl)-1-(2-chloro-4-fluoro-benzyl)-1H-indazole-6-carboxylic acid; 3-(2-carboxy-vinyl)-1-(2-fluoro-4-chloro-benzyl)-1H-indazole-6-carboxylic acid; 1-(2,4-difluoro-benzyl)-3-(2-methoxycarbonyl-vinyl)-1H-indazole-6-carboxylic acid; 1-(2-chloro-4-fluoro-benzyl)-3-(2-methoxycarbonyl-vinyl)-1H-indazole-6-carboxylic acid; and 1-(2-fluoro-4-chloro-benzyl)-3-(2-methoxycarbonyl-vinyl)-1H-indazole-6-carboxylic acid.

In addition to the foregoing, the derivatives in accordance with Formula I can include $R_2$ as trihaloalkyl: 1-(2,4-dichlorobenzyl)-6-trifluoromethyl-1H-indazole-3-carboxylic acid methyl ester; 1-(2-fluoro-4-chlorobenzyl)-6-trifluoromethyl-1H-indazole-3-carboxylic acid methyl ester; 1-(4-fluoro-2-methyl-benzyl)-6-trifluoromethyl-1H-indazole-3-carboxylic acid methyl ester; 1-(4-methyl-2-chloro-benzyl)-6-trifluoromethyl-1H-indazole-3-carboxylic acid methyl ester; 1-(4-methyl-2-fluoro-benzyl)-6-trifluoromethyl-1H-indazole-3-carboxylic acid methyl ester; 3-[1-(2-fluoro-4-chlorobenzyl)-6-trifluoromethyl-1H-indazol-3-yl]-acrylic acid; 3-[1-(4-fluoro-2-methyl-benzyl)-6-trifluoromethyl-1H-indazol-3-yl]-acrylic acid; 3-[1-(4-methyl-2-chloro-benzyl)-6-trifluoromethyl-1H-indazol-3-yl]-acrylic acid; 3-[1-(4-methyl-2-fluoro-benzyl)-6-trifluoromethyl-1H-indazol-3-yl]-acrylic acid; 3-[1-(2,4-difluorobenzyl)-6-trifluoromethyl-1H-indazol-3-yl]-2-methyl-acrylic acid; trans 3-[1-(2,4-difluorobenzyl)-6-trifluoromethyl-1H-indazol-3-yl]-acrylic acid methyl ester; cis 3-[1-(2,4-dichlorobenzyl)-6-trifluoromethyl-1H-indazol-3-yl]-acrylic acid methyl ester; 1-(2-fluoro-4-chlorobenzyl)-6-trifluoromethyl-1H-indazole-3-carboxylic acid hydrazide; 3-[1-(2,4-difluorobenzyl)-6-trifluoromethyl-1H-indazol-3-yl]-acrylic acid hydrazide; 3-[1-(2-chloro-4-fluorobenzyl)-6-trifluoromethyl-1H-indazol-3-yl]-acrylic acid hydrazide; 3-[1-(2-fluoro-4-chlorobenzyl)-6-trifluoromethyl-1H-indazol-3-yl]-acrylic acid hydrazide; 3-[1-(2,4-difluorobenzyl)-6-trifluoromethyl-1H-indazol-3-yl]-propionic acid ethyl ester; 3-[1-(2-chloro-4-fluorobenzyl)-6-trifluoromethyl-1H-indazol-3-yl]-propionic acid ethyl ester; 3-[1-(2-fluoro-4-chlorobenzyl)-6-trifluoromethyl-1H-indazol-3-yl]-propionic acid ethyl ester; 1-(2-chloro-4-fluorobenzyl)-5-trifluoromethyl-1H-indazole-3-carboxylic acid methyl ester; 1-(2-fluoro-4-chlorobenzyl)-5-trifluoromethyl-1H-indazole-3-carboxylic acid methyl ester; 3-[1-(2-chloro-4-fluorobenzyl)-5-trifluoromethyl-1H-indazol-3-yl]-acrylic acid; 3-[1-(2-fluoro-4-chlorobenzyl)-5-trifluoromethyl-1H-indazol-3-yl]-acrylic acid; 3-[1-(2,4-dichlorobenzyl)-5-trifluoromethyl-1H-indazol-3-yl]-acrylic acid methyl ester; 3-[1-(2,4-difluorobenzyl)-5-trifluoromethyl-1H-indazol-3-yl]-acrylic acid methyl ester; 3-[1-(2-chloro-4-fluorobenzyl)-5-trifluoromethyl-1H-indazol-3-yl]-acrylic acid methyl ester; 3-[1-(2-fluoro-4-chlorobenzyl)-5-trifluoromethyl-1H-indazol-3-yl]-acrylic acid methyl ester; 1-(2-chloro-4-fluorobenzyl)-5-trifluoromethyl-1H-indazole-3-carboxylic acid hydrazide; 1-(2-fluoro-4-chlorobenzyl)-5-trifluoromethyl-1H-indazole-3-carboxylic acid hydrazide; 3-[1-(2,4-dichlorobenzyl)-5-trifluoromethyl-1H-indazol-3-yl]-acrylic acid hydrazide; 3-[1-(2,4-difluorobenzyl)-5-trifluoromethyl-1H-indazol-3-yl]-acrylic acid hydrazide; 3-[1-(2-chloro-4-fluorobenzyl)-5-trifluoromethyl-1H-indazol-3-yl]-acrylic acid hydrazide; 3-[1-(2-fluoro-4-chlorobenzyl)-5-trifluoromethyl-1H-indazol-3-yl]-acrylic acid hydrazide; 3-[1-(2,4-dichlorobenzyl)-5-trifluoromethyl-1H-indazol-3-yl]-propionic acid ethyl ester; 3-[1-(2,4-difluorobenzyl)-5-trifluoromethyl-1H-indazol-3-yl]-propionic acid ethyl ester; 3-[1-(2-chloro-4-fluorobenzyl)-5-trifluoromethyl-1H-indazol-3-yl]-propionic acid ethyl ester; and 3-[1-(2-fluoro-4-chlorobenzyl)-5-trifluoromethyl-1H-indazol-3-yl]-propionic acid ethyl ester.

In addition to the foregoing, the derivatives in accordance with Formula I can include $R_2$ as a lower alkyl: 1-(2,4-dichlorobenzyl)-6-methyl-1H-indazole-3-carboxylic acid methyl ester; 1-(2,4-difluorobenzyl)-6-methyl-1H-indazole-3-carboxylic acid methyl ester; 1-(2-chloro-4-fluorobenzyl)-6-methyl-1H-indazole-3-carboxylic acid methyl ester; 1-(2-fluoro-4-chlorobenzyl)-6-methyl-1H-indazole-3-carboxylic acid acid methyl ester; 3-[1-(2,4-difluorobenzyl)-6-methyl-1H-indazol-3-yl]-acrylic acid; 3-[1-(2-chloro-4-fluorobenzyl)-6-methyl-1H-indazol-3-yl]-acrylic acid; 3-[1-(2-fluoro-4-chlorobenzyl)-6-methyl-1H-indazol-3-yl]-acrylic acid; 3-[1-(2,4-dichlorobenzyl)-6-methyl-1H-indazol-3-yl]-acrylic acid methyl ester; 3-[1-(2,4-difluorobenzyl)-6-methyl-1H-indazol-3-yl]-acrylic acid methyl ester; 3-[1-(2-chloro-4-fluorobenzyl)-6-methyl-1H-indazol-3-yl]-acrylic acid methyl ester; 3-[1-(2-fluoro-4-chlorobenzyl)-6-methyl-1H-indazol-3-yl]-acrylic acid methyl ester; 1-(2,4-difluorobenzyl)-6-methyl-1H-indazole-3-carboxylic acid hydrazide; 1-(2-chloro-4-fluorobenzyl)-6-methyl-1H-indazole-3-carboxylic acid hydrazide; 1-(2-fluoro-4-chlorobenzyl)-6-methyl-1H-indazole-3-carboxylic acid hydrazide; 3-[1-(2,4-dichlorobenzyl)-6-methyl-1H-indazol-3-yl]-acrylic acid hydrazide; 3-[1-(2,4-difluorobenzyl)-6-methyl-1H-indazol-3-yl]-acrylic acid hydrazide; 3-[1-(2-chloro-4-fluorobenzyl)-6-methyl-1H-indazol-3-yl]-acrylic acid hydrazide; 3-[1-(2-fluoro-4-chlorobenzyl)-6-methyl-1H-indazol-3-yl]-acrylic acid hydrazide; 3-[1-(2,4-dichlorobenzyl)-6-methyl-1H-indazol-3-yl]-propionic acid ethyl ester; 3-[1-(2,4-difluorobenzyl)-6-methyl-1H-indazol-3-yl]-propionic acid ethyl ester; 3-[1-(2-chloro-4-fluorobenzyl)-6-methyl-1H-indazol-3-yl]-propionic acid ethyl ester; and 3-[1-(2-fluoro-4-chlorobenzyl)-6-methyl-1H-indazol-3-yl]-propionic acid ethyl ester.

In addition to the foregoing, the derivatives in accordance with Formula I can include $R_2$ as a dihaloalkyl: 1-(2,4-difluorobenzyl)-6-difluoromethyl-1H-indazole-3-carboxylic acid methyl ester; 1-(2-chloro-4-fluorobenzyl)-6-difluoromethyl-1H-indazole-3-carboxylic acid methyl ester; 1-(2-fluoro-4-chlorobenzyl)-6-difluoromethyl-1H-indazole-3-carboxylic acid methyl ester; 3-[1-(2,4-difluorobenzyl)-6-difluoromethyl-1H-indazol-3-yl]-acrylic acid; 3-[1-(2-chloro-4-fluorobenzyl)-6-difluoromethyl-1H-indazol-3-yl]-acrylic acid; 3-[1-(2-fluoro-4-chlorobenzyl)-6-difluoromethyl-1H-indazol-3-yl]-acrylic acid; 3-[1-(2,4-difluorobenzyl)-6-difluoromethyl-1H-indazol-3-yl]-acrylic acid methyl ester; 3-[1-(2-chloro-4-fluorobenzyl)-6-difluoromethyl-1H-indazol-3-yl]-acrylic acid methyl ester; 3-[1-(2-fluoro-4-chlorobenzyl)-6-difluoromethyl-1H-indazol-3-yl]-acrylic acid methyl ester; 1-(2,4-dichlorobenzyl)-6-difluoromethyl-1H-indazole-3-carboxylic acid hydrazide; 1-(2,4-difluorobenzyl)-6-difluoromethyl-1H-indazole-3-carboxylic acid hydrazide; 1-(2-chloro-4-fluorobenzyl)-6-difluoromethyl-1H-indazole-3-carboxylic acid hydrazide; 1-(2-fluoro-4-chlorobenzyl)-6-difluoromethyl-1H-indazole-3-carboxylic acid hydrazide; 3-[1-(2,4-dichlorobenzyl)-6-difluoromethyl-1H-indazol-3-yl]-acrylic acid hydrazide; 3-[1-(2,4-difluorobenzyl)-6-difluoromethyl-1H-indazol-3-yl]-acrylic acid hydrazide; 3-[1-(2-chloro-4-fluorobenzyl)-6-difluoromethyl-1H-indazol-3-yl]-acrylic acid hydrazide; and 3-[1-(2-fluoro-4-chlorobenzyl)-6-difluoromethyl-1H-indazol-3-yl]-acrylic acid hydrazide.

In addition to the foregoing, the derivatives in accordance with Formula I can include $R_2$ as a monohaloalkyl: 1-(2,4-difluorobenzyl)-6-fluoromethyl-1H-indazole-3-carboxylic acid methyl ester; 1-(2-chloro-4-fluorobenzyl)-6-fluoromethyl-1H-indazole-3-carboxylic acid methyl ester; 1-(2-fluoro-4-chlorobenzyl)-6-fluoromethyl-1H-indazole-3-carboxylic acid methyl ester; 3-[1-(2,4-difluorobenzyl)-6-fluoromethyl-1H-indazol-3-yl]-acrylic acid; 3-[1-(2-chloro-4-fluorobenzyl)-6-fluoromethyl-1H-indazol-3-yl]-acrylic acid; 3-[1-(2-fluoro-4-chlorobenzyl)-6-fluoromethyl-1H-indazol-3-yl]-acrylic acid; 3-[1-(2,4-difluorobenzyl)-6-fluoromethyl-1H-indazol-3-yl]-acrylic acid methyl ester; 3-[1-(2-chloro-4-fluorobenzyl)-6-fluoromethyl-1H-indazol-3-yl]-acrylic acid methyl ester; 3-[1-(2-fluoro-4-chlorobenzyl)-6-fluoromethyl-1H-indazol-3-yl]-acrylic acid methyl ester; 1-(2,4-dichlorobenzyl)-6-fluoromethyl-1H-indazole-3-carboxylic acid hydrazide; 1-(2,4-difluorobenzyl)-6-fluoromethyl-1H-indazole-3-carboxylic acid hydrazide; 1-(2-chloro-4-fluorobenzyl)-6-fluoromethyl-1H-indazole-3-carboxylic acid hydrazide; 1-(2-fluoro-4-chlorobenzyl)-6-fluoromethyl-1H-indazole-3-carboxylic acid hydrazide; 3-[1-(2,4-dichlorobenzyl)-6-fluoromethyl-1H-indazol-3-yl]-acrylic acid hydrazide; 3-[1-(2,4-difluorobenzyl)-6-fluoromethyl-1H-indazol-3-yl]-acrylic acid hydrazide; 3-[1-(2-chloro-4-fluorobenzyl)-6-fluoromethyl-1H-indazol-3-yl]-acrylic acid hydrazide; and 3-[1-(2-fluoro-4-chlorobenzyl)-6-fluoromethyl-1H-indazol-3-yl]-acrylic acid hydrazide.

In addition to the foregoing, the derivatives in accordance with Formula I can include $R_2$ as an alcohol: 1-(2,4-difluorobenzyl)-6-hydroxymethyl-1H-indazole-3-carboxylic acid methyl ester; 1-(2-chloro-4-fluorobenzyl)-6-hydroxymethyl-1H-indazole-3-carboxylic acid methyl ester; 1-(2-fluoro-4-chlorobenzyl)-6-hydroxymethyl-1H-indazole-3-carboxylic acid methyl ester; 3-[1-(2,4-difluorobenzyl)-6-hydroxymethyl-1H-indazol-3-yl]-acrylic acid; 3-[1-(2-chloro-4-fluorobenzyl)-6-hydroxymethyl-1H-indazol-3-yl]-acrylic acid; 3-[1-(2-fluoro-4-chlorobenzyl)-6-hydroxymethyl-1H-indazol-3-yl]-acrylic acid; 3-[1-(2,4-difluorobenzyl)-6-hydroxymethyl-1H-indazol-3-yl]-acrylic acid methyl ester; 3-[1-(2-chloro-4-fluorobenzyl)-6-hydroxymethyl-1H-indazol-3-yl]-acrylic acid methyl ester; 3-[1-(2-fluoro-4-chlorobenzyl)-6-hydroxymethyl-1H-indazol-3-yl]-acrylic acid methyl ester; 1-(2,4-dichlorobenzyl)-6-hydroxymethyl-1H-indazole-3-carboxylic acid hydrazide; 1-(2,4-difluorobenzyl)-6-hydroxymethyl-1H-indazole-3-carboxylic acid hydrazide; 1-(2-chloro-4-fluorobenzyl)-6-hydroxymethyl-1H-indazole-3-carboxylic acid hydrazide; 1-(2-fluoro-4-chlorobenzyl)-6-hydroxymethyl-1H-indazole-3-carboxylic acid hydrazide; 3-[1-(2,4-dichlorobenzyl)-6-hydroxymethyl-1H-indazol-3-yl]-acrylic acid hydrazide; 3-[1-(2,4-difluorobenzyl)-6-hydroxymethyl-1H-indazol-3-yl]-acrylic acid hydrazide; 3-[1-(2-chloro-4-fluorobenzyl)-6-hydroxymethyl-1H-indazol-3-yl]-acrylic acid hydrazide; and 3-[1-(2-fluoro-4-chlorobenzyl)-6-hydroxymethyl-1H-indazol-3-yl]-acrylic acid hydrazide.

In addition to the foregoing, the derivatives in accordance with Formula I can include $R_2$ as an alcohol: 1-(2,4-difluorobenzyl)-6-trifluoromethoxy-1H-indazole-3-carboxylic acid methyl ester; 1-(2-chloro-4-fluorobenzyl)-6-trifluoromethoxy-1H-indazole-3-carboxylic acid methyl ester; 1-(2-fluoro-4-chlorobenzyl)-6-trifluoromethoxy-1H-indazole-3-carboxylic acid methyl ester; 1-(4-fluoro-2-methyl-benzyl)-6-trifluoromethoxy-1H-indazole-3-carboxylic acid methyl ester; 1-(4-methyl-2-chloro-benzyl)-6-trifluoromethoxy-1H-indazole-3-carboxylic acid methyl ester; 1-(4-methyl-2-fluoro-benzyl)-6-trifluoromethoxy-1H-indazole-3-carboxylic acid methyl ester; 3-[1-(2,4-difluorobenzyl)-6-trifluoromethoxy-1H-indazol-3-yl]acrylic acid; 3-[1-(2-chloro-4-fluorobenzyl)-6-trifluoromethoxy-1H-indazol-3-yl]acrylic acid; 3-[1-(2-fluoro-4-chlorobenzyl)-6-trifluoromethoxy-1H-indazol-3-yl]acrylic acid; 3-[1-(4-fluoro-2-methyl-benzyl)-6-trifluoromethoxy-1H-indazol-3-yl]-acrylic acid; 3-[1-(4-methyl-2-chloro-benzyl)-6-trifluoromethoxy-1H-indazol-3-yl]-acrylic acid; 3-[1-(4-methyl-2-fluoro-benzyl)-6-trifluoromethoxy-1H-indazol-3-yl]-acrylic acid; 3-[1-(2,4-difluorobenzyl)-6-trifluoromethoxy-1H-indazol-3-yl]acrylic acid methyl ester; 3-[1-(2-chloro-4-fluorobenzyl)-6-trifluoromethoxy-1H-indazol-3-yl]acrylic acid methyl ester; 3-[1-(2-fluoro-4-chlorobenzyl)-6-trifluoromethoxy-1H-indazol-3-yl]acrylic acid methyl ester; 1-(2,4-difluorobenzyl)-6-trifluoromethoxy- 1H-indazole-3-carboxylic acid hydrazide; 1-(2-chloro-4-fluorobenzyl)-6-trifluoromethoxy-1H-indazole-3-carboxylic acid hydrazide; 1-(2-fluoro-4-chlorobenzyl)-6-trifluoromethoxy-1H-indazole-3-carboxylic acid hydrazide; 3-[1-(2,4-dichlorobenzyl)-6-trifluoromethoxy-1H-indazol-3-yl]-acrylic acid hydrazide; 3-[1-(2,4-difluorobenzyl)-6-trifluoromethoxy-1H-indazol-3-yl]-acrylic acid hydrazide; 3-[1-(2-chloro-4-fluorobenzyl)-6-trifluoromethoxy-1H-indazol-3-yl]-acrylic acid hydrazide; and 3-[1-(2-fluoro-4-chlorobenzyl)-6-trifluoromethoxy-1H-indazol-3-yl]-acrylic acid hydrazide.

In addition to the foregoing, the derivatives in accordance with Formula I can include $R_2$ as an amino: 1-(2,4-difluorobenzyl)-6-dimethylamino-1H-indazole-3-carboxylic acid methyl ester; 1-(2-chloro-4-fluorobenzyl)-6-dimethylamino-1H-indazole-3-carboxylic acid methyl ester; 1-(2-fluoro-4-chlorobenzyl)-6-dimethylamino-1H-indazole-3-carboxylic acid methyl ester; 3-[1-(2,4-difluorobenzyl)-6-dimethylamino-1H-indazol-3-yl]acrylic acid; 3-[1-(2-chloro-4-fluorobenzyl)-6-dimethylamino-1H-indazol-3-yl]acrylic acid; 3-[1-(2-fluoro-4-chlorobenzyl)-6-dimethylamino-1H-indazol-3-yl]acrylic acid; 3-[1-(2,4-dichlorobenzyl)-6-dimethylamino-1H-indazol-3-yl]acrylic acid methyl ester; 3-[1-(2,4-difluorobenzyl)-6-dimethylamino-1H-indazol-3-yl]acrylic acid methyl ester; 3-[1-(2-chloro-4-fluorobenzyl)-6-dimethylamino-1H-indazol-3-yl]acrylic acid methyl ester; 3-[1-(2-fluoro-4-chlorobenzyl)-6-dimethylamino-1H-indazol-3-yl]acrylic acid methyl ester; 1-(2,4-dichlorobenzyl)-6-dimethylamino-1H-indazole-3-carboxylic acid hydrazide; 1-(2,4-difluorobenzyl)-6-dimethylamino-1H-indazole-3-carboxylic acid hydrazide; 1-(2-chloro-4-fluorobenzyl)-6-dimethylamino-1H-indazole-3-carboxylic acid hydrazide; 1-(2-fluoro-4-chlorobenzyl)-6-dimethylamino-1H-indazole-3-carboxylic acid hydrazide; 3-[1-(2,4-dichlorobenzyl)-6-dimethylamino-1H-indazol-3-yl]-acrylic acid hydrazide; 3-[1-(2,4-difluorobenzyl)-6-dimethylamino-1H-indazol-3-yl]-acrylic acid hydrazide; 3-[1-(2-chloro-4-fluorobenzyl)-6-dimethylamino-1H-indazol-3-yl]-acrylic acid hydrazide; and 3-[1-(2-fluoro-4-chlorobenzyl)-6-dimethylamino-1H-indazol-3-yl]-acrylic acid hydrazide.

In addition to the foregoing, the derivatives in accordance with Formula I can include $R_1$ according to the Formula I(A):

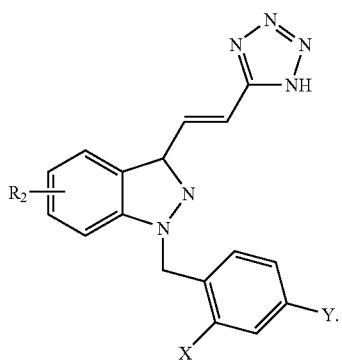

Formula I(A)

Examples of Formula I(A) derivatives include: 1-(2,4-difluoro-benzyl)-3-[2-(1H-tetrazol-5-yl)-vinyl]-6-trifluoromethyl-1H-indazole; 1-(2-chloro-4-fluorobenzyl)-3-[2-(1H-tetrazol-5-yl)-vinyl]-6-trifluoromethyl-1H-indazole; and 1-(2-fluoro-4-chlorobenzyl)-3-[2-(1H-tetrazol-5-yl)-vinyl]-6-trifluoromethyl-1H-indazole.

In addition to the foregoing, the derivatives in accordance with Formula I can include $R_1$ according to the Formula I(B):

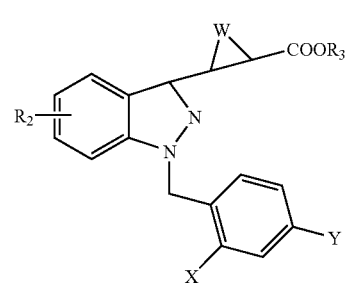

Formula I(B)

wherein $R_3$ is hydrogen, alkyl, aralkyl, or cycloalkyl;
and wherein W is carbon or oxygen;
X and Y are independently halogen; and/or
$R_2$ is trihaloalkyl.

Examples of Formula I(B) derivatives include: 3-[1-(2,4-fluorobenzyl)-6-trifluoromethyl-1H-indazol-3-yl]-oxirane-2-carboxylic acid; 3-[1-(2-chloro-4-fluorobenzyl)-6-trifluoromethyl-1H-indazol-3-yl]-oxirane-2-carboxylic acid; 3-[1-(2-fluoro-4-chlorobenzyl)-6-trifluoromethyl-1H-indazol-3-yl]-oxirane-2-carboxylic acid; 2-[1-(2,4-difluorobenzyl)-6-trifluoromethyl-1H-indazol-3-yl]-cyclopropanecarboxylic acid; 2-[1-(2-chloro-4-fluorobenzyl)-6-trifluoromethyl-1H-indazol-3-yl]-cyclopropanecarboxylic acid; 2-[1-(2-fluoro-4-chlorobenzyl)-6-trifluoromethyl-1H-indazol-3-yl]-cyclopropanecarboxylic acid; 3-[1-(2,4-dichlorobenzyl)-6-halo-1H-indazol-3-yl]-oxirane-2-carboxylic acid; 3-[1-(2,4-fluorobenzyl)-6-halo-1H-indazol-3-yl]-oxirane-2-carboxylic acid; 3-[1-(2-chloro-4-fluorobenzyl)-6-halo-1H-indazol-3-yl]-oxirane-2-carboxylic acid; 3-[1-(2-fluoro-4-chlorobenzyl)-6-halo-1H-indazol-3-yl]-oxirane-2-carboxylic acid; 2-[1-(2,4-dichlorobenzyl)-6-halo-1H-indazol-3-yl]-cyclopropanecarboxylic acid; 2-[1-(2,4-difluorobenzyl)-6-halo-1H-indazol-3-yl]-cyclopropanecarboxylic acid; 2-[1-(2-chloro-4-fluorobenzyl)-6-halo-1H-indazol-3-yl]-cyclopropanecarboxylic acid; and 2-[1-(2-fluoro-4-chlorobenzyl)-6-halo-1H-indazol-3-yl]-cyclopropanecarboxylic acid.

In addition to the foregoing, the derivatives in accordance with Formula I can include $R_1$ as a carboxylic acid ester and $R_2$ as hydrogen: 1-(2,4-difluorobenzyl)indazole-3-carboxylic acid methyl ester; 1-(2-chloro-4-fluorobenzyl)indazole-3-carboxylic acid methyl ester; 1-(2-fluoro-4-chlorobenzyl)indazole-3-carboxylic acid methyl ester; 1-[(2,4-difluorobenzyl)-1H-indazole]-3-carboxylic acid ethyl ester; 1-[(2-chloro-4-fluorobenzyl)-1H-indazole]-3-carboxylic acid ethyl ester; 1-[(2-fluoro-4-chlorobenzyl)-1H-indazole]-3-carboxylic acid ethyl ester; 1-[(2,4-difluorobenzyl)-1H-indazole]-3-carboxylic acid propyl ester; 1-[(2-chloro-4-fluorobenzyl)-1H-indazole]-3-carboxylic acid propyl ester; and 1-[(2-fluoro-4-chlorobenzyl)-1H-indazole]-3-carboxylic acid propyl ester.

In addition to the foregoing, the derivatives in accordance with Formula I can include $R_1$ as a carboxylic acid and $R_2$ as hydrogen, alkoxy, or carboxylic acid: 1-(2-fluoro-4-chlorobenzyl)-6-chloro-1H-indazole-3-carboxylic acid; 1-(2,4-difluorobenzyl)-6-fluoro-1H-indazole-3-carboxylic acid; 1-(2-chloro-4-fluorobenzyl)-6-fluoro-1H-indazole-3-carboxylic acid; 1-(2-fluoro-4-chlorobenzyl)-6-fluoro-1H-indazole-3-carboxylic acid; 1-(2,4-difluorobenzyl)-6-methoxy- 1H-indazole-3-carboxylic acid; 1-(2-chloro-4-fluorobenzyl)-6-methoxy-1H-indazole-3-carboxylic acid; 1-(2-fluoro-4-chlorobenzyl)-6-methoxy-1H-indazole-3-carboxylic acid; 1-(2,4-difluoro-benzyl)-1H-indazole-3,6-dicarboxylic acid; 1-(2-chloro-4-fluoro-benzyl)-1H-indazole-3,6-dicarboxylic acid; and 1-(2-fluoro-4-chloro-benzyl)-1H-indazole-3,6-dicarboxylic acid.

In addition to the foregoing, the derivatives in accordance with Formula I can include $R_1$ as a carboxylic acid and $R_2$ as a trihaloalkyl: 1-(2-fluoro-4-chlorobenzyl)-6-trifluoromethyl-1H-indazole-3-carboxylic acid; 1-(4-fluoro-2-methylbenzyl)-6-trifluoromethyl-1H-indazole-3-carboxylic acid; 1-(4-methyl-2-chloro-benzyl)-6-trifluoromethyl-1H-indazole-3-carboxylic acid; 1-(4-methyl-2-fluoro-benzyl)-6-trifluoromethyl-1H-indazole-3-carboxylic acid; 3-[1-(2,4-difluorobenzyl)-6-trifluoromethyl-1H-indazol-3-yl]-propionic acid; 3-[1-(2-chloro-4-fluorobenzyl)-6-trifluoromethyl-1H-indazol-3-yl]-propionic acid; 3-[1-(2-fluoro-4-chlorobenzyl)-6-trifluoromethyl-1H-indazol-3-yl]-propionic acid; 3-[1-(2,4-dichlorobenzyl)-6-trifluoromethyl-1H-indazol-3-yl]-2-methylpropionic acid; 3-[1-(2,4-fluorobenzyl)-6-trifluoromethyl-1H-indazol-3-yl]-2-methylpropionic acid; 3-[1-(2-chloro-4-fluorobenzyl)-6-trifluoromethyl-1H-indazol-3-yl]-2-methylpropionic acid; 3-[1-(2-fluoro-4-chlorobenzyl)-6-trifluoromethyl-1H-indazol-3-yl]-2-methylpropionic acid; 3-[1-(2,4-dichlorobenzyl)-6-trifluoromethyl-1H-indazol-3-yl]-oxirane-2-carboxylic acid; 3-[1-(2,4-fluorobenzyl)-6-trifluoromethyl-1H-indazol-3-yl]-oxirane-2-carboxylic acid; 3-[1-(2-chloro-4-fluorobenzyl)-6-trifluoromethyl-1H-indazol-3-yl]-oxirane-2-carboxylic acid; 3-[1-(2-fluoro-4-chlorobenzyl)-6-trifluoromethyl-1H-indazol-3-yl]-oxirane-2-carboxylic acid; 2-[1-(2,4-dichlorobenzyl)-6-trifluoromethyl-1H-indazol-3-yl]-cyclopropanecarboxylic acid; 2-[1-(2,4-difluorobenzyl)-6-trifluoromethyl-1H-indazol-3-yl]-cyclopropanecarboxylic acid; 2-[1-(2-chloro-4-fluorobenzyl)-6-trifluoromethyl-1H-indazol-3-yl]-cyclopropanecarboxylic acid; 2-[1-(2-fluoro-4-chlorobenzyl)-6-trifluoromethyl-1H-indazol-3-yl]-cyclopropanecarboxylic acid; 1-(2-chloro-4-fluorobenzyl)-5-trifluoromethyl-1H-indazole-3-carboxylic acid; 1-(2-fluoro-4-chlorobenzyl)-5-trifluoromethyl-1H-indazole-3-carboxylic acid; 3-[1-(2,4-dichlorobenzyl)-5-trifluoromethyl-1H-indazol-3-yl]-propionic acid; 3-[1-(2,4-difluorobenzyl)-5-trifluoromethyl-1H-indazol-3-yl]-propionic acid; 3-[1-(2-chloro-4-fluorobenzyl)-5-trifluoromethyl-1H-indazol-3-yl]-propionic acid; 3-[1-(2-fluoro-4-chlorobenzyl)-5-trifluoromethyl-1H-indazol-3-yl]-propionic acid; 3-[1-(2,4-dichlorobenzyl)-5-trifluoromethyl-1H-indazol-3-yl]-2-methylpropionic acid; 3-[1-(2,4-fluorobenzyl)-5-trifluoromethyl-1H-indazol-3-yl]-2-methylpropionic acid; 3-[1-(2-chloro-4-fluorobenzyl)-5-trifluoromethyl-1H-indazol-3-yl]-2-methylpropionic acid; 3-[1-(2-fluoro-4-chlorobenzyl)-5-trifluoromethyl-1H-indazol-3-yl]-2-methylpropionic acid; 3-[1-(2,4-dichlorobenzyl)-5-trifluoromethyl-1H-indazol-3-yl]-oxirane-2-carboxylic acid; 3-[1-(2,4-fluorobenzyl)-5-trifluoromethyl-1H-indazol-3-yl]-oxirane-2-carboxylic acid; 3-[1-(2-chloro-4-fluorobenzyl)-5-trifluoromethyl-1H-indazol-3-yl]-oxirane-2-carboxylic acid; 3-[1-(2-fluoro-4-chlorobenzyl)-5-trifluoromethyl-1H-indazol-3-yl]-oxirane-2-carboxylic acid; 2-[1-(2,4-dichlorobenzyl)-5-trifluoromethyl-1H-indazol-3-yl]-cyclopropanecarboxylic; 2-[1-(2,4-difluorobenzyl)-5-trifluoromethyl-1H-indazol-3-yl]-cyclopropanecarboxylic; 2-[1-(2-chloro-4-fluorobenzyl)-5-trifluoromethyl-1H-indazol-3-yl]-cyclopropanecarboxylic; and 2-[1-(2-fluoro-4-chlorobenzyl)-5-trifluoromethyl-1H-indazol-3-yl]-cyclopropanecarboxylic.

In addition to the foregoing, the derivatives in accordance with Formula I can include $R_1$ as a carboxylic acid and $R_2$ as a dihaloalkyl: 1-(2,4-difluorobenzyl)-6-difluoromethyl-1H-indazole-3-carboxylic acid; 1-(2-chloro-4-fluorobenzyl)-6-difluoromethyl-1H-indazole-3-carboxylic acid; 1-(2-fluoro-4-chlorobenzyl)-6-difluoromethyl-1H-indazole-3-carboxylic acid; 1-(2,4-dichlorobenzyl)-5-difluoromethyl-1H-indazole-3-carboxylic acid; 1-(2,4-difluorobenzyl)-5-difluoromethyl-1H-indazole-3-carboxylic acid; 1-(2-chloro-4-fluorobenzyl)-5-difluoromethyl-1H-indazole-3-carboxylic acid; and 1-(2-fluoro-4-chlorobenzyl)-5-difluoromethyl-1H-indazole-3-carboxylic acid.

In addition to the foregoing, the derivatives in accordance with Formula I can include $R_1$ as a carboxylic acid and $R_2$ as a monohaloalkyl: 1-(2,4-dichlorobenzyl)-6-fluoromethyl-1H-indazole-3-carboxylic acid; 1-(2,4-difluorobenzyl)-6-fluoromethyl-1H-indazole-3-carboxylic acid; 1-(2-chloro-4-fluorobenzyl)-6-fluoromethyl-1H-indazole-3-carboxylic acid; 1-(2-fluoro-4-chlorobenzyl)-6-fluoromethyl-1H-indazole-3-carboxylic acid; 1-(2,4-dichlorobenzyl)-5-fluoromethyl-1H-indazole-3-carboxylic acid; 1-(2,4-difluorobenzyl)-5-fluoromethyl-1H-indazole-3-carboxylic acid; 1-(2-chloro-4-fluorobenzyl)-5-fluoromethyl-1H-indazole-3-carboxylic acid; and 1-(2-fluoro-4-chlorobenzyl)-5-fluoromethyl-1H-indazole-3-carboxylic acid.

In addition to the foregoing, the derivatives in accordance with Formula I can include $R_1$ as a carboxylic acid and $R_2$ as a trihaloalkoxy: 1-(2,4-difluorobenzyl)-6-trifluoromethoxy-1H-indazole-3-carboxylic acid; 1-(2-chloro-4-fluorobenzyl)-6-trifluoromethoxy-1H-indazole-3-carboxylic acid; 1-(2-fluoro-4-chlorobenzyl)-6-trifluoromethoxy-1H-indazole-3-carboxylic acid; 1-(4-fluoro-2-methyl-benzyl)-6-trifluoromethoxy-1H-indazole-3-carboxylic acid; 1-(4-methyl-2-chloro-benzyl)-6-trifluoromethoxy-1H-indazole-3-carboxylic acid; 1-(4-methyl-2-fluoro-benzyl)-6-trifluoromethoxy-1H-indazole-3-carboxylic acid; 1-(2,4-dichlorobenzyl)-5-trifluoromethoxy-1H-indazole-3-carboxylic acid; 1-(2,4-difluorobenzyl)-5-trifluoromethoxy-1H-indazole-3-carboxylic acid; 1-(2-chloro-4-fluorobenzyl)-5-trifluoromethoxy-1H-indazole-3-carboxylic acid; and 1-(2-fluoro-4-chlorobenzyl)-5-trifluoromethoxy-1H-indazole-3-carboxylic acid.

In addition to the foregoing, the derivatives in accordance with Formula I can include $R_1$ as a carboxylic acid and $R_2$ as an amino: 1-(2,4-difluorobenzyl)-6-dimethylamino-1H-indazole-3-carboxylic acid; 1-(2-chloro-4-fluorobenzyl)-6-dimethylamino-1H-indazole-3-carboxylic acid; 1-(2-fluoro-4-chlorobenzyl)-6-dimethylamino-1H-indazole-3-carboxylic acid; 1-(2,4-dichlorobenzyl)-5-dimethylamino-1H-indazole-3-carboxylic acid; 1-(2,4-difluorobenzyl)-5-dimethylamino-1H-indazole-3-carboxylic acid; 1-(2-chloro-4-fluorobenzyl)-5-dimethylamino-1H-indazole-3-carboxylic acid; 1-(2-fluoro-4-chlorobenzyl)-5-dimethylamino-1H-indazole-3-carboxylic acid; 1-(2,4-dichlorobenzyl)-4-dimethylamino-1H-indazole-3-carboxylic acid; 1-(2,4-fluorobenzyl)-4-dimethylamino-1H-indazole-3-carboxylic acid; 1-(2-chloro-4-fluorobenzyl)-4-dimethylamino-1H-indazole-3-carboxylic acid; and 1-(2-fluoro-4-chlorobenzyl)-4-dimethylamino-1H-indazole-3-carboxylic acid.

In addition to the foregoing, the derivatives in accordance with Formula I can include $R_1$ as a carboxylic acid and $R_2$ as a lower alkyl: 1-(2,4-difluorobenzyl)-6-methyl-1H-indazole-3-carboxylic acid; 1-(2-chloro-4-fluorobenzyl)-6-methyl-1H-indazole-3-carboxylic acid; 1-(2-fluoro-4-chlorobenzyl)-6-methyl-1H-indazole-3-carboxylic acid; 1-(2,4-dichlorobenzyl)-5-methyl-1H-indazole-3-carboxylic acid;

1-(2,4-difluorobenzyl)-5-methyl-1H-indazole-3-carboxylic acid; 1-(2-chloro-4-fluorobenzyl)-5-methyl-1H-indazole-3-carboxylic acid; 1-(2-fluoro-4-chlorobenzyl)-5-methyl-1H-indazole-3-carboxylic acid; 1-(2,4-fluorobenzyl)-4-methyl-1H-indazole-3-carboxylic acid; 1-(2-chloro-4-fluorobenzyl)-4-methyl-1H-indazole-3-carboxylic acid; and 1-(2-fluoro-4-chlorobenzyl)-4-methyl-1H-indazole-3-carboxylic acid.

In addition to the foregoing, the derivatives in accordance with Formula I can include $R_1$ as a carboxylic acid and $R_2$ as an alcohol: 1-(2,4-difluorobenzyl)-6-hydroxymethyl-1H-indazole-3-carboxylic acid; 1-(2-chloro-4-fluorobenzyl)-6-hydroxymethyl-1H-indazole-3-carboxylic acid; 1-(2-fluoro-4-chlorobenzyl)-5-hydroxymethyl-1H-indazole-3-carboxylic acid; 1-(2,4-dichlorobenzyl)-5-hydroxymethyl-1H-indazole-3-carboxylic acid; 1-(2,4-difluorobenzyl)-5-hydroxymethyl-1H-indazole-3-carboxylic acid; 1-(2-chloro-4-fluorobenzyl)-5-hydroxymethyl-1H-indazole-3-carboxylic acid; and 1-(2-fluoro-4-chlorobenzyl)-5-hydroxymethyl-1H-indazole-3-carboxylic acid.

It is also contemplated that the compounds of the present invention can be used in the treatment for polycystic kidney disease, can inhibit the cystic fibrosis transmembrane conductance regulator, and can be used in treating cancer.

It has previously been shown using embryonic mouse kidneys in organ culture (metanephric organ culture) that the intracellular second messenger, 3',5'-cyclic adenosine monophosphate (cAMP or cyclic AMP) causes cystic dilation (cyst formation) over several days in culture. This effect of cAMP was particularly significant in kidneys from a genetic model of polycystic kidney disease (PKD), the Pkd1m1bei mouse, which has a mutation in the Pkd1 gene. It is believed that cAMP stimulates fluid secretion by promoting chloride transport into the tubule lumen. Chloride transport is dependent on the chloride channels, NKCC1 (which brings chloride into cells from the basolateral or blood side) and CFTR (which allows chloride to exit cells into the tubule or cyst lumen). This chloride is then followed by sodium and water causing fluid secretion into the cyst lumen. These findings were proven by using a CFTR inhibitor CFTR172inh, an NKCC1 inhibitor bumetanide, and by using kidneys from mice with inactivating mutations in the genes for CFTR and NKCC1 (Cftr and Nkcc1, respectively). It is also believed that cyst formation is dependent on increased or abnormal cell proliferation. Thus, inhibition of cyst formation should occur with inhibition of fluid secretion and cell proliferation.

Gamendazole as used herein refers to H2-gamendazole (i.e., JWS-2-72 or GMZ), which is a novel indazole carboxylic acid derivative has been shown to be a reversible inhibitor of male spermatogenesis. GMZ is well-tolerated in animal studies with no apparent histopathology in any organ at 25 mg/kg of IP dosage. In rats administered GMZ, there was no evidence of behavioral or body weight changes in the five days post-treatment. The parent compound of GMZ, Lonidamine, inhibits the chloride channel CFTR, interferes with cellular energy output and has been used as an anticancer drug. Recent studies have found that GMZ acts as an Hsp90 inhibitor in rat sertoli cells. GMZ binds directly to Hsp90-beta and eukaryotic elongation factor eEF1A as shown by affinity chromatography and direct binding studies.

Kidney cyst growth can be dependent on both cyst-filling fluid secretion and abnormal cell proliferation. Models have shown that PKD can initiate by some event at a location in a tubule, and the tubule then dilates by abnormal cell growth that increases the area and volume for cyst formation. Continued cell proliferation and fluid secretion enlarges the cyst, which inhibits proper kidney function. As such, inhibiting cyst formation and growth can be used in a therapy for PKD. The phonotypic switch to PKD may be attributed to: decreased intracellular calcium; de-repression of B-Raf; and/or stimulation of the Ras/MAPK pathway by cAMP.

Genetic models of CFTR and NKCC1 have shown that cyst formation and cyst-filling fluid accumulation is dependent in chloride secretion, which provides an approach to PKD: inhibit this function. Also, abnormal cell proliferation can be stimulated in PKD kidneys by cAMP-dependent activation of the Ras/B-Raf/MEK/ERK pathway, and B-Raf is critical to the activation of this pathway. This information provides targets for therapies for PKD. Since CFTR and B-Raf are clients of Hsp90, inhibition of Hsp90 can be used to modulate CFTR and B-Raf as a therapy for PKD.

It has now been found that gamendazole can inhibit the CFTR channel activity, and thereby inhibit chloride secretion. Also, gamendazole can inhibit "short circuit current" in cell monolayers, which would be disruptive to cyst formation in vivo. Moreover, gamendazole can block cyst enlargement in an organ culture of a genetic Pkd1 model, and thereby, is likely to block cyst enlargement in kidneys in vivo. The inhibition of cyst enlargement can be beneficial in preserving kidney function in patients with PKD.

In one embodiment, a compound of the invention (e.g., gamendazole or analogue thereof) can inhibit PKD cell proliferation and induce cytoskeletal rearrangements. It has now been found that the Hsp90 inhibitor gamendazole (GMZ) has antiproliferative effects on primary human PKD cyst epithelial cells. Gamendazole, a lonidamine-derived indazole carboxylate compound, is well-tolerated in animal studies. Additionally, gamendazole is an inhibitor of multiple Hsp90 targets such as CFTR, B-Raf/ERK, ErbB2, and Cdk4 and possibly others. These properties make gamendazole or other analog a therapeutic agent for PKD.

Also, the lonidamine analogue gamendazole inhibits cyst growth in Pkd1-deficient kidneys in metanephric culture by targeting both fluid secretion and cell proliferation. Cyst growth and expansion in PKD involves a number of abnormal processes including increased fluid secretion and abnormal cell proliferation. Because there is a large number of abnormal cellular pathways potentially involved in cyst formation in PKD, lonidamine analogues were tested to determine if they were inhibitors that might act on multiple targets, and in particular on those involved in Cl-driven fluid secretion and Ras/MAPK signaling, both stimulated by cAMP.

Gamendazole inhibits the heat-shock protein HSP90AB1, and thus may cause decreased levels of the HSP90 client proteins B-Raf, Src, CFTR, and NKCC1, all of which have been implicated in cAMP-stimulated cyst formation. Gamendazole was shown to almost completely block forskolin-induced Cl-secretion in human ADPKD cells as measured by short-circuit current in the presence of benzamil.

The lonidamine analogs of the present invention may have the potential to be capable of inhibiting CFTR and Hsp90 pathways. The dual activity can provide for effective therapeutic agents that function in multiple biological pathways in order to provide a therapy for PKD.

Experimental data has shown that gamendazole and other lonidamine derivatives may be useful in a therapy for ADPKD. At the low doses (1-5 uM GMZ) there was inhibition of anion secretion in ADPKD monolayers, which measured the inhibition of cyst-filling CFTR channel activity. These low doses also inhibited cyst formation in metanephric culture and reduced NKCC1 and PCNA protein levels, an indication of Hsp90 inhibition. At moderate to higher doses (10-50 uM) there were effects on ADPKD cell migration, morphology, actin dynamics, cell proliferation, and decreases in the Hsp90 client proteins, ErbB2 and Cdk4. Accordingly, lonidamine derivatives can be effective in inhibiting the proliferation of ADPKD cells; effective in decreasing levels of Hsp90 client proteins involved in cell cycle regulation and cell growth; and effective in causing rearrangement of the actin cytoskeleton and inhibiting ADPKD cell migration. These properties show that lonidamine derivatives can be useful in PKD therapies.

The indazole carboxylic acid derivatives of lonidamine are an example of potential drugs for treating, inhibiting, and/or preventing PKD. Examples of indazole carboxylic acid derivatives of lonidamine have been shown to inhibit cell proliferation. These derivatives can include different substituents on the aromatic ring; however, other lonidamine derivatives may also be useful for PKD.

In view of the foregoing, the lonidamine derivative can be administered in a therapeutically effective amount for treating, inhibiting, and/or preventing PKD. Based on the data, it is contemplated that the lonidamine derivative can be administered in an amount sufficient to obtain at least about 0.25 uM in or adjacent to kidney cells; however, more effective derivatives may be effective at lower concentrations, such as for example, an order of magnitude less. Examples of concentration in or adjacent to kidney cells can be at least about 0.5 uM, at least about 1 uM, at least about 5 uM, or from 5 to 50 uM. Also, based on cell migration, morphology, actin dynamics, cell proliferation, and decreases in the Hsp90 client proteins, ErbB2 and Cdk4, the concentration in or adjacent to kidney cells can be at least about 10 uM, at least about 25 uM, at least about 50 uM, or from 5 to 50 uM. Also, the concentration can be in a range between any of the recited concentrations.

The term "micro" can be represented by the symbol "µ" and the letter "u." As such, uL refers to microliters.

The term "amino" signifies a primary, secondary or tertiary amino group bonded via the nitrogen atom, with the secondary amino group carrying an alkyl or cycloalkyl substituent and the tertiary amino group carrying two similar or different alkyl or cycloalkyl substituents or the two nitrogen substituents together forming a ring, such as, for example, —NH$_2$, methylamino, ethylamino, dimethylamino, diethylamino, methyl-ethylamino, pyrrolidino, piperidino, piperazino, morpholino, etc.

The term "alcohol" indicates an optionally substituted hydrocarbon group having one or more hydroxy substituents. At the 6-position or 5-position, primary, secondary, and tertiary alcohols are contemplated, such as mono-alcohols as well as polyhydroxy variants—e.g., alkandiols, alkantriols, alkantetrols, etc. Preferred alkanols are those containing from about one up to twelve carbon atoms, with alkanols having one to up to six carbon atoms being most preferred. Exemplary of preferred aliphatic alcohols are: methanol, ethanol, 1-propanol, 2-propanol, 1-propen-2-ol, 1-butanol, 2-butanol, 2-methyl-2-propanol, 1-pentanol, 2-pentanol, 3-pentanol, 3-methyl-1-butanol, 1,2-ethandiol (ethylene glycol), 1,2,3-propantriol (glycerol), i-1,2,3,4-butantetrol (i-erythritol), and 2,2-dihydroxymethyl-1,3-propandiol (pentaerythritol).

The term "alkyl" refers to a branched or unbranched saturated hydrocarbon group of one to 24 carbon atoms, such as methyl, ethyl, n-propyl, isopropyl, n-butyl, isobutyl, t-butyl, octyl, decyl, tetradecyl, hexadecyl, eicosyl, tetracosyl and the like. Preferred "alkyl" groups herein contain one to twelve carbon atoms. "Lower alkyl" refers to an alkyl group of one to six, more preferably one to four, carbon atoms.

The term "alkoxy" denotes oxy-containing groups substituted with an alkyl group. Examples include, without limitation, methoxy, ethoxy, and tert-butoxy. Most preferred are "lower alkoxy" groups having one to six carbon atoms. Examples of such groups include methoxy, ethoxy, propoxy, butoxy, isopropoxy, and tert-butoxy alkyls.

The term "aryl" means a carbocyclic aromatic group containing one, two or three rings wherein such rings may be attached together in a pendant manner or may be fused. The term "fused" means that a second ring is present (i.e., attached or formed) by having two adjacent atoms in common (i.e., shared) with the first ring. The term "fused" is equivalent to the term "condensed". The term "aryl" embraces aromatic groups such as phenyl, naphthyl, tetrahydronaphthyl, indane and biphenyl.

The term "aralkyl" embraces aryl-substituted alkyl group. Preferable aralkyl groups are "lower aralkyl" groups having aryl groups attached to alkyl groups having one to six carbon atoms. Examples of such groups include benzyl, diphenylmethyl, triphenylmethyl, phenylethyl and diphenylethyl. The terms benzyl and phenylmethyl are interchangeable.

The term "carbocyclic" refers to an alkyl group that contains one or more covalently closed ring structures, and that the atoms forming the backbone of the ring are all carbon atoms. The term thus distinguishes carbocyclic from heterocyclic rings in which the ring backbone contains at least one non-carbon atom.

The term "heterocyclic" or "heterocycle" means a saturated or unsaturated cyclic hydrocarbon group with three to about 12 carbon atoms, preferably about five to about six, wherein one to about four carbon atoms are replaced by nitrogen, oxygen or sulfur. The preferred heterocycles are selected from the group consisting of benzimidazole, dihydrothiophene, dioxin, dioxane, dioxolane, dithiane, dithiazine, dithiazole, dithiolane, furan, epoxide, imidazole, morpholine, oxazole, oxadiazole, oxathiazole, oxathiazolidine, oxazine, oxadiazine, piperazine, piperadine, pyran, pyrazine, pyrazole, pyridine, pyrimidine, pyrrole, pyrrolidine, tetrahydrofuran, tetrazine, thiadiazine, thiadiazole, thiatriazole, thiazine, thiazole, thiomorpholine, thiophene, thiopyran, triazine, and triazole.

The term "carboxyl" refers to —R$_1$C(═O)O—R$_2$, wherein R$_1$ is substituted or unsubstituted alkyl, cycloalkyl, heterocyclic, or aryl or R$_1$ can additionally be a covalent bond and wherein R$_2$ is hydrogen, alkyl, cycloalkyl, heterocyclic, aryl, aralkyl, and wherein R$_2$ may optionally be substituted with a hydroxyl or amino group.

The term "carboxylic acid" refers to a carboxyl group in which R$_2$ is hydrogen. Such acids include formic, acetic, propionic, butryic, valeric acid, 2-methyl propionic acid, oxirane-carboxylic acid, and cyclopropane carboxylic acid.

The term "carboxylic acid ester" or "ester" refers to a carboxyl group in which R$_2$ is alkyl, cycloalkyl, aryl, aralkyl, and wherein R$_2$ may optionally be substituted with a hydroxyl or amino group.

The term "cycloalkane" or "cyclic alkane" or "cycloalkyl" is a carbocyclic group in which the ring is an optionally substituted cyclic aliphatic hydrocarbon, for example, a cyclic alkyl group preferably with three to 12 ring carbons. "Cycloalkyl" includes, by way of example, cyclopropyl, cyclobutyl, cyclopentyl, cyclohexyl, cycloheptyl, or cyclooctyl, and the like. Most preferred are cyclopropyl.

The term "halo" or "halogen" refers to fluoro, chloro, bromo or iodo, usually regarding halo substitution for a hydrogen atom in an organic compound. Of the halos, chloro and bromo are generally preferred with fluoro generally being the more preferred.

The term "hydroxyl" means —OH.

The term "haloalkyl" refers to an alkyl or cycloalkyl group having at least one halogen thereon. The term includes mono-haloalkyl, dihaloalkyl, and trihaloalkyl groups. Examples of haloalkyl groups include fluoromethyl, difluoromethyl, trifluoromethyl, fluoroethyl, pentafluoroethyl, 2,2,2-trifluoroethyl, and 2,2,3,3,3-pentafluoropropyl. Preferably, the haloalkyl comprises one to three halo groups, such as a hydrocarbon comprising a dichloromethyl group, or a monohalo-substituted hydrocarbon.

The term "haloalkoxy" refers to an alkoxy or cycloalkoxy group having at least one halogen thereon. The term includes monohaloalkoxy, dihaloalkoxy, and trihaloalkoxy groups. Examples of haloalkoxy groups include fluoromethoxy, difluoromethoxy, trifluoromethoxy, and fluoroethoxy. Preferably, the haloalkyl comprises 1 to 3 halo groups, such as a hydrocarbon comprising a dichloromethyl group, or a monohalosubstituted hydrocarbon.

The term "acryl" includes where one of four hydrogen atoms in which ethene is replaced with a different functional group. The term includes substituted and unsubstituted acrylic acids and acrylic acid esters, as well as acrylic acid hydrazides. Non-limiting examples include alkyl(meth)acrylates, hydroxyalkyl(meth)acrylates, alkyl(meth)acrylamides, alkyl di(meth)acrylates, ethylenically unsaturated carboxylic acids, epoxy(meth)acrylates (e.g., glycidyl(meth)acrylate), cyclopropyl(methy)acrylates, ethoxylated (meth)acrylates, cyanoacrylates, etc. Also included are acrylic-, (meth)acrylamido-, and (meth)acrylonitrile. Carbocylic and heterocyclic (especially aryl and aralkyl)acrylates and methacrylates, e.g., cyclohexyl acrylate, isobornyl acrylate, are also included. Exemplary acryl groups are methylacrylate, ethylacrylate, butylacrylate, isobutylacrylate, tert-butylacrylate, di(meth)acrylate, hydroxyethylacrylate ("HEA"), hydroxypropylacrylate, dimethylaminoethylacrylate, glycidylacrylates, ethyl(meth)acrylate, butyl(meth)acrylate, hydroxyethyl (meth)acrylate, hydroxypropyl(meth)acrylate ("HEMA"), dimethylaminoethyl(meth)acrylate, glycidyl(meth)acrylates, acrylonitrile, (meth)acrylonitrile, acrylamide or methacrylamide, N-methylol(meth)acrylamide, N-ethanol acrylamide, N,N-dimethyl(meth)acrylamide, N-t-butyl acrylamide, octyl-acrylamide, etc. In one embodiment, the acryl group comprise an ethene substituted with a tetrazole group. In another aspect, the acryl group comprises and ethene substituted with an oxadiazolone, sulfonamide, sulfonate, or phosphate group.

"Acrylic acid" means the group $-(CR_1=CR_2)_n-$COOH, wherein $R_1$ and $R_2$ are independently hydrogen, alkyl, cycloalkyl, aryl, or aralkyl, and n is between an integer, e.g., 1, 2, 3, 4, and is preferably less than 10.

"Acrylic acid ester" means the group $-(CR_1=CR_2)_n-$COOR$_3$ where $R_1$ and $R_2$ are independently hydrogen, alkyl, cycloalkyl, aryl, or aralkyl, and $R_3$ is alkyl or cycloalkyl. Examples of acrylic acid esters include methyl acrylate, ethyl acrylate, n-butyl acrylate, 2-methyl acrylate, and 2-ethylhexyl acrylate, and the like, and n is between an integer, e.g., 1, 2, 3, 4, and is preferably less than 10.

"Acrylic acid hydrazide" refers to the group $-(CR_1=CR_2)_n-CONR_3NR_4R_5$, wherein $R_1, R_2, R_3, R_4$, and $R_5$ are independently hydrogen, alkyl, cycloalkyl, aryl, or aralkyl hydrogen or alkyl, and n is between an integer, e.g., 1, 2, 3, 4, and is preferably less than 10.

"Carboxylic acid hydrazide" refers to the group $-C(O)NR_1NR_2R_3$ wherein $R_1, R_2$, and $R_3$ are independently hydrogen, alkyl, cycloalkyl, aryl, or aralkyl.

The term "epoxide" is understood as meaning and optionally substituted saturated or unsaturated aliphatic compounds containing at least one ether in which the oxygen atom is part of a ring of three atoms. Exemplary epoxides according to the invention include oxirane (ethylene oxide), oxirane carboxylic acids, epoxypropane, epoxybutane, 2-methylepoxypropane, 2-methylepoxybutanes, glycidol and epichlorohydrin, 2-methyl-2,3-epoxybutane.

"Optional" or "optionally" means that the subsequently described event or circumstance may or may not occur, and that the description includes instances where said event or circumstance occurs and instances in which it does not. "Optionally" is inclusive of embodiments in which the described conditions is present and embodiments in which the described condition is not present. For example, "optionally substituted phenyl" means that the phenyl may or may not be substituted, and that the description includes both unsubstituted phenyl and phenyl wherein there is substitution. The term also includes one or more heteroatoms in the phenyl ring. "Optionally" is inclusive of embodiments in which the described conditions is present and embodiments in which the described condition is not present.

The "patient" to be treated in the case of PKD with the compounds of the present invention can be any animal, and is preferably a mammal, such as a wild or domesticated animal or a livestock animal or human.

The term "treatment" as used herein with respect to PKD refers to the treatment of the PKD in a patient, such as a mammal (particularly a human), and includes: (a) preventing the PKD from occurring, i.e., prophylactic treatment of a patient; (b) ameliorating the PKD, i.e., eliminating or causing regression of the disease or medical condition in a patient; (c) suppressing the PKD, i.e., inhibiting, slowing or arresting the development of the disease or medical condition in a patient; or (d) alleviating the symptoms of the PKD condition in a patient.

The term "inhibit" or "inhibiting" refers to a statistically significant and measurable reduction in activity, preferably a reduction of at least about 10% versus control, more preferably a reduction of about 50% or more, still more preferably a reduction of about 80% or more. In the case of inhibiting PKD, the cysts can be reduced by at least about 10%.

According to another aspect, the present invention provides a pharmaceutical composition, which comprises a therapeutically-effective amount of one or more compounds of the present invention or a pharmaceutically-acceptable salt, ester or prodrug thereof, together with a pharmaceutically-acceptable diluent or carrier.

The compositions may be formulated for any route of administration, in particular for oral, rectal, transdermal, subcutaneous, intravenous, intramuscular or intranasal administration. The compositions may be formulated in any conventional form, for example, as tablets, capsules, caplets, solutions, suspensions, dispersions, syrups, sprays, gels, suppositories, patches and emulsions.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically-acceptable carrier" as used herein means a pharmaceutically-acceptable material, composition or vehicle, such as a liquid or solid filler, diluent, excipient, solvent or encapsulating material, involved in carrying or transporting the subject lonidamine analogue or derivative from one organ, or portion of the body, to another organ, or portion of the body. Each carrier must be "acceptable" in the sense of being compatible with the other ingredients of the formulation and not injurious to the patient. Some examples of materials which may serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

The compounds of the present invention may be administered in free form or in pharmaceutically acceptable salt form. Such salts may be prepared in conventional manner and exhibit the same order of activity as the free compounds. As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge, et al. describe pharmaceutically acceptable salts in detail in J. Pharmaceutical Sciences, 66: 1-19 (1977), incorporated herein by reference. The salts can be prepared in situ during the final isolation and purification of the compounds of the invention, or separately by reacting the free base function with a suitable organic acid. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include, but are not limited to, adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed.

As used herein, the term "pharmaceutically acceptable ester" refers to esters which hydrolyze in vivo and include, but are not limited to, those that break down readily in the human body to leave the parent compound or a salt thereof. Suitable ester groups include, for example, those derived from pharmaceutically acceptable aliphatic carboxylic acids, particularly alkanoic, alkenoic, cycloalkanoic and alkanedioic acids, in which each alkyl or alkenyl moiety advantageously has not more than 6 carbon atoms. Examples of particular esters include formates, acetates, propionates, butyrates, acrylates and ethylsuccinates.

The term "pharmaceutically acceptable prodrugs" as used herein refers to those prodrugs of the compounds of the present invention which are, within the scope of sound medical judgment, suitable for use in contact with the tissues of humans and lower animals without undue toxicity, irritation, allergic response and the like, commensurate with a reasonable risk/benefit ratio, and effective for their intended use, where possible, of the compounds of the invention. The term "prodrug" refers to compounds that are rapidly transformed in vivo to yield the parent compound of the above formulae, for example, by hydrolysis in blood. A thorough discussion is provided in T. Higuchi and V. Stella, *Prodrugs as Novel delivery Systems*, Vol. 14 of the A.C.S. Symposium Series and in Edward B. Roche, ed., *Bioreversible Carriers in Drug Design*, American Pharmaceutical Association and Pergamon Press, 1987, both of which are incorporated by reference herein.

A "therapeutically effective amount" is an amount of a compound of the present invention or a combination of two or more such compounds, which inhibits, totally or partially, the progression of the condition or alleviates, at least partially, one or more symptoms of the condition. A therapeutically effective amount can also be an amount that is prophylactically effective. The amount that is therapeutically effective will depend upon the patient's size and gender, the condition to be treated, the severity of the condition and the result sought. For a given patient, a therapeutically effective amount can be determined by methods known to those of skill in the art.

In reference to the treatment of PKD using the compounds of the present invention, a "therapeutically effective amount" refers to that amount which has the effect of (1) reducing the size of the cysts, (2) inhibiting (that is, slowing to some extent, preferably stopping) cyst growth or new cyst formation, (3) inhibiting to some extent (that is, slowing to some extent, preferably stopping) cyst growth, and/or, (4) relieving to some extent (or, preferably, eliminating) one or more symptoms associated with the PKD, including extrarenal manifestations of the disease.

In the context of the present invention, a therapeutic effective amount will be that concentration which is effective to cause diminution or cessation of PKD. For example, for RC-MC-110, JSW-2-72, and JSW-1-190, it is currently thought that a formulation containing between about 25.0 mg/kg of body weight and about 0.3 mg/kg, preferably less than 6.0 mg/kg, of body weight will constitute a therapeutically effective concentration for intravenous or oral application, with routine experimentation providing adjustments to these concentrations for other routes of administration if necessary.

In the context of cancer or PKD treatment, it is contemplated that some of the compounds of the present invention may be used with other anti-neoplastic agents. As used herein, the phrase "anti-neoplastic agent" is synonymous with "chemotherapeutic agent" and refers to compounds that prevent cancer cells from multiplying (i.e. anti-proliferative agents). Such compounds include, but are not limited to, paclitaxel, docetaxel, vinblastine, vincristine, vindesine and vinorelbine; see for example the review: *Cancer, Principles and Practice of Oncology*, Lippincott-Raven Ed. (1997), 467-483. Platinum derivatives used in clinical practice include, but are not limited to cisplatin, carboplatin, oxaliplatin, nedaplatin and lobaplatin; see review *Cancer, Principles and Practice of Oncology*, Lippincott-Raven Ed. (1997), 418-432. Other potential anti-neoplastic agents include alkylating agents (including, without limitation, nitrogen mustards, ethylenimine derivatives, alkyl sulfonates, nitrosoureas and triazenes): uracil mustard, chlormethine, cyclophosphamide, ifosfamide, melphalan, chlorambucil, pipobroman, triethylene-melamine, triethylenethiophosphoramine, busulfan, carmustine, lomustine, streptozocin, dacarbazine, and temozolomide. Antimetabolites (including, without limitation, folic acid antagonists, pyrimidine analogs, purine analogs and adenosine deaminase inhibitors): methotrexate, 5-fluorouracil, floxuridine, cytarabine, 6-mercaptopurine, 6-thioguanine, fludarabine phosphate, pentostatine, and gemcitabine. Natural products and their derivatives (for example, vinca alkaloids, antitumor antibiotics, enzymes, lymphokines and epipodophyllotoxins): vinblastine, vincristine, vindesine, bleomycin, dactinomycin, daunorubicin, doxorubicin, epirubicin, idarubicin, ara-C, paclitaxel, mithramycin, deoxycoformycin, mitomycin-C, L-asparaginase, interferons (especially IFN-a), etoposide, and teniposide. Other antiproliferative cytotoxic agents are navelbene, CPT-11, anastrazole, letrazole, capecitabine, reloxafine, cyclophosphamide, ifosamide, and droloxafine.

Microtubule affecting agents interfere with cellular mitosis and are well known in the art for their anti-cancer activity. Microtubule affecting agents useful in the invention include, but are not limited to, allocolchicine (NSC 406042), Halichondrin B (NSC 609395), colchicine (NSC 757), colchicine derivatives (e.g., NSC 33410), dolastatin 10 (NSC 376128), maytansine (NSC 153858), rhizoxin (NSC 332598), paclitaxel (Taxol®, NSC 125973), Taxol® derivatives (e.g., derivatives (e.g., NSC 608832), thiocolchicine NSC 361792), trityl cysteine (NSC 83265), vinblastine sulfate (NSC 49842), vincristine sulfate (NSC 67574), natural and synthetic epothilones including but not limited to epothilone A, epothilone B, and discodermolide (see Service, (1996) Science, 274:2009) estramustine, nocodazole, MAP4, and the like. Examples of such agents are also described in the scientific and patent literature, see, e.g., Bulinski (1997) J. Cell Sci. 110:3055 3064; Panda (1997) Proc. Natl. Acad. Sci. USA 94:10560-10564; Muhlradt (1997) Cancer Res. 57:3344-3346; Nicolaou (1997) Nature 387:268-272; Vasquez (1997) Mol. Biol. Cell. 8:973-985; Panda (1996) J. Biol. Chem. 271:29807-29812.

Additional anti-cancer agents include, melphalan, hexamethyl melamine, thiotepa, cytarabin, idatrexate, trimetrexate, dacarbazine, L-asparaginase, camptothecin, topotecan, bicalutamide, flutamide, leuprolide, pyridobenzoindole derivatives, interferons, and interleukins. Preferred classes of antiproliferative cytotoxic agents are the EGFR inhibitors, Her-2 inhibitors, CDK inhibitors, and Herceptin (trastuzumab). Some especially preferred anti-proliferative cytostatic agents are paclitaxel, cis-platin, carboplatin, epothilones, gemcytabine, CPT-11,5-fluorouracil, tegafur, leucovorin, and EGFR inhibitors such as Iressa® (ZD 1839, 4-(3-chloro-4-fluorophenylamino)-7-methoxy-6-(3-(4-morpholinyl)propoxy)quinazoline and OSI-774 (4-(3-ethynylphenylamino)-6,7-bis(2-methoxyethoxy)quinazoline).

An exemplary synthesis of the compounds of the present invention is generally set forth in the scheme below. Although the exemplary scheme is for the carboxylic acid and carboxylic acid ester derivatives of the present invention, it will be appreciated by those skilled in the art that a similar scheme can be used to produce the ester, hydrazide, or carboxylic acid hydrazide, etc. derivatives of the present invention.

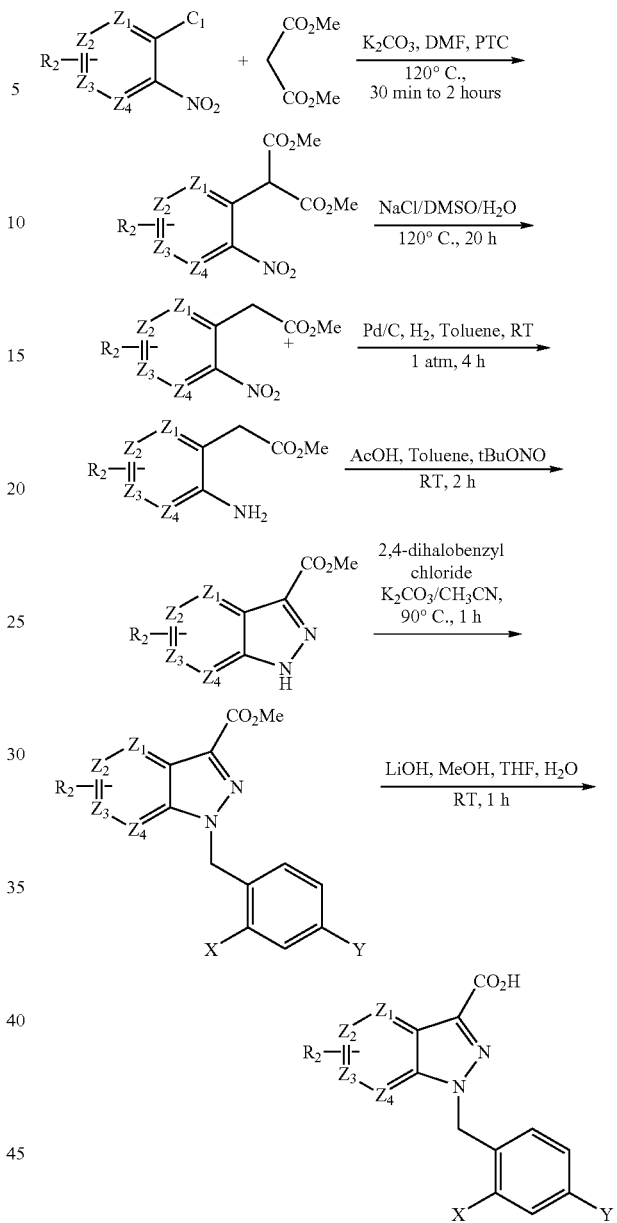

wherein $R_2$ is hydrogen, halogen, alcohol, alkyl, alkoxy, aralkyl, cycloalkyl, haloalkyl, haloalkoxy, amino, or carboxyl;

wherein X and Y are the same or different from each other and are halogen or lower alkyl; and wherein $Z_1$, $Z_2$, $Z_3$, and $Z_4$ are independently nitrogen or carbon, In a similar manner, the compounds of the present invention having an acryl derivatives.

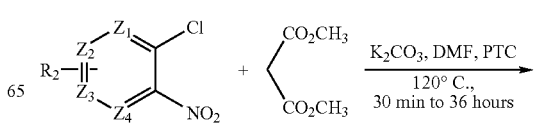

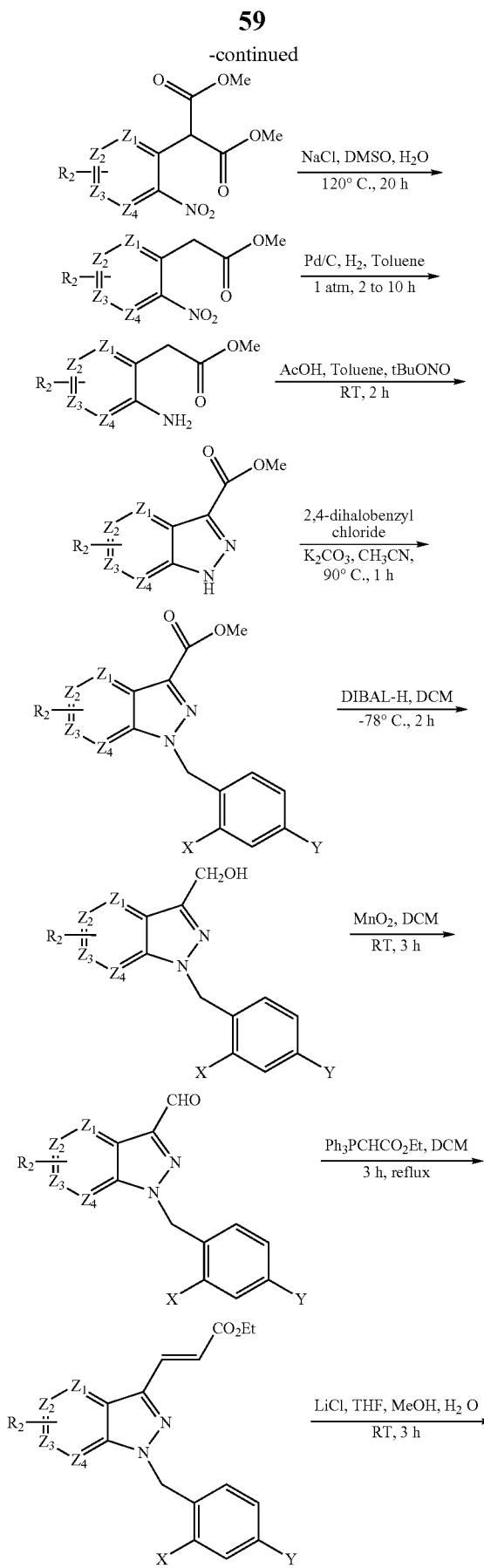

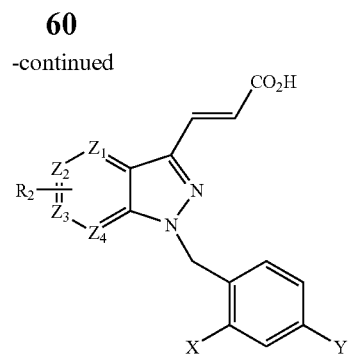

Various derivatives can be synthesized from the acrylic acids and acrylic acid esters of the present invention. For example proprionic acid and ester derivatives can be prepared by using any well known hydrogenation technique. In addition, cycloalkyl derivatives, most preferably cyclopropyl, and heterocylic derivatives, most preferably epoxides, can be prepared.

Those skilled in the art will recognize that minor modifications can be made to the starting materials and other precursors in order to prepare the compounds of the present invention. For example, when a methyl, trifluoromethyl, chlorine, or fluorine is desired in the 6-position of the compounds of the present invention, the starting material is, for example, 4-chloro-3-nitro-methylbenzene, 1-chloro-2-nitro-4-trifluoromethyl-benzene, 1,4-dichloro-2-nitro-benzene, 1-chloro-4-fluoro-2-nitrobenzene, respectively. Likewise, when a trifluoromethyl is desired to be in the 5-position, the starting material is 1-chloro-2-nitro-5-trifluoromethyl-benzene. All of these starting materials are commercially available from Marshallton Research Lab (King, N.C.).

Further, synthesis of the halogenated alkoxy substituents can be performed using by starting with commercially available 1-chloro-4-fluoromethoxybenzene. This on nitration with $HNO_3$ and $H_2SO_4$ at 50° C. about 3 h. The yield (2 isomers) obtained in 98% (scheme-1). 2-Chloro-4-trifluoromethoxy nitrobenzene is readily synthesized according to the following scheme from Michel Dury, U.S. Pat. No. 6,121,492, which is incorporated by reference.

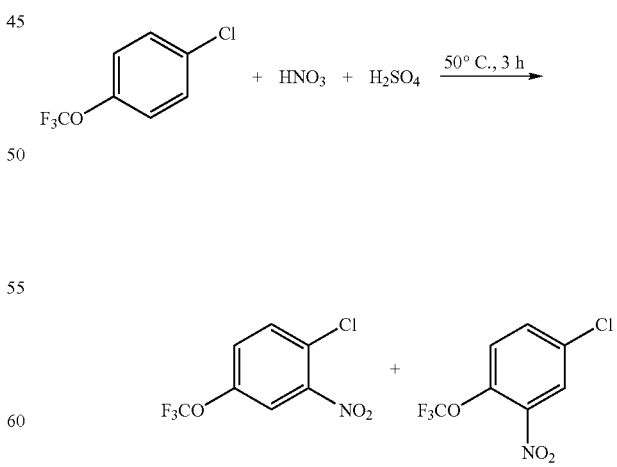

The above two isomers were condensed with dimethylmalonate in DMF in the presence of $K_2CO_3$ at 120° C. for about 8 h. The required product obtained by recrystallization in methanol. The yield was about 55%.

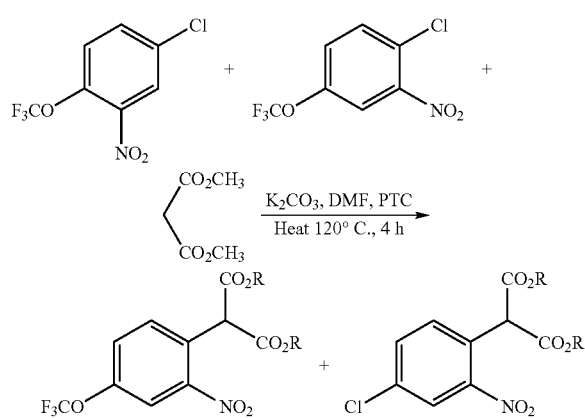

When it is desirable to have one or more nitrogens in the six-membered ring, suitable starting materials include, for example, 2-chloro-3-nitropyridine, 4-hydroxy-3-nitropyridine, 2-chloro-6-methoxy-3-nitro-pyridine, 5-trifluoromethyl-2-pyridonol, 2,3-dichloropyrazine, 4-chloro-3-nitroaniline, and 2-chloro-pyridine. All of these compounds are commercially available from Sigma Aldrich or can be readily synthesized.

It will be appreciated that 4-chloro-3-nitropyridine is readily synthesized according to the following scheme from Reich et al., J. Med. Chem. 1989, 32, 2474-2485.

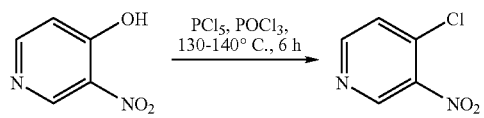 [SMILES: O=[N+]([O-])c1cnccc1O ; O=[N+]([O-])c1cnccc1Cl]

It will be appreciated that 2-chloro-3-nitro-5-trifluoromethyl-pyridine can be synthesized according to the following scheme according to European Patent Application 0272824:

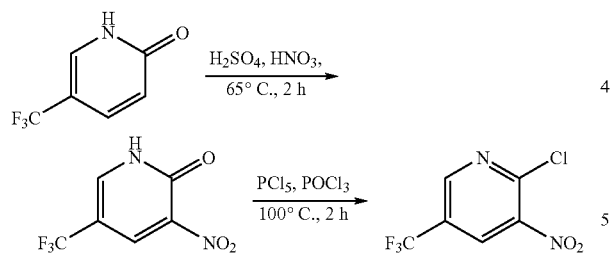

Suitable pyrazine precursors can also be readily synthesized. For example 2-amino-3-chloropyrazineis is readily synthesized according to the following scheme from A. P. Komin et al., J. Het. Chem., Vol., 13, 13-22 (1976), which is incorporated by reference.

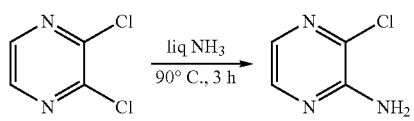 [SMILES: Clc1nccnc1Cl ; Nc1nccnc1Cl]

The S,S-dimethyl-N-(3-chloropyrazin-2-yl)sulfilimine is readily synthesized according to the following scheme from Hartman, U.S. Pat. No. 4,609,659, which is incorporated by reference. Oxidation of the sulfilimine with MCPBA furnishes the nitro derivative.

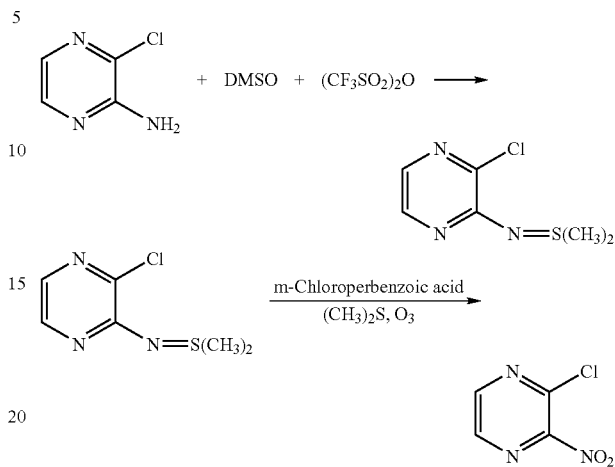

The pyrimidine series can also be synthesized using commercially available 5-nitro-4-chloro pyrimidine (Magical Scientific).

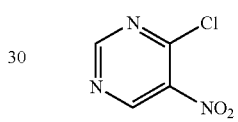

The 4-chloro-2-methyl-benzyl chloride is readily synthesized according to the following scheme from T. S Osdene and et al, Journal of Medicinal Chemistry., 10, 431-434 (1967).

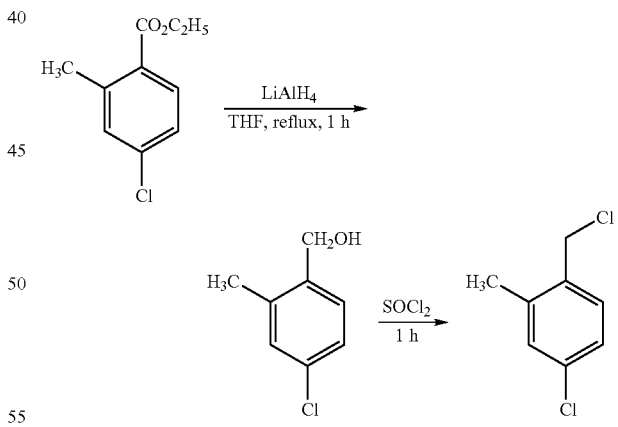

The following synthetic examples are offered to illustrate the invention, and are not to be construed in any way as limiting the scope of the invention.

Example 1

Synthesis of 1-(2,4-dichlorobenzyl)-1H-indazole-3-carboxylic Acid Methyl Ester (RC-MC-30)

For the synthesis of RC-MC-30, methyl indazole-3-carboxylate was first formed. Acetyl chloride (7 mL, excess) was added dropwise to ice-cooled methanol (20 mL) and the solution was stirred at the same temperature for 10 minutes. Commercially available indazole-3-carboxylic acid (2.3 g, 14 mmol) was then added to the solution in one lot and the mixture was allowed to warm to room temperature and stirred overnight. The solvent was removed under vacuum, then the residual solid was dissolved in CHCl$_3$ (100 mL), and washed with std. NaHCO$_3$ solution. The aqueous layer was extracted with CHCl$_3$ and the combined organic extract was washed with brine and dried over anhydrous Na$_2$SO$_4$. Removal of solvent left the product as a light yellow solid. Yield=2.05 g (85%); m.p.=168°-170° C.; 1H NMR (400 MHz, CDCl$_3$) δ 8.25 (d, J=8.8 Hz, 1H), 7.89 (d, J=8.8 Hz, 1H), 7.50 (t, J=7.8 Hz, 1H), 7.37 (t, J=7.8 Hz, 1H), 4.10 (s, 3H).

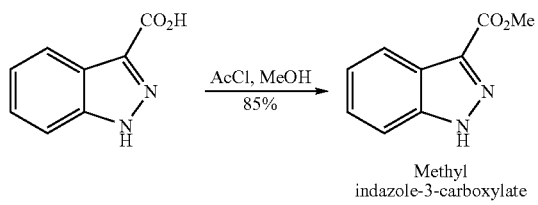 [SMILES: O=C(O)c1n[nH]c2ccccc12 ; COC(=O)c1n[nH]c2ccccc12]

Methyl indazole-3-carboxylate

Next, a mixture of methyl indazole-3-carboxylate (2.05 g, 11.4 mmol), 2,4-dichlorobenzyl chloride (3.35 mL, 12.54 mml), and K$_2$CO$_3$ (7.0 g, 50 mmol) in acetone (22 mL) was refluxed overnight at a temperature of 70° C. The reaction mixture was cooled to room temperature, filtered, and the residue was washed with acetone. The combined filtrate was concentrated under vacuum (rotovapor). The solid thus obtained was dissolved in CH$_2$Cl$_2$ and filtered to remove any undissolved solid. The solution was then concentrated, diluted with hexane and left in the refrigerator overnight. The precipitated solid was then filtered, washed with a mixture of hexane/ethyl acetate (9:1) to yield the pure product as a white solid. Yield=3.5 g (89%); m.p.=144°-146° C.; 1H NMR (400 MHz, CDCl$_3$) δ 8.31 (d, J=8.8 Hz, 1H), 7.39-7.47 (m, 4H), 7.12 (d, J=8.8 Hz, 1H), 6.71 (d, J=8.8 Hz, 1H), 5.81 (s, 2H), 4.11 (s, 3H).

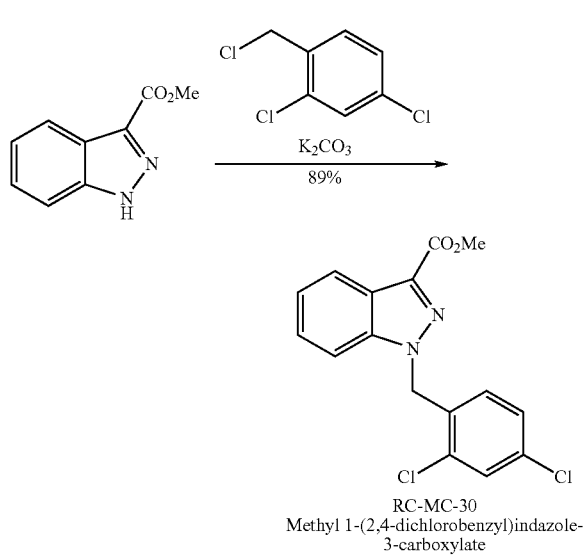

RC-MC-30
Methyl 1-(2,4-dichlorobenzyl)indazole-3-carboxylate

Example 2

Synthesis of 3-[1-(2,4-dichlorobenzyl)-6-trifluoromethyl-1H-indazol-3-yl]-acrylic Acid (RC-MC-110)

Step 1: 2-(2-nitro-4-trifluoromethylphenyl)-malonic Acid Dimethyl Ester

Dimethyl malonate (59.7 g, 0.44 mol) was added dropwise to a stirred solution of potassium tert-butoxide (51 g, 0.44 mol) in dry t-butanol (500 mL). To the resultant suspension, a warm solution of 2-chloro-5-trifluoromethylnitrobenzene (50 g, 0.22 mol) in t-butanol (100 mL) was added and the mixture was refluxed for 6 h (reaction monitored by TLC). After completion of the reaction, most of the t-butanol was distilled off under vacuum, and chilled water was then added to the reaction mixture. The pH was adjusted to neutral with dilute hydrochloric acid, which resulted in the precipitation of the product. The mixture was stirred for 30 minutes and the product was filtered off (68 g, 95%). This material was used without further purification in the next step. A small amount was crystallized (EtOAc/hexane, 4:6) for analysis, to yield a yellow crystalline material, mp 65-67° C. $^1$H NMR (CDCl$_3$) 8.30 (s, 1H), 7.92 (d, J=8.4 Hz, 1H), 7.69 (d, J=8.4 Hz, 1H), 5.37 (s, 1H), 3.80 (s, 6H). MS (FAB) m/z: 322.1 (M$^+$+1).

Step 2: (2-nitro-4-trifluoromethylphenyl)-acetic Acid Methyl Ester 2-(2-Nitro-4-trifluoromethylphenyl)-malonic acid dimethyl ester (68 g, 0.21 mol) was dissolved in dimethyl sulfoxide (200 mL). Sodium chloride (34 g, 0.58 mol) and water (60 mL) were added and the mixture was stirred for 16-20 h at 120° C. (reaction monitored by TLC). The reaction mixture was then cooled to room temperature and quenched into water, which caused precipitation of the product. After stirring for 30 minutes, the product (45 g, 80%) was isolated by filtration. The product was used without further purification in the next reaction. A small sample was crystallized (EtOAc/hexane, 2:8) for analysis, to yield yellow crystals, mp 104-

105° C. ¹H NMR (CDCl₃) 8.3 (s, 1H), 7.88 (d, J=8.4 Hz, 1H), 7.50 (d, J=8.4 Hz, 1H), 4.12 (s, 2H), 3.60 (s, 3H). MS (FAB) m/z: 275.2 (M⁺+1).

Step 3: (2-Acetylamino-4-trifluoromethylphenyl)-acetic Acid Methyl Ester

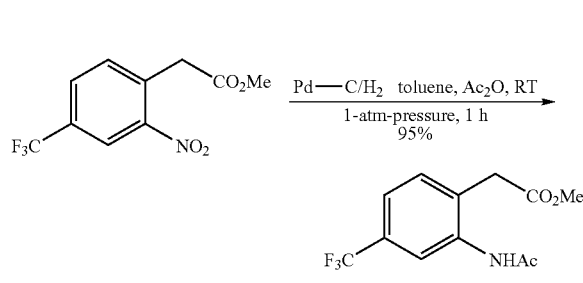

Hydrogenation and acetylation of (2-nitro-4-trifluoromethylphenyl)-acetic acid methyl ester (25 g, 0.095 mol) in the presence of 5% Pd—C (2.5 g, 50% wet) and acetic anhydride (38 g, 0.37 mol) in toluene (200 mL) was carried out under vigorous stirring at room temperature and atmospheric pressure for about 4-5 h (reaction monitored by TLC). The catalyst was removed by filtration and washed with toluene two times. The combined organics were evaporated in vacuo to yield the product (24.8 g, 95%), which was used without further purification in the next step. A small sample was crystallized from hexane to yield the product as a yellow solid, mp 92-94° C. ¹H NMR (CDCl₃) 8.86 (s, 1H), 8.21 (s, 1H), 7.36 (d, J=8.1 Hz, 1H), 7.31 (d, J=8.1 Hz, 1H), 3.74 (s, 3H), 3.68 (s, 2H), 2.23 (s, 3H).

Step 4: 6-Trifluoromethyl-1H-indazole-3-carboxylic Acid Methyl Ester

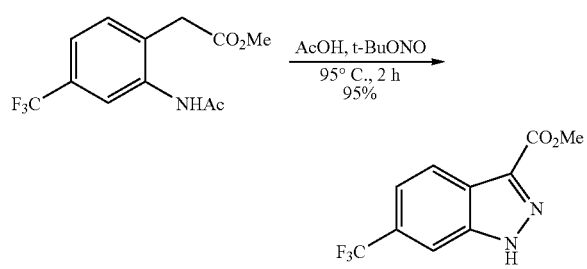

To a solution of (2-acetylamino-4-trifluoromethylphenyl)-acetic acid methyl ester (16 g, 0.058 mol) in acetic acid (50 mL) was added dropwise t-butyl nitrite (90%) (7.35 g, 0.063 mol) over a period of 20 min. at 90-95° C. The mixture was then stirred for 0.5 h at 95° C., poured into cold water and stirred for 1 h. The precipitates were collected by filtration and washed with water. The crude material was dissolved in ethyl acetate and dried over sodium sulfate. The solvent was removed in vacuo. This material (13.4 g, 95%) was used without further purification in the next step. A small sample was crystallized from ethyl acetate to yield a white solid, mp 240-242° C. ¹H NMR (DMSO-d-6) 8.25 (d, J=8.5 Hz, 1H), 8.04 (s, 1H), 7.58 (d, J=8.5 Hz, 1H), 3.95 (s, 3H). MS (FAB) m/z: 245.1 (M⁺+1).

Step 5: 1-(2,4-Dichlorobenzyl)-6-trifluoromethyl-1H-indazole-3-carboxylic Acid Methyl Ester

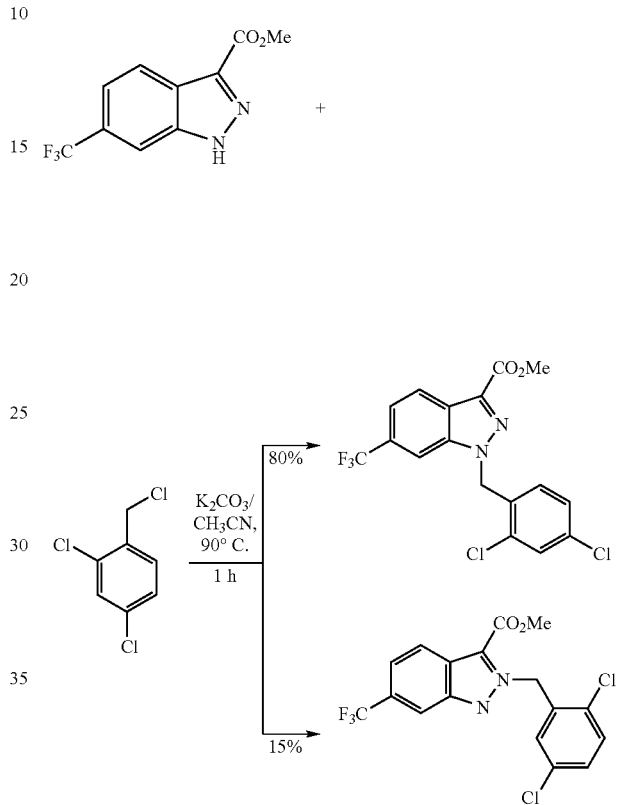

6-Trifluoromethyl-1H-indazole-3-carboxylic acid methyl ester (2.75 g, 0.0112 mol) was dissolved in acetonitrile (50 mL), and potassium carbonate (10 g, 0.07 mol), 2,4-dichlorobenzyl chloride (2.42 g, 0.01239 mol) and tetrabutylammonium iodide (catalytic) were added. The reaction mixture was heated to reflux and refluxed for 2 h under good stirring. The progress of the reaction was monitored by TLC. After completion of the reaction, potassium carbonate was filtered while hot and then washed with acetone. The combined solvents were distilled off under reduced pressure to afford the crude mixture of N1 and N2 benzylated products. The isomers were separated by column chromatography (silica gel, eluent started with hexane then changed to 8:2 hexane, ethyl acetate).

1-(2,4-Dichlorobenzyl)-6-trifluoromethyl-1H-indazole-3-carboxylic acid methyl ester. Yield: 3.62 g (80%), white crystals mp 118-120° C. ¹H NMR (CDCl₃) 8.39 (d, J=8.4 Hz, 1H) 7.74 (s, 1H), 7.57 (d, J=8.4 Hz, 1H), 7.45 (d, J=2.1 Hz, 1H), 7.12 (dd, J=8.4 and 2.1 Hz, 1H), 6.78 (d, J=8.4 Hz, 1H), 5.82 (s, 2H), 4.07 (s, 3H). MS (FAB) m/z: 403 (M⁺+1).

2-(2,4-Dichlorobenzyl)-6-trifluoromethyl-2H-indazole-3-carboxylic acid methyl ester. Yield: 680 mg (15%), white crystals mp 132-134° C. ¹H NMR (DMSO-d-6) 8.27 (s, 1H), 8.20 (d, J=8.7 Hz, 1H), 7.76 (d, J=1.8 Hz, 1H), 7.57 (d, J=8.7

Hz, 1H), 7.30 (dd, J=8.3 and 1.8 Hz, 1H), 6.78 (d, J=8.3 Hz, 1H), 6.17 (s, 2H), 3.96 (s, 3H).

Step 6: [1-(2,4-Difluorobenzyl)-6-trifluoromethyl-1H-indazol-3-yl]-methanol

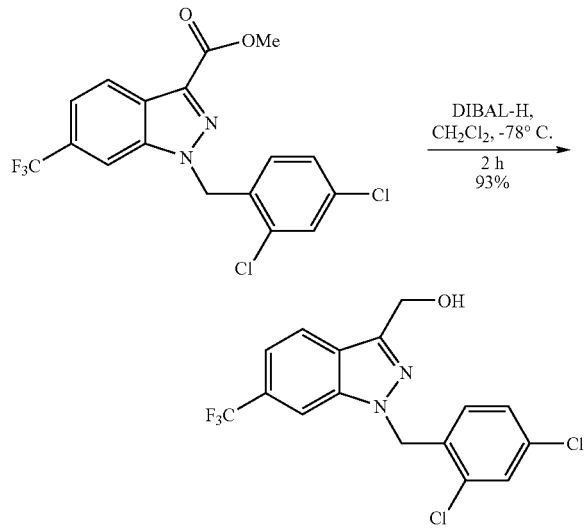

1-(2,4-Dichlorobenzyl)-6-trifluoromethyl-1H-indazole-3-carboxylic acid methyl ester (3.0 g, 0.0075 mol) dissolved in CH$_2$Cl$_2$ (50 mL) was cooled to −78° C. DIBAL-H (8.18 mL, 0.00818 mol) was added slowly dropwise via a syringe under an argon blanket over a period of 15 minutes. After the complete addition of DIBAL-H, the reaction mixture was stirred at −78° C. for another 2 h (reaction monitored by TLC). The reaction was quenched carefully with methanol at −78° C. The reaction mixture was then carefully poured into water and the layers were separated. The organic layer was washed with water and dried over sodium sulfate. Removal of the solvent yielded the crude alcohol (2.6 g, 93%), which was used without purification in the next step. The alcohol was a white solid, mp 137-139° C. $^1$H NMR (CDCl$_3$) 7.97 (d, J=8.4 Hz, 1H), 7.66 (s, 1H), 7.44 (d, J=2.0 Hz, 1H), 7.42 (d, J=8.5 Hz, 1H), 7.12 (dd, J=8.3 and 2.0 Hz, 1H), 6.93 (d, J=8.3 Hz, 1H), 5.65 (s, 2H), 5.09 (s, 2H). MS (FAB) m/z: 375 (M$^+$+1).

Step 7: 1-(2,4-Dichlorobenzyl)-6-trifluoromethyl-1H-indazole-3-carbaldehyde

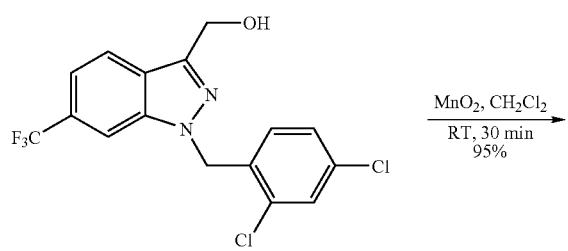

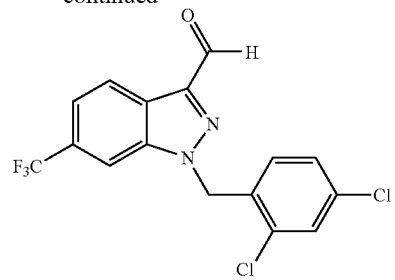

[1-(2,4-Difluorobenzyl)-6-trifluoromethyl-1H-indazol-3-yl]-methanol (3.75 g, 0.01 mol) was dissolved in CH$_2$Cl$_2$ (100 mL) and manganese(IV) oxide (8.7 g, 0.1 mol) was added and stirred for 2-3 h at room temperature (reaction monitored by TLC). The solids were removed by filtration and the removal of the CH$_2$Cl$_2$ in vacuo yielded the crude aldehyde. The aldehyde was used without further purification in the next step. The aldehyde (3.54 g, 95%) was a white solid, mp 97-98° C. $^1$H NMR (CDCl$_3$) 10.25 (s, 1H), 8.45 (d, J=8.5 Hz, 1H), 7.79 (s, 1H), 7.60 (d, J=8.5 Hz, 1H), 7.48 (d, J=2.0 Hz, 1H), 7.20 (dd, J=8.3 Hz and 2.0 Hz, 1H), 6.93 (d, J=8.3 Hz, 1H), 5.79 (s, 2H). MS (FAB) m/z: 373 (M$^+$+1).

Step 8: 3-[1-(2,4-Dichlorobenzyl)-6-trifluoromethyl-1H-indazol-3-yl]-acrylic Acid Ethyl Ester

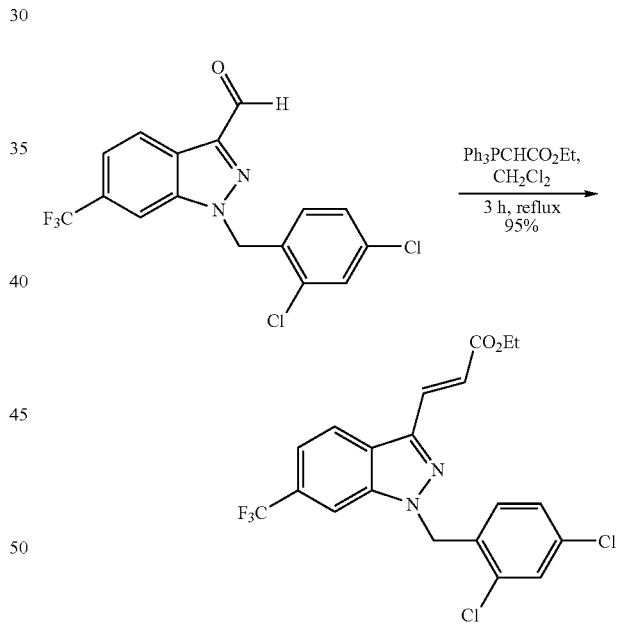

1-(2,4-Dichlorobenzyl)-6-trifluoromethyl-1H-indazole-3-carbaldehyde (2.0 g, 0.00536 mol) was dissolved in CH$_2$Cl$_2$ (50 mL) and Wittig reagent (carbethoxymethylene) triphenylphosphorane (1.06 g, 0.0536 mol) was added to the solution. The homogeneous reaction mixture was heated to reflux in an oil bath for 12 h. The reaction progress was monitored by TLC. The reaction mixture was cooled to room temperature and worked up by quenching into water and separating the organic layer. Removal of the CH$_2$Cl$_2$ yielded the crude product, which was purified by column chromatography to yield the pure product (2.25 g, 95%) as a white solid, mp 186-188° C. $^1$H NMR (CDCl$_3$) 8.08 (d, J=8.5 Hz, 1H), 7.99 (d, J=16.2 Hz, 1H), 7.74 (s, 1H), 7.52 (d, J=8.5 Hz, 1H), 7.47 (d, J=2.0 Hz, 1H), 7.16 (dd, J=8.3 and 2.0 Hz, 1H), 6.84 (d, J=8.3 Hz, 1H), 6.82 (d, J=16.2 Hz, 1H), 5.72 (s, 2H), 4.32 (q, J=7.1 Hz, 2H), 1.38 (t, J=7.1 Hz, 3H). MS (FAB) m/z: 443 (M$^+$+1).

It will be appreciated that the acrylic acid ethyl ester can be hydrogenated using 5% Pd—C in the presence of methanol, DCM at RT and 1 atm-pressure to give the propionic acid ester derivative. For example, treatment under such conditions yields 3-[1-(2,4-dichlorobenzyl)-6-trifluoromethyl-1H-indazol-3-yl]-propionic acid ethyl ester (JWS-2-70).

Step 9: 1-(2,4-Dichlorobenzyl)-3-[6-trifluoromethyl-1H-indazol-3-yl]-acrylic Acid

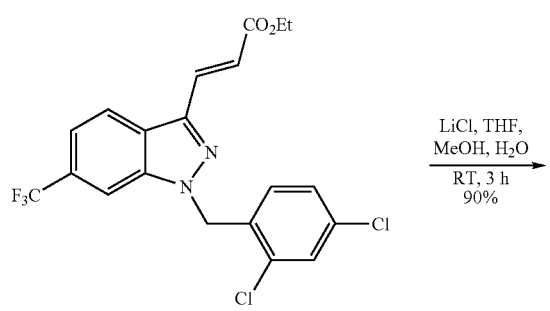

1-(2,4-Dichlorobenzyl)-3-[6-trifluoromethyl-1H-indazol-3-yl]-acrylic acid ethyl ester (2.0 g, 0.0045 mol) was dissolved in a mixture of tetrahydrofuran (50 mL) and methanol (25 mL). A lithium hydroxide solution (0.33 g, 0.013 mol lithium hydroxide in 7.5 mL water) was added slowly at room temperature under good stirring. The reaction mixture was then warmed to 40° C. and held at that temperature for 2 h. The reaction mixture was diluted with water and extracted with ethyl acetate in order to remove neutral impurities. The layers were separated and the aqueous layer was cooled to 0° C. and then acidified with 20% sulfuric acid to pH 2. White solids precipitated and were filtered and dried to constant weight. The crude product was recrystallized from ethyl acetate and hexane (1:1) to afford the pure product (1.68 g, 90%) as a white solid, mp 186-188° C. $^1$H NMR (DMSO-d-6) 8.39 (s, 1H), 8.36 (d, J=8.5 Hz, 1H), 7.79 (d, J=16.2 Hz, 1H), 7.66 (d, J=1.6 Hz, 1H), 7.55 (d, J=8.5 Hz, 1H), 7.35 (dd, J=8.3 and 1.6 Hz, 1H), 6.93 (d, J=8.3 Hz, 1H), 6.76 (d, J=16.2 Hz, 1H), 5.89 (s, 2H). Anal. calcd. for $C_{18}H_{11}Cl_2F_3N_2O_2$: C, 52.02; H, 2.65; N, 6.74. Found: C, 50.63; H, 2.63; N, 6.63. HRMS (FAB+) m/z calcd. for $C_{18}H_{11}Cl_2F_3N_2O_2$ 415.01, found 415.0233. MS (FAB) m/z: 415 (M$^+$+1).

It will be appreciated that proprionic derivatives of the acrylic acid derivatives of the, such as RC-MC-110, present invention can be prepared by was hydrogenated using 5% Pd—C in the presence of methanol, DCM at RT and 1 atm-pressure to give desired product. For example, treatment of RC-MC-110 under such conditions yields 3-[1-(2,4-dichlorobenzyl)-6-trifluoromethyl-1H-indazol-3-yl]-propionic acid (JWS-2-72).

Similarly, three-membered cycloalkyl heterocyclic ring systems can be prepared from the acrylic acid and ester compounds of the present invention. For example, compounds comprising cis- and trans-3-[1-(2,4-dichlorobenzyl)-6-trifluoromethyl-1H-indazol-3-yl]-oxirane-2-carboxylic acid were prepared by treating RC-MC-110 or its cis isomer with 30% hydrogen peroxide in the presence of sodium hydroxide, methanol and water at room temperature for 6 hours. Similarly, compounds comprising cis- and trans-2-[1-(2,4-dichloro-benzyl)-6-trifluoromethyl-1H-indazol-3-yl]-cyclopropanecarboxylic acid were prepared by refluxing RC-MC-110 and its cis analogue with methylene iodide and zinc-copper couple in anhydrous ethyl ether for 48 hours.

Example 3

Synthesis of 1-(2,4-dichlorobenzyl)-1H-pyrazolo[3,4-b]pyridine-3-carboxylic Acid (RC-MC-86)

Step 1: 1-(2-Chloropyridin-3-yl)ethanol

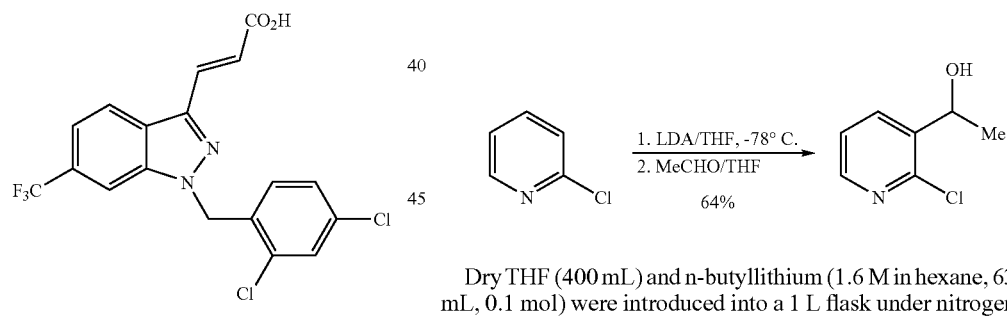

Dry THF (400 mL) and n-butyllithium (1.6 M in hexane, 63 mL, 0.1 mol) were introduced into a 1 L flask under nitrogen at −70° C. A solution of dry diisopropylamine (10.1 g, 0.1 mol) in THF (25 mL) was added dropwise to the mixture at −70° C. The mixture was then kept for 1 h at 0° C. and then cooled to −70° C. A solution of 2-chloropyridine (11.3 g, 0.1 mol) in THF (25 mL) was added dropwise to the mixture at −70° C. and the mixture was stirred for 3 h at this temperature. A solution of acetaldehyde (4.85 g, 0.11 mol) in dry THF (50 mL) was then added dropwise and the mixture was kept for 3 h at −70° C. A solution of water (4 mL) in THF (40 mL), acidified by a few drops of concentrated hydrochloric acid, was added to the mixture at −40° C. and then water (200 mL) was introduced at −10° C. Extraction with diethyl ether (3×150 mL), drying over anhydrous sodium sulfate, and evaporation gave a crude product, which was purified by column chromatography to yield an oil (10 g, 64%). *$^1$H NMR (CDCl$_3$) 8.15 (dd, J=5 and 2 Hz, 1H), 7.95 (dd, J=8 and 2 Hz, 1H), 7.20 (dd, J=8 and 5 Hz, 1H), 5.15 (d, J=7 Hz, 1H), 3.90 (s, 1H), 1.45 (d, J=7 Hz, 3H).

*NMR values reported in Journal of Chemical Society Perkin Trans 1: Organic and Bio-organic Chemistry, 1990, 9, 2409-2415.

Step 2: 1-(2-Chloropyridin-3-yl)ethanone

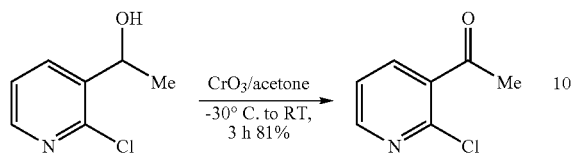

A solution of 1-(2-chloropyridin-3-yl)ethanone (10 g, 0.0635 mol) in dry acetone (200 mL) was introduced under argon into a 1 L flask. The mixture was cooled to −30° C. and pure, pulverized chromic anhydride (19 g, 0.19 mol) was added. The reaction mixture was kept at room temperature for 3 h. 2-Propanol (100 mL) was added, followed by aqueous sodium hydrogen carbonate to pH 8. After filtration, solids were washed with chloroform. The organic and aqueous layers were then separated and the aqueous layer was extracted with chloroform (2×100 mL). The combined organics were dried over anhydrous sodium sulfate and evaporated to yield the crude pyridyl ketone as an oil. This product was purified by column chromatography (8 g, 81%). *$^1$H NMR (CDCl$_3$) 8.44 (dd, J=5 and 2 Hz, 1H) 7.91 (dd, J=7.5 and 2 Hz, 1H), 7.34 (dd, J=7.5 and 5 Hz, 1H), 2.68 (s, 3H).
*NMR values reported in Journal of Chemical Society Perkin Trans 1: Organic and Bio-organic Chemistry, 1990, 9, 2409-2415.

Step 3: 3-Methyl-1H-pyrazolo[3,4b]pyridine

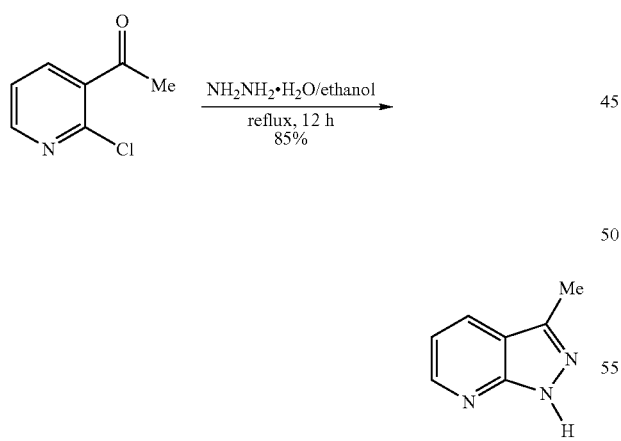

A solution of 1-(2-chloropyridin-3-yl)ethanone (22 g, 0.1415 mol) and hydrazine hydrate 98% (113 g, 2.21 mol) in ethanol (300 mL) was refluxed for 12 h. About 80% of the ethanol was distilled off under reduced pressure using a rotary evaporator. The residue was allowed to come to room temperature. The precipitated solid was filtered and washed with water. The product was dried at 90° C. to constant weight (16 g, 85%) mp 152-154° C. $^1$H NMR (CDCl$_3$) 8.62 (dd, J=4.5 and 1.4 Hz, 1H), 8.08 (dd, J=8.0 and 1.4 Hz, 1H), 7.15 (dd J=8.0 and 4.5 Hz, 1H), 2.64 (s, 3H). MS (FAB) m/z: 133 (M$^+$+1).

Step 4: 1H-Pyrazolo[3,4b]pyridine-3-carboxylic Acid

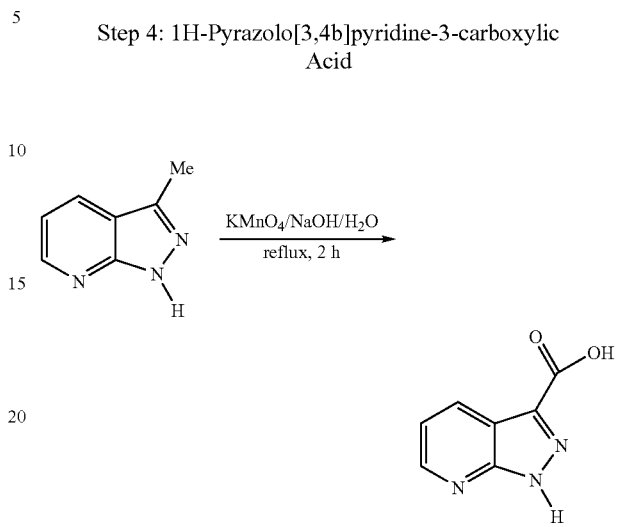

Sodium hydroxide (35 g, 0.88 mol) was dissolved in water (800 mL), then 3-methyl-1H-pyrazolo[3,4b]pyridine (16 g, 0.12 mol) was added to a solution of sodium hydroxide and stirred at room temperature for 10 minutes. The reaction mixture was heated to 80° C. Under good stirring potassium permanganate solution (68.5 g, 0.433 mol of KMnO$_4$ in 300 mL water) was slowly added dropwise over a period of 2 h, keeping the oil bath temperature at 100° C. After completing the addition of potassium permanganate, the reaction mixture was further heated for 1 hr. The progress of the reaction was monitored by TLC. The reaction mixture was cooled to 70-80° C. and the byproduct manganese dioxide was filtered off. The manganese dioxide cake was washed with hot water. The main filtrate and the washings were combined and acidified to pH 2 with concentrated sulfuric acid. The water was then distilled off under reduced pressure using a rotary evaporator. The yellow solid obtained was a mixture of the desired 1H-pyrazolo[3,4b]pyridine-3-carboxylic acid, sodium sulfate and potassium sulfate (95 g). This mixture of solids was taken without purification to the next step. A small sample was purified by column chromatography for analytical purposes to afford white crystals mp 175-176° C. $^1$H NMR (CDCl$_3$) 8.28 (dd, J=4.9 and 1.6 Hz, 1H), 7.82 (dd, J=7.5 and 1.6 Hz, 1H), 7.39 (dd J=7.5 and 4.9 Hz, 1H). MS 9FAB) m/z: 147 (M$^+$+1).

Step 5: 1H-Pyrazolo[3,4b]pyridine-3-carboxylic Acid Methyl Ester

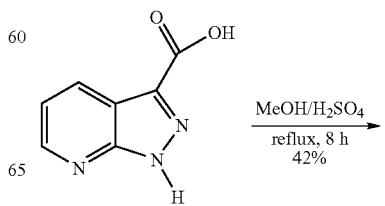

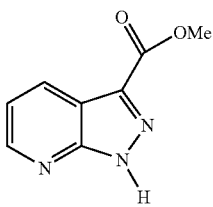

The mixture of solids from the preceding step 4 (95 g) was suspended in methanol (500 mL) and sulfuric acid (5 mL) was added carefully. The reaction mixture was then heated to reflux for 6-8 h, and the reaction was monitored using TLC. After completion of the reaction, inorganic solids were filtered off from the reaction mixture and the solid cake was washed with hot methanol. The main filtrate and the washings were combined, then methanol was distilled off under reduced pressure on the rotary evaporator. The resulting solids were suspended in 5% sodium bicarbonate solution (300 mL) and stirred for 5 min. at room temperature. The white solids were filtered off and dried in an oven at 90-95° C. to constant weight (8.07 g, 42% based on 3-methyl-1H-pyrazolo[3,4b]pyridine), mp 201-203° C. $^1$H NMR: (CDCl$_3$) 14.4 (brs, 1H), 8.74 (dd, J=4.6 and 1.5 Hz, 1H), 8.64 (dd, J=8.1 and 1.5 Hz, 1H), 7.39 (dd J=8.1 and 4.6 Hz, 1H), 4.10 (s, 3H).

Step 6: 1-(2,4-Dichlorobenzyl)-1H-pyrazolo[3,4b]pyridine-3-carboxylic Acid Methyl Ester

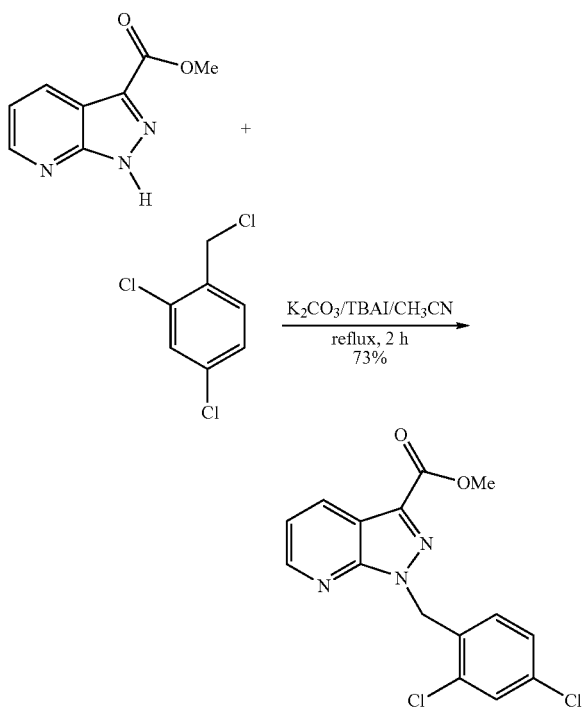

1H-Pyrazolo[3,4b]pyridine-3-carboxylic acid methyl ester (8 g, 0.0452 mol) was suspended in acetonitrile (200 mL) and the resulting suspension was stirred under heating for 10 min. in order to homogenize the solution. Potassium carbonate (31.2 g, 0.226 mol) was then added in one lot, followed by the addition of the tetrabutylammonium iodide (0.08 g, catalytic) and 2,4-dichlorobenzyl chloride (10.6 g, 0.0543 mol). The reaction mixture was heated to reflux for 2 h under good stirring. The reaction progress was monitored by TLC. After completion of the reaction, the mixture was cooled to room temperature and potassium carbonate was filtered off. Acetonitrile was distilled off under reduced pressure to afford the crude benzylated product. The crude product was purified using column chromatography (silica gel, eluent started with hexane then 8:2 hexane/ethyl acetate) to yield the pure product as white crystals (11 g, 73%) mp 135-136° C. $^1$H NMR (CDCl$_3$) 8.04 (dd, J=4.5 and 1.6 Hz, 1H), 8.58 (dd, J=8.1 and 1.6 Hz, 1H), 7.45 (d, J=2.0 Hz, 1H), 7.36 (dd, J=8.1 and 4.5 Hz, 1H), 7.10 (dd, J=8.3 and 2.0 Hz, 1H), 6.72 (d, J=8.3 Hz, 1H), 5.92 (s, 2H), 4.06 (s, 3H). MS (FAB) m/z: 336 (M$^+$+1).

Step 7: 1-(2,4-Dichlorobenzyl)-1H-pyrazolo[3,4b]pyridine-3-carboxylic Acid

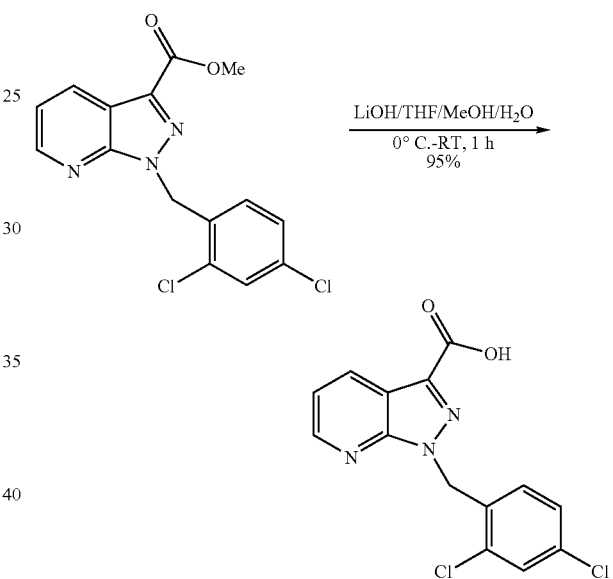

The benzylated methyl ester (4 g, 0.012 mol) was dissolved in a mixture of tetrahydrofuran (60 mL) and methanol (30 mL). A lithium hydroxide solution (1 g, 0.040 mol, lithium hydroxide in 15 mL water) was added slowly at room temperature under good stirring. The reaction was completed (monitored by TLC) after stirring for 1 h. The reaction mixture was diluted with water and extracted with ethyl acetate in order to remove neutral impurities. The layers were separated and the aqueous layer was cooled to 0° C. and acidified with 20% sulfuric acid to pH 2. The white solids that precipitated were filtered and dried to constant weight. The crude product was recrystallized from ethyl acetate and hexane (6:4) to afford the pure product (3.48 g, 95%), mp 233-235° C. HPLC purity 99.98%. $^1$H NMR (CDCl$_3$) 9.12 (dd, J=4.5 and 1.5 Hz, 1H), 9.00 (dd, J=8.1 and 1.5 Hz, 1H), 8.06 (d, J=2.1 Hz, 1H), 7.90 (dd J=8.1 and 4.5 Hz, 1H), 7.81 (d, J=8.3 Hz, 1H), 7.57 (d, J=8.3 Hz, 1H), 6.41 (2H, s). $^{13}$C NMR (DMSO/acetone-d-6) δ 169.9, 152.0, 150.7, 136.6, 134.7, 134.5, 134.3, 132.4, 132.2, 130.0, 128.6, 120.4, 116.1, 48.8. Anal. calcd. for C$_{14}$H$_{10}$ClNO$_2$: C, 52.17; H, 2.79; N, 13.04. Found: C, 51.94; H, 2.51; N, 13.06. HRMS (FAB) m/z calcd. for C$_{14}$H$_{10}$ClNO$_2$ 322.0150, found 322.0159.

Example 4

Ames Test for Mutigenicity

The Ames test was performed on the compounds of the present invention. The procedure involved the following steps:

1. Bacteria Culture (Strain *Salmonella Typhimurium* TA 100)

A lyophilized disc of *S. typhimurium* TA 100 left over from the Muta-Chromoplate Kit Version 3.0 (obtained from Environmental Bio-Detection Products, inc. (EBIP), 14 Abacus Road, Brampton, Ontario, Canada, L6T 5B7) was placed in 5.0 ml of Difco Nutrient Broth (2 g/L, pH 7.40) or Oxoid broth No. 2 in a 13×100 mm sterile culture tube. The material was incubated for 24 hours at 37° C. with the cap slightly loosened. Turbidity was evaluated the next day.

Following the above initial preparation, the bacteria were mixed with DMSO (0.09 ml of DMSO per 1.0 ml of bacteria culture) and divided into 500 µl aliquots in sterile centrifuge tubes and stored at −80° C. For this assay, one tube was thawed and placed into 5.0 ml of Oxoid broth the night before the assay was run. On the following day, checks for the rfa mutation were performed.

2. Rfa Mutation Test

Two nutrient agar plates were placed in a 37° C. incubator 30 minutes to an hour before preparing the top agar. The plates were removed just before adding the culture in step 3.

A bottle of the top agar was melted and 2 ml was placed in a 13×100 mm sterile culture tube. The tube was placed in a heating block at 45° C. About 0.1 ml of a bacteria culture was grown overnight in the 2 ml of agar. As soon as possible after adding the culture, the tube was vortexed and the material was poured onto the nutrient agar plate. The plates were placed on a level surface for several minutes to allow the top agar to become firm.

About 10 µl of sterile Crystal Violet (0.1 g/100 ml) was placed onto a sterile ¼ inch round disk made from Whitman 1 filter paper. The disc was gently pressed into the top agar. The plates were placed into a humidified 37° C. degree incubator. The plates were checked every 12 hours to 16 hours for a zone of inhibition around the disks.

For this test, a zone of inhibition of 12 mm was noted in the first plate and 12 mm in the second indicating the rfa mutation was intact.

3. Histidine Requirement

This test ensures that the His⁻ mutation is still functional. Using a broth culture grown overnight from a frozen aliquot from, a small sample of the culture was spread over a histidine/biotin plate using a platinum 20 µl loop. The plate was inverted and placed in a 37° C. incubator overnight.

At the same time, a small amount of the culture broth was removed and placed in a sterile 500 µl centrifuge tube. The tube was spun for 10 minutes at 3000 rpm on a Fisher Marathon 13K microcentrifuge. The broth was removed and the bacteria was re-suspended in sterile 10 mM Tris, pH 7.40. The bacteria was placed on a biotin plate and incubate overnight.

The histidine/biotin plates should show growth along the streaked areas while the biotin only plates should show no growth. The colonies from the Histidine/Biotin plates can be used as master plates to make new cultures, including those to be frozen and stored at −80° C.

4. Bacteria Cultures for Mutagenicity Assay

About 600 µl of the culture was placed into 7.0 ml of nutrient broth (Oxoid Broth No. 2) in a 13×100 mm culture tube. The tube was incubated at 37° C. for approximately 12 hours. About 600 µl of the culture was placed into another 7.0 ml of nutrient broth in a 13×100 mm culture tube and incubated at 37° C. for approximately 12 hours. Both tubes were combined in a sterile 15 ml conical immediately prior to use. This is the test culture used for inoculating plates and making the dilutions used for determining culture density.

The tubes were rechecked for the His⁻ mutation using the procedure listed above.

5. Bacterial Culture Density Check

The cultures contained around $2 \times 10^8$ bacteria/plate for optimal results. The best means of testing was with a turbidometer at 650 nm. Concentration was determined by making serial dilutions and plating them out in duplicate at the time of the mutagenicity assay.

6. Mutagenicity Assay

About 10 ml of the 0.5 mM histidine/biotin solution was added to 100 ml of top agar. The agar was melted in a water bath at 60-70° C. The minimal glucose plates were placed in a 37° C. incubator 30-45 minutes prior to starting the assay.

The test compound was dissolved in DMSO (Fisher D128-500) and made a 1 to 10 and 1 to 100 dilution. For example:

| Compound | wt. of compound (g) | ml of DMSO |
|---|---|---|
| RC-MC-110 | 0.1001 | 1.0 ml |
| RC-MC-86 | 0.1001 | 1.0 ml |

The solution was sterilized with a 0.22 µM Nylon syringe filter. (Fisher, 09-719C). Then, about 80 µl of the above 100 mg/ml solution was pipetted into 720 µl of sterile DMSO to obtain a 10 mg/ml solution.

The positive mutagens were prepared as follows:

Sodium azide (15 µg/ml). About 3 mg (Actual wt.=0.0030 g, FisherBiotech BP922-500) was dissolved in 2 ml of sterile water and then diluted by placing 1 ml of the above 1500 µg/ml solution in 9 ml of sterile water. About 1 ml of the 150 µg/ml solution was placed in 9 ml of sterile water to yield the final 15 µg/ml solution. This solution was sterilized by placing it in a 10 ml syringe and passing it through a 0.20 µm nylon filter (Fisherbrand 09-719C).

Amino anthracene (25 µg/ml). About 5 mg of amino anthracene (Actual wt.=0.0050 g, 2-Anthramine, Sigma A-1381) was dissolved in 2 ml of ethanol (Fisher A-405-20) to obtain a 2500 µg/ml solution. About 0.5 ml of the 2500 µg/ml solution was placed in 4.5 ml of ethanol to obtain a 250 µg/ml solution. About 0.5 ml of the 250 µg/ml solution was placed in 4.5 ml of ethanol to obtain a 25 µg/ml solution. This solution was sterilized by placing it in a 10 ml syringe and passing it through a 0.20 µm nylon filter (Fisherbrand 09-719C).

The S9 solutions were prepared as follows:

| Ingredient | (+)S9 mix | (−) S9 mix |
|---|---|---|
| Sterile $H_2O$ | 9.88 ml | 10.88 ml |
| 0.2M phosphate buffer (pH 7.4) | 12.5 ml | 12.5 ml |
| 0.1M NADP | 1.0 ml | 1.0 ml |
| 1M glucose-6-phosphate | 0.125 ml | 0.125 ml |
| $MgCl_2$—KCl salt solution | 0.5 ml | 0.5 ml |
| S9 enzyme preparation | 1.0 ml | 0 ml |

The S9 was obtained from Moltox (Sprague-Dawley, Phenobarbital-5,6-Benzoflavone). The solutions were added in the order indicated and kept on ice even during the assay until added to the top agar solution.

Six 13×100 mm culture tubes were placed in a heating block at 45° C. for a few minutes prior to use. About 2 ml of the molten top agar containing the 0.5 mM histidine/biotin solution was pipetted into each tube. The bacterial broth culture was removed placed on a minimal glucose plate for each tube from the incubator. Then, 0.1 ml of the drug, buffer or solvent was added to the top agar.

About 0.1 ml of the bacteria culture was then added. Then, the appropriate S9 solution was added to the tube and immediately vortexed. The top agar was placed onto the pre-warmed minimal glucose plate and swirled to get uniform distribution.

Each test compound was run with both the (+)S9 mix and (−)S9 mix with the following exceptions: (1) sodium azide—(−)S9 only (positive control for bacterial mutation; and (2) amino anthracene—(+)S9 only (positive control for S9 activation).

All plates were incubated for 48 hours at 37° C. The plates were removed and inspected for colony count.

The following table summarizes the results of the Ames test with respect to the compounds of the present invention:

| Compound | (+)S9 10 mg/pl. | (+)S9 1 mg/pl. | (+)S9 0.1 mg/pl. | (−)S9 10 mg/pl. | (−)S9 1 mg/pl. | (−)S9 0.1 mg/pl. |
|---|---|---|---|---|---|---|
| RC-MC-30 | Pass | Pass | Pass | Pass | Pass | Pass |
| RC-MC-60* | Pass | Pass | Pass | Pass | Pass | Pass |
| RC-MC-65 | Fail | Fail | Pass | Fail | Fail | Pass |
| RC-MC-86 | Pass | Pass | Pass | Pass | Pass | Pass |
| RC-MC-100 | Pass | Pass | Pass | Pass | Pass | Pass |
| RC-MC-101 | Pass | Pass | Pass | Pass | Pass | Pass |
| TH-2-178 | Pass | Pass | Pass | Pass | Pass | Pass |
| TH-2-179 | Pass | Pass | Pass | Pass | Pass | Pass |
| RC-MC-110 | Pass | Pass | Pass | Pass | Pass | Pass |
| DD-MC-1 | Pass | Pass | Pass | Pass | Pass | Pass |
| DD-MC-II | Pass | Pass | Pass | Pass | Pass | Pass |
| AD-1-115-21 | Pass | Pass | Pass | Pass | Pass | Pass |
| AD-1-117-19 | Pass | Pass | Pass | Pass | Pass | Pass |
| AD-1-131-14 | Pass | Pass | Pass | Pass | Pass | Pass |
| AG-2-51* | Pass | Pass | Pass | Pass | Pass | Pass |
| JWS-1-110 | Pass | Pass | Pass | Pass | Pass | Pass |
| JWS-1-112* | Pass | Pass | Pass | Fail | Fail | Pass |
| JWS-1-114 | Pass | Pass | Pass | Pass | Pass | Pass |
| JWS-1-130 | Pass | Pass | Pass | Pass | Pass | Pass |
| JWS-1-132 | Pass | Pass | Pass | Pass | Pass | Pass |
| JWS-1-140 | Pass | Pass | Pass | Pass | Pass | Pass |
| JWS-1-142 | Pass | Pass | Pass | Pass | Pass | Pass |
| JWS-1-144 | Pass | Pass | Pass | Pass | Pass | Pass |
| JWS-1-146* | Pass | Pass | Pass | Pass | Pass | Pass |
| JWS-1-158 | Pass | Pass | Pass | Pass | Pass | Pass |
| JWS-1-160 | Pass | Pass | Pass | Pass | Pass | Pass |
| JWS-1-162 | Pass | Pass | Pass | Pass | Pass | Pass |
| JWS-1-170 | Pass | Pass | Pass | Pass | Pass | Pass |
| JWS-1-190 | Pass | Pass | Pass | Pass | Pass | Pass |
| JWS-1-228 | Pass | Pass | Pass | Pass | Pass | Pass |
| JWS-1-230 | Pass | Pass | Pass | Pass | Pass | Pass |
| JWS-1-232 | Pass | Pass | Pass | Pass | Pass | Pass |
| JWS-1-254 | Pass | Pass | Pass | Pass | Pass | Pass |
| JWS-1-258 | Pass | Pass | Pass | Pass | Pass | Pass |
| JWS-1-260 | Pass | Pass | Pass | Pass | Pass | Pass |
| JWS-1-268 | Pass | Pass | Pass | Pass | Pass | Pass |
| JWS-1-270 | Pass | Pass | Pass | Pass | Pass | Pass |
| JWS-1-274 | Pass | Pass | Pass | Pass | Pass | Pass |
| JWS-1-276 | Pass | Pass | Pass | Pass | Pass | Pass |
| JWS-1-280 | Pass | Pass | Pass | Pass | Pass | Pass |
| JWS-1-282 | Fail | Pass | Pass | Pass | Pass | Pass |
| JWS-1-284 | Fail | Fail | Pass | Fail | Fail | Pass |
| JWS-1-294 | Pass | Pass | Pass | Pass | Pass | Pass |
| JWS-1-298 | Fail | Fail | Pass | Fail | Fail | Pass |
| JWS-1-300 | Fail | Fail | Pass | Fail | Fail | Pass |
| JWS-1-302 | Fail | Pass | Pass | Pass | Pass | Pass |
| JWS-2-1 | Pass | Pass | Pass | Fail | Marginal | Pass |
| JWS-2-10 | Pass | Pass | Pass | Pass | Pass | Pass |
| JWS-2-12 | Pass | Pass | Pass | Pass | Pass | Pass |
| JWS-2-14 | Fail | Pass | Pass | Fail | Fail | Pass |
| JWS-2-18 | Fail | Fail | Pass | Marginal | Pass | Pass |
| JWS-2-20 | Fail | Fail | Pass | Fail | Fail | Marginal |
| JWS-2-22 | Pass | Pass | Pass | Pass | Pass | Pass |
| JWS-2-36 | Pass | Pass | Pass | Pass | Fail | Pass |
| JWS-2-40 | Pass | Pass | Pass | Marginal | Pass | Pass |
| RC-MC-156 | Pass | Pass | Pass | Pass | Pass | Pass |
| RC-MC-158 | Pass | Pass | Marginal | Pass | Pass | Pass |
| RC-MC-200 | Fail | Fail | Pass | Pass | Pass | Pass |
| RC-MC-205 | Fail | Fail | Pass | Marginal | Fail | Pass |
| TH-2-192 | Pass | Pass | Pass | Pass | Pass | Pass |

*Compounds indicated showed bactericidal activity at 1 or more high doses.

In the table, "Pass" indicates compounds that were not significantly above the control with respect to colony count (p<0.05).

7. Colormetric Ames Test Procedure

The following procedures were performed aseptically. First, the day before the assay, as late as possible in the day, the vial labeled "G" Nutrient Broth was dispensed into the vial labeled *S. typhimurium* TA100 (lyophilized). The mixture was incubated over night at 37° C. for about 16-18 hours.

In appropriate vial, about 50 mg of the test compound was weighed out. About 1 mL of DMSO was added, and the mixture was filter sterilized with 25 mm syringe filter into a sterile tube. The concentration of DMSO was noted.

In a sterile 50 mL tube, about 15 mL of sterile Davis Mingioli Salt (see Davis & Mingioli, Aromatic biosynthesis, VII. Accumulation of two derivatives of shikimic acid by bacterial mutants, J. Bacteriol. 1953. August; 66(2): 129-36) was pipetted. This salt solution (Muta Component "A") was comprised of (1) Milli-Q, 600 mL; (2) dipotassium phosphate, anhyd., 38.5 g; (3) monopotassium phosphate, anhyd. 11.0 g; (4) ammonium sulfate, 5.5 g; (5) trisodium citrate, 1.375 g; and (6) magnesium sulfate, 0.55 g. Appropriate volume of Milli-Q water was added to bring total volume to 1 L. Each component was dissolved one at a time in the above order. The solution was filtered through a 0.22 μm filter to remove sediment at a pH of about 7.3.

To the salt solution, small amounts of DMSO diluted compound was added, not to exceed 500 μl of DMSO. For example, about 100 μl aliquots of the DMSO diluted compound was added until the highest concentration is reached with compound still in solution. It was found that this may need to be repeated with a lower volume of DMSO diluted compound, if the compound falls out of solution and does not go back into solution with the addition of sterile DMSO and/or sonication for twenty minutes to an hour. The volume of DMSO diluted compound was noted in the total solution. When the highest concentration of compound was determined, an appropriate volume of sterile Davis Mingioli salts was added to bring the total volume of solution to 17.5 mL. The concentration of compound and DMSO in the test solution was then noted.

The components were then mixed in a 50 mL sterile tube labeled Reaction Mixture as follows: 21.62 mL of A+4.75 ml of B (D-glucose, 40% w/v)+2.38 mL of C (bromocresol purple, 5 mg/ml)+1.19 ml of D (D-biotin, 0.1 mg/ml)+0.060 ml (60 µl) of E (L-histidine, 0.1 mg/ml). The vial was vortexed and then set aside.

The S9 Mixture was prepared by reconstituting the S9 enzymes with 2.1 mL of sterile water. This was labeled "S9F." In a 50 mL tube labeled S9 Mixture, the following were mixed together (all available from EBIP): 0.4 mL of S9A ($MgCl_2$, 0.4 M and KCl, 1.65 M)+0.09 mL of S9B (glucose-6-phosphate, 1.0 M)+0.81 mL of S9C (nicotine amide di-nucleotide phosphate, 0.1 M)+9.98 mL of S9D (phosphate buffer, pH 7.4)+6.72 mL of S9E (sterile distilled water)+2 mL of S9F (Rate liver extract). The vial was vortexed and then set aside.

Sterile tubes were labeled as follows: Blank, Background I, Background II, Standard Mutagen, Compound 1 (–), Compound 1 (S9+), Compound 2 (–), Compound 2 (S9+), Compound 3 (–), Compound 3 (S9+). Next, about 2.5 mL of the reaction mix was added to each tube. Then, about 2 mL of the S9 mix was added to the Background II and the S9+ compounds. Next, to each of the compound vials, about 8 mL of the prepared compounds was added. The concentration of the compound in the final solution was noted. Then, about 100 µl of the standard mutagen was added to the Standard mutagen vial. ($NaN_3$ for non S9 activation and 2-aminoanthracene with S9 activation). The appropriate volume of sterile water was next added for a final volume of 17.5 mL. Then, about 5 µl of bacteria was added to each tube except the Blank. Each vial was vortexed and poured into a sterile multi-channel pipette boat, and pipette 200 µl per well into the 96 well plate with a multi channel pipetter. The plates were labeled, covered, placed in zip lock bag, and then incubated for 5 days at 37° C.

On day five of the incubation, the plates were removed from the incubator and placed in a laminar flow hood. The Blank was analyzed first. If there were any wells that were yellow, the test was considered contaminated and the results invalid. The plates were then scored visually in the following manner: (1) all yellow, partially yellow or turbid wells are scored as positives or (2) all purple wells are scored as negative (compare to negative control plates). The number of positive wells for each plate was recorded. The Background plates showed the level of spontaneous or background mutation of the assay organism. The results of each treatment plate were scored against the background mutations. For each treatment-plate, the statistical significance of the difference using the Table 4.1 provided with the kit was determined. See Gilbert, R. I., *The Anslysis of Flucutation Tests, Mutation Research*, at 283-289 (1980), which is incorporated by reference. If a treatment plate contained all purple wells, acute toxicity of the sample to the tester strain may have resulted.

Other references, which are incorporated by reference, with respect to the aformentione Ames Tests protocols, are as follows: Ames, B., F. Lee, and W. Durston. 1973. *An improved bacterial test system for the detection and classification of mutagens and carcinogens*. Proc. Natl. Acad. Sci. USA 70: 782-786; McCann, J., N. Spingarn, J. Kobori, and B. Ames. 1975a. *Detection of carcinogens as mutagens: Bacterial tester strains with R Factor plasmids*. Proc. Natl. Acad. Sci. USA 72 979-983; McCann, J., E. Choi, E. Yamasaki, and B. Ames. 1975b. *Detection of carcinogens as mutagens in the Salmonella/microsome test: Assay of 300 chemicals*. Proc. Natl. Acad. Sci. USA 72: 5135-5139; and Mortelmans K, and E. Zeiger. 2000. *The Ames Salmonella/microsome mutagenicity assay*. Mutat Res. 455: 29-60.

The results of the assay was as follows:

| Compound | Concentration | without S9 | with S9 |
|---|---|---|---|
| JWS-2-132 | 360.1 µM | Pass* | Pass* |
| TH-3-130 | 182.3 µM | Pass* | Pass* |
| JWS-2-92 | 3.40 µM | Pass* | Pass* |
| JWS-2-100 | 246 µM | Pass* | Pass* |
| JWS-2-102 | 3.28 µM | Pass* | Pass* |
| JWS-2-104 | 6.12 µM | Pass* | Pass* |
| JWS-2-110 | 5.77 µM | Pass* | Pass* |
| JWS-2-120 | 11.48 µM | Pass* | Pass* |
| JWS-2-122 | 2.57 µM | Pass* | Pass* |
| LN-2-4 | 11.9 µM | Pass* | Pass* |
| JWS-2-112 | 1.39 µM | Pass* | Pass* |

Example 5

In Vivo Antispermatogenic Testing in Long Evans Rats

Male Long Evans rats were ordered in at day 55 and allowed a quaratine period of 5 days prior to inoculation. Water and food were given ad libitum. The day prior to testing all animals are weighed.

When the rats were 60 days old, the test compound was taken out of the refrigerator, and 480 mg of material was weighed. The material was then dissolved in 6.00 ml of dimethyl sulfoxide ("DMSO") (Fisher, Certified ACS, D128-500) to yield an 80 mg/ml solution. This solution was used for injecting the rats in the 200 mg/kg range.

In the case of lonidamine, it was necessary to add 1% concentrated HCl and sonicate for approximately 15 minutes to solubilize and suspend the material. Ice was placed in the sonicator to prevent overheating during this time.

About 1.00 ml of the 80 mg/ml solution was then added to 7 ml of DMSO to yield a final concentration of 10 mg/ml. This solution was used for injecting the rats in the 25 mg/kg range.

Both the 80 mg/kg and 10 mg/kg solutions were kept wrapped in foil until immediately prior to use. For controls, the animals were injected with DMSO only (or DMSO+1% HCl in the case of lonidamine). The rats were then weighed immediately prior to injection. The weight was converted to kilograms, multiplied by the treatment concentration and then divided by the concentration of the solution for that group. As an example, 250 g in the 200 mg/kg treatment group would be calculated as follows:

(a.) (0.250 kg)(200 mg/kg)/(80 mg/ml)=0.625 or 0.63

(b) The injections for the controls were done in the same manner by calculating the amount they would receive if they were in one of the treatment groups. That is, a 250 g control rat would also receive 0.63 ml (c) The amount of solution calculated for each rat was then drawn up in a sterile 1 cc tuberculin syringe capped with a 21 gauge needle and injected i.p. into the upper part of the left lower quadrant of the animal. The syringe was pulled back prior to injection to insure that the needle was not in a blood vessel or organ.

The animal was placed back in its cage and observed closely for the next few hours, and thereafter were checked at least once a day. All surviving animal were re-weighed on the second day post-injection. Five days following injection, the animals were re-weighed for the final time and then euthanized by carbon dioxide asphyxiation. Immediately following asphyxiation the animal was opened with a mid-sagittal abdominal incision and both the left and right testes were removed. The testes were trimmed of any extraneous tissue and weighed.

Following weighing, about 7-10 puncture holes were placed in the tunica albuginea using a number 11 scalpel blade, and the testes was then placed into 6 ml of Bouin's fixative for at least 48 hours at 4° C. The Bouin's fixative was prepared by mixing together: 125 ml of saturated picric acid (Sigma), 25 ml of glacial acetic acid (Fisher, A38-500), 375 ml of 37% Formaldehyde (Fisher F79-500). Alternatively, the testes were fixed in 10% formalin.

In at least two of the animals in each group, the pancreas, right kidney and part of the liver, heart, spleen, and lung were removed and evaluated for toxic effects. See Example 6 below.

After 48 hours, the testes were removed and cut in half in the mid-coronal region, then placed back in Bouin's for an additional 48 hours. A similar process was performed with the 10% formalin for testes fixed in formalin. Following the second 48 hours, the tissues were removed, placed in embedding cassettes, and then in two washes of 70% Ethanol to attempt to remove some of the fixative. The tissues were then embedded in paraffin using the following protocol. (a) 70% Ethanol, 1 hour, (b) 80% Ethanol, 1 hour, (c) 95% Ethanol, 40 min, (d) 95% Ethanol, 40 min, (e) 95% Ethanol, 40 min, (f) 100% Ethanol, 40 min, (g) 100% Ethanol, 40 min, (h) 100% Ethanol, 40 min, (i) Xylene subst., 1 hour, (j) Xylene subst., 1 hour, (k) Paraffin, 1.5 hour, (l) Paraffin, 1.5 hour. Then sections at 5 μm were cut and stained with H&E.

FIGS. 1A, 1B, 1C, 1D, 1E, 2A, 2B (RC-MC-30), 3A, 3B, 3C, 3D, 3E, 4A, 4B (RC-MC-86), 5A, 5B, 5C, 5D, 5E, 6A, 6B, 6C, 6D, 6E, 6G (RC-MC-110) show the change in body weight, left and/or right testes weight, staging, tubular development, and histologic testes effects for some of the compounds in accordance with the present invention. These results show that spermatogenesis was inhibited using the compounds of the present invention without adversely affecting the body weight of the subject. See J. M. Whitsett et al., *Effect of Transitional Photoperiods on Testicular Development and Puberty in Male Deer Mice, J. Reprod. Fertil.* 72 (2):277-286 (1984).

The dose response for the compounds of the present invention is shown in the following table:

| Compound | Response 25 mg/kg | Mortality | Response 200 mg/kg | Mortality | Staging 25 mg/kg | Staging 200 mg/kg |
|---|---|---|---|---|---|---|
| Lonidamine | 2/5 | 0/5 | 5/5 | 0/5 | 4.7 | 1.8 |
| AF2785 | 1/5 | 0/5 | 3/4 | 2/6 | 5.5 | 3.4 |
| AF2364 | 3/5 | 0/5 | 5/5 | 0/5 | 3.5 | 2.1 |
| RC-MC-30 | 3/5 | 0/5 | 4/5 | 0/5 | 4.1 | 3.1 |
| RC-MC-60 | 0/5 | 0/5 | 0/5 | 0/5 | NA | NA |
| RC-MC-86 | 0/5 | 0/5 | 5/5 | 0/5 | 5.9 | 2.4 |
| RC-MC-101 | 0/5 | 0/5 | 0/5 | 0/5 | NA | NA |
| RC-MC-100 | 0/5 | 0/5 | 0/5 | 0/5 | 5.9 | 5.9~ |
| TH-2-192 | 0/5 | 0/5 | 0/4 | 4/5 | 5.9 | 5.8 |
| RC-MC-110 | 5/5 | 0/5 | 2/2 | 3/5 | NA | NA |
| DD-MC-1 | 0/5 | 0/5 | 2/5 | 0/5 | NA | NA |
| JWS-1-254 | 0/5 | 0/5 | 0/5 | 0/5 | NA | NA |
| JWS-1-270 | 0/5 | 0/5 | 0/5 | 0/5 | NA | NA |
| JWS-1-274 | 0/5 | 0/5 | 0/5 | 0/5 | NA | NA |
| JWS-1-276 | 0/5 | 0/5 | 0/5 | 0/5 | NA | NA |
| JWS-1-280 | 0/5 | 0/5 | 0/5 | 0/5 | NA | NA |
| JWS-2-12 | 0/5 | 0/5 | 0/5 | 0/5 | NA | NA |
| DD-MC-I | 0/5 | 0/5 | 2/5 | 0/5 | 5.9 | 4.5 |
| JWS-1-110 | 0/5 | 0/5 | 0/5 | 0/5 | NA | NA |
| JWS-1-114 | 1/5 | 0/5 | 0/5 | 0/5 | NA | NA |
| JWS-130 | 0/5 | 0/5 | 0/5 | 0/5 | NA | NA |
| JWS-1-142 | 0/5 | 0/5 | 0/5 | 0/5 | NA | NA |
| JWS-1-144 | 0/5 | 0/5 | Not tested due to insolubility | N/A | NA | NA |
| JWS-1-146 | 0/5 | 0/5 | Not tested due to insolubility | N/A | NA | NA |
| JWS-1-158 | 4/5 | 0/5 | 5/5 | 0/5 | NA | NA |
| JWS-1-160 | 3/5 | 0/5 | 3/3 | 2/5 | NA | NA |
| JWS-1-170 | 3/5 | 0/5 | 3/3 | 0/5 | 3.7 | 2.8 |
| JWS-1-190 | 5/5 | 0/5 | 0/0 | 5/5 | NA | |
| RC-MC-156 | 2/5 | 0/5 | 4/5 | 0/5 | NA | |
| RC-MC-158 | 2/5 | 0/5 | 5/5 | 0/5 | NA | |
| TH-2-178 remake TH-2-193 | 0/5 | 0/5 | 4/5 | 0/5 | 5.4 | 2.9 |
| TH-2-179 remake TH-2-194 | 2/5 | 0/5 | 5/5 | 0/5 | 4.7 | 2.0 |
| JWS-1-190 | 4/5 | 0/5 | 2/5 | 0/5 | 5/5 | 0/5 |

For dose response, the fraction represents the number of animals responding out of five and the animals surviving out of five. For the mortality, the fraction represents the number of animals dead out of five injected.

Example 6

The toxicology of animals receiving some of the compounds of the present invention IP and/or oral was examined. At the time of sacrifice samples of liver, pancreas, heart, lung, spleen and kidney were removed, visually inspected, and immersion fixed in Bouin's solution for a minimum of 48 hours. All organs were then sectioned and examined for evidence of necrosis, inflammation, hemorrhage, and possible tumors. The major veins in each tissue were also examined for distention, especially in the liver and pancreas, and any other abnormalities are compared to known histopathological states. In addition to the above, the heart was examined for evidence of fibrosis in the muscular walls, and to compare the thickness of the ventricular walls. The pancreas was examined mainly for calcium deposits, while the lung was checked for signs of any exudates or hemorrhage, especially in the alveolar spaces. Finally, the kidney was examined mainly for microscopic hemorrhages, tubular necrosis or alterations in the glomeruli in the cortex.

Example 6A

Toxicology Comparison RC-MC-30 Versus Lonidamine

In this example, the effects of RC-MC-30 were compared with those of lonidamine in sexually mature rats. As discussed above, each of the rats (8 total) received a single injection and were sacrificed five days after injection and examined. The following tables illustrates the findings:

| Lonidamine | | | |
|---|---|---|---|
| | Liver and Pancreas | Kidney | Dosage mg/kg |
| Animal 101 | Non-remarkable, no evidence of inflammation, necrosis, hemorrhage or tumor | Non-remarkable, no evidence of inflammation, necrosis, hemorrhage or tumor | 25 |
| Animal 104 | Non-remarkable, no evidence of inflammation, necrosis, hemorrhage or tumor | Non-remarkable, no evidence of inflammation, necrosis, hemorrhage or tumor | 25 |
| Animal 37 | Some areas of the liver contained arteries and veins engorged with blood, while other areas did not appear to be congested. Otherwise, no evidence of inflammation, necrosis, hemorrhage or tumor. | Some engorgement of arteries, otherwise non-remarkable with no evidence of inflammation, necrosis, hemorrhage or tumor | 200 |
| Animal 40 | Same as for Animal 37 except that the Pancreas also had engorged arteries and veins | Swollen arterioles, large amounts of blood mainly between the proximal tubules | 200 |

| RC-MC-30 | | | |
|---|---|---|---|
| | Liver and Pancreas | Kidney | Dosage mg/kg |
| Animal 126 | Non-remarkable, no evidence of inflammation, necrosis, hemorrhage or tumor | Small areas with blood between the tubules, may have been due to the way it was cut. Otherwise no evidence of inflammation, necrosis, hemorrhage or tumor | 25 |
| Animal 127 | Non-remarkable, no evidence of inflammation, necrosis, hemorrhage or tumor | Same as for animal 126, a few more areas of possible hemorrhage | 25 |
| Animal 131 | Non-remarkable, no evidence of inflammation, necrosis, hemorrhage or tumor | Patchy hemorrhagic areas, some showing evidence of hemosiderin. Again could be due to cutting. Otherwise, no evidence of inflammation, necrosis, hemorrhage or tumor | 200 |
| Animal 132 | Non-remarkable, no evidence of inflammation, necrosis, hemorrhage or tumor | Patchy hemorrhagic areas, some showing evidence of hemosiderin. Again could be due to cutting. Otherwise, no evidence of inflammation, necrosis, hemorrhage or tumor | 200 |

Example 6B

Toxicology Results for RC-MC-110

In this example, the toxicology results of RC-MC-110 were investigated compared to controls. Two controls and four animals receiving RC-MC-110 were investigated.

In the two controls (Animal 261 and 262), the liver, lung, pancreas, spleen, heart and kidney all appeared within normal limits. No sign of necrosis or hemorrhage were apparent in any of the tissues. The heart showed no signs of dilation or hypertrophy in the ventricular walls.

Animals receiving 25 mg/kg and 200 mg/kg of RC-MC-110 were also investigated. The liver, lung, pancreas, spleen, heart and kidney all appear within normal limits in the two animals receiving 25 mg/kg (animal 266 and 267) and those receiving 200 mg/kg (animal 271 and 274). No sign of necrosis or hemorrhage in any of the tissues were revealed. The heart showed no signs of dilation or hypertrophy in the ventricular walls.

In a separate experiment, five animals were given 200 mg/kg of RC-MC-100. Approximately 10 minutes after IP injection, all 5 animals tested became lethargic and ceased moving. At 15 to 20 minutes post-injection, all of the animals in this group began to have minor tremors in both hindlimbs which lasted approximately 30 minutes. Two of the animals also had wet rales with their breathing being audible within 5 feet of their cage. Three of the animals died 2-3 hours later, while the other two recovered and did not show any other symptoms.

In a follow-up experiment, the toxicology of animals receiving 6 mg/kg and 12 mg/kg of RC-MC-110 were investigated. For Animal 286 (6 mg/kg), the lung, pancreas, spleen, heart and kidney all appeared within normal limits. There was no evidence of necrosis, tumor or hemorrhage in any of the tissues. The heart showed no sign of dilatation or hypertrophy in the ventricular walls. The liver did have isolated, scattered, small necrotic patches. For Animal 287 (6 mg/kg), the lung, pancreas, spleen, heart and kidney all appeared within normal limits. There was no evidence of necrosis, tumor or hemorrhage in any of the tissues. The heart showed no sign of dilatation or hypertrophy in the ventricular walls. The liver did have isolated, scattered, small necrotic patches, resembling what is often found in subacute hepatic necrosis.

For Animal 291 (12 mg/kg), the lung, pancreas, spleen, heart and kidney all appeared within normal limits. There was no evidence of necrosis, tumor or hemorrhage in any of the tissues. The heart showed no sign of dilatation or hypertrophy in the ventricular walls. The liver did have isolated, scattered, small necrotic patches, resembling what is often found in subacute hepatic necrosis. For Animal 292 (12 mg/kg), the pancreas, spleen, heart and kidney all appeared within normal limits. There was no evidence of necrosis, tumor or hemorrhage in any of the tissues. The heart did not show any signs of dilatation or hypertrophy in the ventricular walls. The liver contained small, patchy areas of necrosis resembling what is often described for subacute hepatic necrosis. The lungs also had multiple, small hemorrhagic areas around the respiratory and terminal bronchioles.

Example 6C

Toxicology Results for RC-MC-110 Compared to Lonidamine

In this example, the toxicology of animals receiving varying amounts of RC-MC-110 and 25 mg/kg of lonidamine were investigated. Controls were corn oil only.

In the two controls using corn oil (Animals 326 and 327) and those receiving 25 mg/kg of lonidamine (Animals 356 and 357), the liver, lung, pancreas, spleen, heart and kidney all appeared normal. There was no evidence of necrosis, tumor or hemorrhage in any of the tissues. The heart showed no sign of dilatation or hypertrophy in the ventricular walls.

In two animals from each of the four dose levels of oral 6 mg/kg, 3 mg/kg, 1 mg/kg and 0.5 mg/kg of RC-MC-110 (Animal 331 and 332), the liver, lung, pancreas, spleen, heart and kidney all appeared within normal limits. There was no evidence of necrosis, tumor or hemorrhage in any of the tissues. In one animal receiving 1.5 mg/kg of RC-MC-110 (Animal 341), the liver showed a small number of randomly scattered, small necrotic patches, but was otherwise normal. The other animal receiving 1.5 mg/kg appeared normal.

Example 6D

Toxicology Results for JWS-1-110

In this example, the toxicology of animals receiving 25 mg/kg and 200 mg/kg of JWS-1-110 were investigated. Controls were DMSO only. For Animal 306 (25 mg/kg), the liver, lung, pancreas, heart and kidney all appeared within normal limits. There was no sign of necrosis, tumor or hemorrhage in any of the tissues. The heart did not have any signs of dilatation or hypertrophy in the ventricular walls. The spleen had distended veins and necrosis in the white pulp, often early indicators of portal hypertension. The pancreas, heart and kidney of Animal 307 (25 mg/kg) all appeared within normal limits. There was no sign of necrosis, tumor, or hemorrhage in any of the tissues. The heart did not have any signs of dilatation or hypertrophy in the ventricular walls. The liver had distended portal veins with surrounding small patches of hepatic necrosis. The lung contained scattered hemorrhagic areas around the alveoli and terminal bronchioles. Also, the spleen had distended veins and diminished amounts of white pulp containing necrotic cells.

For Animal 311 (200 mg/kg), the kidney, heart and pancreas appeared to be within normal limits with no signs of necrosis, tumor or hemorrhage. The heart did not have any signs of dilatation or hypertrophy in the ventricular walls. The liver showed distended portal veins with scattered, small patches of necrosis. The lung contained multiple hemorrhagic areas throughout the alveoli, and terminal and respiratory bronchioles. Some of these hemorrhagic patches were causing distention between adjacent compartments. Finally, the spleen demonstrated distended veins, and diminished white pulp with necrotic cells. For Animal 312 (200 mg/kg), the kidney, heart, and lung appeared to be within normal limits with no signs of necrosis, tumor or hemorrhage. The heart was split so it was not possible to determine if ventricular dilatation is present, but there did not appear to be any hypertrophy of the ventricular walls. The liver had distended veins, with scattered, small patches of necrosis throughout. The pancreas had distended veins, but no other noticeable abnormalities. Finally, the spleen demonstrated distended veins, and diminished white pulp with necrotic cells.

Example 6E

Toxicology Results for JWS-1-114

In this example, the toxicology of animals receiving 25 mg/kg and 200 mg/kg of JWS-1-114 were investigated. Controls were DMSO only. Animals 316 and 317 (25-mg/kg) had a liver, lung, pancreas, spleen, heart and kidney that appeared within normal limits. There was no sign of necrosis, tumor or hemorrhage in any of the tissues. The heart did not have any signs of dilatation or hypertrophy in the ventricular walls.

Animal 321 (200 mg/kg) had a pancreas, heart, and kidney that appeared within normal limits. There was no sign of necrosis, tumor or hemorrhage in any of the tissues. The heart did not have any signs of dilatation or hypertrophy in the ventricular walls. The lung had massive pulmonary hemorrhaging around the bronchioles, with congested, distended regions between the alveolar clusters. The liver had moderate sized (5-10 cell in diameter) necrotic patches generally in the periportal areas, however, there was no evidence of venous distension. There was no spleen sample for this animal. Animal 322 (200 mg/kg) exhibited a liver, lung, pancreas, spleen, heart and kidney that appeared within normal limits. There was no sign of necrosis, tumor or hemorrhage in any of the tissues. The heart did not have any signs of dilatation or hypertrophy in the ventricular walls.

Example 6F

Toxicology Results for JWS-1-130

In this example, the toxicology of animals receiving 25 mg/kg and 200 mg/kg of JWS-1-130 were investigated. Controls were corn oil only. For Animal 366 (25 mg/kg), the lung, pancreas, spleen, heart and kidney all appeared within normal limits. There was no sign of necrosis, tumor or hemorrhage, although the heart did have some artificial tears from cutting the section out from the ventricles. The heart showed no evidence of hypertrophy or dilation in the ventricular walls. The liver appeared to have distended veins throughout, but no other abnormalities were noted. For Animal 367 (25 mg/kg), the lung, pancreas, spleen, heart and kidney all appeared within normal limits. There was no sign of necrosis, tumor or hemorrhage in any of the tissues. The heart did not have any signs indicating dilation or hypertrophy in the ventricular walls. The liver did have distended veins throughout, with small scattered patches of necrosis, usually located around the periportal areas.

For Animal 371 (200 mg/kg), the liver, lung, pancreas, spleen, heart and kidney all appeared within normal limits. There was no sign of necrosis, tumor or hemorrhage in any of the tissues. The heart did not have any signs indicating dilation or hypertrophy in the ventricular walls. For Animal 372, the lung, pancreas, spleen, heart and kidney all appeared within normal limits. There was no sign of necrosis, tumor or hemorrhage in any of the tissues. The heart did not have any signs indicating dilation or hypertrophy in the ventricular walls. The liver did have distended veins throughout, with small scattered patches of necrosis, usually located around the periportal areas.

Example 6G

Toxicology Results for JWS-1-142

In this example, the toxicology of animals receiving 25 mg/kg and 200 mg/kg of JWS-1-142 were investigated. Controls were corn oil only. For both Animal 376 and 377 (25 mg/kg), the liver, lung, pancreas, spleen, heart and kidney all appeared within normal limits. There was no sign of necrosis, tumor or hemorrhage in any of the tissues. The heart did not have any signs indicating dilation or hypertrophy in the ventricular walls.

For Animal 381 (200 mg/kg), the lung, pancreas, spleen, heart and kidney all appeared within normal limits. There was no sign of necrosis, tumor or hemorrhage in any of the tissues. The heart did not have any signs indicating dilation or hypertrophy in the ventricular walls. The liver contained a small, confined cluster of lymphocytes in the parenchyma. For Animal 382 (200 mg/kg), the liver, lung, pancreas, spleen, heart and kidney all appeared within normal limits. There was no sign of necrosis, tumor or hemorrhage in any of the tissues. The heart did not have any signs indicating dilation or hypertrophy in the ventricular walls.

Example 6H

Toxicology Results for JWS-1-146

In this example, the toxicology of animals receiving 25 mg/kg of JWS-1-146 were investigated. Controls were corn oil only. Animal 396 and 397 (25 mg/kg) had a liver, lung, pancreas, spleen, heart and kidney that appeared within normal limits. There was no sign of necrosis, tumor or hemorrhage in any of the tissues. The heart did not have any signs indicating dilation or hypertrophy in the ventricular walls.

Example 6I

Toxicology Results for JWS-1-144

In this example, the toxicology of animals receiving 25 mg/kg of JWS-1-144 were investigated. Controls were DMSO only. Animal 441 and 442 (25 mg/kg) had a liver, lung, pancreas, spleen, heart and kidney that appeared within normal limits. There was no sign of necrosis, tumor or hemorrhage in any of the tissues. The heart did not have any signs indicating dilation or hypertrophy in the ventricular walls.

Example 6J

Toxicology Results for JWS-1-170

In this example, the toxicology of animals receiving 25 mg/kg and 200 mg/kg of JWS-1-170 were investigated. Controls were DMSO only. Animal 456 and 457 (25 mg/kg) had a liver, lung, pancreas, spleen, heart and kidney that appeared within normal limits. There was no sign of necrosis, tumor or hemorrhage in any of the tissues. The heart did not have any signs indicating dilation or hypertrophy in the ventricular walls For Animal 462 (200 mg/kg), the liver, lung, pancreas, spleen, heart and kidney all appeared within normal limits. There was no evidence of necrosis, tumor, or hemorrhage in any of the tissues. The heart showed no sign of dilatation or hypertrophy in the ventricular walls. For Animal 463 (200 mg/kg), the lung, pancreas, spleen, heart and kidney all appeared within normal limits. There was no evidence of necrosis, tumor, or hemorrhage in any of the tissues. The heart showed no sign of dilatation or hypertrophy in the ventricular walls. The liver did have moderate patches (5-10 cells in diameter) of necrosis mainly in the periportal areas.

Example 6K

Toxicology Results for JWS-1-190

In this example, the toxicology of animals receiving 25 mg/kg of JWS-1-190 were investigated. Controls were DMSO only. For Animal 466, the liver, pancreas, spleen, heart and kidney all appeared within normal limits. There is no evidence of necrosis, tumor, or hemorrhage in any of the tissues. The heart did not show any sign of dilatation or hypertrophy in the ventricular walls. The lung did have multiple, scattered hemorrhagic patches in the alveolar clusters, and many of the alveoli were filled with a clear exudates that appeared to stain lightly with eosin. For Animal 467, the liver, lung, pancreas, spleen, heart and kidney all appeared within normal limits. There was no evidence of necrosis, tumor, or hemorrhage in any of the tissues. The heart showed no sign of dilatation or hypertrophy in the ventricular walls.

Example 6L

Toxicology Results for RC-MC-156

In this example, the toxicology of animals receiving 25 mg/kg and 200 mg/kg of RC-MC-156 were investigated. Controls were DMSO only. For Animal 476 (25 mg/kg), the liver, pancreas, spleen, heart and kidney all appeared within normal limits. There was no evidence of necrosis, tumor, or hemorrhage in any of the tissues. The heart did not show any signs of dilatation or hypertrophy in the ventricular walls. The lung did have scattered small, hemorrhagic patches, mainly in the alveolar and terminal bronchiole regions. For Animal 477 (25 mg/kg), the liver, pancreas, spleen, heart and kidney all appear within normal limits. There was no evidence of necrosis, tumor, or hemorrhage in any of the tissues. The heart did not show any signs of dilatation or hypertrophy in the ventricular walls. The lung showed widespread hemorrhagic regions throughout the alveoli and terminal bronchioles with small hemosiderin deposits around a few smaller bronchioles.

For Animal 481 (200 mg/kg), the liver, lung, pancreas, spleen, heart and kidney all appeared within normal limits. There was no evidence of necrosis, tumor, or hemorrhage in any of the tissues. The heart shows no sign of dilatation or hypertrophy in the ventricular walls. For Animal 482 (200 mg/kg), the pancreas, spleen, heart and kidney all appear within normal limits. There was no evidence of necrosis, tumor, or hemorrhage in any of the tissues. The heart showed no sign of dilatation or hypertrophy in the ventricular walls. The lung had small, scattered areas of hemorrhage mainly around the alveoli and small bronchioles. The liver had small (4-5 cells in diameter) patches of necrosis scattered throughout the parenchyma which resembles what is normally found in subacute necrosis.

Example 6M

Toxicology Results for RC-MC-158

In this example, the toxicology of animals receiving 25 mg/kg and 200 mg/kg of RC-MC-158 were investigated. Controls were DMSO only. For Animal 486 (25 mg/kg), the liver, lung, pancreas, spleen, heart and kidney all appeared within normal limits. There was no evidence of necrosis, tumor, or hemorrhage in any of the tissues. The heart shows no sign of dilatation or hypertrophy in the ventricular walls. For Animal 487 (25 mg/kg), the liver, pancreas, spleen, heart and kidney all appeared within normal limits. The lung did have small scattered hemorrhagic areas, mainly around the alveoli and terminal bronchioles.

For Animal 491 (200 mg/kg), the liver, pancreas, spleen, heart and kidney all appeared within normal limits. There was no evidence of necrosis, tumor or hemorrhage in any of the tissues. The heart showed no sign of dilatation or hypertrophy in the ventricular walls. The lung had multiple, large hemorrhagic areas, mainly in the alveolar regions with some hemosiderin deposits. For Animal 492, the pancreas, spleen, heart and kidney all appeared within normal limits. There was no evidence of necrosis, tumor or hemorrhage in any of the tissues. The heart showed no sign of dilatation or hypertrophy. The lung contained multiple large hemorrhagic areas, mainly in the alveoli. The liver contained small, scattered necrotic areas, generally around the portal veins.

Example 6N

Toxicology Results for JSW-1-158

In this example, the toxicology of animals receiving 25 mg/kg and 200 mg/kg of JSW-1-158 were investigated. Controls were DMSO only. Both controls had moderate areas of necrosis between the periportal areas, and the cytoplasm appeared to be washed out in many areas. For Animal 406 (25 mg/kg), the liver, lung, pancreas, spleen, heart and kidney all appeared within normal limits. There was no sign of necrosis, tumor or hemorrhage in any of the tissues. The heart showed no signs of dilatation or hypertrophy in the ventricles. For Animal 407, the liver, pancreas, spleen, heart and kidney all appeared within normal limits. There was no sign of necrosis, tumor or hemorrhage in any of the tissues. The heart showed no signs of dilatation or hypertrophy in the ventricles. The lung had thickening of the alveolar and bronchiole walls, and scattered areas of moderate sized hemorrhaging covering several adjacent alveoli.

For Animal 411 (200 mg/kg), the liver, lung, spleen, heart and kidney all appeared within normal limits. There was no sign of necrosis, tumor or hemorrhage in any of the tissues. The heart shows no signs of dilatation or hypertrophy in the ventricles. The pancreas had areas of lymphocytic infiltrates extending from the periphery inwards between the acinar cells. For Animal 412 (200 mg/kg), the liver, lung, pancreas, spleen, heart and kidney all appeared within normal limits. There was no sign of necrosis, tumor or hemorrhage in any of the tissues. The heart showed no signs of dilatation or hypertrophy in the ventricles.

Example 6O

Toxicology Results for JSW-1-160

In this example, the toxicology of animals receiving 25 mg/kg and 200 mg/kg of JSW-1-160 were investigated. Controls were DMSO only. Both controls had moderate areas of necrosis between the periportal areas, and the cytoplasm appeared to be washed out in many areas. For Animal 416 (25 mg/kg), the lung, pancreas, spleen and heart all appeared within normal limits. There was no sign of necrosis, tumor, or hemorrhage in any of the tissues. The heart showed no signs of dilatation or hypertrophy in the ventricles. The kidney does have scattered, small patches of tubular necrosis in the inner cortex, closer to the medullary-cortical border than the periphery. The liver had several distended veins, but no other abnormalities were noted. For Animal 417 (25 mg/kg), the liver, lung, pancreas, spleen, heart and kidney all appeared within normal limits. There was no sign of necrosis, tumor or hemorrhage in any of the tissues. The heart showed no signs of dilatation or hypertrophy in the ventricles.

For Animal 421 (200 mg/kg), the liver, lung, pancreas, spleen, and heart all appeared within normal limits. There was no sign of necrosis, tumor or hemorrhage in any of the tissues. The heart showed no signs of dilatation or hypertrophy in the ventricles. The kidney did have scattered, small patches of tubular necrosis in the inner cortex. For Animal 422, the liver, lung, pancreas, spleen, heart and kidney all appeared within normal limits. There was no sign of necrosis, tumor or hemorrhage in any of the tissues. The heart showed no signs of dilatation or hypertrophy in the ventricles.

Example 6P

Toxicology Results for JSW-1-162

In this example, the toxicology of animals receiving 25 mg/kg and 200 mg/kg of JSW-1-162 were investigated. Controls were DMSO only. Both controls had moderate areas of necrosis between the periportal areas, and the cytoplasm appeared to be washed out in many areas. For Animals 426 and 427 (25 mg/kg), the liver, lung, pancreas, spleen, heart and kidney all appeared within normal limits. There was no sign of necrosis, tumor or hemorrhage in any of the tissues. The heart showed no signs of dilatation or hypertrophy in the ventricles For Animal 431 (200 mg/kg), the liver, pancreas, spleen, heart and kidney all appeared within normal limits. There was no sign of necrosis, tumor or hemorrhage in any of the tissues. The heart showed no signs of dilatation or hypertrophy in the ventricles. The lung had scattered hemorrhagic patches surrounding many of the small bronchioles, generally with thickening of the alveolar walls in the immediate vicinity. For Animal 432 (200 mg/kg), the liver, pancreas, spleen, heart and kidney all appeared within normal limits. There was no sign of necrosis, tumor or hemorrhage in any of the tissues. The heart showed no signs of dilatation or hypertrophy in the ventricles. The lung had moderate regions showing thickening of the alveolar walls, with a clear exudates slightly stained by eosin filling the alveoli.

Example 7

Use as Anti-Cancer Agent

RC-MC-110 has been found to bind heat shock 90 proteins, HSP90, a ubiquitous protein found in many cancer cells. 3-D docking experiments with HSP90 (HSP83) N-terminal ATP binding site suggest that RC-MC-110 probably does not bind to the N-terminal ATP pocket, but may be a new more potent analogue that likely binds to the C-terminal ATP binding pocket of HSP-90.

To analyze the binding of the compounds of the present invention, the following procedure is used.

a. Basic Pre-Lysis buffer—50 mM Tris, pH 7.40, 0.050 M NaCl, 0.001% NP-40, 5 mM EDTA, 50 mM NaF b. Na Orthovanadate—Add 600 µl of 50 mM per 30 ml of lysis buffer c. Na pyrophosphate—Add 600 µl of 50 mM per 30 ml of lysis buffer d. Benzamidine—Add 3 ml of 100 mM per 30 ml of lysis buffer e. PMSF—Add 1.5 ml of 1 mg/ml per 30 ml of lysis buffer f. TPCK—Add 300 µl of 1 mg/ml per 30 ml of lysis buffer g. Aprotinin—Add 10 µl of 1 mg/ml per 30 ml of lysis buffer h. Trypsin inhibitor—Add 10 µl of 1 mg/ml per 30 ml of lysis buffer 2. Wash four 150 mm plates of TM4 cells (sertoli cells) or ID-8 cells (ovarian cancer) once with PBS (20 mM concentration pH 7.5). Add enough volume to trypsinize cells. Aspirate and spin cells for 10 minutes at 4° C. at 250×g. Add enough Lysis buffer to the cells.

3. Transfer the sample in a Dounce glass homogenizer. Use the tight pestle and homogenize the sample with 5-10 strokes to break the cells.

4. Let stand on ice for 30 minutes, then centrifuge at 16,500 rpm (37,500×g) using a JA-17 rotor for 10 minutes at 4° C.

5. Remove the cell lysate and apply the sample into a 2 ml avidin-sepharose (tetramer form) column (pre-equilibrated with 50 mM Tris-HCl/0.001% NP-40, pH 7.4) to remove native biotinylated compounds.

6. Take 2.7 ml of pre-cleared cell lysate and incubate the sample with RC-MC-110.

Tube 1: 2.7 ml of pre-cleared lysate plus 150 µl of 1.2 mg/ml biotinylated RC-MC-110+150 µl of DMSO (maintaining the same amount of DMSO in both tubes).

Tube 2: 2.7 ml of pre-cleared lysate plus 150 µl of 1.2 mg/ml of biotinylated RC-MC-110 (RC-MC-150, see structure below), and add 150 µl of 12 mg/ml RC-MC-110 stock. Incubate the sample overnight at 40° C. on a rocking platform (or gentle stirring) with gentle agitation.

7. Load samples on an avidin-sepharose column pre-equilibrated with buffer (50 mM Tris-HCl pH 7.4, 0.1% NP-40=TD buffer). Wash column until background is reached.

8. Wash column with 2.5 ml of 0.6 mg/ml of RC-MC-110 in TD buffer (stock 12 mg/ml) until peak elutes (if any) and stable background. Pool fractions.

9. Wash column with 2.5 ml of 250 mM NaCl in TD buffer. Pool fractions and proceed to next step.

10. Wash column with 2.5 ml 600 mM NaCl in TD buffer. Pool fractions and proceed to the next step.

11. Concentrate samples in a Centricon Y-10. Spin pooled fractions for 2 hours at 4° C. at 5000×g (6000 rpm JA-17); concentrate samples until a volume of 100-200 µl is obtained, this may take longer or less time than noted.

12. Invert the Centricon and spin for 5 minutes at 5000×g at 4° C. Add enough 4×SDS polyacrylated gel electrophoresis sample buffer to give a final 1× solution for SDS-Page. See Laemmli, *Cleavage of Structural Proteins During the Assembly of the Head of Bacteriophage T*4, Nature, Vol. 228, at pp. 680-85 (1970), which is incorporated by reference. Keep some protein for protein assay prior to adding sample buffer.

13. Perform electrophoresis on a 5-20% acrylamide gradient gel. (Large gel)

14. At the end of the run, stain the gel with Coomassie brilliant blue ("CBB")-G250.

15. CBB G-250 Coomassie Staining Solution a. Dissolve 1 g (Actual wt. 1.0006 g, CBB G-250, Fisher-Biotech, BP100-25) in 20 ml of MilliQ water. Do not filter. Store at room temperature.

b. Dissolve 2 g of 85% Phosphoric Acid (Fisher A242-500) in 90 ml of MilliQ water. Dilute to a final volume of 100 ml with water.

c. Dissolve 10 g ammonium sulfate (Actual wt. 10.0010 g, Fisher A938-500) in approximately 80 ml of the 2% phosphoric acid prepared in step 11 b. Dissolve and dilute to a final volume of 99 ml.

d. Add 1 ml of the 5% CBB solution prepared in step 11 a to 99 ml of the ammonium sulfate/phosphoric acid solution prepared in step 11 c. Store at room temperature as a stock solution until immediately prior to use.

e. Immediately prior to use add 80 ml of the stock solution prepared in 11 d to 20 ml of methanol (Fisher, Certified ACS, A434-20)

16. Destaining solution—Add 250 ml of methanol to 750 ml of MilliQ water.

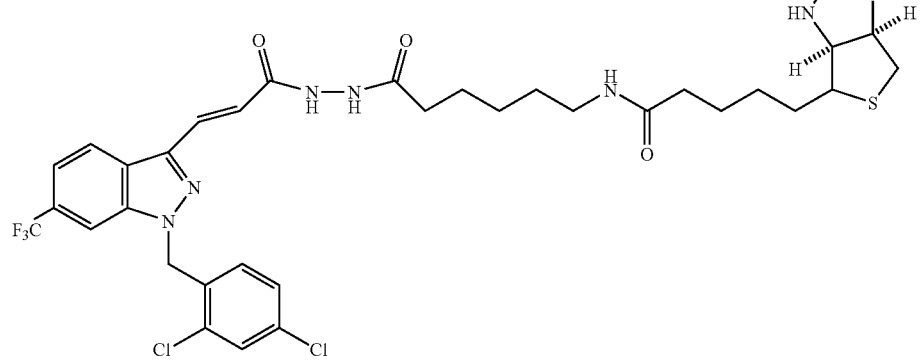

17. Silver stain method is preferred since there not enough protein for the coomassie blue staining. See Shevchenko et al., *Mass Spectrometric Sequencing of Proteins from Silver-Stained Polyacrylamide Gels*, Anal. Chem., Vol. 68, at pp. 850-58 (1996), which is incorporated by reference.

If at the end of the staining procedure there is an absence of any bands in the elution fractions, a silver stain is performed according to the method described below. (Suitable for MALDI-TOF).

After electrophoresis, the gel slabs are fixed for 20 minutes in 50% methanol, 5% Acetic acid. Then wash the gel with 50% methanol for 10 minutes followed with water for an additional 10 minutes. The gel is sensitized with 2% sodium thoisulfate for 1 min. Rinse the gels with 2 changes of water for one minute each. Incubate the gel for 20 minutes at 4° C. with chilled 0.1% silver nitrate. The silver nitrate solution is discarded and the gel rinsed twice with water for 1 minute each.

Develop the gel with 0.04%/(v/v) formalin [make the sodium carbonate solution (2% (w/v) and then add the necessary volume of formaldehyde to give a final concentration of 0.04% (v/v); 200 µl of formaldehyde (37% (w/w) stock, and weigh out 10 g of sodium carbonate (anhydrous) in 500 ml total volume. It is essential that the developing is carried out in clear solution in order to maintain a clear background. When desired intensity is achieved stop the reaction with 5% acetic acid in water, and store the gel in 1% acetic acid at 4° C.

Figure 7A:
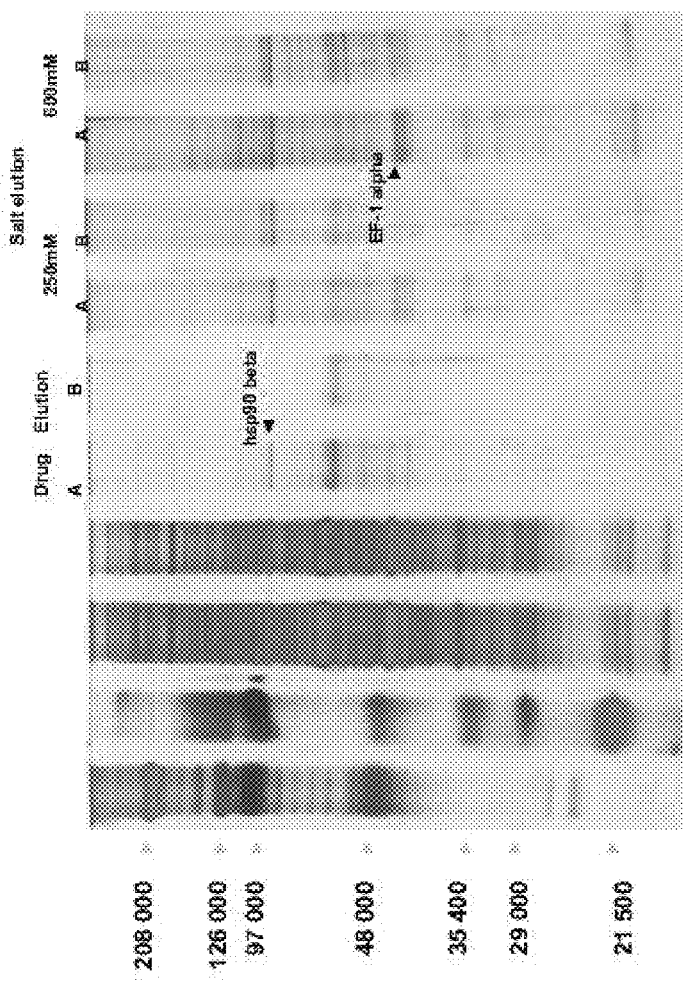
FIG. 7A shows the drug specific elution of Hsp90 from TM4 sertoli cell lines (mouse) for RC-MC-110.
Figure 7B:
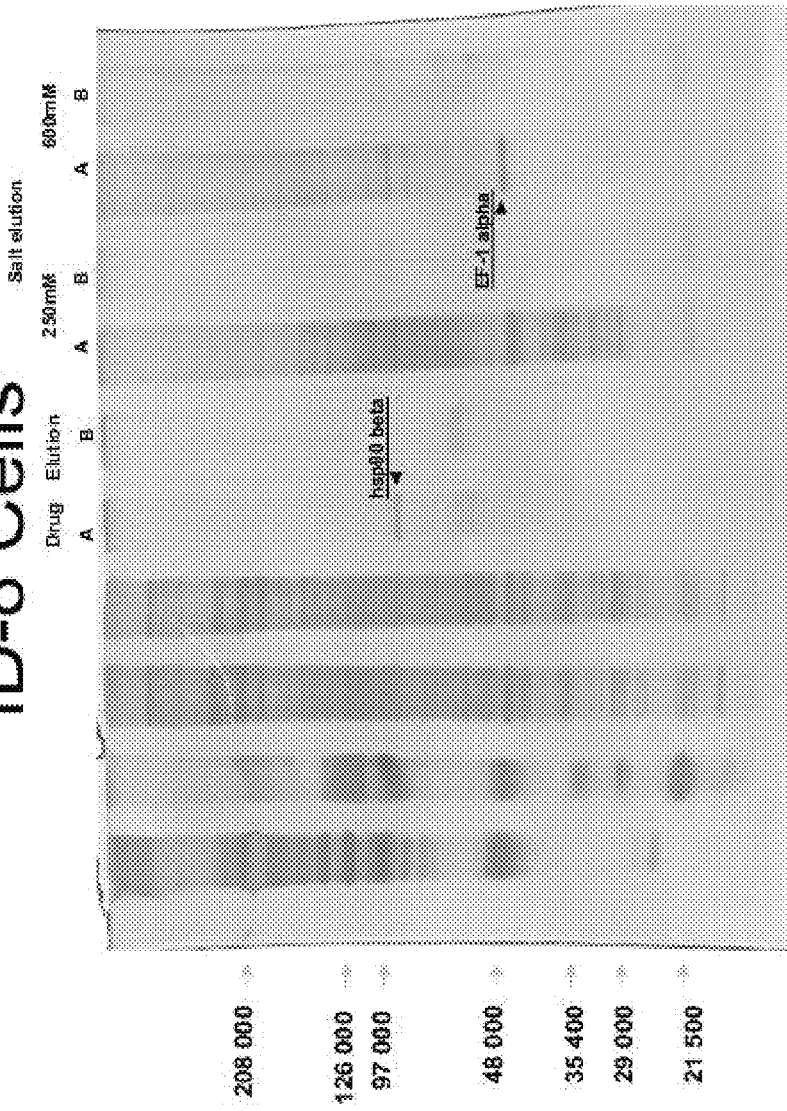
FIG. 7B shows the drug-specific elution of Hsp90 for ID8 cell lines using RC-MC-110.

When RC-MC-110 is added to a variety of cancer cells: ovarian (ID8), taxol-resistant ovarian (ID8), prostate (LNCaP and PC-3), kidney (293). Growth of all of these cell lines in vitro was inhibited by RC-MC-110 in a dose-dependent manner. ID8 cell growth is more sensitive to RC-MC-110 than lonidamine. The drug specific elution of Hsp90 from TM4 serolid cell lines (mouse) is shown in FIG. 7A and in ID8 cell lines FIG. 7B.

Example 8

Use as Anti-Cancer Agent

Figure 8A:
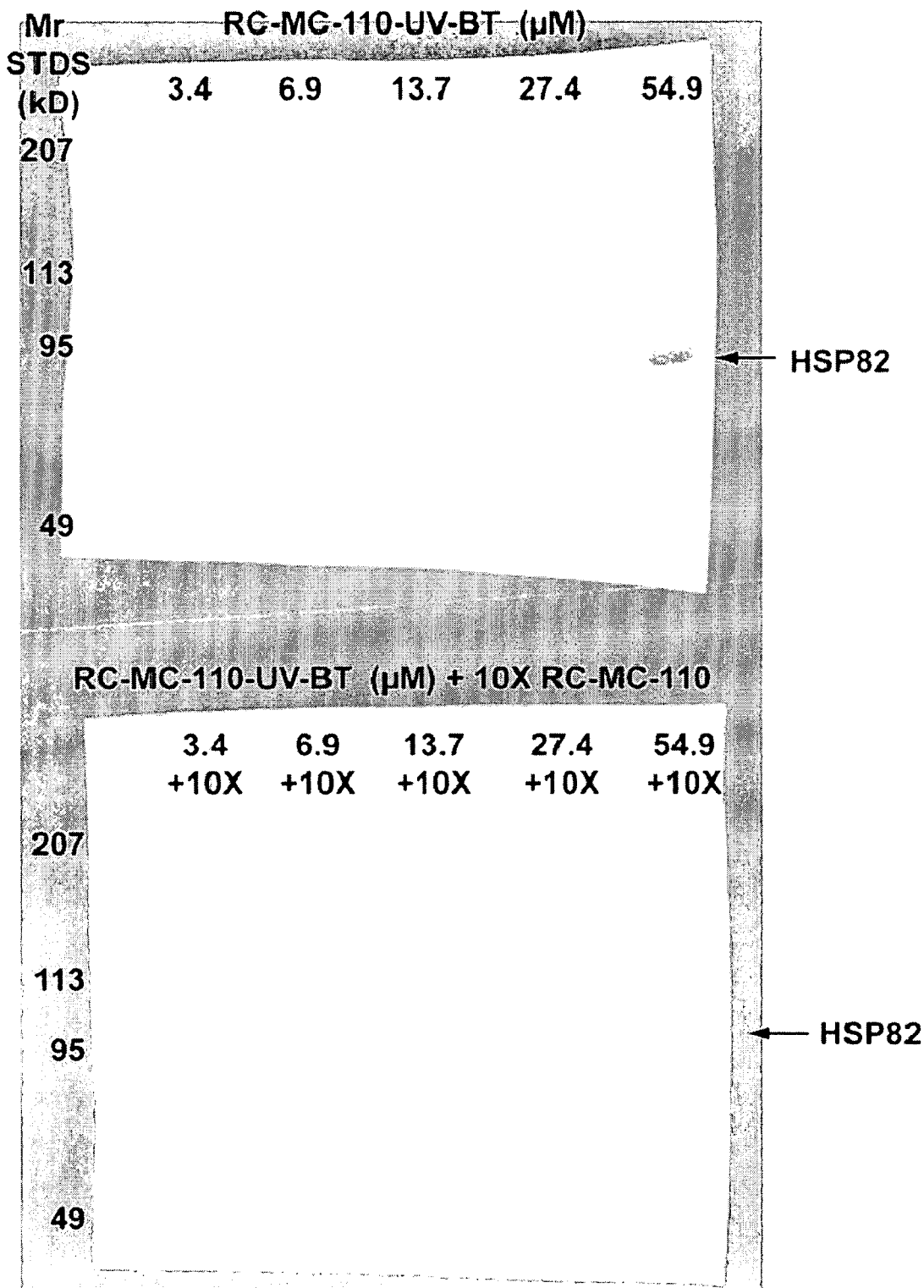
FIG. 8A shows the direct binding of purified Hsp82, a yeast homologue of Hsp90, by a cross-linked biotinylated analogue of RC-MC-110, as well as the effects when excess RC-MC-110 is added to the protocol.

In this example, the binding of cross-linked biotinylated RC-MC-110 (RC-MC-200) to Hsp82 (the yeast homologue of Hsp90) was investigated by a cross-linking and biotinylated analogue of RC-MC-110. The examples show that the binding competes with excess RC-MC-110. The results are shown in FIG. 8A.

Since a purified protein was used in this example, there was no need for any affinity chromatography.

The buffer solution in this examples was comprised of 50 mM Tris-HCl, pH 7.4, 50 mM NaCl, 5 mM EDTA, and 50 mM NaF.

First, the protein was diluted with the buffer solution above to give a final concentration of 0.278 mg/ml. The stock protein concentration was 22 mg/ml in 5 µl aliquots.

Next the drug was diluted as follows. Stock concentrations of RC-MC-210 (see structure below) were 0.6 mg/ml (cross-linked biotinylated analogue of RC-MC-110). A 300 µl aliquot was thawed, and separated into two 150 µl aliquots. Dilutions were in the order of 1, ½, ¼, ⅛, 1/16 of the stock solutions. The stock concentration of the competition solution was 0.6 mg/ml RC-MC-210 (549 µM), and about 0.9 mg of RC-MC-110 was dissolved in 150 µl of RC-MC-210 solution to give a final concentration of 6 mg/ml (14.5 mM).

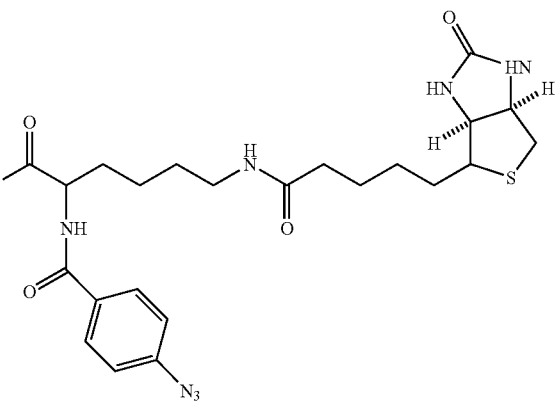

The competition solution had the same concentration of RC-MC-210, but a 10-fold excess of RC-MC-110 (non-biotinylated) to its respective concentration (e.g: ½ RC-MC-210, then the RC-MC-110 was 10× that concentration.)

To prepare of the incubation reactions, 18 µl of protein from a 0.277 mg/ml diluted stock (about 5 µg of protein) was incubated with 2 µl of drug for 1 hr at 4° C. with gentle rocking. The concentration of the drug was diluted another 10-fold, and the same for the competition tubes (e.g: for the highest drug concentration, then the final concentration of RC-MC-210 is 549 µM×(2 µl/20 µl)=54.9 µM in the assay, and for the competition the RC-MC-110 had a final concentration in the assay tube of 1.45 mM).

The 18 µl of protein (5 µg) was incubated with 2 µl of drug for 1 hr at 4° C., for each tube at the various concentrations, with its respective competition tube (10 tubes total). After one hour, the samples were exposed to a UV-vis mineral lamp. The UV light exposure was for 20 minutes at 4° C. using the long wavelength setting. After UV incubation, 4× sample buffer was added and boiled for 5 minutes. The samples were electrophoresed on a 7.5% polyacrylamide gel, and transferred on PVDF membrane overnight. The membrane was blocked for 1 hr in 5% BSA in TTBS at room temperature. The membrane was then washed 3 times 5 minutes each in TTBS+0.1% bovine serum albumin ("BSA") (reduces background). The membrane was incubated with the Horseradish peroxidase ("HRP") Avidin D for 20 minutes. (25 µl in 25 ml of TTBS+0.1% BSA). The membrane was washed 3×5 minutes with TTBS+0.1% BSA.

During the last 3 washes, the AEC substrated (chromogenic kit from ZYMED) was used to visualize the HRP reaction. The protocol for preparing the solution from the Kit was according to the manufacture's instructions. The blot was then incubated with the AEC solution. Once the desired intensity has been achieved, Wash the blot 3×10 minutes each with 20 mM PBS, pH 7.5.

Example 9

Fertility Trials Following Oral Administration of Compounds

The following table illustrates the results of a single oral does of 6 mg/kg of RC-MC-110 orally to male rats. The compounds were dissolved in a minimum amount of 10% ethyl alcohol and mixed with corn oil. The ethyl alcohol was evaporated 10% prior to administration. The "embryos normal" and "embryos abnormal" represents the mean number of embryos per pregnant female.

TABLE 9A

Fertility of Male Rats Following Seven Consecutive Daily Oral Doses of 6 mg/day of RC-MC-110

| | CONTROLS | | | | EXPERIMENTAL | | | |
|---|---|---|---|---|---|---|---|---|
| WEEK | Males mated | Males fertile | Embryos normal[1] | Embryos abnormal[1] | Males mated | Males fertile | Embryos normal[1] | Embryos abnormal[1] |
| 1 | 7 | 7 | 15 | 0.1 | 7 | 7 | 15 | 0.2 |
| 2 | 7 | 7 | 14 | 0.6 | 7 | 7 | 13 | 0.3 |
| 3 | 7 | 7 | 14 | 0.2 | 7 | 2 | 7 | 0 |
| 4 | 7 | 7 | 14 | 0.1 | 7 | 3 | 7 | 0.5 |
| 5 | 7 | 7 | 14 | 0.6 | 7 | 0 | 0 | 0 |
| 6 | 7 | 7 | 15 | 0.3 | 7 | 0 | 0 | 0 |
| 7 | 7 | 7 | 14 | 0.3 | 7 | 0 | 0 | 0 |
| 8 | 7 | 7 | 14 | 0.3 | 6 | 0 | 0 | 0 |
| 9 | 7 | 7 | 14 | 0.5 | 7 | 1 | 9 | 1 |
| 10 | 7 | 7 | 14 | 0.5 | 7 | 1 | 2 | 0 |
| 12 | 7 | 7 | 14 | 0.4 | 7 | 2 | 14 | 0.3 |
| 13 | 7 | 7 | 13 | 0.3 | 7 | 2 | 15 | 0.3 |
| 14 | 7 | 7 | 15 | 0.3 | 7 | 2 | 14 | 0 |
| 18 | 7 | 7 | 15 | 0.4 | 7 | 2 | 14 | 0 |

[1]Mean number of normal or abnormal embryos per pregnant female

The following table illustrates the results of a single oral does of 6 mg/kg/day of RC-MC-110 orally to male rats.

TABLE 9B

Fertility of Male Rats Following a Single Oral Dose of 6 mg/kg of RC-MC-110.

| | CONTROLS | | | | EXPERIMENTAL | | | |
|---|---|---|---|---|---|---|---|---|
| WEEK | Males mated | Males fertile | Embryos normal[2] | Embryos abnormal[1] | Males mated | Males fertile | Embryos normal[1] | Embryos abnormal[1] |
| 1 | 7 | 7 | 15 | 0.1 | 7 | 7 | 15 | 0.2 |
| 2 | 7 | 7 | 14 | 0.6 | 7 | 7 | 12 | 0.3 |
| 3 | 7 | 7 | 14 | 0.2 | 7 | 2 | 6 | 2 |
| 4 | 7 | 7 | 14 | 0.1 | 7 | 0 | 0 | 0 |
| 5 | 7 | 7 | 14 | 0.6 | 7 | 0 | 0 | 0 |
| 6 | 7 | 7 | 15 | 0.3 | 7 | 1 | 10 | 1 |
| 7 | 7 | 7 | 14 | 0.3 | 7 | 2 | 13 | 0 |
| 8 | 7 | 7 | 14 | 0.3 | 7 | 3 | 12 | 1 |
| 9 | 7 | 7 | 14 | 0.5 | 7 | 4 | 12 | 0.4 |
| 10 | 7 | 7 | 14 | 0.5 | 7 | 3 | 11 | 1 |
| 12 | 7 | 7 | 14 | 0.4 | 7 | 4 | 14 | 0.1 |
| 13 | 7 | 7 | 13 | 0.3 | 7 | 3 | 14 | 1.0 |
| 14 | 7 | 7 | 15 | 0.3 | 7 | 4 | 11 | 0.7 |
| 18 | 7 | 7 | 15 | 0.4 | 7 | 4 | 14 | 0.7 |
| 26 | 7 | 7 | 15 | 0.6 | 7 | 3 | 13 | 0.6 |

[2]Mean number of normal or abnormal embryos per pregnant female

The following table illustrates the results of a single oral does of four different doses of RC-MC-110 orally to male rats.

TABLE 9C

Challenge Mating Studies Following a Single Oral Dose of RC-MC-110 in 10% Ethyl Alcohol and Sesame Oil

| WEEK | MALES MATED/MALES FERTILE | | | |
|------|-----------|----------|----------|----------|
|      | 0.75 MG/KG | 1.5 MG/KG | 3.0 MG/KG | 6.0 MG/KG |
| 1  | 6/6 | 6/5 | 6/6 | 7/7 |
| 2  | 8/8 | 6/6 | 6/6 | 7/7 |
| 3  | 6/6 | 6/5 | 6/3 | 7/2 |
| 4  | 6/6 | 6/5 | 6/2 | 7/0 |
| 5  | 6/6 | 6/6 | 6/6 | 7/0 |
| 6  | 6/6 | 6/6 | 6/6 | 7/1 |
| 7  | 6/6 | 6/6 | 6/6 | 7/2 |
| 8  | 6/6 | 6/6 | 6/6 | 7/3 |
| 9  |     | 6/6 | 6/6 | 7/4 |
| 10 |     |     |     | 7/3 |
| 12 |     |     |     | 7/4 |
| 13 |     |     |     | 7/3 |
| 14 |     |     |     | 7/4 |

Example 10

Compounds that Inhibit Spermatogenesis

As discussed above, it has been shown that some of the compounds of the present invention bind to Hsp90 and EF1-alpha and function to inhibit spermatogenesis. It is thus contemplated that other compounds that bind to one of both of these proteins may inhibit spermatogenesis. Thus, the present invention is broadly directed to a method of inhibiting spermatogenesis by administering a therapeutically effective amount of a compound that inhibits the action of Hsp90 and/or EF1-alpha.

Several known Hsp90 inhibitors are listed above. With regard to HSP90, RC-MC-110 likely a novel inhibitor of the N-terminal ATP binding site or a novel site on Hsp90. It should be noted that mutants of Hsp90 in *Drosophila* (fruitfly) produce sterile males and females. See Yue L, Karr T L, Nathan D F, Swift H, Srinivasan S, Lindquist S. *Genetic analysis of viable Hsp90 alleles reveals a critical role in Drosophila spermatogenesis.* Genetics. 1999 March; 151(3): 1065-79. When lonidamine and RC-MC-110 were provided to a fruitfly, both inhibited reproduction. However, RC-MC-110 was more potent than lonidamine.

In addition, since elongation factor 1-alpha (EF1a) is a GTP binding protein, it is contemplated that certain nucleotide analogues or certain inhibitors of GTP binding pockets should work as contraceptives. Ubiquitin-aldehyde, an inhibitor of certain peptidases may also inhibit EF1a. See Gonen H, Smith C E, Siegel N R, Kahana C, Merrick W C, Chakraburtty K, Schwartz A L, Ciechanover A. *Protein synthesis elongation factor EF-1 alpha is essential for ubiquitin-dependent degradation of certain N alpha-acetylated proteins and may be substituted for by the bacterial elongation factor EF-Tu.* Proc Natl Acad Sci USA. 1994 Aug. 2; 91(16): 7648-52.

Example 11

Cell Proliferation

Various compounds were tested for their effects on cell proliferation. In the study, the cell types were M-1 Clone 20, which is an immortalized cell line that mimics PKD, and human primary cyst epithelial cells, or ADPKD cells. The compounds were tested at 1 µM to 100 µM concentrations.

M-1 clone 20 ("M1 Clone 20") cells are a model of PKD-like cells, which were created by stably transfecting parental "normal" M-1 immortalized renal cortical collecting duct cells with the C-terminal cytosolic domain (or C-tail) of mouse polycystin-1 (the protein product of the Pkd1 gene. The overexpressed C-tail acts in a dominant-negative fashion, conferring the PKD phenotype to these cells. Their characterization is described in: Sutters, M., Yamaguchi, T., Maser, R. L., Magenheimer, B. S., St. John, P. L., Abrahamson, D. R., Grantham, J. J. and Calvet, J. P. (2001) *Polycystin-1 transforms the cAMP growth-responsive phenotype of M-1 cells.* Kidney Int. 60, 484-494.

Figure 9A:
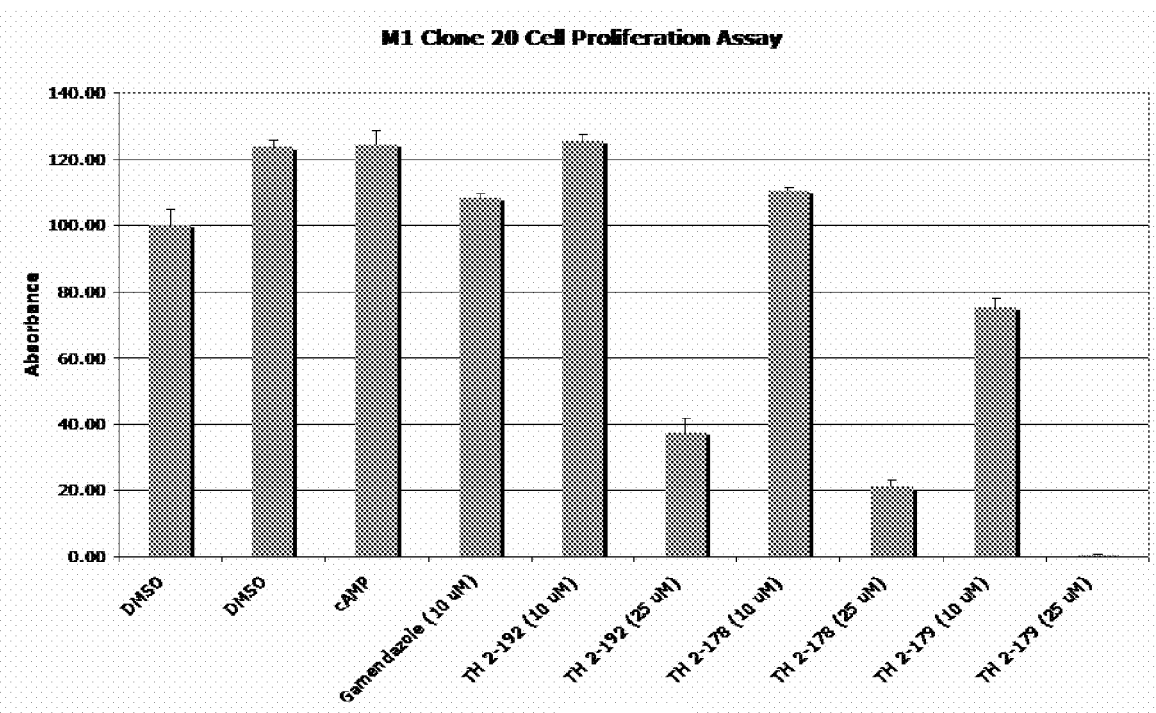
FIGS. 9A-9B are graphs that show a cell proliferation assay and the response to analogues of the invention.
Figure 9B:
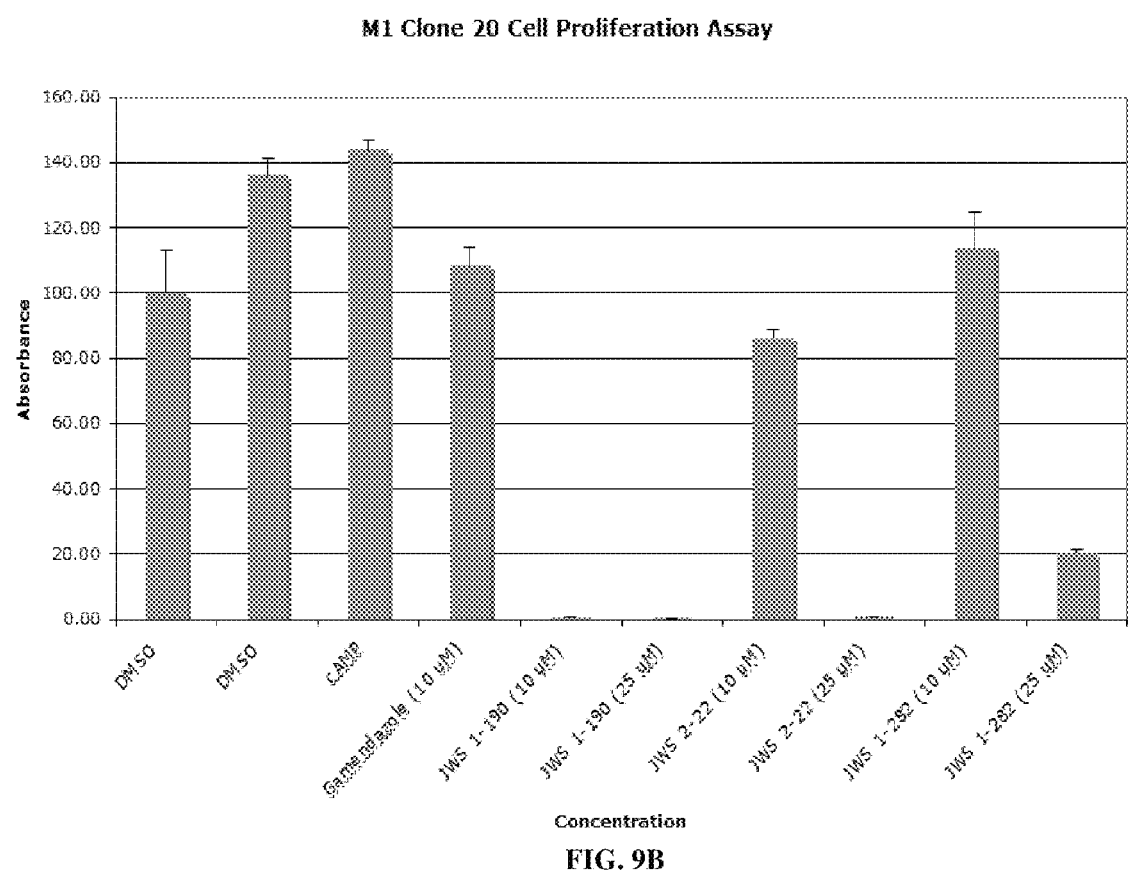

FIGS. 9A-9B include graphs that show cells grown in the vehicle (i.e. DMSO at two different volumes of 1 uL and 5 uL respectively), cAMP only, and then under the treatment drugs, all of which also had cAMP in them. The comparison drug used was 10 uM of gamendazole. The graph shows Absorbance in a spectrophotometer after the cells were treated for 48 hours and then exposed to the MTT assay reagent to evaluate uptake and thus overall Absorbance. Absorbance is a measure of cell number.

FIG. 9A shows cells grown in the vehicle (i.e. DMSO at two different volumes of 1 uL and 5 uL respectively), cAMP only, and then under the treatment drugs, all of which also had cAMP with them. The comparison drug used was 10 uM Gamendazole. The MTT cell proliferation assay was carried out to assess cell number—cell proliferation is essentially cell number. The graph shows absorbance measurements after 48 hours treatment with the drugs. Thus, absorbance is a measure of cell number, or cell proliferation. The reference bar is the third bar from the left (cAMP)—the degree of inhibition should be compared to that bar. 25 microM doses of these drugs were quite effective in inhibiting cell proliferation. As shown, TH 2-192, TH 2-178, and TH 2-179 were each more effective in inhibition of cell proliferation at 25 uM compared to 10 uM. TH 2-179 was more effective at 10 uM followed by TH 2-178.

FIG. 9B also shows cells grown in the vehicle (i.e. DMSO at two different volumes of 1 microL and 5 microL respectively), cAMP only, and then with treatment drugs, all of which also had cAMP with them, with other parameters being similar to FIG. 9A. As shown, the 25 uM doses of JWS 1-190, JWS 2-22, and JWS 1-282 were quite effective in inhibiting cell proliferation. Additionally, 10 uM of JWS 1-190 was also very effective. These results suggest that other lonidamine derivatives may be effective therapies for the abnormal cell proliferation associated with cyst formation and enlargement in ADPKD. Thus, various lonidamine derivatives, such as indazole carboxylic acids or others, may be useful for treating, inhibiting, and/or preventing PKD.

Example 12

Cell Proliferation

Gamendazole (GMZ) was studied to determine the effect on cAMP and EGF treated ADPKD cyst-lining epithelial cells. The cells were treated with 100 uM cAMP or 25 ng/ml EGF to stimulate cell proliferation. Increasing concentrations of gamendazole were added to the medium of the cells. After 72 hours of treatment, MTT assays were performed.

Figure 10A:
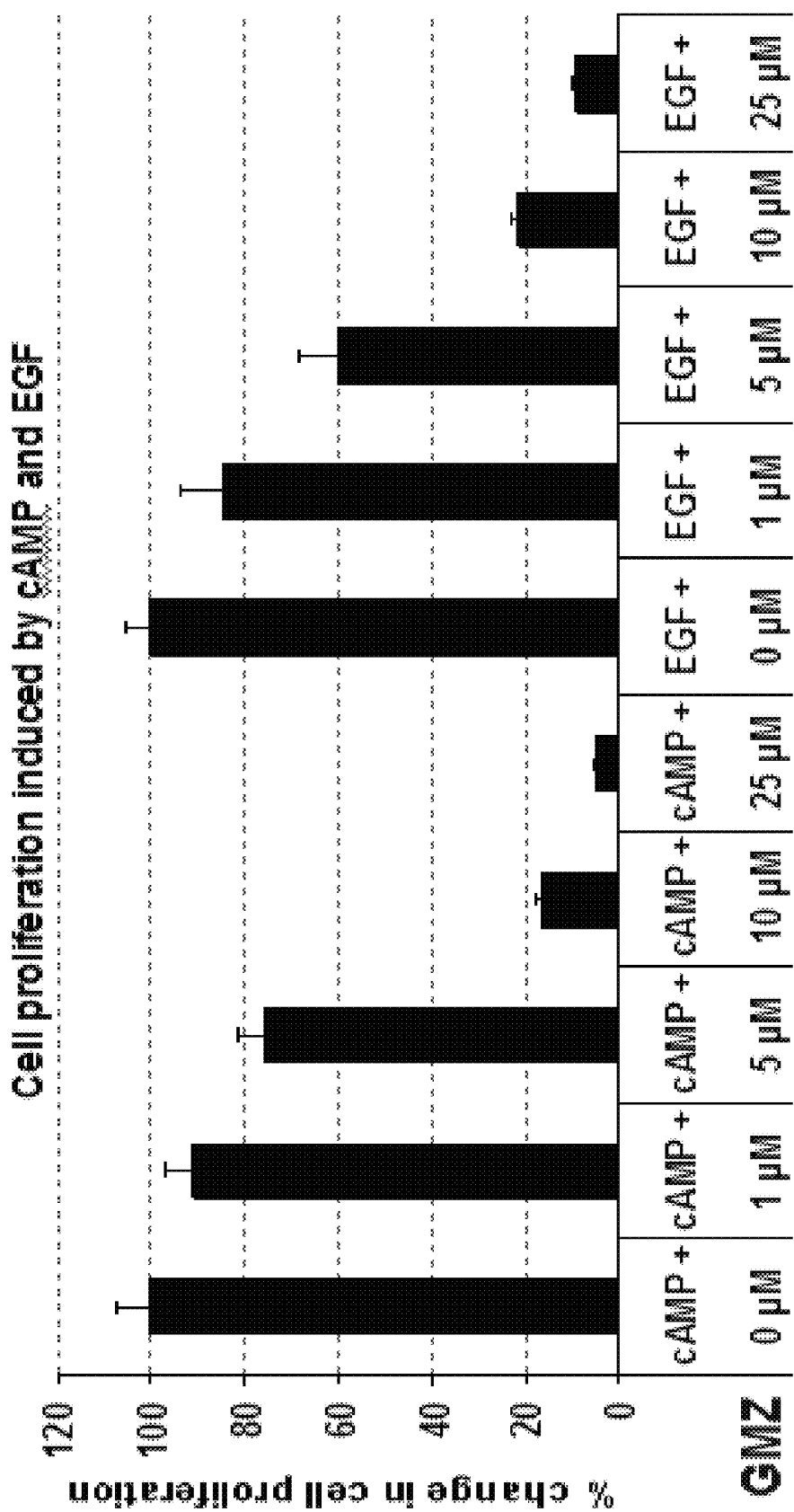
FIGS. 10A-10B are graphs for MTT assays that show gamendazole significantly inhibited both cAMP- and EGF-induced proliferation of PKD (e.g., ADPKD) cells in a dose-dependent manner (1 uM-25 uM GMZ for 72 h).
Figure 10B:
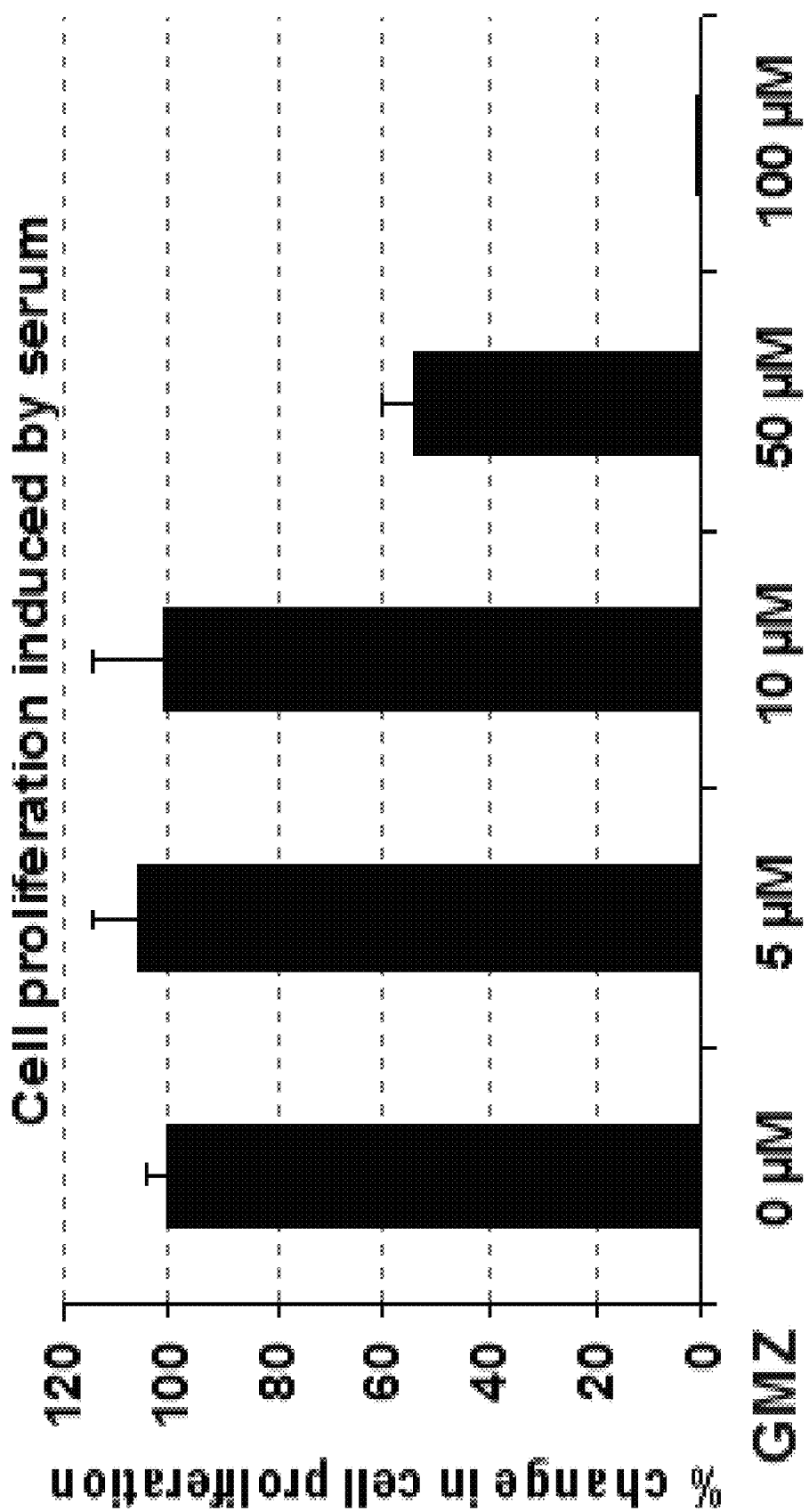

As shown in FIG. 10A, MTT assays showed that gamendazole significantly inhibited both cAMP- and EGF-induced proliferation of PKD (e.g., ADPKD) cells in a dose-dependent manner (1 uM to 25 uM GMZ for 72 h). For the MTT assay shown in FIG. 10A, ADPKD cyst-lining epithelial cells were plated at a density of $4 \times 10^3$ cells per well in a 96-well cell culture plate (n=6). Cells were serum-starved for 24 hours and treated either with 100 μM cAMP or 25 ng/ml EGF to stimulate cell proliferation. For the MTT assay shown in FIG. 10B, ADPKD cells were plated at a density of $2 \times 10^3$ cells per well in medium containing 1% FBS. After 24 hours, medium was changed to include 5% FBS. Increasing concentrations of GMZ were added to the medium for the cells of both FIGS. 10A and 10B to determine the effect of GMZ on cell proliferation. After 72 hours of treatment, MTT assays were performed by adding dye solution to the cells and stopping the reaction four hours later. Optical densities were measured using a spectrophotometer. In each group, results were expressed as a percentage of the control group (not treated with GMZ). As shown, GMZ more effectively inhibited cell proliferation as the concentration was increased.

Figure 10C:
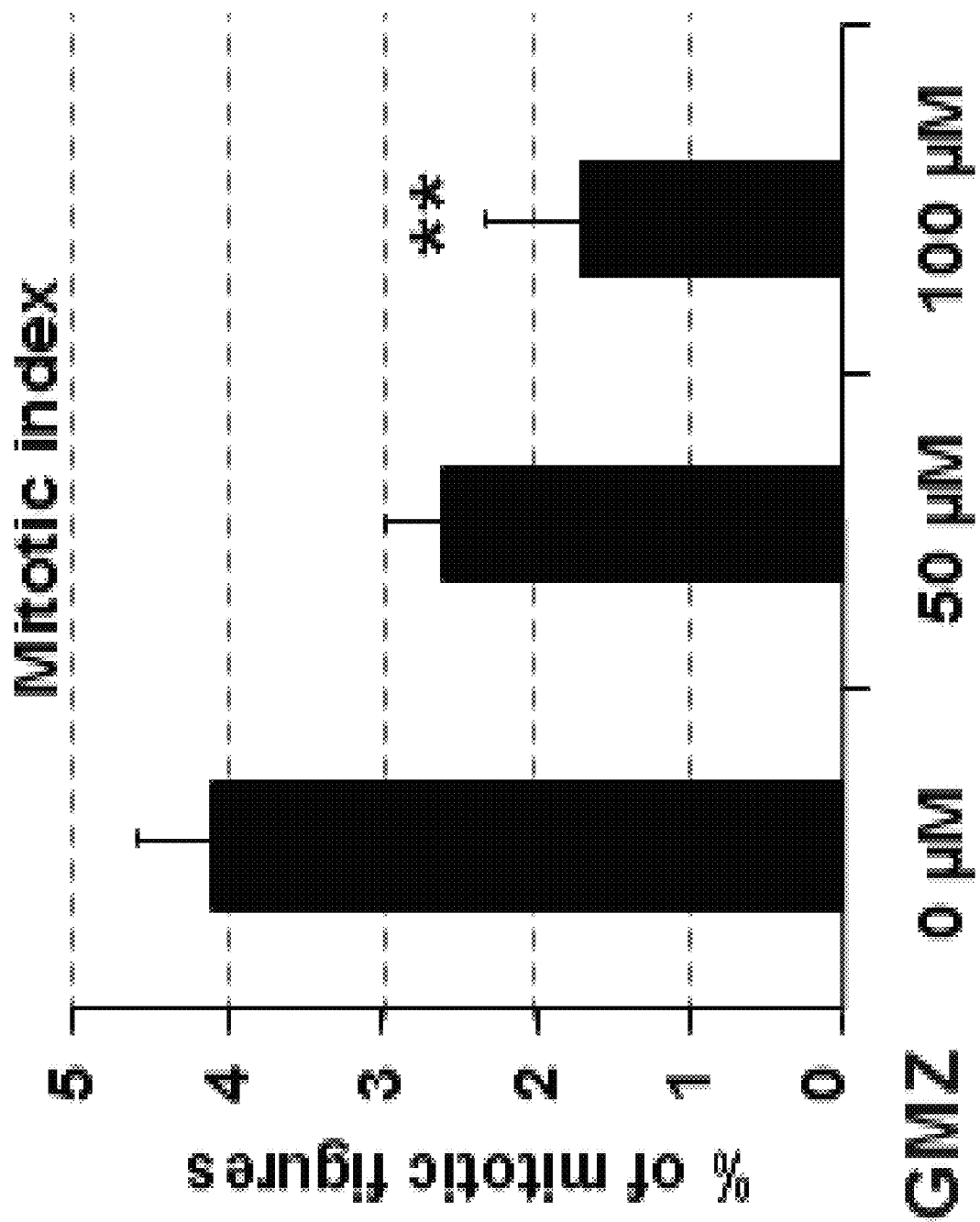
FIG. 10C is a graph showing the mitotic index of PKD cells in response to gamendazole.

For the MTT assay shown in FIG. 10C, $5 \times 10^3$ ADPKD cells were plated in a 4-well chamber slide. After 24 hours, medium was changed to include 5% FBS. Cells were treated with increasing concentrations of GMZ for 16 hours, fixed with 4% paraformaldehyde and permeabilized with 0.2% Triton-X100. Cells were mounted with DAPI-containing mounting medium and observed by fluorescence microscopy. Eight to ten separate fields were examined at 10× magnification and the number of mitotic figures (nuclei) were counted and expressed as a percentage of the total number of nuclei per field. Statistical analysis was done to compare the GMZ-treated cells to untreated cells at each time point using One-way ANOVA and the Tukey HSD test for pair-wise comparisons. GMZ treatment (50 μM for 16 h) decreased the mitotic index in comparison to untreated controls (2.6% vs. 4.1%), and 100 μM GMZ was even more effective (1.7% vs. 4.1%, p<0.01). The results indicate that GMZ effectively inhibits the proliferation of ADPKD cystic cells in culture.

Example 13

Western Blot Assay

Gamendazole (GMZ) was tested to determine if treatment decreases Hsp90 client protein levels in ADPKD cells. Briefly, ADPKD cells were treated with 50 μM GMZ for 24, 48 or 72 hours. Proteins from 20 μg total cell lysate were separated by SDS-PAGE, transferred to a PVDF membrane and probed with antibodies against the Hsp90 client proteins ErbB2 (185 kD), and cdk4 (34 kD).

Figure 11:
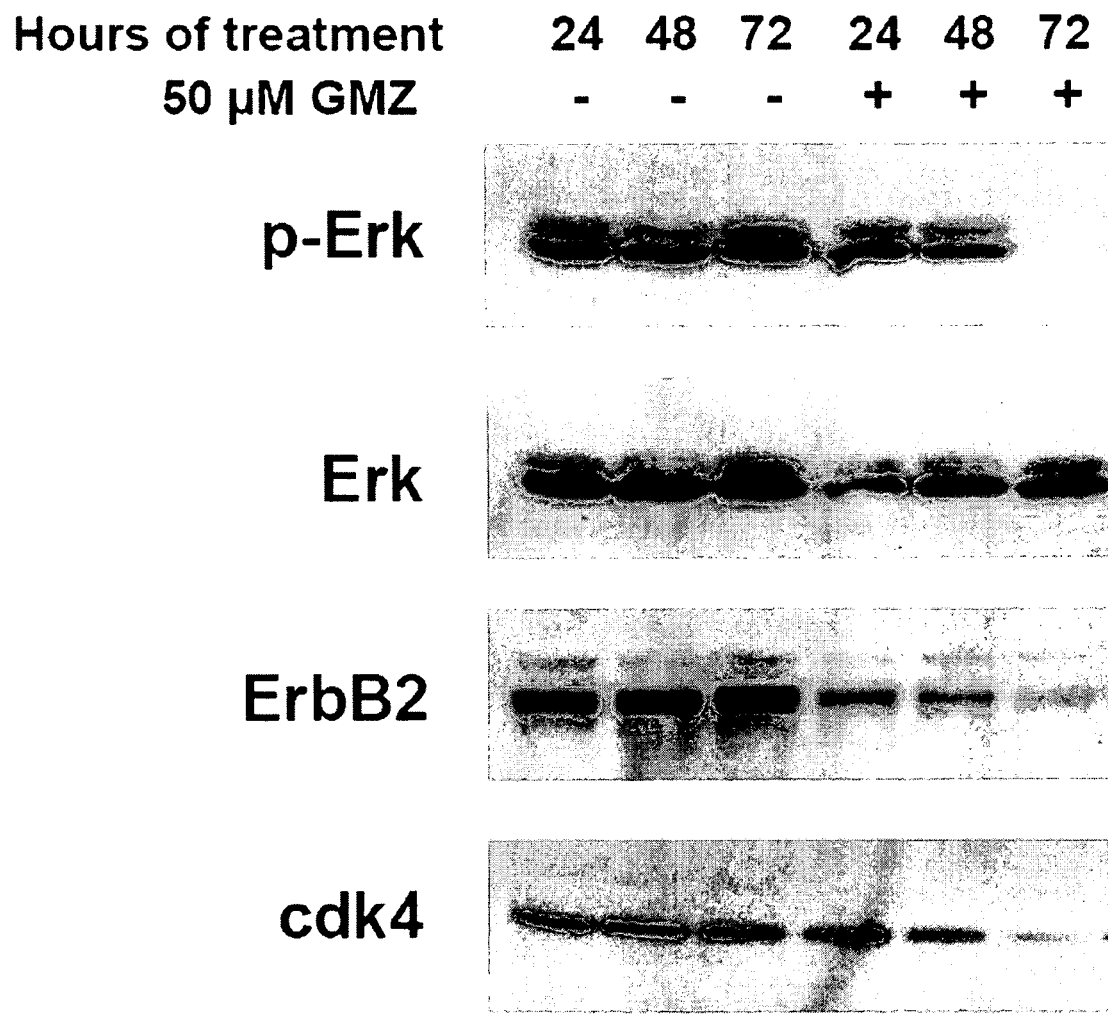
FIG. 11 is a picture of a Western blot that shows gamendazole-treated ADPKD cells (50 uM for 24-72 h) showed decreased P-ERK levels, while total ERK levels were unchanged; and decreased levels of the Hsp90 client proteins ErbB2 and Cdk4.

FIG. 11 is a picture of a Western blot that shows gamendazole-treated ADPKD cells (50 uM for 48 h) had decreased P-ERK levels (71.2% of controls; n=2), while total ERK levels were unchanged; and decreased levels of the Hsp90 client proteins ErbB2 and Cdk4. GMZ decreased the total levels of these client proteins in ADPKD cells. A decrease in P-ERK correlates with the inhibition of cell proliferation by GMZ. The results indicate that GMZ can decrease protein levels that are relevant for cell proliferation or propagation, and such a decrease shows GMZ can be useful in inhibiting PKD. The data also provides an indication that other lonidamine derivatives may be useful in therapies for PKD.

Example 14

Inhibiting Cyst Formation

The lonidamine derivative H2-Gamendazole (GMZ) was studied to determine whether it could inhibit cyst formation in Pkd1 metanephric kidneys by inhibiting cell proliferation and fluid secretion. The rationale for using GMZ was that it was known to be an Hsp90 (Heat-shock protein 90) inhibitor, hence affecting CFTR and NKCC1 protein levels as well the levels of a number of potential intracellular signaling intermediates, thus inhibiting both fluid secretion and cell proliferation, which are both important for cyst formation, and cyst growth and enlargement in PKD kidneys. Lonidamine had also previously been shown by others to inhibit CFTR channel activity, and thus it was possible that GMZ might also.

Using metanephric organ culture with Pkd1m1Bei null kidneys, we had previously shown that cAMP-driven fluid secretion and cyst-like tubule expansion is CFTR- and NKCC1-dependent: by treatment with CFTR172inh, a CFTR inhibitor, or bumetanide, an inhibitor of NKCC1; or using double knockout embryos of Pkd1:Cftr and Pkd1:Nkcc1. (see FIG. 12B).

In this study, we have tested whether the Lonidamine derivative Gamendazole can: inhibit proliferation and cAMP-stimulated tubule expansion using metanephric cultures; or inhibit cAMP-driven chloride secretion using monolayers of primary ADPKD cells. Since it is known that Lonidamine can block forskolin-induced CFTR-dependent channel activity, the inventors wanted to test Gamendazole's ability to inhibit fluid secretion either directly by inhibiting CFTR channel activity or by targeting the Hsp90 client proteins, CFTR and NKCC1. Forskolin (FSK) is a small molecule agonist of adenylyl cyclase, the enzyme that makes cAMP. Thus, FSK treatment of cells increases the levels of intracellular cAMP.

To determine whether gamendazole alters the cyst-forming process in response to cAMP, kidneys from Pkd1+/+, +/−, and −/− mice were placed in metanephric culture at E15.5 and treated with 100 uM 8-Br-cAMP with or without gamendazole (100 nM-10 uM) for 4 days. Gamendazole did not appear to be toxic to the kidneys, yet it significantly inhibited cystic dilation.

Figure 12A:
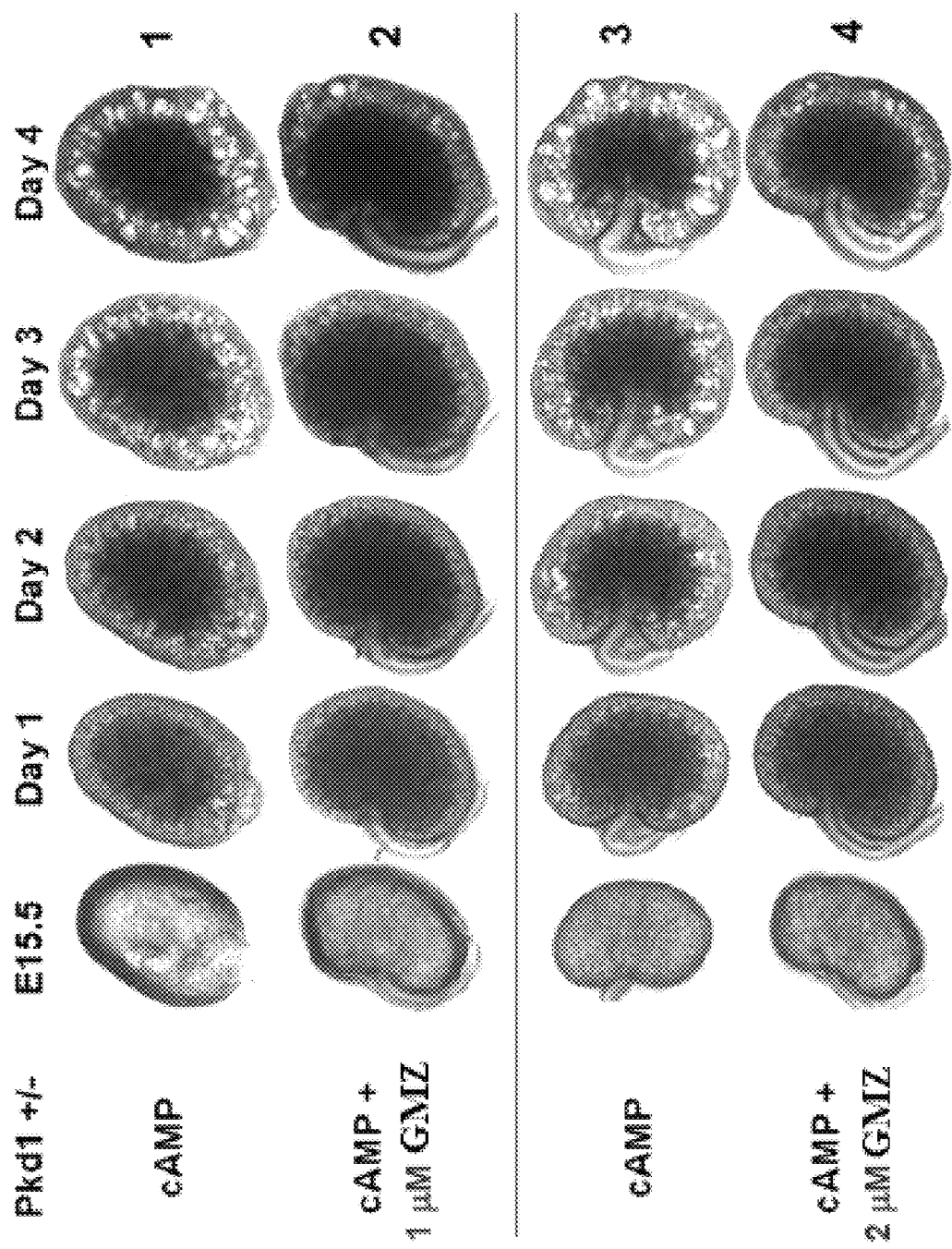
FIG. 12A shows that 1-2 uM gamendazole was effective in Pkd1+/− kidneys, essentially preventing cyst formation.

FIG. 12A shows that 1-2 uM gamendazole was effective in Pkd1+/− kidneys, essentially preventing cyst formation, while other data not shown indicated that 5-10 uM gamendazole resulted in dramatic cyst reduction in Pkd1−/− kidneys.

Figure 12B:
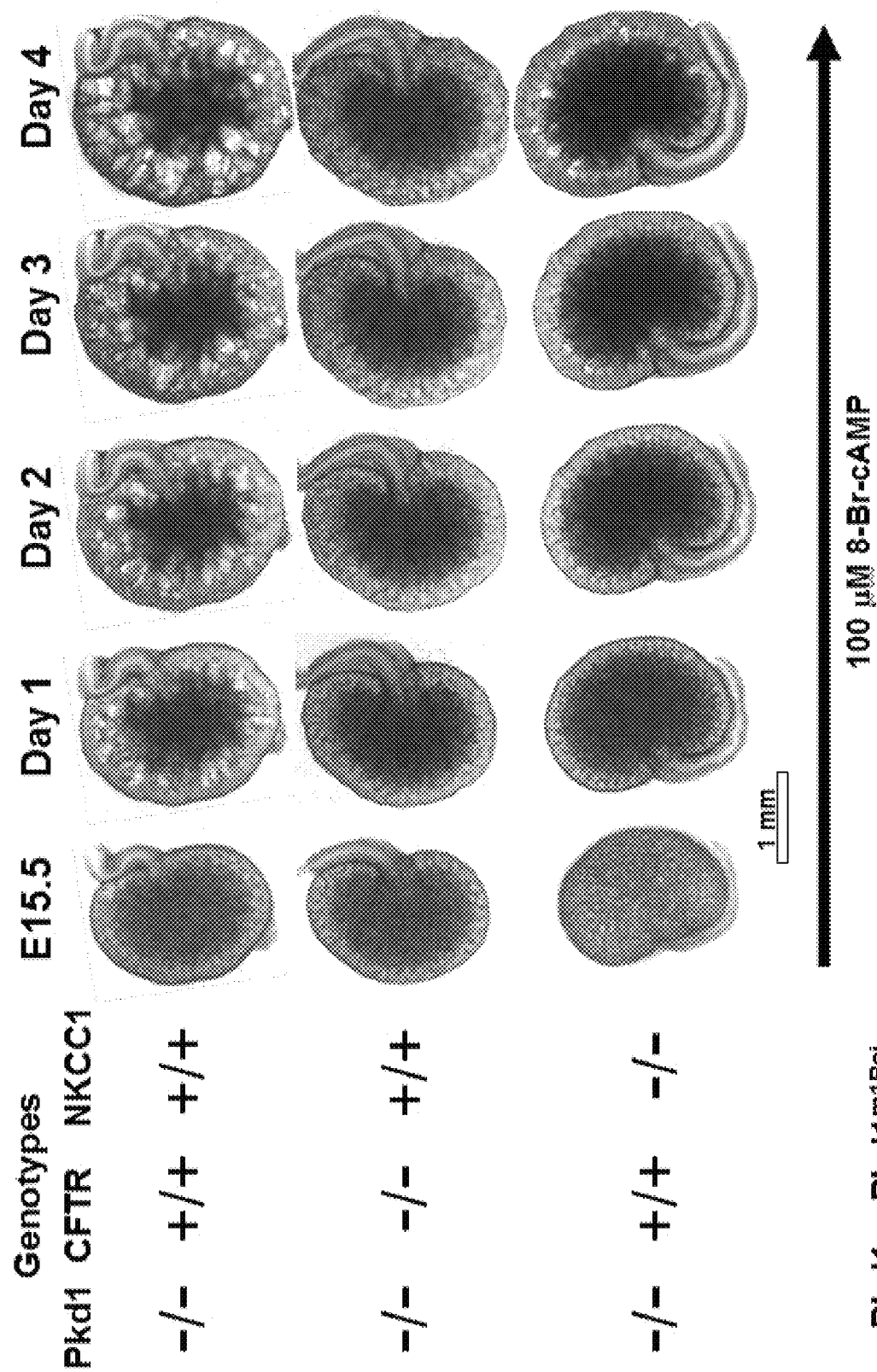
FIG. 12B shows that embryonic day 15.5 kidneys from Pkd1 null, compound Pkd1:Cftr or compound Pkd1:Nkcc1 mutant mice were placed in organ culture in the presence of 8-Bromo-cAMP for 4 days (8-Bromo-cAMP is a cell-permeable form of cAMP), and that both Cftr and Nkcc1 are required for cyst formation.

FIG. 12B shows embryonic day 15.5 kidneys from Pkd1 null, compound Pkd1:Cftr or compound Pkd1:Nkcc1 mutant mice in organ culture in the presence of 8-Bromo-cAMP for 4 days (this is a cell-permeable form of cAMP). Pkd1 mutant kidneys with wildtype CFTR and NKCC1 develop numerous, large cysts in the presence of cAMP (dilated tubules or cysts are the clear or light-colored areas within the kidneys), while the kidneys from Pkd1:Cftr double-deficient mice had absolutely no evidence of cyst formation, and the Pkd1:Nkcc1 double-deficient mice had significantly reduced cyst formation. This shows the importance of these chloride transporters for cyst formation.

Figure 12C:
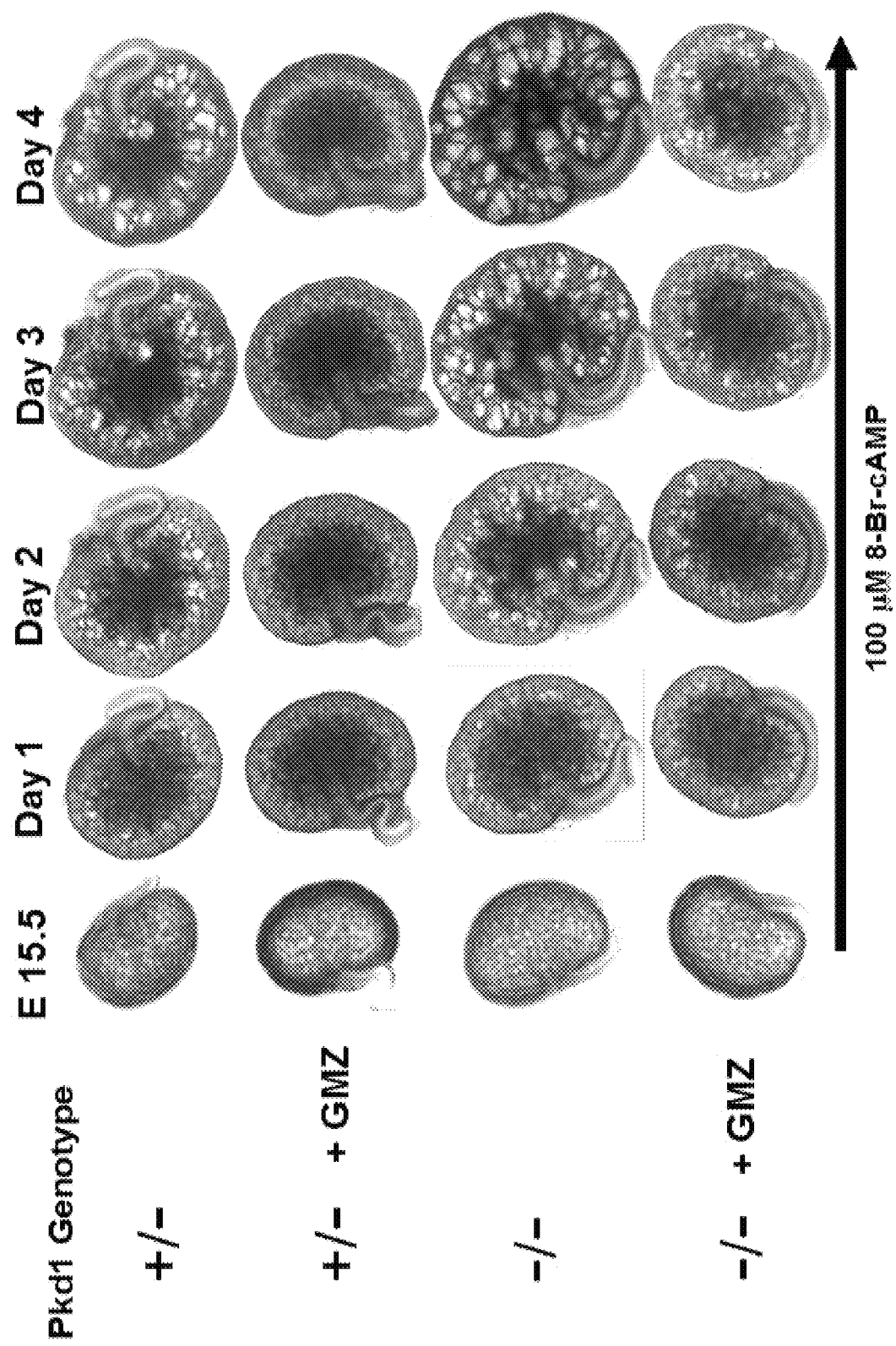
FIG. 12C shows that 5 µM GMZ significantly inhibited cAMP-mediated cyst formation in both the heterozygous and null metanephric kidneys

To determine whether GMZ treatment had an effect on cAMP-driven tubule expansion, E15.5 kidneys were treated with cAMP in the presence or absence of 5 microM Gamendazole. FIG. 12C shows that GMZ significantly inhibited cAMP-mediated cyst formation in both the heterozygous and null metanephric kidneys.

Figure 12D:
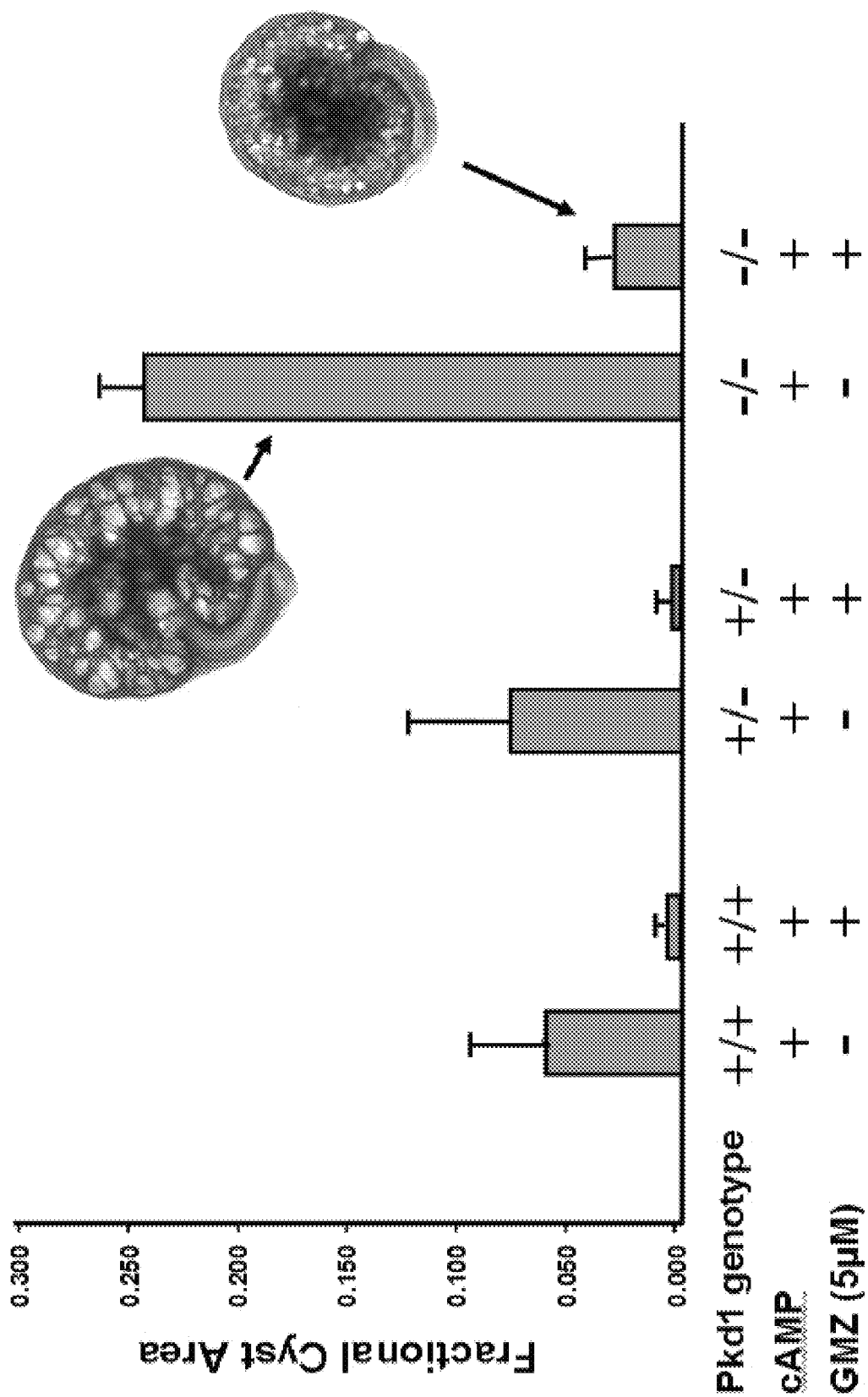
FIG. 12D shows quantification of the cystic index in the presence or absence of Gamendazole for the three Pkd1 genotypes again showing the dramatic decrease in cystic index with 5 uM GMZ treatment.

FIG. 12D shows quantification of the cystic index in the presence or absence of Gamendazole for the three Pkd1 genotypes again showing the dramatic decrease in cystic index with 5 microM GMZ treatment. This indicates that gamendazole had a potent effect on cyst formation in the embryonic kidneys.

Figure 12E:
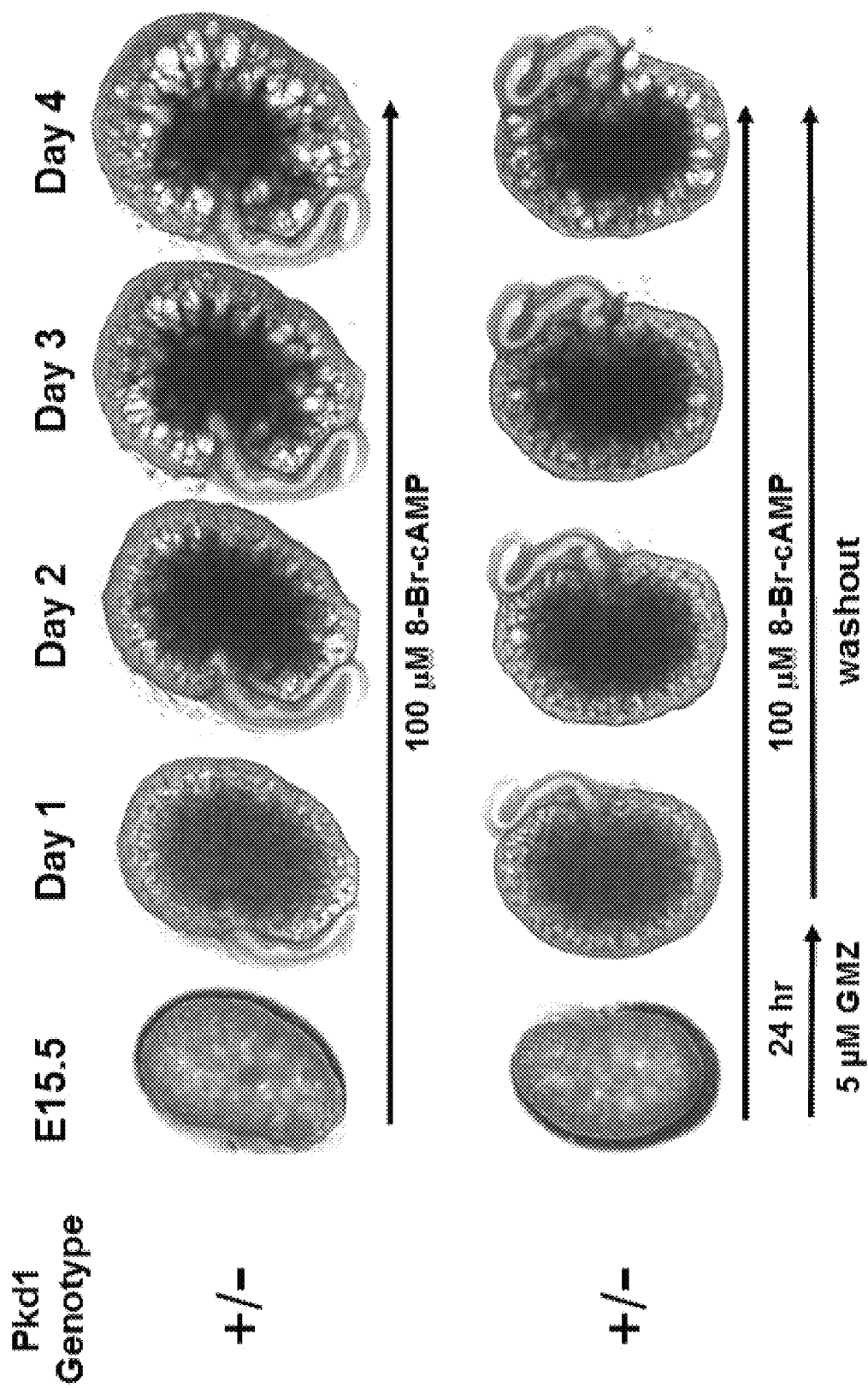
FIG. 12E shows that even after a short 24 hour treatment with gamendazole, the inhibitory effects appeared to persist in culture by the reduced number and size of the tubule dilations on Day 4.

The length of time that Gamendazole was able to block fluid secretion in embryonic kidneys using a washout technique was studied. Briefly, E15.5 kidneys were treated with cAMP alone or with cAMP plus 5 microM Gamendazole. 24 hrs later, culture medium was removed from the GMZ+cAMP-treated kidneys and was replaced with fresh medium containing cAMP only. FIG. 12E shows that even after this short treatment with gamendazole, the inhibitory effects appeared to persist in culture. This was evident by the reduced number and size of the tubule dilations on Day 4.

Figure 12F:
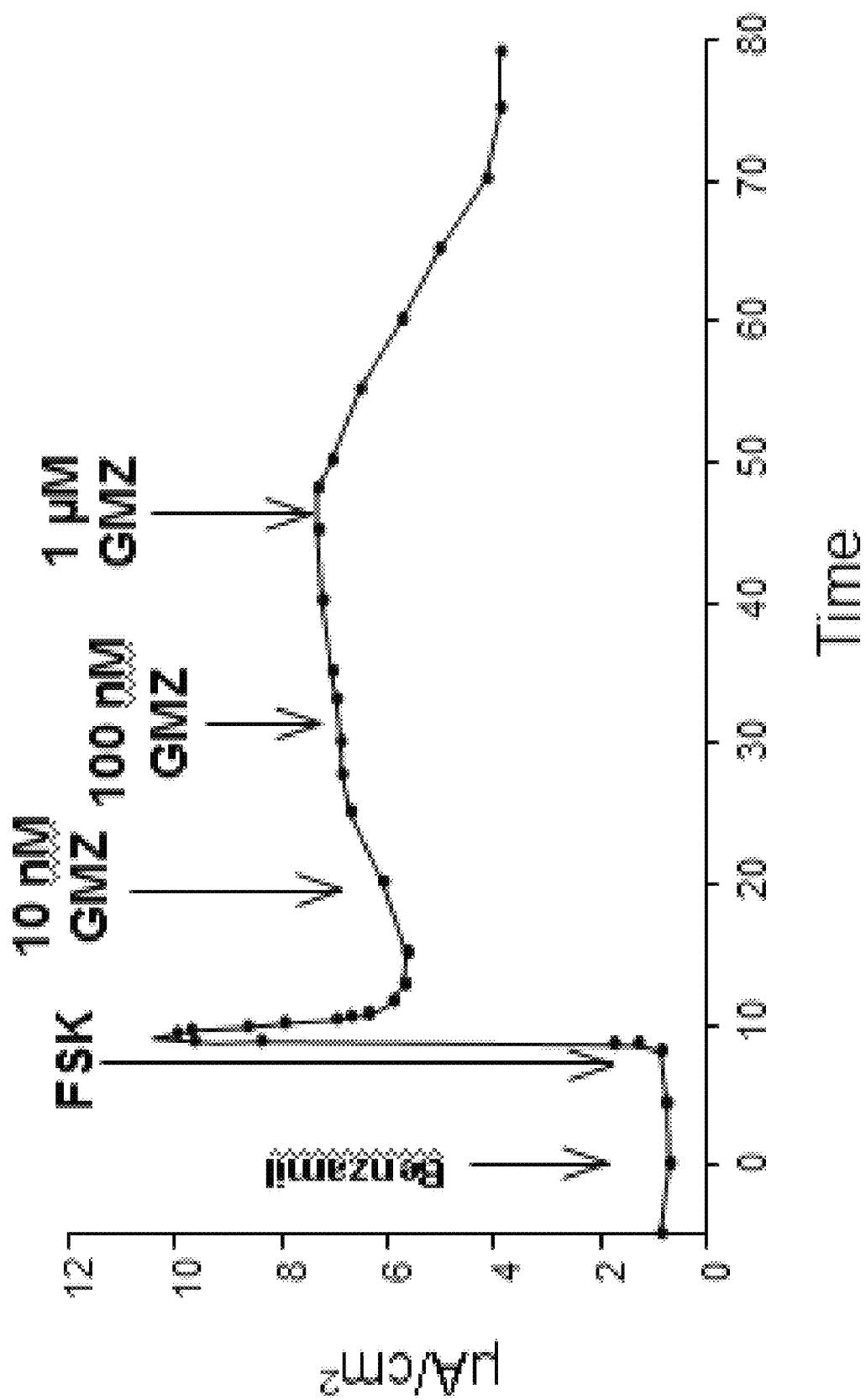
FIG. 12F shows an example of a tracing from one ADPKD cell monolayer showing that GMZ at 1 µM inhibits anion currents.
Figure 12G:
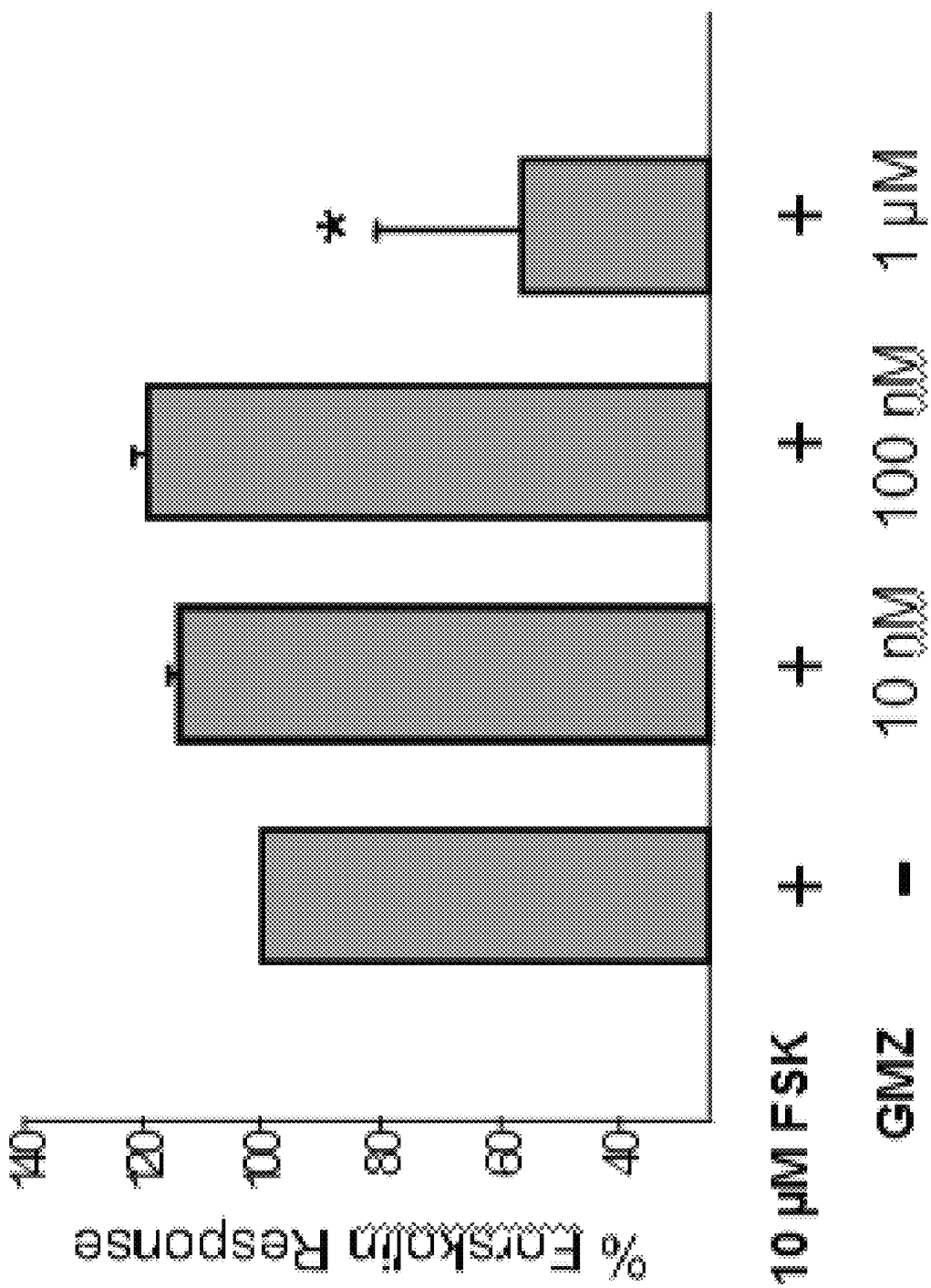
FIG. 12G shows that gamendazole decreases the forskolin-stimulated transepithelial chloride transport from FIG. 12F.

To determine if the ability of GMZ to inhibit cAMP-stimulated tubule expansion was due to inhibition of CFTR-mediated chloride transport, forskolin-induced short-circuit current was measured with cyst-lining epithelial cells derived from two human ADPKD (autosomal dominant PKD) kidneys. FSK is an adenylyl cyclase agonist, which increases the levels of intracellular cAMP. The cAMP then opens the CFTR chloride channel. FIG. 12F shows an example of a tracing from one ADPKD cell monolayer. FIG. 12F shows that 10 microM forskolin (FSK) was added, then GMZ at 10 nM, which was then increased to 100 nM, then to 1 microM. As shown in FIG. 12G, there was an effect at 1 microM where a decrease in short-circuit current is apparent. The bars in FIG. 12G show the results for the three treatments. 1 microM gamendazole applied to the apical side of the cell monolayer was effective in inhibiting greater than 40 percent of the forskolin-stimulated transepithelial chloride transport. This suggested that GMZ, like LND but surprisingly at much lower concentration, can inhibit CFTR-mediated chloride channel activity.

To also test whether GMZ can target the Hsp90 client protein NKCC1, sections of E15.5 organ culture kidneys treated with cAMP or cAMP plus GMZ were immunostained with an antibody for NKCC1 (methods in Magenheimer, et al., 2006). While not shown, images indicated that NKCC1 staining was reduced in the GMZ-treated kidneys. Consistent with the known localization of NKCC1 in the kidney, the immunolabeling appeared to be decreased in the metanephric mesenchyme and collecting ducts when GMZ was used at 1-5 uM.

It was also observed that GMZ-treated kidneys in organ culture were somewhat reduced in size compared to their untreated counterparts. Since GMZ affects Hsp90 client proteins involved in cell proliferation, it was hypothesized that GMZ could also be inhibiting cell proliferation in the metanephric organ cultures. To test this idea, organ culture sections were immunostained with an antibody to PCNA (proliferating cell nuclear antigen), a marker of cell proliferation. While not shown, there was overall less staining, and fewer tubule cells staining for PCNA in kidneys treated with GMZ.

In conclusion, these experiments show the dramatic effects of Gamendazole on cyst formation and enlargement in kidney organ culture, using a mouse model of PKD, the Pkd1m1bei mouse. The Pkd1 gene is orthologous to the gene involved in ~85% of human ADPKD cases. It is suggested by these experiments that GMZ directly and rapidly inhibits CFTR channel activity. This inhibition of anion (chloride) transport using human cyst epithelial cells (ADPKD cells) demonstrated that GMZ was effective at lower doses than was Lonidamine itself. This is the first demonstration of this property of GMZ, which had previously been shown for the parent compound Lonidamine, and thus, importantly, it is likely that other Lonidamine derivatives will also prove to be effective CFTR channel inhibitors. It was also suggested that GMZ inhibits Hsp90, as was shown previously by Tash J S, Chakrasali R, Jakkaraj S R, Hughes J, Smith S K, Hornbaker K, Heckert L L, Ozturk S B, Hadden M K, Kinzy T G, Blagg B S, Georg G I. *Gamendazole, an orally active indazole carboxylic acid male contraceptive agent, targets HSP90AB1 (HSP90BETA) and EEF1A1 (eEF1A), and stimulates Il1a transcription in rat Sertoli cells.* Biol Reprod. 78(6):1139-52 (2008). If so, it could be reducing the levels of the Hsp90 client proteins, CFTR and NKCC1, both important for cyst-filling chloride secretion. Evidence is shown here that NKCC1 protein levels were reduced by GMZ treatment of metanephric kidneys in organ culture. Evidence was also shown for decreased PCNA levels, which is consistent with a general decrease in cell proliferation in these kidneys in organ culture, due probably to Hsp90 inhibition. The efficacy of GMZ on inhibition of cyst growth in vivo is currently being tested in the pcy mouse, a mouse model of nephronophthisis-3 (NPHP3) which has a slowly progressive renal cystic disease. So far, the treated mice appear to be tolerating GMZ (1 mg/kg IP, three times weekly from 5-20 weeks of age) after 12 weeks of treatment. Accordingly, gamendazole inhibits cell proliferation and cAMP-stimulated cyst-like expansion (in metanephric organ cultures). The mechanisms may involve: a direct and rapid inhibition of forskolin-stimulated CFTR channel activity; inhibition of Hsp90 chaperone function leading to long-term reduction of NKCC1 protein levels; or reduction of PKD proliferation pathway components. Thus, GMZ appears to be a potent inhibitor of these two important processes involved in PKD pathogenesis.

The lonidamine analogue GMZ inhibits cyst growth in Pkd1-deficient kidneys in metanephric culture by targeting both fluid secretion and cell proliferation. Cyst growth and expansion in PKD involves a number of abnormal processes including increased fluid secretion and abnormal cell proliferation. Because there is a large number of abnormal cellular pathways potentially involved in cyst formation in PKD, lonidamine analogues were tested to determine if they were inhibitors that might act on multiple targets, and in particular on those involved in Cl-driven fluid secretion and Ras/MAPK signaling, both stimulated by cAMP.

Example 15

Cell Morphology Changes

To determine if gamendazole treatment alters actin cytoskeleton dynamics, ADPKD cells were stained with phalloidin and examined by fluorescence microscopy. Gamendazole-treated cultures had a higher proportion of smaller cells with fewer and smaller lamellipodia and decreased cytoplasmic actin staining. Briefly, ADPKD cells or M-1 cortical collecting duct cells were plated in a 4-well chamber slide in 5% FBS-containing medium. After 24 hours, the cells were treated with increasing concentrations of GMZ. Cells were fixed using 4% paraformaldehyde and permeabilized with 0.2% Triton-X 100. Cells were then incubated for 20 min with TRITC-conjugated phalloidin, washed with PBS and mounted with DAPI-containing mounting medium. Images were captured at 10× (FIG. 13A) or 60× (FIG. 13B), using the same exposure settings for treated and untreated cells. Red color (peripheral staining) shows phalloidin bound to actin filaments in the cell. Blue (internal staining) indicates DAPI-stained nuclei.

Figure 13A:
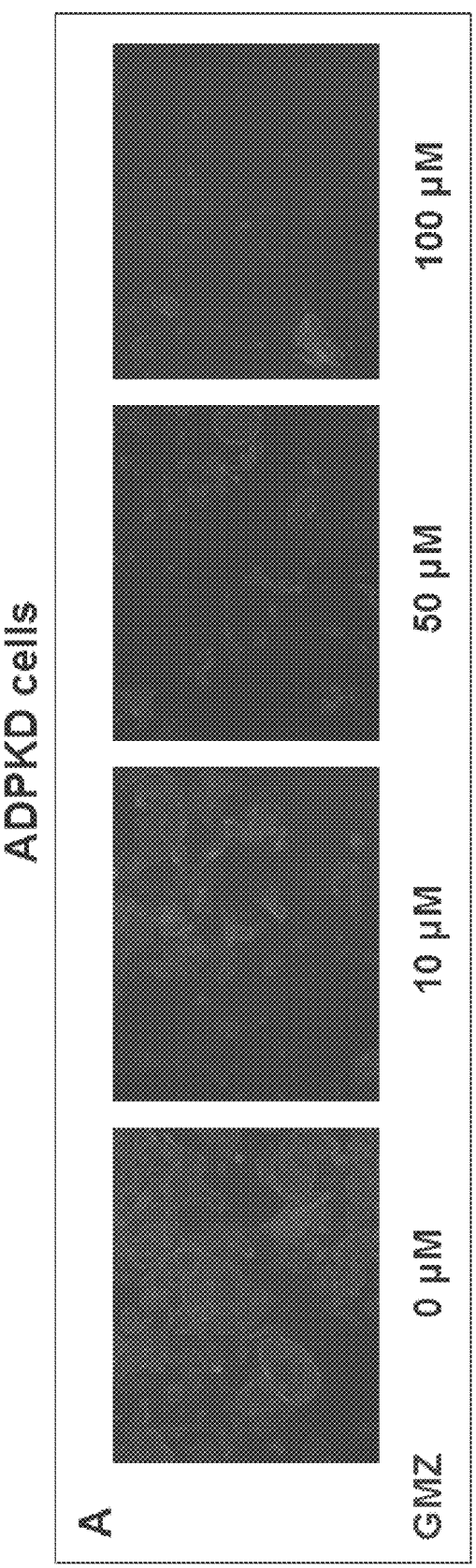
FIGS. 13A-13B show the morphology of the actin cytoskeleton is changed by treatment with gamendazole.
Figure 13B:
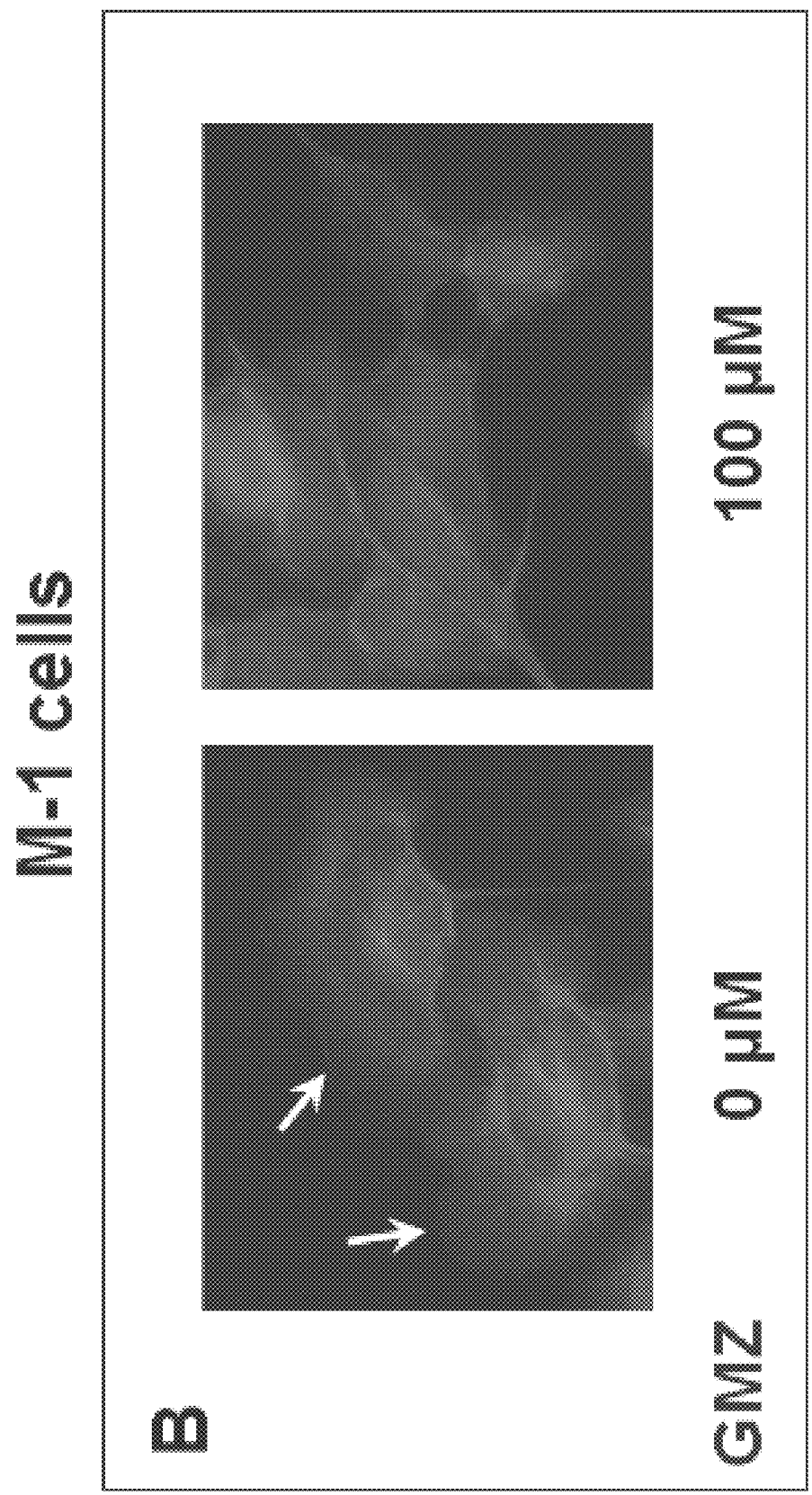

FIGS. 13A-13B show the morphology of the actin cytoskeleton is changed by treatment with gamendazole (GMZ). Untreated cells exhibited leading edges (lamellipodia) characteristic of migrating cells whereas GMZ-treated cells were smaller, without leading edges and with less filamentous actin, consistent with an inhibition of cell motility.

Example 16

Cell Migration

Gamendazole (GMZ) was tested to determine if it inhibits cell migration. Briefly, ADPKD cells were plated on a 12-well cell culture plate in 5% FBS-containing medium and allowed to form a confluent monolayer. The monolayer was wounded using a P-200 pipette tip and the medium changed to include increasing concentrations of gamendazole. Images of three different fields per well were captured at 10× magnification immediately after wounding and at 4, 8 and 24 hours post-wounding. GMZ was tested at 0, 10, 50, and 100 uM.

Figure 14A:
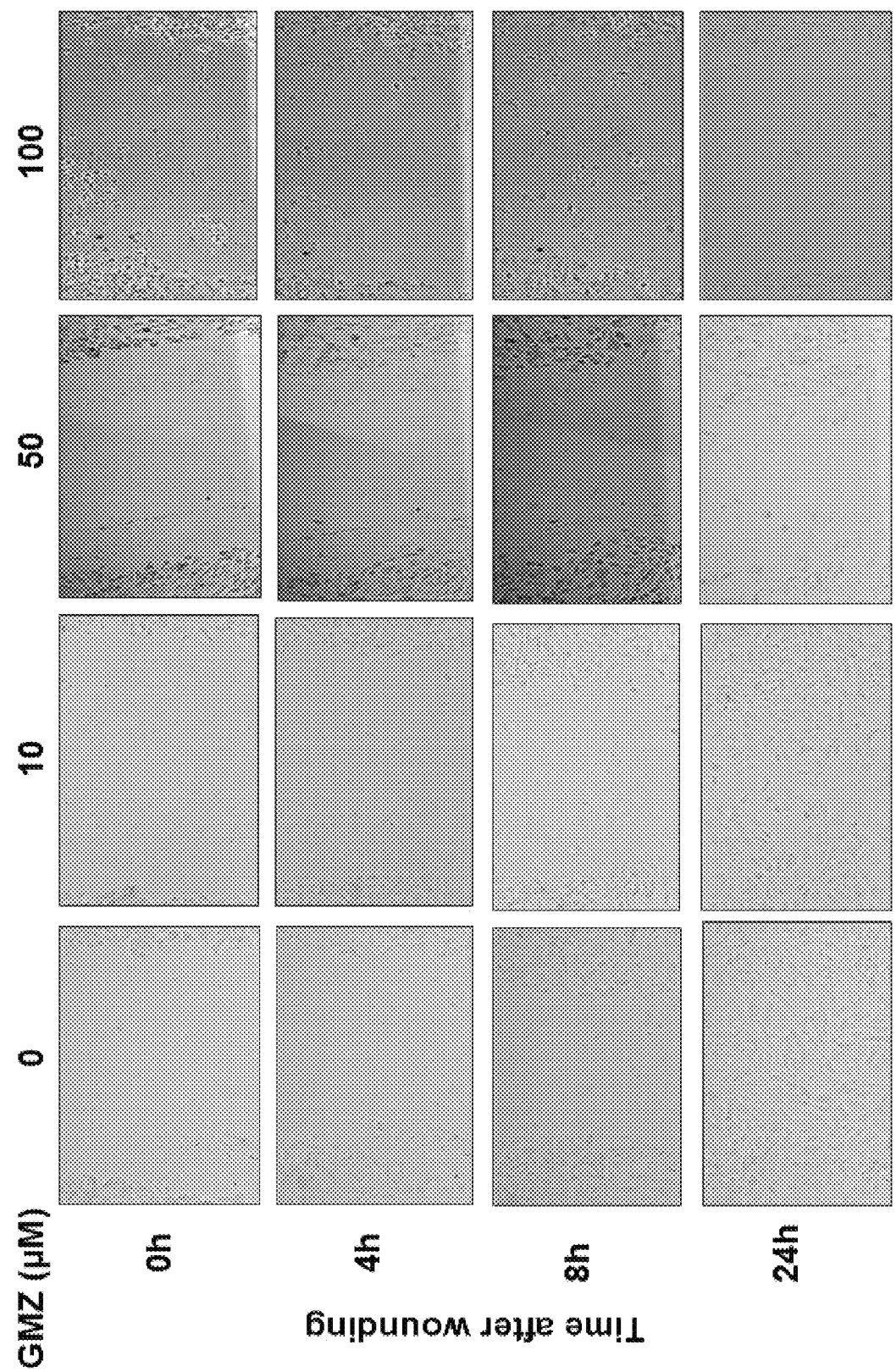
FIG. 14A includes pictures of wound-healing scratch assays which showed that gamendazole-treated ADPKD cells were unable to accomplish wound closure even at low gamendazole concentration (10 uM), consistent with an alteration in the actin cytoskeleton and effects on cell motility.

FIG. 14A include pictures of wound-healing scratch assays which showed that gamendazole-treated ADPKD cells were unable to accomplish wound closure even at low gamendazole concentration (10 uM), consistent with an alteration in the actin cytoskeleton and effects on cell motility. Thus, gamendazole treatment decreases ADPKD cell proliferation and motility and as such may slow cyst formation. These properties, along with its low toxicity, make gamendazole and its analogues attractive candidates for treatment of ADPKD.

Area of the wound was measured at each time point using NIH Image J program. Percentage of wound closure was calculated by subtracting the area of the wound at any given time point from the 0 h wound area expressed as a percentage of the 0 h wound area. Statistical analysis was done to compare the GMZ-treated cells to untreated cells at each time point using One-way ANOVA and the Tukey HSD test for pair-wise comparisons.

Figure 14B:
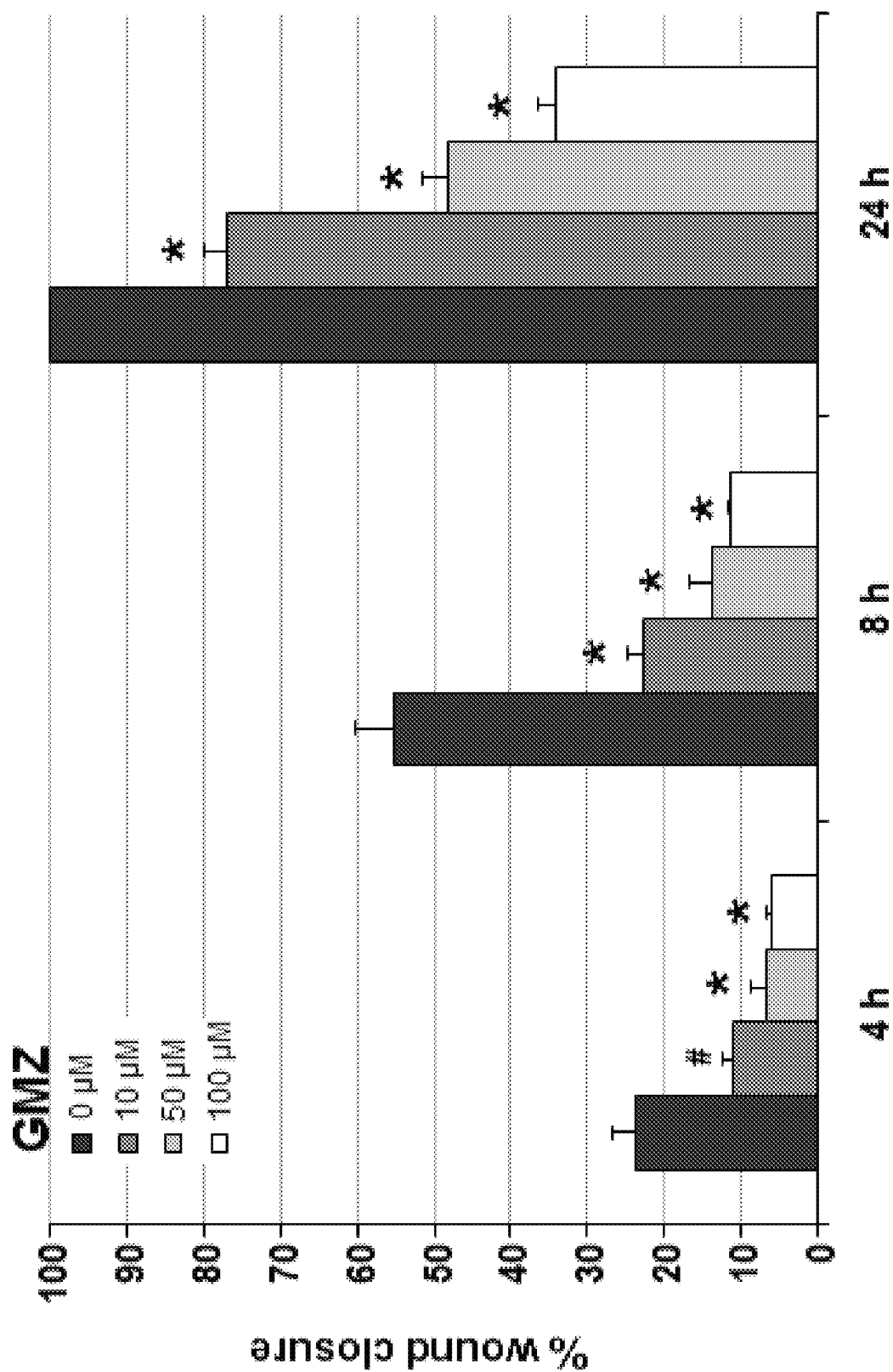
FIG. 14B provides the data showing the percentage of wound closure from FIG. 14A.

FIG. 14B provides the data showing the percentage of wound closure from FIG. 14A. The data shows that there was significant inhibition of cell migration at all concentrations of GMZ tested and at all time points. GMZ inhibited cell migration, preventing wound closure even at the low 10 μM concentration which had no effect on cell proliferation.

From the foregoing it will be seen that this invention is one well adapted to attain all ends and objectives herein-above set forth, together with the other advantages which are obvious and which are inherent to the invention. Those skilled in the art will recognize, or be able to ascertain using no more than routine experimentation, numerous equivalents to the lonidamine analogues and methods of use thereof described herein. Such equivalents are considered to be within the scope of this invention and are covered by the following claims. All references recited herein are incorporated herein by specific reference.

The invention claimed is:

1. A method for inhibiting and/or alleviating the symptoms of polycystic kidney disease (PKD) in a subject, the method comprising:
identifying a subject in need of treatment of PKD;
administering to the subject a compound according to Formula I:

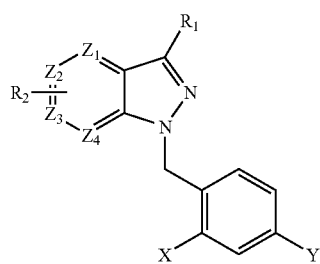

Formula 1 wherein $R_1$ is propionic acid, carboxyl, acryl, or carboxylic acid hydrazide;
wherein $R_2$ is halogen, alcohol, alkoxy, aralkyl, cycloalkyl, haloalkyl, haloalkoxy, amino, or carboxyl;
wherein X and Y are the same or different from each other and are halogen or lower alkyl;
wherein $Z_1$, $Z_2$, $Z_3$, and $Z_4$ are carbon; and
pharmaceutically acceptable salts and esters thereof.

2. A method as in claim 1, wherein $R_2$ is a trihaloalkyl at the 6-position.

3. A method as in claim 1, wherein the compound is selected from the group consisting of:
3-[1-(2,4-dichlorobenzyl)-6-trifluoromethyl-1H-indazol-3-yl]-acrylic acid;
6-chloro-1-(2,4-dichlorobenzyl)-1H-indazole-3-carboxylic acid hydrazide;
1-(2,4-dichlorobenzyl)-6-fluoro-1H-indazole-3-carboxylic acid methyl ester;
6-fluoro-1-(2,4-dichlorobenzyl)-1H-indazole-3-carboxylic acid hydrazide;
3-[1-(2,4-dichlorobenzyl)-6-fluoro-1H-indazol-3-yl]-acrylic acid;
3-[1-(2,4-dichlorobenzyl)-6-chloro-1H-indazol-3-yl]-acrylic acid;
3-[1-(2,4-dichlorobenzyl)-6-trifluoromethoxy-1H-indazol-3-yl]acrylic acid;
3-[1-(2,4-dichlorobenzyl)-6-chloro-1H-indazol-3-yl]-propionic acid;
3-[1-(2,4-dichlorobenzyl)-6-trifluoromethyl-1H-indazol-3-yl]-propionic acid; and
pharmaceutically acceptable salts and esters thereof.

4. A method as in claim 1, wherein the compound is selected from the group consisting of:
gamendazole;
3-[1-(2,4-dichlorobenzyl)-6-trifluoromethyl-1H-indazol-3-yl]-propionic acid (JWS-2-72 or H2-gamendazole);
3-[1-(2,4-dichlorobenzyl)-6-methyl-1H-indazol-3-yl]acrylic acid (TH 2-192);
1-(2,4-dichlorobenzyl)-6-methyl-1H-indazole-3-carboxylic acid (TH 2-178);
3-[1-(2,4-dichlorobenzyl)-6-chloro-1H-indazol-3-yl]-acrylic acid (JWS 1-190);
1-(2-chloro-4-fluorobenzyl)-6-chloro-1H-indazole-3-carboxylic acid hydrazide (JWS 2-22);
1-(2,4-difluorobenzyl)-6-chloro-1H-indazole-3-carboxylic acid hydrazide (JWS 1-282); and
pharmaceutically acceptable salts and esters thereof.

5. A method as in claim 1, wherein $R_1$ is a carboxylic acid hydrazide.

6. A method as in claim 1, wherein the compound is administered in a therapeutically effective amount for inhibiting polycystic kidney disease (PKD) in the subject.

7. A method as in claim 1, wherein the compound is administered in a therapeutically effective amount for inhibiting CFTR and/or Hsp90 or biological pathway thereof.

8. A method as in claim 7, wherein the compound is administered in a therapeutically effective amount for inhibiting ErbB2, Src, Raf-1, B-Raf, MEK, Cdk4, NKCC1, or combinations thereof.

9. A method for inhibiting cystic fibrosis transmembrane conductance regulator (CFTR), the method comprising:
identifying a subject in need of treatment of PKD and administering a compound according to Formula I:

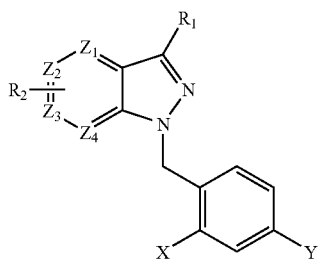

Formula 1 wherein $R_1$ is propionic acid, carboxyl, acryl, or carboxylic acid hydrazide;
wherein $R_2$ is halogen, alcohol, alkoxy, aralkyl, cycloalkyl, haloalkyl, haloalkoxy, amino, or carboxyl;
wherein X and Y are the same or different from each other and are halogen or lower alkyl;
wherein $Z_1$, $Z_2$, $Z_3$, and $Z_4$ are carbon; and
pharmaceutically acceptable salts and esters thereof.

10. A method as in claim 9, wherein $R_2$ is a trihaloalkyl at the 6-position.

11. A method as in claim 9, wherein the compound is selected from the group consisting of:
- 3-[1-(2,4-dichlorobenzyl)-6-trifluoromethyl-1H-indazol-3-yl]-acrylic acid;
- 6-chloro-1-(2,4-dichlorobenzyl)-1H-indazole-3-carboxylic acid hydrazide;
- 1-(2,4-dichlorobenzyl)-6-fluoro-1H-indazole-3-carboxylic acid methyl ester;
- 6-fluoro-1-(2,4-dichlorobenzyl)-1H-indazole-3-carboxylic acid hydrazide;
- 3-[1-(2,4-dichlorobenzyl)-6-fluoro-1H-indazol-3-yl]-acrylic acid;
- 3-[1-(2,4-dichlorobenzyl)-6-chloro-1H-indazol-3-yl]-acrylic acid;
- 3-[1-(2,4-dichlorobenzyl)-6-trifluoromethoxy-1H-indazol-3-yl]acrylic acid;
- 3-[1-(2,4-dichlorobenzyl)-6-chloro-1H-indazol-3-yl]-propionic acid;
- 3-[1-(2,4-dichlorobenzyl)-6-trifluoromethyl-1H-indazol-3-yl]-propionic acid; and
pharmaceutically acceptable salts and esters thereof.

12. A method as in claim 9, wherein the compound is selected from the group consisting of:
- gamendazole;
- 3-[1-(2,4-dichlorobenzyl)-6-trifluoromethyl-1H-indazol-3-yl]-propionic acid (JWS-2-72 or H2-gamendazole);
- 3-[1-(2,4-dichlorobenzyl)-6-methyl-1H-indazol-3-yl] acrylic acid (TH 2-192);
- 1-(2,4-dichlorobenzyl)-6-methyl-1H-indazole-3-carboxylic acid (TH 2-178);
- 3-[1-(2,4-dichlorobenzyl)-6-chloro-1H-indazol-3-yl]-acrylic acid (JWS 1-190);
- 1-(2-chloro-4-fluorobenzyl)-6-chloro-1H-indazole-3-carboxylic acid hydrazide (JWS 2-22);
- 1-(2,4-difluorobenzyl)-6-chloro-1H-indazole-3-carboxylic acid hydrazide (JWS 1-282); and
and pharmaceutically acceptable salts and esters thereof.

* * * * *